US005849870A

United States Patent [19]
Warren et al.

[11] Patent Number: 5,849,870
[45] Date of Patent: *Dec. 15, 1998

[54] PESTICIDAL PROTEINS AND STRAINS

[75] Inventors: Gregory W. Warren; Michael G. Koziel, both of Cary; Martha A. Mullins, Raleigh; Gordon J. Nye, Apex; Brian Carr; Nalini M. Desai, both of Cary; Kristy Kostichka, Durham; Nicholas B. Duck, Cary; Juan J. Estruch, Durham, all of N.C.

[73] Assignee: Novartis Finance Corporation, New York, N.Y.

[ * ] Notice: The term of this patent shall not extend beyond the expiration date of Pat. No. 5,770,696.

[21] Appl. No.: 463,483

[22] Filed: Jun. 5, 1995

Related U.S. Application Data

[63] Continuation-in-part of Ser. No. 314,594, Sep. 28, 1994, abandoned, which is a continuation-in-part of Ser. No. 218,018, Mar. 23, 1994, abandoned, which is a continuation-in-part of Ser. No. 037,057, Mar. 19, 1993, abandoned.

[51] Int. Cl.$^6$ .................................................. C07K 14/325
[52] U.S. Cl. ................. 530/350; 435/252.31; 435/252.5; 435/320.1; 536/23.1; 536/23.7; 536/13.71
[58] Field of Search ........................ 530/350; 536/23.71, 536/23.1, 23.7; 435/193, 252.31, 252.5, 320.1

[56] References Cited

U.S. PATENT DOCUMENTS

| | | | |
|---|---|---|---|
| 3,632,747 | 1/1972 | Satohiro et al. ........................... | 424/93 |
| 3,651,215 | 3/1972 | Satohiro et al. ........................... | 424/93 |
| 4,996,155 | 2/1991 | Sick et al. ............................. | 435/252.3 |
| 5,262,323 | 11/1993 | Baird et al. ........................... | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO88/08880 | 11/1988 | WIPO . |
| WO90/13651 | 11/1990 | WIPO . |
| WO91/16432 | 10/1991 | WIPO . |
| WO91/16434 | 10/1991 | WIPO . |
| 94/03131 | 7/1994 | WIPO . |
| WO 94/21795 | 9/1994 | WIPO . |
| WO 95/15383 | 6/1995 | WIPO . |

OTHER PUBLICATIONS

European International Search Report dated May 3, 1996 for PCT/EP95/03826.

Bernier et al., "*Bacillus thuringiensis* Strains A20 and A29 and Insecticidal Compounds Therefrom, and Compositions Containing These Compounds", Abstract No. 227249, *New Zealand Patent OFfice Journal*, 80(6):798, (1988).

Jellis et al., "*Bacillus thuringiensis* δ–Endotoxin Variants and Insecticidal Compositions", Abstract No. 228108, *New Zealand Patent Office Journal*, 81(3):359, (1992).

Schurter et al., "Genetic Manifpulation of *B. thuringiensis* and *B. cereus* Vectors and Inspecticidal Composition", Abstract No. 229191, *New Zealand Patent Office Journal*, 81(3):363, (1992).

Tayabali et al., "Semiautomated Quantification of Cytotoxic Damage Induced in Cultured Insect Cells Exposed to Commercial *Bacillus thuringiensis* Biopesticides", *Journal of Applied Toxicology*, 15(5): 365–373 (1995).

Thanabalu et al., "Cytotoxicity and ADP–Ribosylating Activity of the Mosquitocidal Toxin from *Bacillus sphaericus* SSII–1: Possible Roles of the 27–and 70–Kilodalton Peptides", *Journal of Bacteriology*, 175(8): 2314–2320 (1993).

Vaithlingam et al., "Anti–Coleopteran Toxin and Gene", Abstract No. 226442, *New Zealand Patent Office Journal*, 80 (7):931, (1991).

Wahisaka et al., "*Bacillus thuringiensis* Mutant and Bacterial Insecticide", Abstract No. 199725, *New Zealand Patent Office Journal*, (1982).

Walther et al., "Analysis of Mosquito Larvicidal Potential Exhibited by Vegetative Cells of *Bacillus thuringiensis* subsp. *israelensis*", *Applied and Environmental Microbiology*, 52(4):650–653 (1986).

Ward et al., "*Bacillus thuringiensis* var. *israelensis* δ–Endotoxin Cloning and Expression of the Toxin in Sporogenic and Asporogenic Strains of *Bacillus subtilis*", *Journal of Molecular Biology*, 191(1): 13–22 (1986).

Arellano, A., et al., "Evidence of a New *Bacillus thuriengiensis* Toxin Active Against the Australian Sheep Blowfly *Lucilla cuprina*", *Proceedings and Abstracts of the 5th International Colloquium on Invertebrate Pathology and Microbial Control, Adelaide, Austrailia*, 20–24 Aug. 1990, p. 291.

Beecher, Douglas J., et al., "A Novel Bicomponent Hemolysin from *Bacillus cereus*", *Inspection and Immunity*, 58(7):2220–2227 (1990).

Faust, R.M., "Bacterial Diseases", In: *Insect Diseases*, G. Cantwell, ed., Marcel Dekker, NY 1974, pp. 90–102.

Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

(List continued on next page.)

Primary Examiner—Robert A. Wax
Assistant Examiner—Nashaat T. Nashed
Attorney, Agent, or Firm—Gary M. Pace, Ph.D.

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

9 Claims, 1 Drawing Sheet

OTHER PUBLICATIONS

Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", *Can. J. Zool.*, 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).

Hofte, H., et al., "Insecticidal Crystal Proteins of *Bacillus thuringiensus*", *Microbiological Reviews*, 53(2):242–255 (1989).

Koziel, M.G., et al., "Field Performance of Elite Tansgenic Maize Plants Expressing an Insecticidal Protein Derived from *Bacillus thuringiensis*", *Bio/Technology*, 11:194–200 (1993).

Krieg, A., "Thuricin, a Bacteriocin Produced by *Bacillus thuringiensis*", *J. Invert. Path.*, 15:291 (1970).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

Myers, P.S., et al., "Localization of a Mosquito–Larval Toxin of *Bacillus sphaericus* 1593", *Appl. Environ. Microbiol.*, 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var, *tenebropmos*", *Current Microbiology*, 17:347–349.

Shivakumar, A.G., et al., Abstract, :Cloned Crystal Protein Genes Express Vegetatively in *Bacillus subtilis, Plasmid,* 16(3):230 (1986).

Thanabalu, T., et al., "Proteolytic Processing of the Mosquitocidal Toxin from *Bacillus sphaericus* SSII–1", *Bacteriol.*, 174(15):5051–5056 (1992).

Yoshisue, H., et al., "Effects of *Bacillus thuringiensus* var. *israelensis* 20 kDa Protein on Production of the Bti 130–kDa Crystal Protein in *escherichia coli* ", *Bioscience, Biotechnology, and Biochemistry*, 56(9):1429–1433 (1992).

Thirumaran et al. "Cloning, sequencing, and expression of a gene encoding a 100–kilodalton mosquitocidal toxin from *Bacillus sphaericus* SSII–1" J Bacteriol. 173, 2776–2785, May 1991.

Krieg, A. "Concerning alpha–toxin produced by vegetative cells of *Bacillus thuringiensis* and *Bacillus cereus*" J. Inverteb. Path. 17, 134–135, Jan. 1971.

Chambers et al., Isolation and Characterization of a Novel Isecticidal Crystal Protein Gene from *Bacillus thuringiensis* subsp. aizawai, Journal of Bacteriology, Jul. 1991, 3966–3976.

Gleave, et al., Screening by Poymerase Chain Reaction of *Bacillus thuringiensis* Serotypes for the Presence of cryV–like Insecticidal Protein Genes and Characterization of a cryV Gene Cloned from *B. thuringiensis* subsp. kurstaki, Applied and Environmental.

Kostichka, et al. Cloning of a cryV–type Isecticidal Protein Gene from *Bacillus thuringiensis*: the cry–V encoded Protein Is Expressed Early in Stationary Phase.

Tailor et al., Identification and characterization of a novel *Bacillus thuringiensis* –(endotoxin entomocidal to coleopteran and lepidopteran larvae, Molecular Microbiology, 1992:6(9), 1211–1217.

Characterization of pCIB6022

Functional Complementation of VIP Clones

PESTICIDAL PROTEINS AND STRAINS

The present invention is a continuation-in-part application of U.S. application Ser. No. 08/314,594 filed Sep. 28, 1994, now abandoned, which is a continuation-in-part application of U.S. application Ser. No. 08/218,018 filed Mar. 23, 1994, now abandoned, which is a continuation-in-part application of U.S. application Ser. No. 08/037,057 filed Mar. 25, 1993, now abandoned, the disclosures of which are herein incorporated by reference.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (*Bt*). *Bt* is a gram-positive spore forming Bacillus which produces an insecticidal crystal protein (ICP) during sporulation.

Numerous varieties of *Bt* are known that produce more than 25 different but related ICP's. The majority of ICP's made by *Bt* are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*. the western corn rootworm (WCRW) or *Diabrotica longicornis barberi*, the northern corn rootworm.

*Bacillus cereus* (*Bc*) is closely related to *Bt*. A major distinguishing characteristic is the absence of a parasporal crystal in *Bc*. *Bc* is a widely distributed bacterium that is commonly found in soil and has been isolated from a variety of foods and drugs. The organism has been implicated in the spoilage of food.

Although *Bt* has been very useful in controlling insect pests, there is a need to expand the number of potential biological control agents.

SUMMARY OF THE INVENTION

Figure 1:
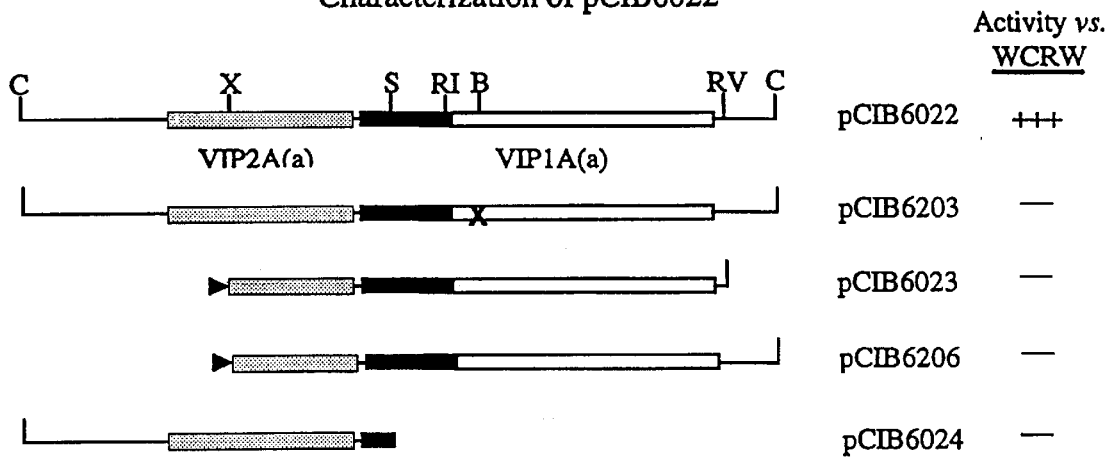
FIG. 1: Characterization of pCIB6022. Boxed regions represent the extent of VIP|A(a) and VIP2A(a). White box represents the portion of VIP 1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI-Eco RI; B-Bgl II; RV-Eco RV.
Figure 1:
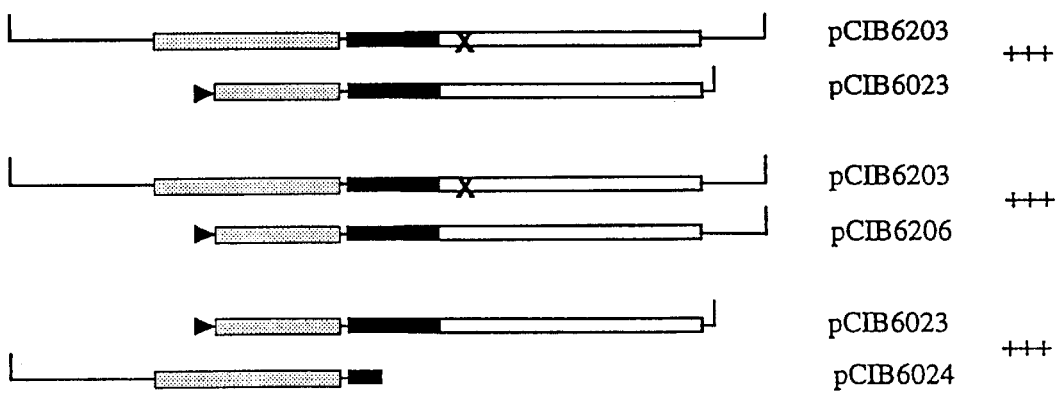

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera, Tables 1–10 gives a list of pests associated with major crop plants and pests of human and veterinary importance. Such pests are included within the scope of the present invention.

TABLE 1

| Lepidoptera (Butterflies and Moths) | |
|---|---|
| Maize | Sunflower |
| *Ostrinia nubilalis*, European corn borer | *Suleima helianthana*, sunflower bud moth |
| *Agrotis ipsilon*, black cutworm | *Homoeosoma electellum*, sunflower moth |
| *Helicoverpa zea*, corn earworm | Cotton |
| *Spodoptera fugiperda*, fall armyworm | *Heliothis virescens*, cotton boll worm |
| *Diatraea grandiosella*, southwestern corn borer | *Helicoverpa zea*, cotton bollworm |
| *Elasmopalpus lignosellus*, lesser cornstalk borer | *Spodoptera exigua*, beet armyworm |
| *Diatraea saccharalis*, sugarcane borer | *Pectinophora gossypiella*, pink bollworm |
| | Rice |
| | *Diatraea sacchaalis*, sugarcane borer |

TABLE 1-continued

Lepidoptera (Butterflies and Moths)

| | |
|---|---|
| Sorghum | *Spodoptera frugioerda*, fall armyworm |
| *Chilo partellus*, sorghum borer | *Helicoverpa zea*, corn earworm |
| *Spodoptera frugiperda*, | Soybean |
| fall armyworm | *Pseudoplusia includens*, soybean looper |
| *Helicoverpa zea*, corn earworm | *Anticarsia gemmatalis*, velvetbean |
| *Elasmopalpus lignosellus*, lesser cornstalk borer | caterpillar |
| *Feltia subterranea*, granulate cutworm | *Plathypena scabra*, green cloverworm |
| | *Ostrinia nubilalis*, European corn borer |
| | *Agrotis ipsilon*, black cutworm |
| Wheat | *Spodoptera exigua*, beet armyworm |
| *Pseudaletia unipunctata*, army worm | *Heliothis virescens*, cotton boll worm |
| *Spodoptera frugiperda*, | *Helicoverpa zea*, cotton bollworm |
| | Barley |
| fall armyworm | *Ostrinia nubilalis*, European corn borer |
| *Elasmopalpus lignosellus*, lesser cornstalk borer | *Agrotis ipsilon*, black cutworm |
| *Agrotis orthogonia*, pale western cutworm | |
| *Elasmopalpus lignosellus*, lesser cornstalk borer | |

TABLE 2

Coleoptera (Beetles)

| | |
|---|---|
| Maize | *Diabrotica virgifera* virgifera, western corn rootworm |
| | *Diabrotica longicornis* barberi, northern corn rootworm |
| | *Diabrotica undecimpunctata* howardi, southern corn rootworm |
| | *Melanotus spp.*, wireworms |
| | *Cyclocephala borealis*, northern masked chafer (white grub) |
| | *Cyclocephala immaculata*, southern masked chafer (white grub) |
| | *Popillia japonica*, Japanese beetle |
| | *Chaetocnema pulicaria*, corn flea beetle |
| | *Sphenophorus maidis*, maize billbug |
| Sorghum | *Phyllophaga crinita*, white grub |
| | *Eleodes, Conoderus,* and *Aeolus spp.*, wireworms |
| | *Oulema melanopus*, cereal leaf beetle |
| | *Chaetocnema pulicaria*, corn flea beetle |
| | *Sphenophorus maidis*, maize billbug |
| Wheat | *Oulema melanopus*, cereal leaf beetle |
| | *Hypera punctata*, clover leaf weevil |
| | *Diabrotica undecimpunctata* howardi, southern corn rootworm |
| Sunflower | *Zygogramma exclamationis*, sunflower beetle |
| | *Bothyrus gibbosus*, carrot beetle |
| Cotton | *Anthonomus grandis*, boll weevil |
| Rice | *Colaspis brunnea*, grape colaspis |
| | *Lissorhoptrus oryzophilus*, rice water weevil |
| | *Sitophilus oryzae*, rice weevil |
| Soybean | *Epilachna varivestis*, Mexican bean beetle |

TABLE 3

Homoptera (Whiteflies, Aphids etc..)

| | |
|---|---|
| Maize | *Rhopalosiphum maidis*, corn leaf aphid |
| | *Anuraphis maidiradicis*, corn root aphid |
| Sorghum | *Rhopalosiphum maidis*, corn leaf aphid |
| | *Sipha flava*, yellow sugarcane aphid |
| Wheat | Russian wheat aphid |
| | *Schizaphis graminum*, greenbug |
| | *Macrosiphum avenae*, English grain aphid |
| Cotton | *Aphis gossypii*, cotton aphid |
| | *Pseudatomoscelis seriatus*, cotton fleahopper |
| | *Trialeurodes abutilonea*, bandedwinged whitefly |
| Rice | *Nephotettix nigropictus*, rice leafhopper |

TABLE 3-continued

Homoptera (Whiteflies, Aphids etc..)

| | |
|---|---|
| Soybean | *Myzus persicae*, green peach aphid |
| | *Empoasca fabae*, potato leafhopper |
| Barley | *Schizaphis graminum*, greenbug |
| Oil Seed Rape | *Brevicoryne brassicae*, cabbage aphid |

TABLE 4

Hemiptera (Bugs)

| | |
|---|---|
| Maize | *Blissus leucopterus* leucopterus, chinch bug |
| Sorghum | *Blissus leucopterus* leucopterus, chinch bug |
| Cotton | *Lygus lineolans*, tarnished plant bug |
| Rice | *Blissus leucopterus* leucopterus, chinch bug |
| | *Acrosternum hilare*, green stink bug |
| Soybean | *Acrosternum hilare*, green stink bug |
| Barley | *Blissus leucopterus* leucopterus, chinch bug |
| | *Acrosternum hilare*, green stink bug |
| | *Euschistus servus*, brown stink bug |

TABLE 5

Orthoptera (Grasshoppers Crickets and Cockroaches)

| | |
|---|---|
| Maize | *Melanoplus femurrubrum*, redlegged grasshopper |
| | *Melanoplus sanguinipes*, migratory grasshopper |
| Wheat | *Melanoplus femurrubrum*, redlegged grasshopper |
| | *Melanoplus differentialis*, differential grasshopper |
| | *Melanoplus sanguinipes*, migratory grasshopper |
| Cotton | *Melanoplus femurrubrum*, redlegged grasshopper |
| | *Melanoplus differentialis*, differential grasshopper |
| Soybean | *Melanoplus femurrubrum*, redlegged grasshopper |
| | *Melanoplus differentialis*, differential grasshopper |
| Structural/Household | *Periplaneta americana*, American cockroach |
| | *Blattella germanica*, German cockroach |
| | *Blatta orientalis*, oriental cockroach |

TABLE 6

Diptera (Flies and Mosquitoes)

| | |
|---|---|
| Maize | *Hylemya platura*, seedcorn maggot |
| | *Agromyza parvicornis*, corn blotch leafminer |
| Sorghum | *Contarinia sorghicola*, sorghum midge |
| Wheat | *Mayetiola destructor*, Hessian fly |
| | *Sitodiplosis mosellana*, wheat midge |
| | *Meromyza americana*, wheat stem maggot |
| | *Hylemya coarctata*, wheat bulb fly |
| Sunflower | *Neolasioptera murtfeldtiana*, sunflower seed midge |
| Soybean | *Hylemya platura*, seedcorn maggot |
| Barley | *Hylemya platura*, seedcorn maggot |
| | *Mayetiola destructor*, Hessian fly |
| Insects attacking humans and animals and disease carriers | |
| | *Aedes aegypti*, yellowfever mosquito |
| | *Aedes albopictus*, forest day mosquito |
| | *Phlebotomus papatasii*, sand fly |
| | *Musca domestica*, house fly |
| | *Tabanus atratus*, black horse fly |
| | *Cochliomyia hominivorax*, screwworm fly |

TABLE 7

Thysanoptera (Thrips)

| | |
|---|---|
| Maize | *Anaphothrips obscurus*, grass thrips |
| Wheat | *Frankliniella fusca*, tobacco thrips |
| Cotton | *Thrips tabaci*, onion thrips |
| | *Frankliniella fusca*, tobacco thrips |

TABLE 7-continued

Thysanoptera (Thrips)

| | |
|---|---|
| Soybean | *Sericothrios variabilis*, soybean thrips |
| | *Thrips tabaci*, onion thrips |

TABLE 8

Hymenoptera (Sawflies, Ants, Wasps, etc.)

| | |
|---|---|
| Maize | *Solenopsis milesta*, thief ant |
| Wheat | *Cephus cinctus*, wheat stem sawfly |

TABLE 9

Other Orders and Representative Species

| | |
|---|---|
| Dermaptera (Earwigs) | *Forficula auricularia*, European earwig |
| Isoptera (Termites) | *Reticulitermes flavipes*, eastern subterranean termite |
| Mallophaga (Chewing Lice) | *Cuclotogaster heterographa*, chicken head louse |
| | *Bovicola bovis*, cattle biting louse |
| Anoplura (Sucking Lice) | *Pediculus humanus*, head and body louse |
| Siphonaptera (Fleas) | *Ctenocephalides felis*, cat flea |

TABLE 10

Acari (Mites and Ticks)

| | |
|---|---|
| Maize | *Tetranychus urticae*, twospotted spider mite |
| Sorghum | *Tetranychus cinnabarinus*, carmine spider mite |
| | *Tetranychus urticae*, twospotted spider mnite |
| Wheat | *Aceria tulipae*, wheat curl mite |
| Cotton | *Tetranychus cinnabarinus*, carmine spider mite |
| | *Tetranychus urticae*, twospotted spider mite |
| Soybean | *Tetranychus turkestani*, strawberry spider mite |
| | *Tetranychus urticae*, twospotted spider mite |
| Barley | *Petrobia latens*, brown wheat mite |
| | Important human and animal Acari |

*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al. (eds.), The Prokaryotes: A Handbook on Habitats, Isolation, and Identification of Bacteria, Vol. II, Springer-Verlag Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| | Unassigned Strains |
|---|---|
| Morphological Group 1 | Subgroup A |
| *B. megaterium* | *B. apiarus*\* |
| *B. cereus*\* | *B. filicolonicus* |
| *B. cereus* var. mycoides | *B. thiaminolyticus* |
| *B. thuringiensis*\* | *B. alcalophilus* |
| *B. licheniformis* | Subgroup B |
| *B. subtilis*\* | *B. cirroflagellosus* |
| *B. pumilus* | *B. chitinosporus* |
| *B. firmus*\* | *B. lentus* |
| *B. coagulans* | Subgroup C |
| Morphological Group 2 | *B. badius* |
| *B. polymyxa* | *B. aneurinolyticus* |
| *B. macerans* | *B. macroides* |
| *B. circulans* | *B. freundenreichii* |
| *B. stearothermophilus* | Subgroup D |
| *B. alvei*\* | *B. pantothenticus* |
| *B. laterosporus*\* | *B. epiphytus* |
| *B. brevis* | Subgroup E1 |
| *B. pulvifaciens* | *B. aminovorans* |
| *B. popilliae*\* | *B. globisporus* |
| *B. lentimorbus*\* | *B. insolitus* |
| *B. larvae*\* | *B. psychrophilus* |
| Morphological Group 3 | Subgroup E2 |
| *B. sphaericus*\* | *B. psychrosaccharolyticus* |
| *B. pasteurii* | *B. macquariensis* |

\*= Those Bacillus strains that have been previously found associated with insects Grouping according to Parry, J. M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, NY (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP2 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with *Bt* endotoxins or other insecticidal proteins to increase insect target range. Furthermore, the use of the VIPs of the present invention in combination with *Bt* δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more *Bt* δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of *Bt* δ-endotoxin. By crossing Parent 1 with Parent 2, progeny plants are obtained which express all the genes introduced into Parents 1 and 2. Particularly preferred *Bt* δ-endotoxins are those disclosed in U.S. Pat. No. 5,625,136, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*, J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent.

Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff (1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP 1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, insecticidal protein. Such a insecticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. application Ser. No. 07/951,715; EPA 0359472; EPA 0385962; WO 91/16432; Perlak et al. (1991) *Proc. Natl. Acad. Sci. USA* 88:3324–3328; and Murray et al. (1989) *Nucleic Acids Research* 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), *Nucleic Acids Research* 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) *Gene* 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) *Plant Science* 52:111–116; Neuhause et al., (1987) *Theor. Appl. Genet.* 75:30–36; Klein et al., (1987) *Nature* 327:70–73; Howell et al., (1980) *Science* 208:1265; Horsch et al., (1985) *Science* 227: 1229–1231; DeBlock et al., (1 989) *Plant Physiology* 91:694–701; *Methods for Plant Molecular Biology* (Weissbach and Weissbach, eds.) Academic Press, Inc. (1988); and *Methods in Plant Molecular Biology* (Schuler and Zielinski, eds.) Academic Press, Inc. (1989). See also U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al., (1989) *Nucleic Acids Research* 17:477–498; and WO 91/16432.

The construct may also include any other necessary regulators such as terminators, (Guerineau et al., (1991), *Mol. Gen. Genet.,* 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al et al., (1989), *Nucleic Acids Res.,* 17:7891–7903; Joshi et al., (1987), *Nucleic Acid Res.,* 15:9627–9639); plant translational consensus sequences (Joshi, C. P., (1987), *Nucleic Acids Research,* 15:6643–6653), introns (Luehrsen and Walbot, (1991), *Mol. Gen. Genet.,* 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV leader (Tobacco Etch Virus) (Allison et al., (1986); MDMV leader (Maize Dwarf Mosaic Virus); *Virology,* 154:9–20), and Human immunoglobulin heavy-chain binding protein (BiP), (Macejak, D. G., and Sarnow, P., (1991), *Nature,* 353:90–94;

Untranslated leader from the coat protein mRNA of alfalfa mosaic virus (AMV RNA 4), (Jobling, S. A., and Gehrke, L., (1987), *Nature,* 325:622–625;

Tobacco mosaic virus leader (TMV), (Gallie, D. R. et al., (1989), *Molecular Biology of RNA,* pages 237–256; and Maize Chlorotic Mottle Virus leader (MCMV) (Lommel, S. A. et al., (1991), *Virology,* 81:382–385. See also, Della-Cioppa et al., (1987), *Plant Physiology,* 84:965–968.

A plant terminator may be utilized in the expression cassette. See, Rosenberg et al., (1987), *Gene,* 56:125; Guerineau et al., (1991), *Mol. Gen. Genet.,* 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al., (1989), *Nucleic Acids Res.,* 17:7891–7903; Joshi et al., (1987), *Nucleic Acid Res.,* 15:9627–9639.

For tissue specific expression, the nucleotide sequences of the invention can be operably linked to tissue specific promoters. See, for example, U.S. application Ser. No. 07/951,715 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacterium, *Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. Iaurentii, Saccharomyces rosei, S. pretoriensis, S. cerevisiae, Sporobolomyces rosues, S. odorus, Kluyveromyces veronae,* and *Aureobasidium pollulans.* Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonas fluorescens, Saccharomyces cerevisiae, Bacillus thuringiensis, Escherichia coli, Bacillus subtilis,* and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a Bacillus cereus strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.,* 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli,* for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli,* for example, by fusing an appropriate *E. coli* signal peptide to the amino-terminal end of the VIP signal peptide or replacing the VIP signal peptide with the E. coli signal peptide. Signal peptides recognized by E. coli can be found in proteins already known to be secreted in E. coli, for example the OmpA protein (J. Ghrayeb, H. Kimura, M. Takahara, Y. Masui and M. Inouye, EMBO J., 3:2437–2442 (1984)). OmpA is a major protein of the E. coli outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, Methods in Enzymology 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, EMBO J., 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in E. coli would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that *Bacillus thuringiensis* strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such *Bt* strains produce endotoxin protein(s) as well as VIPs. Alternatively, such strains can produce only VIPs. A sporulation deficient strain of *Bacillus subtilis* has been shown to produce high levels of the CryIIIA endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", J. Bacteriol., 17647:34–4741 (1994)). A similar spoOA mutant can be prepared in *Bacillus thuringiensis* and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne , J. Mol. Biol. 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP 1, VIP2 and/or other VIPs of the invention can be eliminated from the sequence thereby making them unrecognizable as secretion proteins in Bacillus. Specifically, a methionine start site can be engineered in front of the proprotein sequence in VIP 1, starting at Asp32, or the proprotein sequence in VIP2, starting at Glu41 using methods known in the art.

VIP genes can be introduced into micro-organisms that multiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide) -producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a *Bacillus cereus* microorganism has been isolated which is capable of killing *Diabrotica virgifera virgifera*, and *Diabrotica longicornis barberi*. The novel *B. cereus* strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the *B. cereus* strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: $NH_2$-Lys-Arg-Glu-Ile-Asp-Glu-Asp-Thr-Asp-Thr-Asx-Gly-Asp-Ser-Ile-Pro-(SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the $NH_2$-terminus has been generated. The probe was synthesized based on the codon usage of a *Bacillus thuringiensis* (*Bt*) δ-endotoxin gene. The nucleotide sequence of the oligonucleotide probe used for Southern hybridizations was as follows:

5'-GAA ATT GAT CAA GAT ACN GAT-3' (SEQ ID NO:9)

where N represents any base.

In addition, the DNA probe for the *Bc* AB78 VIP1 gene described herein, permits the screening of any Bacillus strain or other organisms to determine whether the VIP 1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
|---|---|---|
| VIP1A(a) | VIP1 | VIP1 from strain AB78 as disclosed in SEQ ID NO: 5. |
| VIP2A(a) | VIP2 | VIP2 from strain AB78 as disclosed in SEQ ID NO: 2. |
| VIP1A(b) | VIP1 homolog | VIP1 from *Bacillus thuringiensis* var. *tenebrionis* as disclosed in SEQ ID NO:21. |
| VIP2A(b) | VIP2 homolog | VIP2 from *Bacillus thuringiensis* var. *tenebrionis* as disclosed in SEQ ID NO: 20. |
| VIP3A(a) | — | VIP from strain AB88 as disclosed in SEQ ID NO: 28 of the present application |
| VIP3A(b) | — | VIP from strain AB424 as disclosed in SEQ ID NO: 31 of the present application |

EXPERIMENTAL

EXAMPLE 1

AB78 ISOLATION AND CHARACTERIZATION

*Bacillus cereus* strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g $MnCl_2$; Travers, R. S. 1983). During log phase growth, AB78 gave significant activity against western corn rootworm. Antibiotic activity against gram-positive Bacillus spp. was also demonstrated (Table 12).

TABLE 12

Antibiotic activity of AB78 culture supernatant

| | Zone of inhibition (cm) | |
|---|---|---|
| Bacteria tested | AB78 | Streptomycin |
| *E. coli* | 0.0 | 3.0 |
| *B. megaterium* | 1.1 | 2.2 |
| *B. mycoides* | 1.3 | 2.1 |
| *B. cereus* CB | 1.0 | 2.0 |
| *B. cereus* 11950 | 1.3 | 2.1 |
| *B. cereus* 14579 | 1.0 | 2.4 |
| *B. cereus* AB78 | 0.0 | 2.2 |
| *Bt* var. *israelensis* | 1.1 | 2.2 |
| *Bt* var. *tenebrionis* | 0.9 | 2.3 |

Morphological characteristics of AB78 are as follows:

Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl. Table 13 provides the biochemical profile of AB78.

TABLE 13

Biochemical characteristics of *B. cereus* strain AB7S.

| | | | |
|---|---|---|---|
| Acid from L-arabinose | − | Methylene blue reoxidized | + |
| Gas from L-arabinose | − | Nitrate reduced | + |
| Acid from D-xylose | − | $NO_3$ reduced to $NO_2$ | + |
| Gas from D-xylose | − | VP | + |
| Acid from D-glucose | + | $H_2O_2$ decomposed | + |
| Gas from D-glucose | − | Indole | − |
| Acid from lactose | − | Tyrosine decomposed | + |
| Gas from lactose | − | Dihydroxyacetone | − |
| Acid from sucrose | − | Litmus milk acid | − |
| Gas from sucrose | − | Litmus milk coagulated | − |
| Acid from D-mannitol | − | Litmus milk alkaline | − |
| Gas from D-mannitol | − | Litmus milk peptonized | − |
| Proprionate utilization | + | Litmus milk reduced | − |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

EXAMPLE 2

BACTERIAL CULTURE

A subculture of Bc strain AB78 was used to inoculate the following medium, known as TB broth:

| | |
|---|---|
| Tryptone | 12 g/l |
| Yeast Extract | 24 g/l |
| Glycerol | 4 ml/l |
| KH₂PO₄ | 2.1 g/l |
| K₂HPO₄ | 14.7 g/l |
| pH 7.4 | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3
INSECT BIOASSAYS

*B. cereus* strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli* clone bioassay: *E. coli* cells were grown overnight in broth containing 100 μg/ml ampicillin at 37° C. Ten ml culture was sonicated 3× for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five cm² potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 μl was pipetted onto the surface of 18 cm² of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14
Activity of AB78 culture supernatant against various insect species

| Insect species tested to date | Order | Activity |
|---|---|---|
| Western corn rootworm (*Diabrotica virgifera virgifera*) | Col | +++ |
| Northern corn rootworm (*Diabrotica longicornis barberi*) | Col | +++ |
| Southern corn rootworm (*Diabrotica undecimpunctata howardi*) | Col | – |
| Colorado potato beetle (*Leptinotarsa decemlineata*) | Col | – |
| Yellow mealworm (*Tenebrio molitor*) | Col | – |
| European corn borer (*Ostrinia nubilalis*) | Col | – |
| Tobacco budworm (*Heliothis virescens*) | Lep | – |
| Tobacco hornworm (*Manduca sexta*) | Lep | – |
| Beet armyworm (*Spodoptera exigua*) | Lep | – |
| Black cutworm (*Agrotis ipsilon*) | Lep | – |
| Northern house mosquito (*Culex pipiens*) | Dip | – |

The newly discovered *B. cereus* strain AB78 showed a significantly different spectrum of insecticidal activity as compared to known coleopteran active δ-endotoxins from *Bt*. In particular, AB78 showed more selective activity against beetles than known coleopteran-active Bt strains in that it was specifically active against Diabrotica spp. More specifically, it was most active against *D. virgifera virgifera* and *D. longicornis barberi* but not *D. undecimpunctata howardi*.

A number of Bacillus strains were bioassayed for activity during vegetative growth (Table 15) against western corn rootworm. The results demonstrate that AB78 is unique in that activity against western corn rootworm is not a general phenomenon.

TABLE 15
Activity of culture supernatants from various Bacillus spp. against western corn rootworm

| Bacillus strain | Percent WCRW mortality |
|---|---|
| *B. cereus* AB78 (Bat.1) | 100 |
| *B. cereus* AB78 (Bat.2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis* isrealensis | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (µl/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 µl of culture supernatant per ml of western corn rootworm diet.

The cell pellet was also bioassayed and had no activity against WCRW. Thus, the presence of activity only in the supernatant indicates that this VIP is an exotoxin.

EXAMPLE 4
ISOLATION AND PURIFICATION OF CORN ROOTWORM ACTIVE PROTEINS FROM AB78

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

SEQUENCE ANALYSIS OF THE CORN ROOTWORM ACTIVE PROTEIN

The 80 kDa component isolated by SDS-PAGE was transferred to PVDF membrane and was subjected to amino-terminal sequencing as performed by repetitive Edman cycles on an, ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be:

NH2-Lys-Arg-Glu-Ile-Asp-Glu-Asp-Thr-Asp-Thr-Asx-Gly-Asp-Ser-Ile-Pro-(SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

CONSTRUCTION OF DNA PROBE

An oligonucleotide probe for the region of the gene encoding amino acids 3–9 of the N-terminal sequence (Example 5) was generated. The probe was synthesized based on the codon usage of a *Bacillus thuringiensis* (*Bt*) δ-endotoxin gene. The nucleotide sequence

5'-GAA ATT GAT CAA GAT ACN GAT-3' (SEQ ID NO:9)

was used as a probe in Southern hybridizations. The oligonucleotide was synthesized using standard procedures and equipment.

EXAMPLE 7

ISOELECTRIC POINT DETERMINATION OF THE CORN ROOTWORM ACTIVE PROTEIN

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR DATA ON AB78

PCR analysis (See, for example U.S. patent application Ser. No. 08/008,006; and, Carozzi et al. (1991) *Appl. Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

| Bacillus insecticidal crystal protein gene primers tested by PCR against AB78 DNA. | |
|---|---|
| Primers Tested | Product Produced |
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |
| CryIC specific | Negative |
| CryIE specific | Negative |
| 2 sets specific for *B. sphaericus* | Negative |
| 2 sets specific for CryIV | Negative |
| Bacillus control (PI-PLC) | Positive |

EXAMPLE 9
COSMID CLONING OF TOTAL DNA FROM *B. CEREUS* STRAIN AB78

The VIP1A(a) gene was cloned from total DNA prepared from strain AB78 as follows:

Isolation of AB78 DNA was as follows

1. Grow bacteria in 10 ml L-broth overnight. (Use 50 ml sterile centrifuge tube)
2. Add 25 ml of fresh L-broth and ampicillin (30 $\mu$g/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 $\mu$l 20% SDS and 400 $\mu$l Proteinase K stock (20 mg/ml). Incubate at 37° C.
8. Add 200 $\mu$l fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h.
14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:

A. Sau 3A partial digestion of the AB78 DNA.

B. Preparation of vector DNA

C. Ligation and packaging of DNA

D. Tittering the cosmid library

1. Start a culture of HB101 cells by placing 50 ml of an overnight culture in 5 mls of TB with 0.2% maltose. Incubate 3.5 hrs. at 37° C.
2. Spin out cells and resuspend in 0.5 ml 10 mM $MgSO_4$.
3. Add together:
   100 $\mu$l cells
   100 $\mu$l diluted packaging mixture
   100 $\mu$l 10 mM $MgSO_4$
   30 $\mu$l TB
4. Adsorb at room temperature for 30 minutes with no shaking.
5. Add 1 ml TB and mix gently. Incubate 30 minutes at 37° C.
6. Plate 200 $\mu$l onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
|---|---|
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

EXAMPLE 10

IDENTIFICATION OF A 6 KB REGION ACTIVE AGAINST WESTERN CORN ROOTWORM

DNA from P3-12 was partially digested with restriction enzyme Sau 3A, and ligated into the *E. coli* vector pUC 19 and transformed into *E. coli*. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the *E. coli*-Bacillus shuttle vector pHT 3101 (Lereclus, D. et al., *FEMS Microbiology Letters* 60:211–218 (1989)) to yield pCIB6201. This construct confers anti-western corn rootworm activity upon both Bacillus and *E. coli* strains, in either orientation. pCIB6022 contains this same 6 kb Cla I fragment in pBluescript SK(+) (Stratagene), produces equivalent VIP1A(a) protein (by western blot), and is also active against western corn rootworm.

The nucleotide sequence of pCIB6022 was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in FIG. 1. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11
FUNCTIONAL DISSECTION OF THE VIP1A(a) DNA REGION

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was re-ligated and transformed into E. coli. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm. (See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) region, in combination with VIP1A (a), to confer maximal western corn rootworm activity. (See FIG. 1)

EXAMPLE 12
AB78 ANTIBODY PRODUCTION

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3x63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on nitrocellulose in DMSO for ELISA screening:

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 $\mu$l of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:

1. Coat with AB78/DMSO in BBS. Incubate overnight at 4° C.
2. Wash plate 3× with 1×ELISA wash buffer.
3. Block (1% BSA & 0.05% Tween 20 in PBS) for 30 minutes at Room Temperature.
4. Wash plate 3× with 1×ELISA wash buffer.
5. Add rat serum. Incubate 1.5 hours at 37° C.
6. Wash plate 3× with 1×ELISA wash buffer.
7. Add goat anti-rat at a concentration of 2 $\mu$g/ml in ELISA diluent. Incubate 1 hr. at 37° C.
8. Wash plate 3× with 1×ELISA wash buffer.
9. Add rabbit anti-goat alkaline phosphatase at 2 $\mu$g/ml in ELISA diluent. Incubate 1 hr. at 37° C.
10. Wash 3× with 1×ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

EXAMPLE 13
ACTIVATION OF INSECTICIDAL ACTIVITY OF NON-ACTIVE BT STRAINS WITH AB78 VIP CLONES

Adding pCIB6203 together with a 24 h culture (early to mid-log phase) supernatant from Bt strain GC91 produces 100% mortality in *Diabrotica virgifera virgifera*. Neither pCIB6203 nor GC91 is active on *Diabrotica virgifera virgifera* by itself. Data are shown below:

| Test material | Percent Diabrotica mortality |
| --- | --- |
| pCIB6203 | 0 |
| GC91 | 16 |
| pCIB6203 + GC91 | 100 |
| Control | 0 |

EXAMPLE 14
ISOLATION AND BIOLOGICAL ACTIVITY OF *B. CEREUS* AB81

A second *B. cereus* strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
| --- | --- |
| *Ostrinia nubilalis* | 0 |
| *Agrotis ipsilon* | 0 |
| *Diabrotica virgifera* virgifera | 55 |

EXAMPLE 15
ISOLATION AND BIOLOGICAL ACTIVITY OF *B. THURINGIENSIS* AB6

A *B. thuringiensis* strain, designated AB6, was isolated from grain bin dust samples by standard methods known in the art. A subculture of AB6 was grown and prepared for bioassay as described in Example 2. Half of the presence of β-exotoxin.

Biological activity was evaluated as described in Example 3. The results are as follows:

| Insect species tested | Percent Mortality |
| --- | --- |
| *Ostrinia nubilalis* | 0 |
| *Agrotis ipsilon* | 100 |
| *Agrotis ipsilon* (autoclaved sample) | 0 |
| *Diabrotica virgifera* virgifera | 0 |

The reduction of insecticidal acitivity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16
ISOLATION AND BIOLOGICAL CHARACTERIZATION OF *B. thuringiensis* AB88

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| | | Percent mortality of culture supernatant | |
| --- | --- | --- | --- |
| Insect species tested | Order | Non-autoclaved | Autoclaved |
| *Agrotis ipsilon* | Lepidoptera | 100 | 5 |
| *Ostrinia nubilalis* | Lepidoptera | 100 | 0 |
| *Spodoptera frugiperda* | Lepidoptera | 100 | 4 |
| *Helicoverpa zea* | Lepidoptera | 100 | 12 |
| *Heliothis virescens* | Lepidoptera | 100 | 12 |
| *Leptinotarsa decemlineata* | Coleoptera | 0 | 0 |
| *Diabrotica virgifera* virgifera | Coleoptera | 0 | 5 |

The reduction of insecticidal acitivity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against *Agrotis ipsilon*.

EXAMPLE 17
PURIFICATION OF VIPS FROM STRAIN AB88

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromotography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins.

| | |
|---|---|
| anion exchange fraction 23 (smaller): | xEPFVSAxxxQxxx (SEQ ID NO: 10) |
| anion exchange fraction 28 (larger): | xEYENVEPFVSAx (SEQ ID NO: 11) |

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18
CHARACTERIZATION OF AB88 VIP

Fractions containing the various lepidopteran active vegetative proteins were generated as described in Example 17. Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa |
| | MDNNPNINE (SEQ ID NO: 14) |
| 80 kDa | 80 kDa |
| MNKNNTKLPTRALP | MDNNPNINE (SEQ ID NO: 15) |
| (SEQ ID NO: 12) | 60 kDa |
| | MNVLNSGRTTI (SEQ ID NO: 16) |
| 35 kDa | |
| ALSENTGKDGGYIVP | |
| (SEQ ID NO: 13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A
ISOLATION AND BIOLOGICAL ACTIVITY OF *B. thuringiensis* AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| *Ostrinia nubilalis* | 100 |
| *Agrotis ipsilon* | 100 |
| *Diabrotica virgifera* virgifera | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

EXAMPLE 18B
CLONING OF THE VIP3A(a) and VIP3A(b) GENES WHICH ENCODE PROTEINS ACTIVE AGAINST BLACK CUTWORM DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis ipsilon* (black cutworm). Four out of 400 recombinant clones were positive. Insect bioassays of the positive recombinants exhibited toxicity to black cutworm larvae comparable to that of AB88 or AB424 supernatants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C
IDENTIFICATION OF NOVEL VIP3-LIKE GENES BY HYBRIDIZATION

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. *Molecular Cloning: A Laboratory Manual*

(1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D
CHARACTERIZATION OF A *B. thuringiensis* STRAIN M2194 CONTAINING A CRYPTIC VIP3-LIKE GENE A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immuno-blot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19
ISOLATION AND BIOLOGICAL ACTIVITY OF OTHER BACILLUS SP

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
| --- | --- | --- |
| AB6 | + | 100 |
| AB53 | - | 80 |
| AB88 | + | 100 |
| AB195 | - | 60 |
| AB211 | - | 70 |
| AB217 | - | 83 |
| AB272 | - | 80 |
| AB279 | - | 70 |
| AB289 | + | 100 |
| AB292 | + | 80 |
| AB294 | - | 100 |
| AB300 | - | 80 |
| AB359 | - | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
| --- | --- | --- |
| AB52 | - | 50 |
| AB59 | - | 71 |
| AB68 | + | 60 |
| AB78 | - | 100 |
| AB122 | - | 57 |
| AB218 | - | 64 |
| AB256 | - | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

EXAMPLE 20
IDENTIFICATION OF NOVEL VIP1/VIP2 LIKE GENES BY HYBRIDIZATION

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis* var *tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21
CLONING OF A VIP1A(a)/VIP2A(a) HOMOLOG FROM BACILLUS thuringiensis VAR. TENEBRIONIS Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)/VIP2A(a) like sequences. DNA from Bt strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a) homologs. In contrast, Bacillus thuringiensis var. tenebrionis (Btt) contained sequences that hybridized to the VIP1A(a)/VIP2A (a) region. Further analysis confirmed that Btt contains VIP1A(a)/VIP2A(a) like sequences.

To characterize the Btt homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into E. coli to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77% amino acid identity to VIP1A(a) from AB78. An alignment of these two VIP1 proteins is provided in Table 20. The alignment shown in Table 20 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20) of the two proteins exhibit 91% identity, while the carboxy-terminal third (from aa 619–833 of VIP1A(b)) exhibit only 35% identity.

Western blot analysis indicated that Bacillus thuringiensis var. tenebrionis (Btt) produces both VIP1A(a) like and VIP2A(a) like proteins. However, these proteins do not appear to have activity against western corn rootworm. Bioassay for activity against western corn rootworm was performed using either a 24 h culture supernatant from Btt or E. coli clone pCIB7100 (which contains the entire region of the VIP1A(a)/VIP2A(a) homologs). No activity against western corn rootworm was detected in either case.

Given the similarity between the VIP2 proteins from Btt and AB78, the ability of VIP2A(b) from Btt to substitute for VIP2A(a) from AB78 was tested. Cells containing pCIB6206 (which produces AB78 VIP1A(a) but not VIP2A (a) protein) were mixed with Btt culture supernatant, and tested for activity against western corn rootworm. While neither Btt culture supernatant nor cells containing pCIB6206 had activity on WCRW, the mixture of Btt and pCIB6206 gave high activity against WCRW. Furthermore, additional bioassay showed that the Btt clone pCIB7100, which contains the Btt VIP1A(b)NIP2A(b) genes in E. coli, also confers activity against WCRW when mixed with pCIB6206. Thus, the VIP2A(b) protein produced by Btt is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/ VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences from Bacillus thuringiensis var. tenebrionis
(VIP2A(b)) vs. AB78 (VIP2A(a))

| Btt | 1 M Q R M E G K L F V V S K T L Q V V T R T V L L S T V Y S I T L L N N V V I K A D Q L N I N S Q S K | 50 SEQ ID NO: 20 |
|---|---|---|
| | \| . \| \| \| \| \| \| \| \| : \| \| \| . \| \| \| \| \| : \| \| \| \| \| \| \| \| : \| \| . \| \| \| \| \| \| \| \| : \| \| \| \| \| \| \| \| | |
| AB78 | 1 M K R N E G K L F M V S K K L Q V V T K T V L L S T V F S I S L L N N E V I K A E Q L N I N S Q S K | 50 SEQ ID NO: 2 |

TABLE 19-continued

Alignment of VIP2 Amino Acid Sequences from *Bacillus thuringiensis* var. *tenebrionis*
(VIP2A(b)) vs. AB78 (VIP2A(a))

```
 51 YTNLQNLKI PDNAEDF KEDKGKAKE WG KE KGE E WR P P ATE KGE MNNF LDN 100
    ||||||||| .|.. |||||||| : ||||||||||| : . ||: . ||||| . ||||||
 51 YTNLQNLKI TDKVEDF KEDKE KAKE WG KE KE KE WKL T ATE KG KMNNF LDN 100

101 KNDI KTNYKEI TFS MAGS CEDEI KDLEEI DKI FDKANLS SS I I TYKNVEP 150
    |||| ||||||||||||| ||||| . |||| . ||| . ||| . ||||||||||
101 KNDI XTNYKEI TFS MAGS FEDEI KDLKEI DKMFDKTNLS NS I I TYKNVEP 150

151 ATI GF NKS LTEGNTI NS DAMAQF KEQF LGKDMKF DS YLDTHLTAQQVS S K 200
    . ||||||||||||||||||||||||||||: : | : ||||||||||||||||||
151 TTI GF NKS LTEGNTI NS DAMAQF KEQF LDRDI KF DS YLDTHLTAQQVS S K 200

201 KRVI LKVTVPS GKGS TTP TKAGVI LNNNEYKMLI DNGYVL HVDKVS KVVK 250
    . |||||||||||||||||||||||||. ||||||||||||: : |||||||||
201 ERVI LKVTVPS GKGS TTP TKAGVI LNNS EYKMLI DNGYMVHVDKVS KVVK 250

251 KGMECLQVEGTLKKS LDF KNDI NAE AHS WGMKI YEDWAKNLTAS QREALD 300
    || : |||| : |||||||||||||||||||||| || : ||| : || . ||||||
251 KGVECLQI EGTLKKS LDF KNDI NAE AHS WGMKNYEE WAKDLTDS QREALD 300

301 GYARQDYKEI NNYLRNQGGS GNE KLDAQL KNI SDALGKKPI PENI TVYRW 350
    ||||||||||||||||||||||||||||||: |||||||||||||||||||
301 GYARQDYKEI NNYLRNQGGS GNE KLDAQI KNI SDALGKKPI PENI TVYRW 350

351 CGMP EF GYQI SDP LP SLKDF EEQF LNTI KEDKGYMS TS LS S ERLAAF GS R 400
    |||||||||||||||||||||||||||||||||||||||||||||||||
351 CGMP EF GYQI SDP LP SLKDF EEQF LNTI KEDKGYMS TS LS S ERLAAF GS R 400

401 KI I LRLQVP KGS TGAYLS AI GGF AS E KEI LLDKDS KYHI DKATE VI I KGV 450
    || ||||||||||||||||||||||||||||||||||||||| . ||||||||
401 KI I LRLQVP KGS TGAYLS AI GGF AS E KEI LLDKDS KYHI DKVTE VI I KGV 450

451 KRYVVDATLLTN 462
    ||||||||||||
451 KRYVVDATLLTN 462
```

TABLE 20

Alignment of VIP1 Amino Acid Sequences from *Bacillus thuringiensis* var. *tenebrionis*
(VIP1A(b)) vs. AB78 (VIP1A(a))

```
Btt    1 MKNMKKKLAS VVTCMLLAP MFLNGNVNAVNADS KI NQI STTQENQQKEMD  50 SEQ ID NO: 21
         ||||||||||||||||| |||||||||||| |||| . ||||||| . ||||||
AB78   1 MKNMKKKLAS VVTCTLLAP MFLNGNVNAVYADS KTNQI STTQKNQQKEMD  50 SEQ ID NO: 5

51 RKGLLGYYF KGKDF NNLTMF AP TRDNTLMYDQQTANALLDKKQQEYQS I R 100
         ||||||||||||||| . |||||||||| . || : ||||||| |||||||||
      51 RKGLLGYYF KGKDF SNLTMF AP TRDSTLI YDQQTANKLLDKKQQEYQS I R 100

101 WI GLI QRKETGDF TF NLS KDEQAI I EI DGKI I SNKGKE KQVVHLE KE KLV 150
         |||||. |||||||||||. ||||||||: |||||||||||||||||: |||
     101 WI GLI QS KETGDF TF NLS EDRQAI I EI NGKI I SNKGKE KQVVHLE KGLLV 150

151 PI KI EYQS DTKF NI DS KTF KELKLF KI DS QNQS QQVQ . . . LRNPE F NKKE 197
         |||||||||||||||||||||||||||||||. |||| |||||||||||
     151 PI KI EYQS DTKF NI DS KTF KELKLF KI DS QNQP QQVQQDELRNPE F NKKE 200

198 SQEF LAKAS KTNLF KQKMKRDI DEDTDTDGDS I PDLWEENGYTI QNKVAV 247
         |||||||: ||. ||||||| ||||||||||||||||||||||||: : ||
     201 SQEF LAKPSKI NLF TQKMKREI DEDTDTDGDS I PDLWEENGYTI QNRI AV 250

248 KWDDS LAS KGYTKF VS NPLDS HTVGDP YTDYE KAARDLDLS NAKETF NPL 297
         ||||||||||||||||||| : ||||||||||||||||||||||||||||
     251 KWDDS LAS KGYTKF VS NPLES HTVGDP YTDYE KAARDLDLS NAKETF NPL 300

298 VAAF PS VNVS MEKVI LS PNENLS NS VES HS S TNWS YTNTE GAS I EAGGGP 347
         ||||||||||||||||||||||||||||||||||||||||| : ||| ||
     301 VAAF PS VNVS MEKVI LS PNENLS NS VES HS S TNWS YTNTE GAS VEAGI GP 350

348 LGLS FGVS VTYQHS ETVAQE WGTS TGNTS QF NTAS AGYLNANVRYNNVGT 397
         | : ||||||. |||||||||||||||||||||||||||||||||||||||
     351 KGI SFGVS VNYQHS ETVAQE WGTS TGNTS QF NTAS AGYLNANVRYNNVGT 400

398 GAI YDVKPTTS FVLNNNTI ATI TAKS NS TALRI SPGDS YPEI GENAI AI T 447
         ||||||||||| : |||||| ||||||||||||. |||| : ||| .  | : | : ||||
     401 GAI YDVKPTTS FVLNNDTI ATI TAKS NS TALNI SPGES YPKKGQNGI AI T 450
```

TABLE 20-continued

Alignment of VIP1 Amino Acid Sequences from *Bacillus thuringiensis* var. *tenebrionis*
(VIP1A(b)) vs. AB78 (VIP1A(a))

```
      448 S MD D F N S  HP I  T L N K Q Q V N Q L I  N N K P I  M L E T D Q T D G V Y K I  R D T H G N I  V T G G  497
          | | | | | | | | | | | | | . | | : | | : | | | | : | | | | : | | | | | | | | : | | | | | | | | |
      451 S MD D F N S  HP I  T L N K K Q V D N L  L N N K P MM L E T N Q T D G V Y K I  K D T H G N I  V T G G  500

498 E WN G V T Q Q I  K A K T A S I  I  V D D G K Q V A E K R V A A K D Y G H P E D K T P  P L T L K D T L  547
          | | | | | . | | | | | | | | | | | | | | | | . . | | | | | | | | | | | | : : | | | | | | . | | | | | . |
      501 E WN G V I  Q Q I  K A K T A S I  I  V D D G E R V A E K R V A A K D Y E N P E D K T P  S L T L K D A L  550

548 K L S  Y P  D E I  K E T N G L L  Y Y D D K P I  Y E S S V M T  Y L D E N T A K E V K K Q I  N D T T G K F  597
          | | | | | | | | | | | . : | | | | | . : | | | | | | | | | | | | | | | | | | | . | | : | | | | | | |
      551 K L S  Y P  D E I  K E I  E G L L  Y Y K N K P I  Y E S S V M T  Y L D E N T A K E V T K Q L N D T T G K F  600
```

Btt     598 K D V N H L  Y D V K L  T P  K M N F  T I  K M A S  L Y D G A E  N N H N S  L G T W Y L  T Y N V A G G N T G   647 SEQ ID NO: 21
               | | | . | | | | | | | | | | | . | | | : .     | | | . | | : . | | : | . |     |     | . | | | . |
Ab78   600 K D V S H L  Y D V K L  T P  K M N V T I  K L S I  L Y D N A E  S N D N S I  G K W T N T N I  V S G G N N G   650 SEQ ID NO: 5

```
      648 K R Q Y R S  A H S  C A H V A L S  S E A K K K L  N Q N A N Y Y L S  M Y M K A D S T T E P T I  E V A G E  697
          | : | | . | . : .   | : : . | . . . : | . . | | | . |   : | | : | : | | | . : . . | : . . | . : | |
      651 K K Q Y S  S N N P  D A A L T L N T D A Q E K L  N K N R D Y Y I  S L Y M K S E K N T Q C E I  T I  D G E  700

698 K S  A I  T S K K V K L  N N Q N Y Q R V D I  L V K N S E R N P  M D K I  Y I  R G N G T T N V Y G D D V T  747
          : | | . | . | . : | . : | | . | : | | : . . |   . . | | : . . . : | : . | : . . . . : :   | | : .
      701 I  Y P I  T T K T V N V N K D N Y K R L D I  I  A H N I  K S N P I  S S L H I  K T N D E I  T L F WD D I  S  750

748 I  P E V S  A I  N P  A S  L S D E E I  Q E I  F K D S T I  E Y G N P S F V A D A V T F K . . . . . . . . . .  788
          | . : | . . | . | . . | . | . | | . : | :      . | . . . : : .    : : . .    . . : .
      751 I  T D V A S I  K P  E N L T D S E I  K Q I  Y S  R Y G I  K L E D G I  L I  D K K G   I  H Y G E F I  N E A S  800

789 . NI  K P  L Q N Y V K E Y E I  Y H K . . . . . . . S H R Y E K K T V F  D I  M G V H Y E Y S I  A R E Q  830
          | | . | | | | | | . . | . :    . .       | . .   | . . . : : .    . : . : : : .     . . .
      801 F NI  E P  L Q N Y V T K Y K V T Y S  S E L G Q N V S D T L E S D K I  Y K D G T I  K F D F T K Y S K N  850

831 K K A  833
          . . :
      851 E Q G  853
```

EXAMPLE 22
FUSION OF VIP PROTEINS TO MAKE A SINGLE POLYPEPTIDE

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the $NH_2$ terminus of the fusion protein, or they can be fused to produce the larger of the polypeptides as the $NH_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example patent application U.S. Pat. No. 5,625,136 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-<u>CCCGGG</u> CCT TCT ACT CCC CCA ACT CCC TCT CCT AGC ACG CCT CCG ACA CCT AGC <u>GAT ATC</u> <u>GGA TC C</u>-3' (SEQ ID NO:48). Oligonucleotides were synthesized to represent: both the upper and lower strands and cloned into a pUC vector following hybridization and phosphorylation using standard procedures. The stop codon in VIP2A(a) was removed using PCR and replaced by the BglII restriction site with a SmaI site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23
TARGETING OF VIP2 TO PLANT ORGANELLES

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263: 15104–15109 (1988)). These signal sequences can be fused to heterologous gene products such as VIP2 to effect the import of those products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad. Sci. USA 82:6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205:446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell*, 1:381–390 (1989), Denecke et al., *The Plant Cell*, 2:51–59 (1990). Amino-terminal sequences have been identified that are responsible for targeting to the ER, the apoplast, and extracellular secretion from aleurone cells (Koehler & Ho, Plant Cell 2:769–783 (1990)).

The presence of additional signals are required for the protein to be retained in the endoplasmic reticulum or the vacuole. The peptide sequence KDEL/HDEL at the carboxy-terminal of a protein is required for its retention in the endoplasmic reticulum (reviewed by Pelham, *Annual Review Cell Biol.*, 5:1–23 (1989). The signals for retention of proteins in the vacuole have also been characterized. Vacuolar targeting signals may be present either at the amino-terminal portion, (Holwerda et al., *The Plant Cell*, 4:307–318 (1992), Nakamura et al., *Plant Physiol.*, 101:1–5 (1993)), carboxy-terminal portion, or in the internal sequence of the targeted protein. (Tague et al., *The Plant Cell*, 4:307–318 (1992), Saalbach et al., *The Plant Cell*, 3:695–708 (1991)). Additionally, amino-terminal sequences in conjunction with carboxy-terminal sequences are responsible for vacuolar targeting of gene products (Shinshi et al. Plant Molec. Biol. 14: 357–368 (1990)). Similarly, proteins may be targeted to the mitochondria or plastids using specific carboxy terminal signal peptide fusions (Heijne et al., *Eur. J. Biochem.*, 180:535–545 (1989), Archer and Keegstra, *Plant Molecular Biology*, 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell*, 1:381–390 (1989), Denecke, et al., *The Plant Cell*, 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant* Cell, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-<u>GGATCC</u>ACC ATG GGC TGG AGC TGG ATC TTC CTG TTC CTG CTG AGC GGC <u>GCC GCG GGC G</u>TG CAC TGC <u>CTGCAG</u>-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-<u>CCG CGG</u> GCG TGC ACT GCC TCA GCA GCA GCA GCT TCG CCG ACA GCA ACC CCA TCC GCG TGA CCG ACC GCG CCG CCA GCA CC<u>C TGC AG</u>-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A
REMOVAL OF BACILLUS SECRETION SIGNAL FROM VIP1A(a) AND VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucleotide position 507. A 527 bp amplification product was obtained containing the restriction sites BamHI at the 5' end and HindIII site at the 3' end. The amplification product was cloned into a T-vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A (a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC-3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T-vector, sequenced and ligated to a BamHI/HindIII digested root-preferred promoter cassette containing the maize optimized VIP2A(a). The construct obtained was designated pCIB5527. The maize optimized coding region for VIP2A (a) with the Bacillus secretion signal removed is disclosed as SEQ ID NO:39 and the encoded protein is disclosed as SEQ ID NO:40.

EXAMPLE 24
CONSTRUCTION AND CLONING OF THE VIP1A(a) AND VIP2A(a) MAIZE OPTIMIZED GENES

Design: The maize optimized genes were designed by reverse translation of the native VIP1A(a) and VIP2A(a) protein sequences using codons that are used most often in maize (Murray et al., *Nucleic Acid Research*, 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever necessary, nucleotides were changed to decrease the stability of the secondary structure without changing the amino acid sequence of the protein. A plant ribosomal binding site consensus sequence, TAAACAATG (Joshi et al., *Nucleic Acid Res.*, 15:6643–6653 (1987)) or eukaryotic ribosomal binding site concensus sequence CCACCATG (Kozak, *Nucleic Acid Research*, 12:857–872 (1984)) was inserted at the translational start codon of the gene.

Cloning: Oligos were synthesized by IDT Inc., and were supplied as lyophilized powders. They were resuspended at a concentration of 200 μM. To 30 μl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in $dH_2O$ at a concentration of 2.5 μM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation: Homologous double stranded oligo pairs were obtained by mixing 5 μl of the upper and of the lower oligo for each oligo pair with buffer containing 1×polynucleotide kinase (PNK) buffer (70 mM Tris-HCl (pH 7.6), 10 mM $MgCl_2$ 5 mM dithiothreitol (DTT)), 50 mM KCl, and 5% formamide in a final volume of 50 μl. The oligos were boiled for 10 minutes and slow cooled to 37° C. or room temperature. 10 μl was removed for analysis on a 4% agarose in a TAE buffer system (Metaphore®; FMC). Each hybridized oligo pair was kinased by the addition of ATP at a final concentration of 1 mM, BSA at a final concentration of 100 μg per ml and 200 units of polynucleotide kinase and 1 μl of 10×PNK buffer in a volume of 10 μl. Following hybridization and phosphorylation, the reaction was incubated at 37° C. for 2 hours to overnight. 10 μl of each of the oligo pairs for a particular fragment, were mixed in a final volume of 50 μl. The oligo pairs were hybridized by heating at 80° C. for 10 minutes and slow cooling to 37° C. 2 μl of oligos was mixed with about 100 ng of an appropriate vector and ligated using a buffer containing 50 mM Tris-HCl (pH 7.8), 10 mM $MgCl_2$, 10 mM DTT, 1 mM ATP. The reaction was incubated at room temp. for 2 hours to overnight and transformed into DH5α strain of *E. coli*, plated on L-plates containing ampicillin at a concentration of 100 μg/ml using standard procedures. Positive clones were further characterized and confirmed by PCR miniscreen described in detail in U.S. Pat. No. 5,625,136 using the universal primers "Reverse" and M13 "−20" as primers. Positive clones were identified by digestion of DNA with appropriate enzymes followed by sequencing. Recombinants that had the expected DNA sequence were then selected for further work.

PCR Amplification and cloning into T-vector:

PCR amplification was carried out by using a mixture of all the oligomers that represented the upper and the lower strand of a particular fragment (final concentration 5 mM each) as template, specific end primers for the particular fragment (final concentration 2 μM) 200 μM of each dATP, dTTP, dCTP and dGTP, 10 mM Tris-HCl (pH 8.3), 50 mM KCl, 1.5 mM $MgCl_2$, 0.01% gelatin and 5 units of Taq polymerase in a final reaction volume of 50 μl. The amplification reaction was carried out in a Perkin Elmer thermocycler 9600 by incubation at 95° C. for 1 min (1 cycle ), followed by 20 cycles of 95° C. for 45 sec., 50° C. for 45 sec., 72° C. for 30 sec. Finally the reaction was incubated for 5 min at 72° C. before analyzing the product. 10 μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research* 19:1154(1991). pBluescriptsk+ (Stratagene®, Ca.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. Pat. No. 5,466,785 herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

EXAMPLE 25

NAD AFFINITY CHROMATOGRAPHY

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon-10. Yield is typically about 7–15 $\mu$g of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

EXAMPLE 26
EXPRESSION OF MAIZE OPTIMIZED VIP1A(a) AND VIP2A(a)

E. coli strains containing different plasmids comprising VIP genes were assayed for expression of VIPs. E. coli strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

Expression of VIPs in *E. coli*

| Extract of *E. coli* Strain Harboring | % Mortality | | Protein |
|---|---|---|---|
| Indicated Plasmid | Assay No. 1 | Assay No. 2 | Detected |
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5S21 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG-40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

Expression of VIPs in Plant Protoplasts

| | % Mortality | | Protein |
|---|---|---|---|
| Extract Tested | Assay No. 1 | Assay No. 2 | Detected |
| No DNA control | 27 | 10 | no |
| pCIB5521 (p) (maize optimized VIP1A(a)) | 20 (0) | 30 | yes |
| pCIB5522 (p) (maize optmizied VIP2A(a)) | 20 (0) | 20 | yes |
| Extracts pCIB5521 (p) + pCIB5522 (p) combined | 87 (82) | 90 | |
| Extracts pCIB5521 (p) + pCIB5522 (e) combined | 100 | — | |
| Extracts pCIB5522 (p) + pCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024(e) (native VIP2A(a)) | 0 | — | yes |
| pCIB6206(e) (native VIP1A(a)) | 20 | — | yes |
| pCIBS521 + pCIB 5522 (plasmids delivered by cotransformation) | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

| | |
|---|---|
| 1. *E.coli* PL2 | Accession No. NRRL B-21221N |
| 2. *E. coli* pCIB6022 | Accession No. NRRL B-21222 |
| 3. *E. coli* pCIB6023 | Accession No. NRRL B-21223N |
| 4. *Bacillus thuringiensis* HD73-78VIP | Accession No. NRRL B-21224 |
| 5. *Bacillus thuringiensis* AB88 | Accession No. NRRL B-21225 |
| 6. *Bacillus thuringiensis* AB359 | Accession No. NRRL B-21226 |
| 7. *Bacillus thuringiensis* AB289 | Accession No. NRRL B-21227 |
| 8. *Bacillus sp.* AB59 | Accession No. NRRL B-21228 |
| 9. *Bacillus sp.* AB294 | Accession No. NRRL B-21229 |
| 10. *Bacillus sp.* AB256 | Accession No. NRRL B-21230 |
| 11. *E. coli* P5-4 | Accession No. NRRL B-21059 |
| 12. *E. coli* P3-12 | Accession No. NRRL B-21061 |
| 13. *Bacillus cereus* AB78 | Accession No. NRRL B-21058 |
| 14. *Bacillus thuringiensis* AB6 | Accession No. NRRL B-21060 |
| 15. *E. coli* pCIB6202 | Accession No. NRRL B-21321 |
| 16. *E. coli* pCIB7100 | Accession No. NRRL B-21322 |
| 17. *E. coli* pCIB7101 | Accession No. NRRL B-21323 |

-continued

| 18. E. coli pCIB7102 | Accession No. NRRL B-21324 |
| 19. E. coli pCIB7102 | Accession No. NRRL B-21325 |
| 20. E. coli pCIB7104 | Accession No. NRRL B-21422 |
| 21. E. coli pCIB7107 | Accession No. NRRL B-21423 |
| 22. E. coli pCIB7108 | Accession No. NRRL B-21438 |
| 23. Bacillus thuringiensis AB424 | Accession No. NRRL B-21439 |

Although the foregoing invention has been described in some detail by way of illustration and example for purposes of clarity of understanding, it will be obvious that certain changes and modifications may be practiced within the scope of the appended claims.

What is claimed is:

1. A substantially pure vegetative insecticidal protein secreted during the vegetative growth phase of Bacillus spp., wherein said vegetative insecticidal protein is insect-specific.

2. The vegetative insecticidal protein of claim 1 wherein said Bacillus is selected from a *Bacillus thuringiensis* and *B. cereus*.

3. The vegetative insecticidal protein of claim 1 wherein said protein is toxic to Coleoptera or Lepidoptera.

4. The vegetative insecticidal protein of claim 2, wherein said *Bacillus cereus* having Accession No. NRRL B-21058.

5. The vegetative insecticidal protein of claim 4, wherein said Bacillus is *Bacillus thuringiensis* selected from Accession Numbers NRRL B-21060, NRRL B-21224, NRRL B-21225, NRRL B-21226, NRRL B-21227 and NRRL B-21439.

6. The vegetative insecticidal protein of claim 1, wherein said protein has a molecular weight of about 60 to about 100 kDa determined by SDS-PAGE analysis.

7. The vegetative insecticidal protein of claim 6, wherein said protein has a molecular weight of about 80 kDa determined by SDS-PAGE analysis.

8. The vegetative insecticidal protein of claim 1, wherein said protein has the amino acid sequence selected from the group consisting of SEQ ID NO:7, SEQ ID NO:5, SEQ ID NO:2, SEQ ID NO:20, SEQ ID NO:21, SEQ ID NO:29 and SEQ ID NO:32.

9. The vegetative insecticidal protein of claim 1, wherein said protein is encoded by a DNA sequence whose complement hybridizes under hybridization conditions of 65° C. followed by washing at 65° C. with 2×SSC containing 0.1% SDS to a coding sequence selected from the group consisting of SEQ ID NO:6, SEQ ID NO:4, SEQ ID NO:1, SEQ ID NO:19, SEQ ID NO:28 and SEQ ID NO:31.

* * * * *

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 6049 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: CDS
        ( B ) LOCATION: 1082..2467
        ( D ) OTHER INFORMATION: /product="VIP2A(a)"

( i x ) FEATURE:
        ( A ) NAME/KEY: misc_feature
        ( B ) LOCATION: 2475..5126
        ( D ) OTHER INFORMATION: /note= "Coding sequence for the 100
            kd VIP1A(a) protein. This coding sequence is repeated
            in SEQ ID NO:4 and translated separately."

( x i ) SEQUENCE DESCRIPTION: SEQ ID NO:1:

| | | | | | | |
|---|---|---|---|---|---|---|
| ATCGATACAA | TGTTGTTTTA | CTTAGACCGG | TAGTCTCTGT | AATTTGTTTA | ATGCTATATT | 60 |
| CTTTACTTTG | ATACATTTTA | ATAGCCATTT | CAACCTTATC | AGTATGTTTT | TGTGGTCTTC | 120 |
| CTCCTTTTTT | TCCACGAGCT | CTAGCTGCGT | TTAATCCTGT | TTTGGTACGT | TCGCTAATAA | 180 |
| TATCTCTTTC | TAATTCTGCA | ATACTTGCCA | TCATTCGAAA | GAAGAATTTC | CCCATAGCAT | 240 |
| TAGAGGTATC | AATGTTGTCA | TGAATAGAAA | TAAAATCTAC | ACCTAGCTCT | TTGAATTTTT | 300 |
| CACTTAACTC | AATTAGGTGT | TTTGTAGAGC | GAGAAATTCG | ATCAAGTTTG | TAAACAACTA | 360 |
| TCTTATCGCC | TTTACGTAAT | ACTTTTAGCA | ACTCTTCGAG | TTGAGGGCGC | TCTTTTTTA | 420 |
| TTCCTGTTAT | TTTCTCCTGA | TATAGCCTTT | CTACACCATA | TTGTTGCAAA | GCATCTATTT | 480 |
| GCATATCGAG | ATTTTGTTCT | TCTGTGCTGA | CACGAGCATA | ACCAAAAATC | AAATTGGTTT | 540 |
| CACTTCCTAT | CTAAATATAT | CTATTAAAAT | AGCACCAAAA | ACCTTATTAA | ATTAAAATAA | 600 |
| GGAACTTTGT | TTTTGGATAT | GGATTTTGGT | ACTCAATATG | GATGAGTTTT | TAACGCTTTT | 660 |
| GTTAAAAAAC | AAACAAGTGC | CATAAACGGT | CGTTTTTGGG | ATGACATAAT | AAATAATCTG | 720 |
| TTTGATTAAC | CTAACCTTGT | ATCCTTACAG | CCCAGTTTTA | TTTGTACTTC | AACTGACTGA | 780 |
| ATATGAAAAC | AACATGAAGG | TTTCATAAAA | TTTATATATT | TTCCATAACG | GATGCTCTAT | 840 |
| CTTTAGGTTA | TAGTTAAATT | ATAAGAAAAA | AACAAACGGA | GGGAGTGAAA | AAAAGCATCT | 900 |

-continued

```
TCTCTATAAT TTTACAGGCT CTTTAATAAG AAGGGGGGAG ATTAGATAAT AAATATGAAT      960

ATCTATCTAT AATTGTTTGC TTCTACAATA ACTTATCTAA CTTTCATATA CAACAACAAA     1020

ACAGACTAAA TCCAGATTGT ATATTCATTT TCAGTTGTTC CTTTATAAAA TAATTTCATA     1080
```

| | | | | | | | | | | | | | | | | |
|---|---|---|---|---|---|---|---|---|---|---|---|---|---|---|---|---|
| A | ATG | AAA | AGA | ATG | GAG | GGA | AAG | TTG | TTT | ATG | GTG | TCA | AAA | AAA | TTA | 1126 |
| | Met | Lys | Arg | Met | Glu | Gly | Lys | Leu | Phe | Met | Val | Ser | Lys | Lys | Leu | |
| | 1 | | | | 5 | | | | | 10 | | | | | 15 | |

| | | | | | | | | | | | | | | | |
|---|---|---|---|---|---|---|---|---|---|---|---|---|---|---|---|
| CAA | GTA | GTT | ACT | AAA | ACT | GTA | TTG | CTT | AGT | ACA | GTT | TTC | TCT | ATA | TCT | 1174 |
| Gln | Val | Val | Thr | Lys | Thr | Val | Leu | Leu | Ser | Thr | Val | Phe | Ser | Ile | Ser | |
| | | | | 20 | | | | | 25 | | | | | 30 | | |

| TTA | TTA | AAT | AAT | GAA | GTG | ATA | AAA | GCT | GAA | CAA | TTA | AAT | ATA | AAT | TCT | 1222 |
|---|---|---|---|---|---|---|---|---|---|---|---|---|---|---|---|---|
| Leu | Leu | Asn | Asn | Glu | Val | Ile | Lys | Ala | Glu | Gln | Leu | Asn | Ile | Asn | Ser | |
| | | | 35 | | | | | 40 | | | | | 45 | | | |

| CAA | AGT | AAA | TAT | ACT | AAC | TTG | CAA | AAT | CTA | AAA | ATC | ACT | GAC | AAG | GTA | 1270 |
|---|---|---|---|---|---|---|---|---|---|---|---|---|---|---|---|---|
| Gln | Ser | Lys | Tyr | Thr | Asn | Leu | Gln | Asn | Leu | Lys | Ile | Thr | Asp | Lys | Val | |
| | | 50 | | | | | 55 | | | | | 60 | | | | |

| GAG | GAT | TTT | AAA | GAA | GAT | AAG | GAA | AAA | GCG | AAA | GAA | TGG | GGG | AAA | GAA | 1318 |
|---|---|---|---|---|---|---|---|---|---|---|---|---|---|---|---|---|
| Glu | Asp | Phe | Lys | Glu | Asp | Lys | Glu | Lys | Ala | Lys | Glu | Trp | Gly | Lys | Glu | |
| | 65 | | | | | 70 | | | | | 75 | | | | | |

| AAA | GAA | AAA | GAG | TGG | AAA | CTA | ACT | GCT | ACT | GAA | AAA | GGA | AAA | ATG | AAT | 1366 |
|---|---|---|---|---|---|---|---|---|---|---|---|---|---|---|---|---|
| Lys | Glu | Lys | Glu | Trp | Lys | Leu | Thr | Ala | Thr | Glu | Lys | Gly | Lys | Met | Asn | |
| 80 | | | | | 85 | | | | | 90 | | | | | 95 | |

| AAT | TTT | TTA | GAT | AAT | AAA | AAT | GAT | ATA | AAG | ACA | AAT | TAT | AAA | GAA | ATT | 1414 |
|---|---|---|---|---|---|---|---|---|---|---|---|---|---|---|---|---|
| Asn | Phe | Leu | Asp | Asn | Lys | Asn | Asp | Ile | Lys | Thr | Asn | Tyr | Lys | Glu | Ile | |
| | | | | 100 | | | | | 105 | | | | | 110 | | |

| ACT | TTT | TCT | ATG | GCA | GGC | TCA | TTT | GAA | GAT | GAA | ATA | AAA | GAT | TTA | AAA | 1462 |
|---|---|---|---|---|---|---|---|---|---|---|---|---|---|---|---|---|
| Thr | Phe | Ser | Met | Ala | Gly | Ser | Phe | Glu | Asp | Glu | Ile | Lys | Asp | Leu | Lys | |
| | | | 115 | | | | | 120 | | | | | 125 | | | |

| GAA | ATT | GAT | AAG | ATG | TTT | GAT | AAA | ACC | AAT | CTA | TCA | AAT | TCT | ATT | ATC | 1510 |
|---|---|---|---|---|---|---|---|---|---|---|---|---|---|---|---|---|
| Glu | Ile | Asp | Lys | Met | Phe | Asp | Lys | Thr | Asn | Leu | Ser | Asn | Ser | Ile | Ile | |
| | | 130 | | | | | 135 | | | | | 140 | | | | |

| ACC | TAT | AAA | AAT | GTG | GAA | CCG | ACA | ACA | ATT | GGA | TTT | AAT | AAA | TCT | TTA | 1558 |
|---|---|---|---|---|---|---|---|---|---|---|---|---|---|---|---|---|
| Thr | Tyr | Lys | Asn | Val | Glu | Pro | Thr | Thr | Ile | Gly | Phe | Asn | Lys | Ser | Leu | |
| | 145 | | | | | 150 | | | | | 155 | | | | | |

| ACA | GAA | GGT | AAT | ACG | ATT | AAT | TCT | GAT | GCA | ATG | GCA | CAG | TTT | AAA | GAA | 1606 |
|---|---|---|---|---|---|---|---|---|---|---|---|---|---|---|---|---|
| Thr | Glu | Gly | Asn | Thr | Ile | Asn | Ser | Asp | Ala | Met | Ala | Gln | Phe | Lys | Glu | |
| 160 | | | | | 165 | | | | | 170 | | | | | 175 | |

| CAA | TTT | TTA | GAT | AGG | GAT | ATT | AAG | TTT | GAT | AGT | TAT | CTA | GAT | ACG | CAT | 1654 |
|---|---|---|---|---|---|---|---|---|---|---|---|---|---|---|---|---|
| Gln | Phe | Leu | Asp | Arg | Asp | Ile | Lys | Phe | Asp | Ser | Tyr | Leu | Asp | Thr | His | |
| | | | | 180 | | | | | 185 | | | | | 190 | | |

| TTA | ACT | GCT | CAA | CAA | GTT | TCC | AGT | AAA | GAA | AGA | GTT | ATT | TTG | AAG | GTT | 1702 |
|---|---|---|---|---|---|---|---|---|---|---|---|---|---|---|---|---|
| Leu | Thr | Ala | Gln | Gln | Val | Ser | Ser | Lys | Glu | Arg | Val | Ile | Leu | Lys | Val | |
| | | | 195 | | | | | 200 | | | | | 205 | | | |

| ACG | GTT | CCG | AGT | GGG | AAA | GGT | TCT | ACT | ACT | CCA | ACA | AAA | GCA | GGT | GTC | 1750 |
|---|---|---|---|---|---|---|---|---|---|---|---|---|---|---|---|---|
| Thr | Val | Pro | Ser | Gly | Lys | Gly | Ser | Thr | Thr | Pro | Thr | Lys | Ala | Gly | Val | |
| | | 210 | | | | | 215 | | | | | 220 | | | | |

| ATT | TTA | AAT | AAT | AGT | GAA | TAC | AAA | ATG | CTC | ATT | GAT | AAT | GGG | TAT | ATG | 1798 |
|---|---|---|---|---|---|---|---|---|---|---|---|---|---|---|---|---|
| Ile | Leu | Asn | Asn | Ser | Glu | Tyr | Lys | Met | Leu | Ile | Asp | Asn | Gly | Tyr | Met | |
| | 225 | | | | | 230 | | | | | 235 | | | | | |

| GTC | CAT | GTA | GAT | AAG | GTA | TCA | AAA | GTG | GTG | AAA | AAA | GGG | GTG | GAG | TGC | 1846 |
|---|---|---|---|---|---|---|---|---|---|---|---|---|---|---|---|---|
| Val | His | Val | Asp | Lys | Val | Ser | Lys | Val | Val | Lys | Lys | Gly | Val | Glu | Cys | |
| 240 | | | | | 245 | | | | | 250 | | | | | 255 | |

| TTA | CAA | ATT | GAA | GGG | ACT | TTA | AAA | AAG | AGT | CTT | GAC | TTT | AAA | AAT | GAT | 1894 |
|---|---|---|---|---|---|---|---|---|---|---|---|---|---|---|---|---|
| Leu | Gln | Ile | Glu | Gly | Thr | Leu | Lys | Lys | Ser | Leu | Asp | Phe | Lys | Asn | Asp | |
| | | | | 260 | | | | | 265 | | | | | 270 | | |

| ATA | AAT | GCT | GAA | GCG | CAT | AGC | TGG | GGT | ATG | AAG | AAT | TAT | GAA | GAG | TGG | 1942 |
|---|---|---|---|---|---|---|---|---|---|---|---|---|---|---|---|---|
| Ile | Asn | Ala | Glu | Ala | His | Ser | Trp | Gly | Met | Lys | Asn | Tyr | Glu | Glu | Trp | |
| | | | 275 | | | | | 280 | | | | | 285 | | | |

| GCT | AAA | GAT | TTA | ACC | GAT | TCG | CAA | AGG | GAA | GCT | TTA | GAT | GGG | TAT | GCT | 1990 |
|---|---|---|---|---|---|---|---|---|---|---|---|---|---|---|---|---|
| Ala | Lys | Asp | Leu | Thr | Asp | Ser | Gln | Arg | Glu | Ala | Leu | Asp | Gly | Tyr | Ala | |

```
              290                         295                         300
AGG  CAA  GAT  TAT  AAA  GAA  ATC  AAT  AAT  TAT  TTA  AGA  AAT  CAA  GGC  GGA         2038
Arg  Gln  Asp  Tyr  Lys  Glu  Ile  Asn  Asn  Tyr  Leu  Arg  Asn  Gln  Gly  Gly
     305                      310                      315

AGT  GGA  AAT  GAA  AAA  CTA  GAT  GCT  CAA  ATA  AAA  AAT  ATT  TCT  GAT  GCT         2086
Ser  Gly  Asn  Glu  Lys  Leu  Asp  Ala  Gln  Ile  Lys  Asn  Ile  Ser  Asp  Ala
320                      325                      330                      335

TTA  GGG  AAG  AAA  CCA  ATA  CCG  GAA  AAT  ATT  ACT  GTG  TAT  AGA  TGG  TGT         2134
Leu  Gly  Lys  Lys  Pro  Ile  Pro  Glu  Asn  Ile  Thr  Val  Tyr  Arg  Trp  Cys
                    340                      345                      350

GGC  ATG  CCG  GAA  TTT  GGT  TAT  CAA  ATT  AGT  GAT  CCG  TTA  CCT  TCT  TTA         2182
Gly  Met  Pro  Glu  Phe  Gly  Tyr  Gln  Ile  Ser  Asp  Pro  Leu  Pro  Ser  Leu
               355                      360                      365

AAA  GAT  TTT  GAA  GAA  CAA  TTT  TTA  AAT  ACA  ATC  AAA  GAA  GAC  AAA  GGA         2230
Lys  Asp  Phe  Glu  Glu  Gln  Phe  Leu  Asn  Thr  Ile  Lys  Glu  Asp  Lys  Gly
          370                      375                      380

TAT  ATG  AGT  ACA  AGC  TTA  TCG  AGT  GAA  CGT  CTT  GCA  GCT  TTT  GGA  TCT         2278
Tyr  Met  Ser  Thr  Ser  Leu  Ser  Ser  Glu  Arg  Leu  Ala  Ala  Phe  Gly  Ser
     385                      390                      395

AGA  AAA  ATT  ATA  TTA  CGA  TTA  CAA  GTT  CCG  AAA  GGA  AGT  ACG  GGT  GCG         2326
Arg  Lys  Ile  Ile  Leu  Arg  Leu  Gln  Val  Pro  Lys  Gly  Ser  Thr  Gly  Ala
400                      405                      410                      415

TAT  TTA  AGT  GCC  ATT  GGT  GGA  TTT  GCA  AGT  GAA  AAA  GAG  ATC  CTA  CTT         2374
Tyr  Leu  Ser  Ala  Ile  Gly  Gly  Phe  Ala  Ser  Glu  Lys  Glu  Ile  Leu  Leu
                    420                      425                      430

GAT  AAA  GAT  AGT  AAA  TAT  CAT  ATT  GAT  AAA  GTA  ACA  GAG  GTA  ATT  ATT         2422
Asp  Lys  Asp  Ser  Lys  Tyr  His  Ile  Asp  Lys  Val  Thr  Glu  Val  Ile  Ile
               435                      440                      445

AAA  GGT  GTT  AAG  CGA  TAT  GTA  GTG  GAT  GCA  ACA  TTA  TTA  ACA  AAT              2467
Lys  Gly  Val  Lys  Arg  Tyr  Val  Val  Asp  Ala  Thr  Leu  Leu  Thr  Asn
          450                      455                      460

TAAGGAGATG  AAAAATATGA  AGAAAAAGTT  AGCAAGTGTT  GTAACGTGTA  CGTTATTAGC         2527
TCCTATGTTT  TTGAATGGAA  ATGTGAATGC  TGTTTACGCA  GACAGCAAAA  CAAATCAAAT         2587
TTCTACAACA  CAGAAAAATC  AACAGAAAGA  GATGGACCGA  AAAGGATTAC  TTGGGTATTA         2647
TTTCAAGGA   AAAGATTTTA  GTAATCTTAC  TATGTTTGCA  CCGACACGTG  ATAGTACTCT         2707
TATTTATGAT  CAACAAACAG  CAAATAAACT  ATTAGATAAA  AACAACAAG   AATATCAGTC         2767
TATTCGTTGG  ATTGGTTTGA  TTCAGAGTAA  AGAAACGGGA  GATTTCACAT  TAACTTATC          2827
TGAGGATGAA  CAGGCAATTA  TAGAAATCAA  TGGGAAAATT  ATTTCTAATA  AAGGGAAAGA         2887
AAAGCAAGTT  GTCCATTTAG  AAAAAGGAAA  ATTAGTTCCA  ATCAAAATAG  AGTATCAATC         2947
AGATACAAAA  TTTAATATTG  ACAGTAAAAC  ATTTAAAGAA  CTTAAATTAT  TTAAAATAGA         3007
TAGTCAAAAC  CAACCCCAGC  AAGTCCAGCA  AGATGAACTG  AGAAATCCTG  AATTTAACAA         3067
GAAAGAATCA  CAGGAATTCT  TAGCGAAACC  ATCGAAAATA  AATCTTTTCA  CTCAAAAAAT         3127
GAAAAGGGAA  ATTGATGAAG  ACACGGATAC  GGATGGGGAC  TCTATTCCTG  ACCTTTGGGA         3187
AGAAATGGG   TATACGATTC  ACAATAGAAT  CGCTGTAAAG  TGGGACGATT  CTCTAGCAAG         3247
TAAAGGGTAT  ACGAAATTTG  TTTCAAATCC  ACTAGAAAGT  CACACAGTTG  GTGATCCTTA         3307
TACAGATTAT  GAAAAGGCAG  CAAGAGATCT  AGATTTGTCA  AATGCAAAGG  AAACGTTTAA         3367
CCCATTGGTA  GCTGCTTTTC  CAAGTGTGAA  TGTTAGTATG  GAAAAGGTGA  TATTATCACC         3427
AAATGAAAAT  TTATCCAATA  GTGTAGAGTC  TCATTCATCC  ACGAATTGGT  CTTATACAAA         3487
TACAGAAGGT  GCTTCTGTTG  AAGCGGGGAT  TGGACCAAAA  GGTATTTCGT  TCGGAGTTAG         3547
CGTAAACTAT  CAACACTCTG  AAACAGTTGC  ACAAGAATGG  GGAACATCTA  CAGGAAATAC         3607
```

| | | | | | | |
|---|---|---|---|---|---|---|
| TTCGCAATTC | AATACGGCTT | CAGCGGGATA | TTTAAATGCA | AATGTTCGAT | ATAACAATGT | 3667 |
| AGGAACTGGT | GCCATCTACG | ATGTAAAACC | TACAACAAGT | TTTGTATTAA | ATAACGATAC | 3727 |
| TATCGCAACT | ATTACGGCGA | AATCTAATTC | TACAGCCTTA | AATATATCTC | CTGGAGAAAG | 3787 |
| TTACCCGAAA | AAAGGACAAA | ATGGAATCGC | AATAACATCA | ATGGATGATT | TTAATTCCCA | 3847 |
| TCCGATTACA | TTAAATAAAA | AACAAGTAGA | TAATCTGCTA | AATAATAAAC | CTATGATGTT | 3907 |
| GGAAACAAAC | CAAACAGATG | GTGTTTATAA | GATAAAAGAT | ACACATGGAA | ATATAGTAAC | 3967 |
| TGGCGGAGAA | TGGAATGGTG | TCATACAACA | AATCAAGGCT | AAAACAGCGT | CTATTATTGT | 4027 |
| GGATGATGGG | GAACGTGTAG | CAGAAAAACG | TGTAGCGGCA | AAAGATTATG | AAAATCCAGA | 4087 |
| AGATAAAACA | CCGTCTTTAA | CTTTAAAAGA | TGCCCTGAAG | CTTTCATATC | CAGATGAAAT | 4147 |
| AAAAGAAATA | GAGGGATTAT | TATATTATAA | AAACAAACCG | ATATACGAAT | CGAGCGTTAT | 4207 |
| GACTTACTTA | GATGAAAATA | CAGCAAAAGA | AGTGACCAAA | CAATTAAATG | ATACCACTGG | 4267 |
| GAAATTTAAA | GATGTAAGTC | ATTTATATGA | TGTAAAACTG | ACTCCAAAAA | TGAATGTTAC | 4327 |
| AATCAAATTG | TCTATACTTT | ATGATAATGC | TGAGTCTAAT | GATAACTCAA | TTGGTAAATG | 4387 |
| GACAAACACA | AATATTGTTT | CAGGTGGAAA | TAACGGAAAA | AAACAATATT | CTTCTAATAA | 4447 |
| TCCGGATGCT | AATTTGACAT | TAAATACAGA | TGCTCAAGAA | AAATTAAATA | AAAATCGTGA | 4507 |
| CTATTATATA | AGTTTATATA | TGAAGTCAGA | AAAAAACACA | CAATGTGAGA | TTACTATAGA | 4567 |
| TGGGGAGATT | TATCCGATCA | CTACAAAAAC | AGTGAATGTG | AATAAAGACA | ATTACAAAAG | 4627 |
| ATTAGATATT | ATAGCTCATA | ATATAAAAG | TAATCCAATT | TCTTCACTTC | ATATTAAAAC | 4687 |
| GAATGATGAA | ATAACTTTAT | TTTGGGATGA | TATTTCTATA | ACAGATGTAG | CATCAATAAA | 4747 |
| ACCGGAAAAT | TTAACAGATT | CAGAAATTAA | ACAGATTTAT | AGTAGGTATG | GTATTAAGTT | 4807 |
| AGAAGATGGA | ATCCTTATTG | ATAAAAAAGG | TGGGATTCAT | TATGGTGAAT | TTATTAATGA | 4867 |
| AGCTAGTTTT | AATATTGAAC | CATTGCAAAA | TTATGTGACC | AAATATGAAG | TTACTTATAG | 4927 |
| TAGTGAGTTA | GGACCAAACG | TGAGTGACAC | ACTTGAAAGT | GATAAAATTT | ACAAGGATGG | 4987 |
| GACAATTAAA | TTTGATTTTA | CCAAATATAG | TAAAAATGAA | CAAGGATTAT | TTTATGACAG | 5047 |
| TGGATTAAAT | TGGGACTTTA | AAATTAATGC | TATTACTTAT | GATGGTAAAG | AGATGAATGT | 5107 |
| TTTTCATAGA | TATAATAAAT | AGTTATTATA | TCTATGAAGC | TGGTGCTAAA | GATAGTGTAA | 5167 |
| AAGTTAATAT | ACTGTAGGAT | TGTAATAAAA | GTAATGGAAT | TGATATCGTA | CTTTGGAGTG | 5227 |
| GGGGATACTT | TGTAAATAGT | TCTATCAGAA | ACATTAGACT | AAGAAAAGTT | ACTACCCCCA | 5287 |
| CTTGAAAATG | AAGATTCAAC | TGATTACAAA | CAACCTGTTA | AATATTATAA | GGTTTTAACA | 5347 |
| AAATATTAAA | CTCTTTATGT | TAATACTGTA | ATATAAAGAG | TTTAATTGTA | TTCAAATGAA | 5407 |
| GCTTTCCCAC | AAAATTAGAC | TGATTATCTA | ATGAAATAAT | CAGTCTAATT | TTGTAGAACA | 5467 |
| GGTCTGGTAT | TATTGTACGT | GGTCACTAAA | AGATATCTAA | TATTATTGGG | CAAGGCGTTC | 5527 |
| CATGATTGAA | TCCTCGAATG | TCTTGCCCTT | TTCATTTATT | TAAGAAGGAT | TGTGGAGAAA | 5587 |
| TTATGGTTTA | GATAATGAAG | AAAGACTTCA | CTTCTAATTT | TTGATGTTAA | ATAAATCAAA | 5647 |
| ATTTGGCGAT | TCACATTGTT | TAATCCACTG | ATAAACATA | CTGGAGTGTT | CTTAAAAAAT | 5707 |
| CAGCTTTTTT | CTTTATAAAA | TTTTGCTTAG | CGTACGAAAT | TCGTGTTTTG | TTGGTGGGAC | 5767 |
| CCCATGCCCA | TCAACTTAAG | AGTAAATTAG | TAATGAACTT | TCGTTCATCT | GGATTAAAAT | 5827 |
| AACCTCAAAT | TAGGACATGT | TTTTAAAAAT | AAGCAGACCA | AATAAGCCTA | GAATAGGTAT | 5887 |
| CATTTTAAA | AATTATGCTG | CTTTCTTTTG | TTTTCCAAAT | CCATTATACT | CATAAGCAAC | 5947 |
| ACCCATAATG | TCAAAGACTG | TTTTTGTCTC | ATATCGATAA | GCTTGATATC | GAATTCCTGC | 6007 |

```
AGCCCGGGGG ATCCACTAGT TCTAGAGCGG CCGCCACCGC GG                                6049
```

( 2 ) INFORMATION FOR SEQ ID NO:2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Arg Met Glu Gly Lys Leu Phe Met Val Ser Lys Lys Leu Gln
  1               5                  10                  15
Val Val Thr Lys Thr Val Leu Leu Ser Thr Val Phe Ser Ile Ser Leu
             20                  25                  30
Leu Asn Asn Glu Val Ile Lys Ala Glu Gln Leu Asn Ile Asn Ser Gln
         35                  40                  45
Ser Lys Tyr Thr Asn Leu Gln Asn Leu Lys Ile Thr Asp Lys Val Glu
     50                  55                  60
Asp Phe Lys Glu Asp Lys Glu Lys Ala Lys Glu Trp Gly Lys Glu Lys
 65                  70                  75                  80
Glu Lys Glu Trp Lys Leu Thr Ala Thr Glu Lys Gly Lys Met Asn Asn
                 85                  90                  95
Phe Leu Asp Asn Lys Asn Asp Ile Lys Thr Asn Tyr Lys Glu Ile Thr
            100                 105                 110
Phe Ser Met Ala Gly Ser Phe Glu Asp Glu Ile Lys Asp Leu Lys Glu
        115                 120                 125
Ile Asp Lys Met Phe Asp Lys Thr Asn Leu Ser Asn Ser Ile Ile Thr
    130                 135                 140
Tyr Lys Asn Val Glu Pro Thr Thr Ile Gly Phe Asn Lys Ser Leu Thr
145                 150                 155                 160
Glu Gly Asn Thr Ile Asn Ser Asp Ala Met Ala Gln Phe Lys Glu Gln
                165                 170                 175
Phe Leu Asp Arg Asp Ile Lys Phe Asp Ser Tyr Leu Asp Thr His Leu
            180                 185                 190
Thr Ala Gln Gln Val Ser Ser Lys Glu Arg Val Ile Leu Lys Val Thr
        195                 200                 205
Val Pro Ser Gly Lys Gly Ser Thr Thr Pro Thr Lys Ala Gly Val Ile
    210                 215                 220
Leu Asn Asn Ser Glu Tyr Lys Met Leu Ile Asp Asn Gly Tyr Met Val
225                 230                 235                 240
His Val Asp Lys Val Ser Lys Val Val Lys Lys Gly Val Glu Cys Leu
                245                 250                 255
Gln Ile Glu Gly Thr Leu Lys Lys Ser Leu Asp Phe Lys Asn Asp Ile
            260                 265                 270
Asn Ala Glu Ala His Ser Trp Gly Met Lys Asn Tyr Glu Glu Trp Ala
        275                 280                 285
Lys Asp Leu Thr Asp Ser Gln Arg Glu Ala Leu Asp Gly Tyr Ala Arg
    290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Ile Lys Asn Ile Ser Asp Ala Leu
                325                 330                 335
Gly Lys Lys Pro Ile Pro Glu Asn Ile Thr Val Tyr Arg Trp Cys Gly
            340                 345                 350
```

| Met | Pro | Glu | Phe | Gly | Tyr | Gln | Ile | Ser | Asp | Pro | Leu | Pro | Ser | Leu | Lys |
|---|---|---|---|---|---|---|---|---|---|---|---|---|---|---|---|
| | | 355 | | | | 360 | | | | | | 365 | | | |
| Asp | Phe | Glu | Glu | Gln | Phe | Leu | Asn | Thr | Ile | Lys | Glu | Asp | Lys | Gly | Tyr |
| | 370 | | | | | 375 | | | | 380 | | | | | |
| Met | Ser | Thr | Ser | Leu | Ser | Ser | Glu | Arg | Leu | Ala | Ala | Phe | Gly | Ser | Arg |
| 385 | | | | | 390 | | | | | 395 | | | | | 400 |
| Lys | Ile | Ile | Leu | Arg | Leu | Gln | Val | Pro | Lys | Gly | Ser | Thr | Gly | Ala | Tyr |
| | | | | 405 | | | | | 410 | | | | | 415 | |
| Leu | Ser | Ala | Ile | Gly | Gly | Phe | Ala | Ser | Glu | Lys | Glu | Ile | Leu | Leu | Asp |
| | | | 420 | | | | | 425 | | | | | 430 | | |
| Lys | Asp | Ser | Lys | Tyr | His | Ile | Asp | Lys | Val | Thr | Glu | Val | Ile | Ile | Lys |
| | | 435 | | | | | 440 | | | | | 445 | | | |
| Gly | Val | Lys | Arg | Tyr | Val | Val | Asp | Ala | Thr | Leu | Leu | Thr | Asn | | |
| | 450 | | | | | 455 | | | | | 460 | | | | |

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..20
        ( D ) OTHER INFORMATION: /note= "Signal peptide for vacuolar
            targetting"

( x i ) SEQUENCE DESCRIPTION: SEQ ID NO:3:

| Ser | Ser | Ser | Ser | Phe | Ala | Asp | Ser | Asn | Pro | Ile | Arg | Val | Thr | Asp | Arg |
|---|---|---|---|---|---|---|---|---|---|---|---|---|---|---|---|
| 1 | | | | 5 | | | | | 10 | | | | | 15 | |
| Ala | Ala | Ser | Thr | | | | | | | | | | | | |
| | | | 20 | | | | | | | | | | | | |

( 2 ) INFORMATION FOR SEQ ID NO:4:

( i ) SEQUENCE CHARACTERISTICS:
        ( A ) LENGTH: 2655 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus cereus
        ( B ) STRAIN: AB78
      &nb

| | | | | | | | | | | | | | | | | |
|---|---|---|---|---|---|---|---|---|---|---|---|---|---|---|---|---|
| TTA | GCT | CCT | ATG | TTT | TTG | AAT | GGA | AAT | GTG | AAT | GCT | GTT | TAC | GCA | GAC | 96 |
| Leu | Ala | Pro | Met | Phe | Leu | Asn | Gly | Asn | Val | Asn | Ala | Val | Tyr | Ala | Asp | |
| | 480 | | | | 485 | | | | 490 | | | | | | | |
| AGC | AAA | ACA | AAT | CAA | ATT | TCT | ACA | ACA | CAG | AAA | AAT | CAA | CAG | AAA | GAG | 144 |
| Ser | Lys | Thr | Asn | Gln | Ile | Ser | Thr | Thr | Gln | Lys | Asn | Gln | Gln | Lys | Glu | |
| 495 | | | | | 500 | | | | | 505 | | | | | 510 | |
| ATG | GAC | CGA | AAA | GGA | TTA | CTT | GGG | TAT | TAT | TTC | AAA | GGA | AAA | GAT | TTT | 192 |
| Met | Asp | Arg | Lys | Gly | Leu | Leu | Gly | Tyr | Tyr | Phe | Lys | Gly | Lys | Asp | Phe | |
| | | | | 515 | | | | 520 | | | | | 525 | | | |
| AGT | AAT | CTT | ACT | ATG | TTT | GCA | CCG | ACA | CGT | GAT | AGT | ACT | CTT | ATT | TAT | 240 |
| Ser | Asn | Leu | Thr | Met | Phe | Ala | Pro | Thr | Arg | Asp | Ser | Thr | Leu | Ile | Tyr | |
| | | | 530 | | | | | 535 | | | | | 540 | | | |
| GAT | CAA | CAA | ACA | GCA | AAT | AAA | CTA | TTA | GAT | AAA | AAA | CAA | CAA | GAA | TAT | 288 |
| Asp | Gln | Gln | Thr | Ala | Asn | Lys | Leu | Leu | Asp | Lys | Lys | Gln | Gln | Glu | Tyr | |
| | | 545 | | | | | 550 | | | | | 555 | | | | |
| CAG | TCT | ATT | CGT | TGG | ATT | GGT | TTG | ATT | CAG | AGT | AAA | GAA | ACG | GGA | GAT | 336 |
| Gln | Ser | Ile | Arg | Trp | Ile | Gly | Leu | Ile | Gln | Ser | Lys | Glu | Thr | Gly | Asp | |
| | 560 | | | | | 565 | | | | | 570 | | | | | |
| TTC | ACA | TTT | AAC | TTA | TCT | GAG | GAT | GAA | CAG | GCA | ATT | ATA | GAA | ATC | AAT | 384 |
| Phe | Thr | Phe | Asn | Leu | Ser | Glu | Asp | Glu | Gln | Ala | Ile | Ile | Glu | Ile | Asn | |
| 575 | | | | | 580 | | | | | 585 | | | | | 590 | |
| GGG | AAA | ATT | ATT | TCT | AAT | AAA | GGG | AAA | GAA | AAG | CAA | GTT | GTC | CAT | TTA | 432 |
| Gly | Lys | Ile | Ile | Ser | Asn | Lys | Gly | Lys | Glu | Lys | Gln | Val | Val | His | Leu | |
| | | | | 595 | | | | | 600 | | | | | 605 | | |
| GAA | AAA | GGA | AAA | TTA | GTT | CCA | ATC | AAA | ATA | GAG | TAT | CAA | TCA | GAT | ACA | 480 |
| Glu | Lys | Gly | Lys | Leu | Val | Pro | Ile | Lys | Ile | Glu | Tyr | Gln | Ser | Asp | Thr | |
| | | | 610 | | | | | 615 | | | | | 620 | | | |
| AAA | TTT | AAT | ATT | GAC | AGT | AAA | ACA | TTT | AAA | GAA | CTT | AAA | TTA | TTT | AAA | 528 |
| Lys | Phe | Asn | Ile | Asp | Ser | Lys | Thr | Phe | Lys | Glu | Leu | Lys | Leu | Phe | Lys | |
| | | 625 | | | | | 630 | | | | | 635 | | | | |
| ATA | GAT | AGT | CAA | AAC | CAA | CCC | CAG | CAA | GTC | CAG | CAA | GAT | GAA | CTG | AGA | 576 |
| Ile | Asp | Ser | Gln | Asn | Gln | Pro | Gln | Gln | Val | Gln | Gln | Asp | Glu | Leu | Arg | |
| | 640 | | | | | 645 | | | | | 650 | | | | | |
| AAT | CCT | GAA | TTT | AAC | AAG | AAA | GAA | TCA | CAG | GAA | TTC | TTA | GCG | AAA | CCA | 624 |
| Asn | Pro | Glu | Phe | Asn | Lys | Lys | Glu | Ser | Gln | Glu | Phe | Leu | Ala | Lys | Pro | |
| 655 | | | | | 660 | | | | | 665 | | | | | 670 | |
| TCG | AAA | ATA | AAT | CTT | TTC | ACT | CAA | AAA | ATG | AAA | AGG | GAA | ATT | GAT | GAA | 672 |
| Ser | Lys | Ile | Asn | Leu | Phe | Thr | Gln | Lys | Met | Lys | Arg | Glu | Ile | Asp | Glu | |
| | | | | 675 | | | | | 680 | | | | | 685 | | |
| GAC | ACG | GAT | ACG | GAT | GGG | GAC | TCT | ATT | CCT | GAC | CTT | TGG | GAA | GAA | AAT | 720 |
| Asp | Thr | Asp | Thr | Asp | Gly | Asp | Ser | Ile | Pro | Asp | Leu | Trp | Glu | Glu | Asn | |
| | | | 690 | | | | | 695 | | | | | 700 | | | |
| GGG | TAT | ACG | ATT | CAA | AAT | AGA | ATC | GCT | GTA | AAG | TGG | GAC | GAT | TCT | CTA | 768 |
| Gly | Tyr | Thr | Ile | Gln | Asn | Arg | Ile | Ala | Val | Lys | Trp | Asp | Asp | Ser | Leu | |
| | | 705 | | | | | 710 | | | | | 715 | | | | |
| GCA | AGT | AAA | GGG | TAT | ACG | AAA | TTT | GTT | TCA | AAT | CCA | CTA | GAA | AGT | CAC | 816 |
| Ala | Ser | Lys | Gly | Tyr | Thr | Lys | Phe | Val | Ser | Asn | Pro | Leu | Glu | Ser | His | |
| | 720 | | | | | 725 | | | | | 730 | | | | | |
| ACA | GTT | GGT | GAT | CCT | TAT | ACA | GAT | TAT | GAA | AAG | GCA | GCA | AGA | GAT | CTA | 864 |
| Thr | Val | Gly | Asp | Pro | Tyr | Thr | Asp | Tyr | Glu | Lys | Ala | Ala | Arg | Asp | Leu | |
| 735 | | | | | 740 | | | | | 745 | | | | | 750 | |
| GAT | TTG | TCA | AAT | GCA | AAG | GAA | ACG | TTT | AAC | CCA | TTG | GTA | GCT | GCT | TTT | 912 |
| Asp | Leu | Ser | Asn | Ala | Lys | Glu | Thr | Phe | Asn | Pro | Leu | Val | Ala | Ala | Phe | |
| | | | | 755 | | | | | 760 | | | | | 765 | | |
| CCA | AGT | GTG | AAT | GTT | AGT | ATG | GAA | AAG | GTG | ATA | TTA | TCA | CCA | AAT | GAA | 960 |
| Pro | Ser | Val | Asn | Val | Ser | Met | Glu | Lys | Val | Ile | Leu | Ser | Pro | Asn | Glu | |
| | | | 770 | | | | | 775 | | | | | 780 | | | |
| AAT | TTA | TCC | AAT | AGT | GTA | GAG | TCT | CAT | TCA | TCC | ACG | AAT | TGG | TCT | TAT | 1008 |
| Asn | Leu | Ser | Asn | Ser | Val | Glu | Ser | His | Ser | Ser | Thr | Asn | Trp | Ser | Tyr | |
| | | 785 | | | | | 790 | | | | | 795 | | | | |

| | | | | | | | | | | | | | | | | |
|---|---|---|---|---|---|---|---|---|---|---|---|---|---|---|---|---|
| ACA | AAT | ACA | GAA | GGT | GCT | TCT | GTT | GAA | GCG | GGG | ATT | GGA | CCA | AAA | GGT | 1056 |
| Thr | Asn | Thr | Glu | Gly | Ala | Ser | Val | Glu | Ala | Gly | Ile | Gly | Pro | Lys | Gly | |
| | | 800 | | | | 805 | | | | 810 | | | | | | |
| ATT | TCG | TTC | GGA | GTT | AGC | GTA | AAC | TAT | CAA | CAC | TCT | GAA | ACA | GTT | GCA | 1104 |
| Ile | Ser | Phe | Gly | Val | Ser | Val | Asn | Tyr | Gln | His | Ser | Glu | Thr | Val | Ala | |
| 815 | | | | 820 | | | | | 825 | | | | | | 830 | |
| CAA | GAA | TGG | GGA | ACA | TCT | ACA | GGA | AAT | ACT | TCG | CAA | TTC | AAT | ACG | GCT | 1152 |
| Gln | Glu | Trp | Gly | Thr | Ser | Thr | Gly | Asn | Thr | Ser | Gln | Phe | Asn | Thr | Ala | |
| | | | | 835 | | | | | 840 | | | | | | 845 | |
| TCA | GCG | GGA | TAT | TTA | AAT | GCA | AAT | GTT | CGA | TAT | AAC | AAT | GTA | GGA | ACT | 1200 |
| Ser | Ala | Gly | Tyr | Leu | Asn | Ala | Asn | Val | Arg | Tyr | Asn | Asn | Val | Gly | Thr | |
| | | | 850 | | | | | 855 | | | | | 860 | | | |
| GGT | GCC | ATC | TAC | GAT | GTA | AAA | CCT | ACA | ACA | AGT | TTT | GTA | TTA | AAT | AAC | 1248 |
| Gly | Ala | Ile | Tyr | Asp | Val | Lys | Pro | Thr | Thr | Ser | Phe | Val | Leu | Asn | Asn | |
| | | 865 | | | | | 870 | | | | | 875 | | | | |
| GAT | ACT | ATC | GCA | ACT | ATT | ACG | GCG | AAA | TCT | AAT | TCT | ACA | GCC | TTA | AAT | 1296 |
| Asp | Thr | Ile | Ala | Thr | Ile | Thr | Ala | Lys | Ser | Asn | Ser | Thr | Ala | Leu | Asn | |
| | 880 | | | | | 885 | | | | | 890 | | | | | |
| ATA | TCT | CCT | GGA | GAA | AGT | TAC | CCG | AAA | AAA | GGA | CAA | AAT | GGA | ATC | GCA | 1344 |
| Ile | Ser | Pro | Gly | Glu | Ser | Tyr | Pro | Lys | Lys | Gly | Gln | Asn | Gly | Ile | Ala | |
| 895 | | | | | 900 | | | | | 905 | | | | | 910 | |
| ATA | ACA | TCA | ATG | GAT | GAT | TTT | AAT | TCC | CAT | CCG | ATT | ACA | TTA | AAT | AAA | 1392 |
| Ile | Thr | Ser | Met | Asp | Asp | Phe | Asn | Ser | His | Pro | Ile | Thr | Leu | Asn | Lys | |
| | | | | 915 | | | | | 920 | | | | | 925 | | |
| AAA | CAA | GTA | GAT | AAT | CTG | CTA | AAT | AAT | AAA | CCT | ATG | ATG | TTG | GAA | ACA | 1440 |
| Lys | Gln | Val | Asp | Asn | Leu | Leu | Asn | Asn | Lys | Pro | Met | Met | Leu | Glu | Thr | |
| | | | 930 | | | | | 935 | | | | | 940 | | | |
| AAC | CAA | ACA | GAT | GGT | GTT | TAT | AAG | ATA | AAA | GAT | ACA | CAT | GGA | AAT | ATA | 1488 |
| Asn | Gln | Thr | Asp | Gly | Val | Tyr | Lys | Ile | Lys | Asp | Thr | His | Gly | Asn | Ile | |
| | | 945 | | | | | 950 | | | | | 955 | | | | |
| GTA | ACT | GGC | GGA | GAA | TGG | AAT | GGT | GTC | ATA | CAA | CAA | ATC | AAG | GCT | AAA | 1536 |
| Val | Thr | Gly | Gly | Glu | Trp | Asn | Gly | Val | Ile | Gln | Gln | Ile | Lys | Ala | Lys | |
| | 960 | | | | | 965 | | | | | 970 | | | | | |
| ACA | GCG | TCT | ATT | ATT | GTG | GAT | GAT | GGG | GAA | CGT | GTA | GCA | GAA | AAA | CGT | 1584 |
| Thr | Ala | Ser | Ile | Ile | Val | Asp | Asp | Gly | Glu | Arg | Val | Ala | Glu | Lys | Arg | |
| 975 | | | | | 980 | | | | | 985 | | | | | 990 | |
| GTA | GCG | GCA | AAA | GAT | TAT | GAA | AAT | CCA | GAA | GAT | AAA | ACA | CCG | TCT | TTA | 1632 |
| Val | Ala | Ala | Lys | Asp | Tyr | Glu | Asn | Pro | Glu | Asp | Lys | Thr | Pro | Ser | Leu | |
| | | | | 995 | | | | | 1000 | | | | | 1005 | | |
| ACT | TTA | AAA | GAT | GCC | CTG | AAG | CTT | TCA | TAT | CCA | GAT | GAA | ATA | AAA | GAA | 1680 |
| Thr | Leu | Lys | Asp | Ala | Leu | Lys | Leu | Ser | Tyr | Pro | Asp | Glu | Ile | Lys | Glu | |
| | | | | 1010 | | | | | 1015 | | | | | 1020 | | |
| ATA | GAG | GGA | TTA | TTA | TAT | TAT | AAA | AAC | AAA | CCG | ATA | TAC | GAA | TCG | AGC | 1728 |
| Ile | Glu | Gly | Leu | Leu | Tyr | Tyr | Lys | Asn | Lys | Pro | Ile | Tyr | Glu | Ser | Ser | |
| | | | | 1025 | | | | | 1030 | | | | | 1035 | | |
| GTT | ATG | ACT | TAC | TTA | GAT | GAA | AAT | ACA | GCA | AAA | GAA | GTG | ACC | AAA | CAA | 1776 |
| Val | Met | Thr | Tyr | Leu | Asp | Glu | Asn | Thr | Ala | Lys | Glu | Val | Thr | Lys | Gln | |
| | | | | 1040 | | | | | 1045 | | | | | 1050 | | |
| TTA | AAT | GAT | ACC | ACT | GGG | AAA | TTT | AAA | GAT | GTA | AGT | CAT | TTA | TAT | GAT | 1824 |
| Leu | Asn | Asp | Thr | Thr | Gly | Lys | Phe | Lys | Asp | Val | Ser | His | Leu | Tyr | Asp | |
| 1055 | | | | | 1060 | | | | | 1065 | | | | | 1070 | |
| GTA | AAA | CTG | ACT | CCA | AAA | ATG | AAT | GTT | ACA | ATC | AAA | TTG | TCT | ATA | CTT | 1872 |
| Val | Lys | Leu | Thr | Pro | Lys | Met | Asn | Val | Thr | Ile | Lys | Leu | Ser | Ile | Leu | |
| | | | | 1075 | | | | | 1080 | | | | | 1085 | | |
| TAT | GAT | AAT | GCT | GAG | TCT | AAT | GAT | AAC | TCA | ATT | GGT | AAA | TGG | ACA | AAC | 1920 |
| Tyr | Asp | Asn | Ala | Glu | Ser | Asn | Asp | Asn | Ser | Ile | Gly | Lys | Trp | Thr | Asn | |
| | | | | 1090 | | | | | 1095 | | | | | 1100 | | |
| ACA | AAT | ATT | GTT | TCA | GGT | GGA | AAT | AAC | GGA | AAA | AAA | CAA | TAT | TCT | TCT | 1968 |
| Thr | Asn | Ile | Val | Ser | Gly | Gly | Asn | Asn | Gly | Lys | Lys | Gln | Tyr | Ser | Ser | |
| | | | | 1105 | | | | | 1110 | | | | | 1115 | | |

| | | | | | | | | | | | | | | | |
|---|---|---|---|---|---|---|---|---|---|---|---|---|---|---|---|
| AAT | AAT | CCG | GAT | GCT | AAT | TTG | ACA | TTA | AAT | ACA | GAT | GCT | CAA | GAA | AAA | 2016
| Asn | Asn | Pro | Asp | Ala | Asn | Leu | Thr | Leu | Asn | Thr | Asp | Ala | Gln | Glu | Lys |
| | | 1120 | | | | | 1125 | | | | 1130 | | | | |
| TTA | AAT | AAA | AAT | CGT | GAC | TAT | TAT | ATA | AGT | TTA | TAT | ATG | AAG | TCA | GAA | 2064
| Leu | Asn | Lys | Asn | Arg | Asp | Tyr | Tyr | Ile | Ser | Leu | Tyr | Met | Lys | Ser | Glu |
| 1135 | | | | 1140 | | | | | 1145 | | | | | | 1150 |
| AAA | AAC | ACA | CAA | TGT | GAG | ATT | ACT | ATA | GAT | GGG | GAG | ATT | TAT | CCG | ATC | 2112
| Lys | Asn | Thr | Gln | Cys | Glu | Ile | Thr | Ile | Asp | Gly | Glu | Ile | Tyr | Pro | Ile |
| | | | | 1155 | | | | | 1160 | | | | | 1165 | |
| ACT | ACA | AAA | ACA | GTG | AAT | GTG | AAT | AAA | GAC | AAT | TAC | AAA | AGA | TTA | GAT | 2160
| Thr | Thr | Lys | Thr | Val | Asn | Val | Asn | Lys | Asp | Asn | Tyr | Lys | Arg | Leu | Asp |
| | | | 1170 | | | | | 1175 | | | | | 1180 | | |
| ATT | ATA | GCT | CAT | AAT | ATA | AAA | AGT | AAT | CCA | ATT | TCT | TCA | CTT | CAT | ATT | 2208
| Ile | Ile | Ala | His | Asn | Ile | Lys | Ser | Asn | Pro | Ile | Ser | Ser | Leu | His | Ile |
| | | | | 1185 | | | | | 1190 | | | | | 1195 | |
| AAA | ACG | AAT | GAT | GAA | ATA | ACT | TTA | TTT | TGG | GAT | GAT | ATT | TCT | ATA | ACA | 2256
| Lys | Thr | Asn | Asp | Glu | Ile | Thr | Leu | Phe | Trp | Asp | Asp | Ile | Ser | Ile | Thr |
| | | 1200 | | | | | 1205 | | | | 1210 | | | | |
| GAT | GTA | GCA | TCA | ATA | AAA | CCG | GAA | AAT | TTA | ACA | GAT | TCA | GAA | ATT | AAA | 2304
| Asp | Val | Ala | Ser | Ile | Lys | Pro | Glu | Asn | Leu | Thr | Asp | Ser | Glu | Ile | Lys |
| 1215 | | | | | 1220 | | | | | 1225 | | | | | 1230 |
| CAG | ATT | TAT | AGT | AGG | TAT | GGT | ATT | AAG | TTA | GAA | GAT | GGA | ATC | CTT | ATT | 2352
| Gln | Ile | Tyr | Ser | Arg | Tyr | Gly | Ile | Lys | Leu | Glu | Asp | Gly | Ile | Leu | Ile |
| | | | | 1235 | | | | | 1240 | | | | | 1245 | |
| GAT | AAA | AAA | GGT | GGG | ATT | CAT | TAT | GGT | GAA | TTT | ATT | AAT | GAA | GCT | AGT | 2400
| Asp | Lys | Lys | Gly | Gly | Ile | His | Tyr | Gly | Glu | Phe | Ile | Asn | Glu | Ala | Ser |
| | | | | 1250 | | | | | 1255 | | | | | 1260 | |
| TTT | AAT | ATT | GAA | CCA | TTG | CAA | AAT | TAT | GTG | ACC | AAA | TAT | GAA | GTT | ACT | 2448
| Phe | Asn | Ile | Glu | Pro | Leu | Gln | Asn | Tyr | Val | Thr | Lys | Tyr | Glu | Val | Thr |
| | | | 1265 | | | | | 1270 | | | | | 1275 | | |
| TAT | AGT | AGT | GAG | TTA | GGA | CCA | AAC | GTG | AGT | GAC | ACA | CTT | GAA | AGT | GAT | 2496
| Tyr | Ser | Ser | Glu | Leu | Gly | Pro | Asn | Val | Ser | Asp | Thr | Leu | Glu | Ser | Asp |
| | | 1280 | | | | | 1285 | | | | 1290 | | | | |
| AAA | ATT | TAC | AAG | GAT | GGG | ACA | ATT | AAA | TTT | GAT | TTT | ACC | AAA | TAT | AGT | 2544
| Lys | Ile | Tyr | Lys | Asp | Gly | Thr | Ile | Lys | Phe | Asp | Phe | Thr | Lys | Tyr | Ser |
| 1295 | | | | | 1300 | | | | | 1305 | | | | | 1310 |
| AAA | AAT | GAA | CAA | GGA | TTA | TTT | TAT | GAC | AGT | GGA | TTA | AAT | TGG | GAC | TTT | 2592
| Lys | Asn | Glu | Gln | Gly | Leu | Phe | Tyr | Asp | Ser | Gly | Leu | Asn | Trp | Asp | Phe |
| | | | | 1315 | | | | | 1320 | | | | | 1325 | |
| AAA | ATT | AAT | GCT | ATT | ACT | TAT | GAT | GGT | AAA | GAG | ATG | AAT | GTT | TTT | CAT | 2640
| Lys | Ile | Asn | Ala | Ile | Thr | Tyr | Asp | Gly | Lys | Glu | Met | Asn | Val | Phe | His |
| | | | 1330 | | | | | 1335 | | | | | 1340 | | |
| AGA | TAT | AAT | AAA | TAG | | | | | | | | | | | | 2655
| Arg | Tyr | Asn | Lys | | | | | | | | | | | | |
| | | | 1345 | | | | | | | | | | | | |

( 2 ) INFORMATION FOR SEQ ID NO:5:

( i ) SEQUENCE CHARACTERISTICS:
        ( A ) LENGTH: 884 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Lys | Asn | Met | Lys | Lys | Lys | Leu | Ala | Ser | Val | Val | Thr | Cys | Thr | Leu |
| 1 | | | | 5 | | | | | 10 | | | | | 15 | |
| Leu | Ala | Pro | Met | Phe | Leu | Asn | Gly | Asn | Val | Asn | Ala | Val | Tyr | Ala | Asp |
| | | | 20 | | | | | 25 | | | | | 30 | | |
| Ser | Lys | Thr | Asn | Gln | Ile | Ser | Thr | Thr | Gln | Lys | Asn | Gln | Gln | Lys | Glu |
| | | 35 | | | | | 40 | | | | | 45 | | | |

```
Met Asp Arg Lys Gly Leu Leu Gly Tyr Tyr Phe Lys Gly Lys Asp Phe
     50                  55                  60

Ser Asn Leu Thr Met Phe Ala Pro Thr Arg Asp Ser Thr Leu Ile Tyr
 65                  70                  75                  80

Asp Gln Gln Thr Ala Asn Lys Leu Leu Asp Lys Lys Gln Gln Glu Tyr
                 85                  90                  95

Gln Ser Ile Arg Trp Ile Gly Leu Ile Gln Ser Lys Glu Thr Gly Asp
            100                 105                 110

Phe Thr Phe Asn Leu Ser Glu Asp Glu Gln Ala Ile Ile Glu Ile Asn
            115                 120                 125

Gly Lys Ile Ile Ser Asn Lys Gly Lys Glu Lys Gln Val Val His Leu
        130                 135                 140

Glu Lys Gly Lys Leu Val Pro Ile Lys Ile Glu Tyr Gln Ser Asp Thr
145                 150                 155                 160

Lys Phe Asn Ile Asp Ser Lys Thr Phe Lys Glu Leu Lys Leu Phe Lys
                165                 170                 175

Ile Asp Ser Gln Asn Gln Pro Gln Gln Val Gln Gln Asp Glu Leu Arg
            180                 185                 190

Asn Pro Glu Phe Asn Lys Lys Glu Ser Gln Glu Phe Leu Ala Lys Pro
            195                 200                 205

Ser Lys Ile Asn Leu Phe Thr Gln Lys Met Lys Arg Glu Ile Asp Glu
    210                 215                 220

Asp Thr Asp Thr Asp Gly Asp Ser Ile Pro Asp Leu Trp Glu Glu Asn
225                 230                 235                 240

Gly Tyr Thr Ile Gln Asn Arg Ile Ala Val Lys Trp Asp Asp Ser Leu
                245                 250                 255

Ala Ser Lys Gly Tyr Thr Lys Phe Val Ser Asn Pro Leu Glu Ser His
            260                 265                 270

Thr Val Gly Asp Pro Tyr Thr Asp Tyr Glu Lys Ala Ala Arg Asp Leu
        275                 280                 285

Asp Leu Ser Asn Ala Lys Glu Thr Phe Asn Pro Leu Val Ala Ala Phe
    290                 295                 300

Pro Ser Val Asn Val Ser Met Glu Lys Val Ile Leu Ser Pro Asn Glu
305                 310                 315                 320

Asn Leu Ser Asn Ser Val Glu Ser His Ser Ser Thr Asn Trp Ser Tyr
                325                 330                 335

Thr Asn Thr Glu Gly Ala Ser Val Glu Ala Gly Ile Gly Pro Lys Gly
            340                 345                 350

Ile Ser Phe Gly Val Ser Val Asn Tyr Gln His Ser Glu Thr Val Ala
        355                 360                 365

Gln Glu Trp Gly Thr Ser Thr Gly Asn Thr Ser Gln Phe Asn Thr Ala
370                 375                 380

Ser Ala Gly Tyr Leu Asn Ala Asn Val Arg Tyr Asn Asn Val Gly Thr
385                 390                 395                 400

Gly Ala Ile Tyr Asp Val Lys Pro Thr Thr Ser Phe Val Leu Asn Asn
                405                 410                 415

Asp Thr Ile Ala Thr Ile Thr Ala Lys Ser Asn Ser Thr Ala Leu Asn
            420                 425                 430

Ile Ser Pro Gly Glu Ser Tyr Pro Lys Lys Gly Gln Asn Gly Ile Ala
        435                 440                 445

Ile Thr Ser Met Asp Asp Phe Asn Ser His Pro Ile Thr Leu Asn Lys
450                 455                 460

Lys Gln Val Asp Asn Leu Leu Asn Asn Lys Pro Met Met Leu Glu Thr
```

-continued

```
465                    470                    475                    480
Asn Gln Thr Asp Gly Val Tyr Lys Ile Lys Asp Thr His Gly Asn Ile
                485                    490                    495
Val Thr Gly Gly Glu Trp Asn Gly Val Ile Gln Gln Ile Lys Ala Lys
            500                    505                    510
Thr Ala Ser Ile Ile Val Asp Asp Gly Glu Arg Val Ala Glu Lys Arg
            515                    520                    525
Val Ala Ala Lys Asp Tyr Glu Asn Pro Glu Asp Lys Thr Pro Ser Leu
        530                    535                    540
Thr Leu Lys Asp Ala Leu Lys Leu Ser Tyr Pro Asp Glu Ile Lys Glu
545                    550                    555                    560
Ile Glu Gly Leu Leu Tyr Tyr Lys Asn Lys Pro Ile Tyr Glu Ser Ser
                565                    570                    575
Val Met Thr Tyr Leu Asp Glu Asn Thr Ala Lys Glu Val Thr Lys Gln
            580                    585                    590
Leu Asn Asp Thr Thr Gly Lys Phe Lys Asp Val Ser His Leu Tyr Asp
        595                    600                    605
Val Lys Leu Thr Pro Lys Met Asn Val Thr Ile Lys Leu Ser Ile Leu
    610                    615                    620
Tyr Asp Asn Ala Glu Ser Asn Asp Asn Ser Ile Gly Lys Trp Thr Asn
625                    630                    635                    640
Thr Asn Ile Val Ser Gly Gly Asn Asn Gly Lys Lys Gln Tyr Ser Ser
                645                    650                    655
Asn Asn Pro Asp Ala Asn Leu Thr Leu Asn Thr Asp Ala Gln Glu Lys
            660                    665                    670
Leu Asn Lys Asn Arg Asp Tyr Tyr Ile Ser Leu Tyr Met Lys Ser Glu
        675                    680                    685
Lys Asn Thr Gln Cys Glu Ile Thr Ile Asp Gly Glu Ile Tyr Pro Ile
    690                    695                    700
Thr Thr Lys Thr Val Asn Val Asn Lys Asp Asn Tyr Lys Arg Leu Asp
705                    710                    715                    720
Ile Ile Ala His Asn Ile Lys Ser Asn Pro Ile Ser Ser Leu His Ile
                725                    730                    735
Lys Thr Asn Asp Glu Ile Thr Leu Phe Trp Asp Asp Ile Ser Ile Thr
            740                    745                    750
Asp Val Ala Ser Ile Lys Pro Glu Asn Leu Thr Asp Ser Glu Ile Lys
        755                    760                    765
Gln Ile Tyr Ser Arg Tyr Gly Ile Lys Leu Glu Asp Gly Ile Leu Ile
    770                    775                    780
Asp Lys Lys Gly Gly Ile His Tyr Gly Glu Phe Ile Asn Glu Ala Ser
785                    790                    795                    800
Phe Asn Ile Glu Pro Leu Gln Asn Tyr Val Thr Lys Tyr Glu Val Thr
                805                    810                    815
Tyr Ser Ser Glu Leu Gly Pro Asn Val Ser Asp Thr Leu Glu Ser Asp
            820                    825                    830
Lys Ile Tyr Lys Asp Gly Thr Ile Lys Phe Asp Phe Thr Lys Tyr Ser
        835                    840                    845
Lys Asn Glu Gln Gly Leu Phe Tyr Asp Ser Gly Leu Asn Trp Asp Phe
    850                    855                    860
Lys Ile Asn Ala Ile Thr Tyr Asp Gly Lys Glu Met Asn Val Phe His
865                    870                    875                    880
Arg Tyr Asn Lys
```

( 2 ) INFORMATION FOR SEQ ID NO:6:

( i ) SEQUENCE CHARACTERISTICS:
        ( A ) LENGTH: 2004 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
   &nbs

```
TCT  AAT  TCT  ACA  GCC  TTA  AAT  ATA  TCT  CCT  GGA  GAA  AGT  TAC  CCG  AAA        672
Ser  Asn  Ser  Thr  Ala  Leu  Asn  Ile  Ser  Pro  Gly  Glu  Ser  Tyr  Pro  Lys
               1095                    1100                    1105

AAA  GGA  CAA  AAT  GGA  ATC  GCA  ATA  ACA  TCA  ATG  GAT  GAT  TTT  AAT  TCC        720
Lys  Gly  Gln  Asn  Gly  Ile  Ala  Ile  Thr  Ser  Met  Asp  Asp  Phe  Asn  Ser
     1110                    1115                    1120

CAT  CCG  ATT  ACA  TTA  AAT  AAA  AAA  CAA  GTA  GAT  AAT  CTG  CTA  AAT  AAT        768
His  Pro  Ile  Thr  Leu  Asn  Lys  Lys  Gln  Val  Asp  Asn  Leu  Leu  Asn  Asn
1125                    1130                    1135                    1140

AAA  CCT  ATG  ATG  TTG  GAA  ACA  AAC  CAA  ACA  GAT  GGT  GTT  TAT  AAG  ATA        816
Lys  Pro  Met  Met  Leu  Glu  Thr  Asn  Gln  Thr  Asp  Gly  Val  Tyr  Lys  Ile
                         1145                    1150                    1155

AAA  GAT  ACA  CAT  GGA  AAT  ATA  GTA  ACT  GGC  GGA  GAA  TGG  AAT  GGT  GTC        864
Lys  Asp  Thr  His  Gly  Asn  Ile  Val  Thr  Gly  Gly  Glu  Trp  Asn  Gly  Val
               1160                    1165                    1170

ATA  CAA  CAA  ATC  AAG  GCT  AAA  ACA  GCG  TCT  ATT  ATT  GTG  GAT  GAT  GGG        912
Ile  Gln  Gln  Ile  Lys  Ala  Lys  Thr  Ala  Ser  Ile  Ile  Val  Asp  Asp  Gly
     1175                    1180                    1185

GAA  CGT  GTA  GCA  GAA  AAA  CGT  GTA  GCG  GCA  AAA  GAT  TAT  GAA  AAT  CCA        960
Glu  Arg  Val  Ala  Glu  Lys  Arg  Val  Ala  Ala  Lys  Asp  Tyr  Glu  Asn  Pro
     1190                    1195                    1200

GAA  GAT  AAA  ACA  CCG  TCT  TTA  ACT  TTA  AAA  GAT  GCC  CTG  AAG  CTT  TCA       1008
Glu  Asp  Lys  Thr  Pro  Ser  Leu  Thr  Leu  Lys  Asp  Ala  Leu  Lys  Leu  Ser
1205                    1210                    1215                    1220

TAT  CCA  GAT  GAA  ATA  AAA  GAA  ATA  GAG  GGA  TTA  TTA  TAT  TAT  AAA  AAC       1056
Tyr  Pro  Asp  Glu  Ile  Lys  Glu  Ile  Glu  Gly  Leu  Leu  Tyr  Tyr  Lys  Asn
                         1225                    1230                    1235

AAA  CCG  ATA  TAC  GAA  TCG  AGC  GTT  ATG  ACT  TAC  TTA  GAT  GAA  AAT  ACA       1104
Lys  Pro  Ile  Tyr  Glu  Ser  Ser  Val  Met  Thr  Tyr  Leu  Asp  Glu  Asn  Thr
               1240                    1245                    1250

GCA  AAA  GAA  GTG  ACC  AAA  CAA  TTA  AAT  GAT  ACC  ACT  GGG  AAA  TTT  AAA       1152
Ala  Lys  Glu  Val  Thr  Lys  Gln  Leu  Asn  Asp  Thr  Thr  Gly  Lys  Phe  Lys
     1255                    1260                    1265

GAT  GTA  AGT  CAT  TTA  TAT  GAT  GTA  AAA  CTG  ACT  CCA  AAA  ATG  AAT  GTT       1200
Asp  Val  Ser  His  Leu  Tyr  Asp  Val  Lys  Leu  Thr  Pro  Lys  Met  Asn  Val
     1270                    1275                    1280

ACA  ATC  AAA  TTG  TCT  ATA  CTT  TAT  GAT  AAT  GCT  GAG  TCT  AAT  GAT  AAC       1248
Thr  Ile  Lys  Leu  Ser  Ile  Leu  Tyr  Asp  Asn  Ala  Glu  Ser  Asn  Asp  Asn
1285                    1290                    1295                    1300

TCA  ATT  GGT  AAA  TGG  ACA  AAC  ACA  AAT  ATT  GTT  TCA  GGT  GGA  AAT  AAC       1296
Ser  Ile  Gly  Lys  Trp  Thr  Asn  Thr  Asn  Ile  Val  Ser  Gly  Gly  Asn  Asn
                    1305                    1310                    1315

GGA  AAA  AAA  CAA  TAT  TCT  TCT  AAT  AAT  CCG  GAT  GCT  AAT  TTG  ACA  TTA       1344
Gly  Lys  Lys  Gln  Tyr  Ser  Ser  Asn  Asn  Pro  Asp  Ala  Asn  Leu  Thr  Leu
               1320                    1325                    1330

AAT  ACA  GAT  GCT  CAA  GAA  AAA  TTA  AAT  AAA  AAT  CGT  GAC  TAT  TAT  ATA       1392
Asn  Thr  Asp  Ala  Gln  Glu  Lys  Leu  Asn  Lys  Asn  Arg  Asp  Tyr  Tyr  Ile
     1335                    1340                    1345

AGT  TTA  TAT  ATG  AAG  TCA  GAA  AAA  AAC  ACA  CAA  TGT  GAG  ATT  ACT  ATA       1440
Ser  Leu  Tyr  Met  Lys  Ser  Glu  Lys  Asn  Thr  Gln  Cys  Glu  Ile  Thr  Ile
     1350                    1355                    1360

GAT  GGG  GAG  ATT  TAT  CCG  ATC  ACT  ACA  AAA  ACA  GTG  AAT  GTG  AAT  AAA       1488
Asp  Gly  Glu  Ile  Tyr  Pro  Ile  Thr  Thr  Lys  Thr  Val  Asn  Val  Asn  Lys
1365                    1370                    1375                    1380

GAC  AAT  TAC  AAA  AGA  TTA  GAT  ATT  ATA  GCT  CAT  AAT  ATA  AAA  AGT  AAT       1536
Asp  Asn  Tyr  Lys  Arg  Leu  Asp  Ile  Ile  Ala  His  Asn  Ile  Lys  Ser  Asn
               1385                    1390                    1395

CCA  ATT  TCT  TCA  CTT  CAT  ATT  AAA  ACG  AAT  GAT  GAA  ATA  ACT  TTA  TTT       1584
Pro  Ile  Ser  Ser  Leu  His  Ile  Lys  Thr  Asn  Asp  Glu  Ile  Thr  Leu  Phe
               1400                    1405                    1410
```

```
TGG  GAT  GAT  ATT  TCT  ATA  ACA  GAT  GTA  GCA  TCA  ATA  AAA  CCG  GAA  AAT      1632
Trp  Asp  Asp  Ile  Ser  Ile  Thr  Asp  Val  Ala  Ser  Ile  Lys  Pro  Glu  Asn
          1415                     1420                    1425

TTA  ACA  GAT  TCA  GAA  ATT  AAA  CAG  ATT  TAT  AGT  AGG  TAT  GGT  ATT  AAG      1680
Leu  Thr  Asp  Ser  Glu  Ile  Lys  Gln  Ile  Tyr  Ser  Arg  Tyr  Gly  Ile  Lys
1430                          1435                         1440

TTA  GAA  GAT  GGA  ATC  CTT  ATT  GAT  AAA  AAA  GGT  GGG  ATT  CAT  TAT  GGT      1728
Leu  Glu  Asp  Gly  Ile  Leu  Ile  Asp  Lys  Lys  Gly  Gly  Ile  His  Tyr  Gly
1445                          1450                         1455                    1460

GAA  TTT  ATT  AAT  GAA  GCT  AGT  TTT  AAT  ATT  GAA  CCA  TTG  CCA  AAT  TAT      1776
Glu  Phe  Ile  Asn  Glu  Ala  Ser  Phe  Asn  Ile  Glu  Pro  Leu  Pro  Asn  Tyr
                    1465                     1470                    1475

GTG  ACC  AAA  TAT  GAA  GTT  ACT  TAT  AGT  AGT  GAG  TTA  GGA  CCA  AAC  GTG      1824
Val  Thr  Lys  Tyr  Glu  Val  Thr  Tyr  Ser  Ser  Glu  Leu  Gly  Pro  Asn  Val
               1480                     1485                    1490

AGT  GAC  ACA  CTT  GAA  AGT  GAT  AAA  ATT  TAC  AAG  GAT  GGG  ACA  ATT  AAA      1872
Ser  Asp  Thr  Leu  Glu  Ser  Asp  Lys  Ile  Tyr  Lys  Asp  Gly  Thr  Ile  Lys
          1495                     1500                    1505

TTT  GAT  TTT  ACC  AAA  TAT  AGT  AAA  AAT  GAA  CAA  GGA  TTA  TTT  TAT  GAC      1920
Phe  Asp  Phe  Thr  Lys  Tyr  Ser  Lys  Asn  Glu  Gln  Gly  Leu  Phe  Tyr  Asp
1510                          1515                         1520

AGT  GGA  TTA  AAT  TGG  GAC  TTT  AAA  ATT  AAT  GCT  ATT  ACT  TAT  GAT  GGT      1968
Ser  Gly  Leu  Asn  Trp  Asp  Phe  Lys  Ile  Asn  Ala  Ile  Thr  Tyr  Asp  Gly
1525                          1530                         1535                    1540

AAA  GAG  ATG  AAT  GTT  TTT  CAT  AGA  TAT  AAT  AAA  TAG                          2004
Lys  Glu  Met  Asn  Val  Phe  His  Arg  Tyr  Asn  Lys
                    1545                     1550
```

( 2 ) INFORMATION FOR SEQ ID NO:7:

( i ) SEQUENCE CHARACTERISTICS:
        ( A ) LENGTH: 667 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Lys  Arg  Glu  Ile  Asp  Glu  Asp  Thr  Asp  Thr  Asp  Gly  Asp  Ser  Ile
1                   5                   10                  15

Pro  Asp  Leu  Trp  Glu  Glu  Asn  Gly  Tyr  Thr  Ile  Gln  Asn  Arg  Ile  Ala
               20                  25                  30

Val  Lys  Trp  Asp  Asp  Ser  Leu  Ala  Ser  Lys  Gly  Tyr  Thr  Lys  Phe  Val
          35                  40                  45

Ser  Asn  Pro  Leu  Glu  Ser  His  Thr  Val  Gly  Asp  Pro  Tyr  Thr  Asp  Tyr
     50                  55                  60

Glu  Lys  Ala  Ala  Arg  Asp  Leu  Asp  Leu  Ser  Asn  Ala  Lys  Glu  Thr  Phe
65                  70                  75                  80

Asn  Pro  Leu  Val  Ala  Ala  Phe  Pro  Ser  Val  Asn  Val  Ser  Met  Glu  Lys
               85                  90                  95

Val  Ile  Leu  Ser  Pro  Asn  Glu  Asn  Leu  Ser  Asn  Ser  Val  Glu  Ser  His
               100                 105                 110

Ser  Ser  Thr  Asn  Trp  Ser  Tyr  Thr  Asn  Thr  Glu  Gly  Ala  Ser  Val  Glu
          115                 120                 125

Ala  Gly  Ile  Gly  Pro  Lys  Gly  Ile  Ser  Phe  Gly  Val  Ser  Val  Asn  Tyr
     130                 135                 140

Gln  His  Ser  Glu  Thr  Val  Ala  Gln  Glu  Trp  Gly  Thr  Ser  Thr  Gly  Asn
145                 150                 155                 160

Thr  Ser  Gln  Phe  Asn  Thr  Ala  Ser  Ala  Gly  Tyr  Leu  Asn  Ala  Asn  Val
```

|       |     |     |     |     |     |     |     |     |     |     |     |     |     |
|-------|-----|-----|-----|-----|-----|-----|-----|-----|-----|-----|-----|-----|-----|
|       |     |     | 165 |     |     |     | 170 |     |     |     | 175 |     |     |
| Arg   | Tyr | Asn | Asn | Val | Gly | Thr | Gly | Ala | Ile | Tyr | Asp | Val | Lys | Pro | Thr |
|       |     |     | 180 |     |     |     | 185 |     |     |     | 190 |     |     |
| Thr   | Ser | Phe | Val | Leu | Asn | Asn | Asp | Thr | Ile | Ala | Thr | Ile | Thr | Ala | Lys |
|       |     |     | 195 |     |     |     | 200 |     |     |     | 205 |     |     |
| Ser   | Asn | Ser | Thr | Ala | Leu | Asn | Ile | Ser | Pro | Gly | Glu | Ser | Tyr | Pro | Lys |
|       | 210 |     |     |     |     | 215 |     |     |     | 220 |     |     |     |
| Lys   | Gly | Gln | Asn | Gly | Ile | Ala | Ile | Thr | Ser | Met | Asp | Asp | Phe | Asn | Ser |
| 225   |     |     |     | 230 |     |     |     | 235 |     |     |     |     |     |     | 240 |
| His   | Pro | Ile | Thr | Leu | Asn | Lys | Lys | Gln | Val | Asp | Asn | Leu | Leu | Asn | Asn |
|       |     |     |     | 245 |     |     |     | 250 |     |     |     |     | 255 |     |     |
| Lys   | Pro | Met | Met | Leu | Glu | Thr | Asn | Gln | Thr | Asp | Gly | Val | Tyr | Lys | Ile |
|       |     |     | 260 |     |     |     | 265 |     |     |     |     | 270 |     |     |
| Lys   | Asp | Thr | His | Gly | Asn | Ile | Val | Thr | Gly | Gly | Glu | Trp | Asn | Gly | Val |
|       |     | 275 |     |     |     |     | 280 |     |     |     | 285 |     |     |     |
| Ile   | Gln | Gln | Ile | Lys | Ala | Lys | Thr | Ala | Ser | Ile | Ile | Val | Asp | Asp | Gly |
|       | 290 |     |     |     |     | 295 |     |     |     |     | 300 |     |     |     |
| Glu   | Arg | Val | Ala | Glu | Lys | Arg | Val | Ala | Ala | Lys | Asp | Tyr | Glu | Asn | Pro |
| 305   |     |     |     |     | 310 |     |     |     |     | 315 |     |     |     |     | 320 |
| Glu   | Asp | Lys | Thr | Pro | Ser | Leu | Thr | Leu | Lys | Asp | Ala | Leu | Lys | Leu | Ser |
|       |     |     |     | 325 |     |     |     |     | 330 |     |     |     |     | 335 |     |
| Tyr   | Pro | Asp | Glu | Ile | Lys | Glu | Ile | Glu | Gly | Leu | Leu | Tyr | Tyr | Lys | Asn |
|       |     |     | 340 |     |     |     | 345 |     |     |     |     | 350 |     |     |
| Lys   | Pro | Ile | Tyr | Glu | Ser | Ser | Val | Met | Thr | Tyr | Leu | Asp | Glu | Asn | Thr |
|       |     | 355 |     |     |     |     | 360 |     |     |     | 365 |     |     |     |
| Ala   | Lys | Glu | Val | Thr | Lys | Gln | Leu | Asn | Asp | Thr | Thr | Gly | Lys | Phe | Lys |
|       | 370 |     |     |     |     | 375 |     |     |     |     | 380 |     |     |     |
| Asp   | Val | Ser | His | Leu | Tyr | Asp | Val | Lys | Leu | Thr | Pro | Lys | Met | Asn | Val |
| 385   |     |     |     |     | 390 |     |     |     |     | 395 |     |     |     |     | 400 |
| Thr   | Ile | Lys | Leu | Ser | Ile | Leu | Tyr | Asp | Asn | Ala | Glu | Ser | Asn | Asp | Asn |
|       |     |     |     | 405 |     |     |     |     | 410 |     |     |     | 415 |     |     |
| Ser   | Ile | Gly | Lys | Trp | Thr | Asn | Thr | Asn | Ile | Val | Ser | Gly | Gly | Asn | Asn |
|       |     |     | 420 |     |     |     |     | 425 |     |     |     | 430 |     |     |
| Gly   | Lys | Lys | Gln | Tyr | Ser | Ser | Asn | Asn | Pro | Asp | Ala | Asn | Leu | Thr | Leu |
|       |     | 435 |     |     |     |     | 440 |     |     |     | 445 |     |     |     |
| Asn   | Thr | Asp | Ala | Gln | Glu | Lys | Leu | Asn | Lys | Asn | Arg | Asp | Tyr | Tyr | Ile |
|       | 450 |     |     |     |     | 455 |     |     |     | 460 |     |     |     |     |
| Ser   | Leu | Tyr | Met | Lys | Ser | Glu | Lys | Asn | Thr | Gln | Cys | Glu | Ile | Thr | Ile |
| 465   |     |     |     |     | 470 |     |     |     | 475 |     |     |     |     | 480 |     |
| Asp   | Gly | Glu | Ile | Tyr | Pro | Ile | Thr | Thr | Lys | Thr | Val | Asn | Val | Asn | Lys |
|       |     |     |     | 485 |     |     |     | 490 |     |     |     | 495 |     |     |
| Asp   | Asn | Tyr | Lys | Arg | Leu | Asp | Ile | Ile | Ala | His | Asn | Ile | Lys | Ser | Asn |
|       |     |     | 500 |     |     |     | 505 |     |     |     | 510 |     |     |     |
| Pro   | Ile | Ser | Ser | Leu | His | Ile | Lys | Thr | Asn | Asp | Glu | Ile | Thr | Leu | Phe |
|       |     | 515 |     |     |     |     | 520 |     |     |     | 525 |     |     |     |
| Trp   | Asp | Asp | Ile | Ser | Ile | Thr | Asp | Val | Ala | Ser | Ile | Lys | Pro | Glu | Asn |
|       | 530 |     |     |     |     | 535 |     |     |     | 540 |     |     |     |     |
| Leu   | Thr | Asp | Ser | Glu | Ile | Lys | Gln | Ile | Tyr | Ser | Arg | Tyr | Gly | Ile | Lys |
| 545   |     |     |     |     | 550 |     |     |     | 555 |     |     |     | 560 |     |     |
| Leu   | Glu | Asp | Gly | Ile | Leu | Ile | Asp | Lys | Lys | Gly | Gly | Ile | His | Tyr | Gly |
|       |     |     | 565 |     |     |     | 570 |     |     |     |     | 575 |     |     |
| Glu   | Phe | Ile | Asn | Glu | Ala | Ser | Phe | Asn | Ile | Glu | Pro | Leu | Pro | Asn | Tyr |
|       |     |     | 580 |     |     |     | 585 |     |     |     | 590 |     |     |     |

| Val | Thr | Lys<br>595 | Tyr | Glu | Val | Thr | Tyr<br>600 | Ser | Ser | Glu | Leu | Gly<br>605 | Pro | Asn | Val |

| Ser | Asp<br>610 | Thr | Leu | Glu | Ser | Asp<br>615 | Lys | Ile | Tyr | Lys | Asp<br>620 | Gly | Thr | Ile | Lys |

| Phe<br>625 | Asp | Phe | Thr | Lys | Tyr<br>630 | Ser | Lys | Asn | Glu | Gln<br>635 | Gly | Leu | Phe | Tyr | Asp<br>640 |

| Ser | Gly | Leu | Asn | Trp<br>645 | Asp | Phe | Lys | Ile | Asn<br>650 | Ala | Ile | Thr | Tyr | Asp<br>655 | Gly |

| Lys | Glu | Met | Asn<br>660 | Val | Phe | His | Arg | Tyr<br>665 | Asn | Lys |

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: Peptide
        ( B ) LOCATION: 1..16
        ( D ) OTHER INFORMATION: /note= "N-terminal sequence of
            protein purified from strain AB78"

( x i ) SEQUENCE DESCRIPTION: SEQ ID NO:8:

| Lys<br>1 | Arg | Glu | Ile | Asp<br>5 | Glu | Asp | Thr | Asp | Thr<br>10 | Asx | Gly | Asp | Ser | Ile<br>15 | Pro |

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..21
        ( D ) OTHER INFORMATION: /note= "Oligonucleotide probe based
            on amino acids 3 to 9 of SEQ ID NO:8, using codon usage
            of Bacillus thuringiensis"

( x i ) SEQUENCE DESCRIPTION: SEQ ID NO:9:

GAAATTGATC AAGATACNGA T                                          21

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
            ( A ) ORGANISM: Bacillus thuringiensis
            ( B ) STRAIN: AB88

( i x ) FEATURE:
            ( A ) NAME/KEY: Peptide
            ( B ) LOCATION: 1..14
            ( D ) OTHER INFORMATION: /note= "N-terminal amino acid
                    sequence of protein known as anion exchange fraction 23
                    ( s m a l l e r )"

( x i ) SEQUENCE DESCRIPTION: SEQ ID NO:10:

Xaa  Glu  Pro  Phe  Val  Ser  Ala  Xaa  Xaa  Xaa  Gln  Xaa  Xaa  Xaa
1                   5                        10

( 2 ) INFORMATION FOR SEQ ID NO:11:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( v i ) ORIGINAL SOURCE:
            ( A ) ORGANISM: Bacillus thuringiensis ( x i ) SEQUENCE DESCRIPTION: SEQ ID NO:11:

Xaa  Glu  Tyr  Glu  Asn  Val  Glu  Pro  Phe  Val  Ser  Ala  Xaa
1                   5                        10

( 2 ) INFORMATION FOR SEQ ID NO:12:

( i ) SEQUENCE CHARACTERISTICS:
            ( A ) LENGTH: 14 amino acids
            ( B ) TYPE: amino acid
            ( C ) STRANDEDNESS: single
            ( D ) TOPOLOGY: linear ( v i ) ORIGINAL SOURCE:
            ( A ) ORGANISM: Bacillus thurigiensis ( x i ) SEQUENCE DESCRIPTION: SEQ ID NO:12:

Met  Asn  Lys  Asn  Asn  Thr  Lys  Leu  Pro  Thr  Arg  Ala  Leu  Pro
1                   5                        10

( 2 ) INFORMATION FOR SEQ ID NO:13:

( i ) SEQUENCE CHARACTERISTICS:
            ( A ) LENGTH: 15 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
            ( A ) ORGANISM: Bacillus thuringiensis
            ( B ) STRAIN: AB88

( i x ) FEATURE:
            ( A ) NAME/KEY: Peptide
            ( B ) LOCATION: 1..15
            ( D ) OTHER INFORMATION: /note= "N-terminal amino acid sequence of 35 kDa VIP active against Agrotis ipsilon"

( x i ) SEQUENCE DESCRIPTION: SEQ ID NO:13:

Ala  Leu  Ser  Glu  Asn  Thr  Gly  Lys  Asp  Gly  Gly  Tyr  Ile  Val  Pro
1                   5                        10                            15

( 2 ) INFORMATION FOR SEQ ID NO:14:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( v i ) ORIGINAL SOURCE:
      ( A ) ORGANISM: Bacillus thuringiensis ( x i ) SEQUENCE DESCRIPTION: SEQ ID NO:14:

Met  Asp  Asn  Asn  Pro  Asn  Ile  Asn  Glu
1                   5

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
      ( A ) NAME/KEY: Peptide
      ( B ) LOCATION: 1..9
      ( D ) OTHER INFORMATION: /note= "N-terminal sequence of 80
          kDa delta- endotoxin"

( x i ) SEQUENCE DESCRIPTION: SEQ ID NO:15:

Met  Asp  Asn  Asn  Pro  Asn  Ile  Asn  Glu
1                   5

( 2 ) INFORMATION FOR SEQ ID NO:16:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
      ( A ) ORGANISM: Bacillus thuringiensis ( i x ) FEATURE:
      ( A ) NAME/KEY: Peptide
      ( B ) LOCATION: 1..11
      ( D ) OTHER INFORMATION: /note= "N-terminal sequence from 60
          kDa delta- endotoxin"

( x i ) SEQUENCE DESCRIPTION: SEQ ID NO:16:

Met  Asn  Val  Leu  Asn  Ser  Gly  Arg  Thr  Thr  Ile
1                   5                        10

( 2 ) INFORMATION FOR SEQ ID NO:17:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2652
( D ) OTHER INFORMATION: /note= "Maize optimized DNA sequence for 100 kd VIP1A(a) protein from AB78"

( x i ) SEQUENCE DESCRIPTION: SEQ ID NO:17:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

TACACCAAGT TCGTGAGCAA CCCCCTGGAG AGCCACACCG TGGGCGACCC CTACACCGAC 840

TACGAGAAGG CCGCCCGCGA CCTGGACCTG AGCAACGCCA AGGAGACCTT CAACCCCCTG 900

GTGGCCGCCT TCCCCAGCGT GAACGTGAGC ATGGAGAAGG TGATCCTGAG CCCCAACGAG 960

AACCTGAGCA ACAGCGTGGA GAGCCACTCG AGCACCAACT GGAGCTACAC CAACACCGAG 1020

GGCGCCAGCG TGGAGGCCGG CATCGGTCCC AAGGGCATCA GCTTCGGCGT GAGCGTGAAC 1080

TACCAGCACA GCGAGACCGT GGCCCAGGAG TGGGGCACCA GCACCGGCAA CACCAGCCAG 1140

TTCAACACCG CCAGCGCCGG CTACCTGAAC GCCAACGTGC GCTACAACAA CGTGGGCACC 1200

GGCGCCATCT ACGACGTGAA GCCCACCACC AGCTTCGTGC TGAACAACGA CACCATCGCC 1260

ACCATCACCG CCAAGTCGAA TTCCACCGCC CTGAACATCA GCCCCGGCGA GAGCTACCCC 1320

AAGAAGGGCC AGAACGGCAT CGCCATCACC AGCATGGACG ACTTCAACAG CCACCCCATC 1380

ACCCTGAACA AGAAGCAGGT GGACAACCTG CTGAACAACA AGCCCATGAT GCTGGAGACC 1440

AACCAGACCG ACGGCGTCTA CAAGATCAAG GACACCCACG GCAACATCGT GACCGGCGGC 1500

GAGTGGAACG GCGTGATCCA GCAGATCAAG GCCAAGACCG CCAGCATCAT CGTCGACGAC 1560

GGCGAGCGCG TGGCCGAGAA GCGCGTGGCC GCCAAGGACT ACGAGAACCC CGAGGACAAG 1620

ACCCCCAGCC TGACCCTGAA GGACGCCCTG AAGCTGAGCT ACCCCGACGA GATCAAGGAG 1680

ATCGAGGGCC TGCTGTACTA CAAGAACAAG CCCATCTACG AGAGCAGCGT GATGACCTAT 1740

-continued

| | | | | | | |
|---|---|---|---|---|---|---|
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | GGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:18:

( i ) SEQUENCE CHARACTERISTICS:
( A ) LENGTH: 2004 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2004
( D ) OTHER INFORMATION: /note= "Maize optimized DNA sequence for VIP1A(a) 80 kd protein from AB78"

( x i ) SEQUENCE DESCRIPTION: SEQ ID NO:18:

| | | | | | | |
|---|---|---|---|---|---|---|
| ATGAAGCGCG | AGATCGACGA | GGACACCGAC | ACCGACGGCG | ACAGCATCCC | CGACCTGTGG | 60 |
| GAGGAGAACG | GCTACACCAT | CCAGAACCGC | ATCGCCGTGA | AGTGGGACGA | CAGCCTGGCT | 120 |
| AGCAAGGGCT | ACACCAAGTT | CGTGAGCAAC | CCCCTGGAGA | GCCACACCGT | GGGCGACCCC | 180 |
| TACACCGACT | ACGAGAAGGC | CGCCCGCGAC | CTGGACCTGA | GCAACGCCAA | GGAGACCTTC | 240 |
| AACCCCCTGG | TGGCCGCCTT | CCCCAGCGTG | AACGTGAGCA | TGGAGAAGGT | GATCCTGAGC | 300 |
| CCCAACGAGA | ACCTGAGCAA | CAGCGTGGAG | AGCCACTCGA | GCACCAACTG | GAGCTACACC | 360 |
| AACACCGAGG | GCGCCAGCGT | GGAGGCCGGC | ATCGGTCCCA | AGGGCATCAG | CTTCGGCGTG | 420 |
| AGCGTGAACT | ACCAGCACAG | CGAGACCGTG | GCCCAGGAGT | GGGGCACCAG | CACCGGCAAC | 480 |
| ACCAGCCAGT | TCAACACCGC | CAGCGCCGGC | TACCTGAACG | CCAACGTGCG | CTACAACAAC | 540 |
| GTGGGCACCG | GCGCCATCTA | CGACGTGAAG | CCCACCACCA | GCTTCGTGCT | GAACAACGAC | 600 |
| ACCATCGCCA | CCATCACCGC | CAAGTCGAAT | TCCACCGCCC | TGAACATCAG | CCCCGGCGAG | 660 |
| AGCTACCCCA | AGAAGGGCCA | GAACGGCATC | GCCATCACCA | GCATGGACGA | CTTCAACAGC | 720 |
| CACCCCATCA | CCCTGAACAA | GAAGCAGGTG | GACAACCTGC | TGAACAACAA | GCCCATGATG | 780 |

-continued

```
CTGGAGACCA ACCAGACCGA CGGCGTCTAC AAGATCAAGG ACACCCACGG CAACATCGTG    840
ACCGGCGGCG AGTGGAACGG CGTGATCCAG CAGATCAAGG CCAAGACCGC CAGCATCATC    900
GTCGACGACG GCGAGCGCGT GGCCGAGAAG CGCGTGGCCG CCAAGGACTA CGAGAACCCC    960
GAGGACAAGA CCCCCAGCCT GACCCTGAAG GACGCCCTGA AGCTGAGCTA CCCCGACGAG   1020
ATCAAGGAGA TCGAGGGCCT GCTGTACTAC AAGAACAAGC CCATCTACGA GAGCAGCGTG   1080
ATGACCTATC TAGACGAGAA CACCGCCAAG GAGGTGACCA AGCAGCTGAA CGACACCACC   1140
GGCAAGTTCA AGGACGTGAG CCACCTGTAC GACGTGAAGC TGACCCCCAA GATGAACGTG   1200
ACCATCAAGC TGAGCATCCT GTACGACAAC GCCGAGAGCA ACGACAACAG CATCGGCAAG   1260
TGGACCAACA CCAACATCGT GAGCGGCGGC AACAACGGCA AGAAGCAGTA CAGCAGCAAC   1320
AACCCCGACG CCAACCTGAC CCTGAACACC GACGCCCAGG AGAAGCTGAA CAAGAACCGC   1380
GACTACTACA TCAGCCTGTA CATGAAGAGC GAGAAGAACA CCCAGTGCGA GATCACCATC   1440
GACGGCGAGA TATACCCCAT CACCACCAAG ACCGTGAACG TGAACAAGGA CAACTACAAG   1500
CGCCTGGACA TCATCGCCCA CAACATCAAG AGCAACCCCA TCAGCAGCCT GCACATCAAG   1560
ACCAACGACG AGATCACCCT GTTCTGGGAC GACATATCGA TTACCGACGT CGCCAGCATC   1620
AAGCCCGAGA ACCTGACCGA CAGCGAGATC AAGCAGATAT ACAGTCGCTA CGGCATCAAG   1680
CTGGAGGACG GCATCCTGAT CGACAAGAAG GGCGGCATCC ACTACGGCGA GTTCATCAAC   1740
GAGGCCAGCT TCAACATCGA GCCCCTGCAG AACTACGTGA CCAAGTACGA GGTGACCTAC   1800
AGCAGCGAGC TGGGCCCCAA CGTGAGCGAC ACCCTGGAGA GCGACAAGAT TTACAAGGAC   1860
GGCACCATCA AGTTCGACTT CACCAAGTAC AGCAAGAACG AGCAGGGCCT GTTCTACGAC   1920
AGCGGCCTGA ACTGGGACTT CAAGATCAAC GCCATCACCT ACGACGGCAA GGAGATGAAC   1980
GTGTTCCACC GCTACAACAA GTAG                                          2004
```

(2) INFORMATION FOR SEQ ID NO:19:

(i) SEQUENCE CHARACTERISTICS:
(A) LENGTH: 4074 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1386
(D) OTHER INFORMATION: /product="VIP2A(b) from Btt"

(ix) FEATURE:
(A) NAME/KEY: CDS
(B) LOCATION: 1394..3895
(D) OTHER INFORMATION: /product="VIP1A(b) from Btt"

(ix) FEATURE:
(A) NAME/KEY: misc_feature
(B) LOCATION: 1..4074
(D) OTHER INFORMATION: /note= "Cloned DNA sequence from Btt which contains the genes for both VIP1A(b) and VIP2A(b)"

(xi) SEQUENCE DESCRIPTION: SEQ ID NO:19:

```
ATG CAA AGA ATG GAG GGA AAG TTG TTT GTG GTG TCA AAA ACA TTA CAA     48
Met Gln Arg Met Glu Gly Lys Leu Phe Val Val Ser Lys Thr Leu Gln
        670                 675                 680

GTA GTT ACT AGA ACT GTA TTG CTT AGT ACA GTT TAC TCT ATA ACT TTA     96
Val Val Thr Arg Thr Val Leu Leu Ser Thr Val Tyr Ser Ile Thr Leu
    685                 690                 695
```

| | | | | | | | | | | | | | | | | |
|---|---|---|---|---|---|---|---|---|---|---|---|---|---|---|---|---|
| TTA | AAT | AAT | GTA | GTG | ATA | AAA | GCT | GAC | CAA | TTA | AAT | ATA | AAT | TCT | CAA | 144 |
| Leu | Asn | Asn | Val | Val | Ile | Lys | Ala | Asp | Gln | Leu | Asn | Ile | Asn | Ser | Gln | |
| 700 | | | | | 705 | | | | | 710 | | | | | 715 | |
| AGT | AAA | TAT | ACT | AAC | TTG | CAA | AAT | CTA | AAA | ATC | CCT | GAT | AAT | GCA | GAG | 192 |
| Ser | Lys | Tyr | Thr | Asn | Leu | Gln | Asn | Leu | Lys | Ile | Pro | Asp | Asn | Ala | Glu | |
| | | | 720 | | | | | 725 | | | | | 730 | | | |
| GAT | TTT | AAA | GAA | GAT | AAG | GGG | AAA | GCG | AAA | GAA | TGG | GGG | AAA | GAG | AAA | 240 |
| Asp | Phe | Lys | Glu | Asp | Lys | Gly | Lys | Ala | Lys | Glu | Trp | Gly | Lys | Glu | Lys | |
| | | | | 735 | | | | | 740 | | | | | 745 | | |
| GGG | GAA | GAG | TGG | AGG | CCT | CCT | GCT | ACT | GAG | AAA | GGA | GAA | ATG | AAT | AAT | 288 |
| Gly | Glu | Glu | Trp | Arg | Pro | Pro | Ala | Thr | Glu | Lys | Gly | Glu | Met | Asn | Asn | |
| | | 750 | | | | | 755 | | | | | 760 | | | | |
| TTT | TTA | GAT | AAT | AAA | AAT | GAT | ATA | AAG | ACC | AAT | TAT | AAA | GAA | ATT | ACT | 336 |
| Phe | Leu | Asp | Asn | Lys | Asn | Asp | Ile | Lys | Thr | Asn | Tyr | Lys | Glu | Ile | Thr | |
| 765 | | | | | 770 | | | | | 775 | | | | | | |
| TTT | TCT | ATG | GCA | GGT | TCA | TGT | GAA | GAT | GAA | ATA | AAA | GAT | TTA | GAA | GAA | 384 |
| Phe | Ser | Met | Ala | Gly | Ser | Cys | Glu | Asp | Glu | Ile | Lys | Asp | Leu | Glu | Glu | |
| 780 | | | | | 785 | | | | | 790 | | | | | 795 | |
| ATT | GAT | AAG | ATC | TTT | GAT | AAA | GCC | AAT | CTC | TCG | AGT | TCT | ATT | ATC | ACC | 432 |
| Ile | Asp | Lys | Ile | Phe | Asp | Lys | Ala | Asn | Leu | Ser | Ser | Ser | Ile | Ile | Thr | |
| | | | | 800 | | | | | 805 | | | | | 810 | | |
| TAT | AAA | AAT | GTG | GAA | CCA | GCA | ACA | ATT | GGA | TTT | AAT | AAA | TCT | TTA | ACA | 480 |
| Tyr | Lys | Asn | Val | Glu | Pro | Ala | Thr | Ile | Gly | Phe | Asn | Lys | Ser | Leu | Thr | |
| | | | 815 | | | | | 820 | | | | | 825 | | | |
| GAA | GGT | AAT | ACG | ATT | AAT | TCT | GAT | GCA | ATG | GCA | CAG | TTT | AAA | GAA | CAA | 528 |
| Glu | Gly | Asn | Thr | Ile | Asn | Ser | Asp | Ala | Met | Ala | Gln | Phe | Lys | Glu | Gln | |
| | | 830 | | | | | 835 | | | | | 840 | | | | |
| TTT | TTA | GGT | AAG | GAT | ATG | AAG | TTT | GAT | AGT | TAT | CTA | GAT | ACT | CAT | TTA | 576 |
| Phe | Leu | Gly | Lys | Asp | Met | Lys | Phe | Asp | Ser | Tyr | Leu | Asp | Thr | His | Leu | |
| 845 | | | | | 850 | | | | | 855 | | | | | | |
| ACT | GCT | CAA | CAA | GTT | TCC | AGT | AAA | AAA | AGA | GTT | ATT | TTG | AAG | GTT | ACG | 624 |
| Thr | Ala | Gln | Gln | Val | Ser | Ser | Lys | Lys | Arg | Val | Ile | Leu | Lys | Val | Thr | |
| 860 | | | | | 865 | | | | | 870 | | | | | 875 | |
| GTT | CCG | AGT | GGG | AAA | GGT | TCT | ACT | ACT | CCA | ACA | AAA | GCA | GGT | GTC | ATT | 672 |
| Val | Pro | Ser | Gly | Lys | Gly | Ser | Thr | Thr | Pro | Thr | Lys | Ala | Gly | Val | Ile | |
| | | | | 880 | | | | | 885 | | | | | 890 | | |
| TTA | AAC | AAT | AAT | GAA | TAC | AAA | ATG | CTC | ATT | GAT | AAT | GGG | TAT | GTG | CTC | 720 |
| Leu | Asn | Asn | Asn | Glu | Tyr | Lys | Met | Leu | Ile | Asp | Asn | Gly | Tyr | Val | Leu | |
| | | | 895 | | | | | 900 | | | | | 905 | | | |
| CAT | GTA | GAT | AAG | GTA | TCA | AAA | GTA | GTA | AAA | AAA | GGG | ATG | GAG | TGC | TTA | 768 |
| His | Val | Asp | Lys | Val | Ser | Lys | Val | Val | Lys | Lys | Gly | Met | Glu | Cys | Leu | |
| | | 910 | | | | | 915 | | | | | 920 | | | | |
| CAA | GTT | GAA | GGG | ACT | TTA | AAA | AAG | AGT | CTC | GAC | TTT | AAA | AAT | GAT | ATA | 816 |
| Gln | Val | Glu | Gly | Thr | Leu | Lys | Lys | Ser | Leu | Asp | Phe | Lys | Asn | Asp | Ile | |
| 925 | | | | | 930 | | | | | 935 | | | | | | |
| AAT | GCT | GAA | GCG | CAT | AGC | TGG | GGG | ATG | AAA | ATT | TAT | GAA | GAC | TGG | GCT | 864 |
| Asn | Ala | Glu | Ala | His | Ser | Trp | Gly | Met | Lys | Ile | Tyr | Glu | Asp | Trp | Ala | |
| 940 | | | | | 945 | | | | | 950 | | | | | 955 | |
| AAA | AAT | TTA | ACC | GCT | TCG | CAA | AGG | GAA | GCT | TTA | GAT | GGG | TAT | GCT | AGG | 912 |
| Lys | Asn | Leu | Thr | Ala | Ser | Gln | Arg | Glu | Ala | Leu | Asp | Gly | Tyr | Ala | Arg | |
| | | | | 960 | | | | | 965 | | | | | 970 | | |
| CAA | GAT | TAT | AAA | GAA | ATC | AAT | AAT | TAT | TTG | CGC | AAT | CAA | GGC | GGG | AGT | 960 |
| Gln | Asp | Tyr | Lys | Glu | Ile | Asn | Asn | Tyr | Leu | Arg | Asn | Gln | Gly | Gly | Ser | |
| | | | 975 | | | | | 980 | | | | | 985 | | | |
| GGA | AAT | GAA | AAG | CTG | GAT | GCC | CAA | TTA | AAA | AAT | ATT | TCT | GAT | GCT | TTA | 1008 |
| Gly | Asn | Glu | Lys | Leu | Asp | Ala | Gln | Leu | Lys | Asn | Ile | Ser | Asp | Ala | Leu | |
| | | 990 | | | | | 995 | | | | | 1000 | | | | |
| GGG | AAG | AAA | CCC | ATA | CCA | GAA | AAT | ATT | ACC | GTG | TAT | AGA | TGG | TGT | GGC | 1056 |
| Gly | Lys | Lys | Pro | Ile | Pro | Glu | Asn | Ile | Thr | Val | Tyr | Arg | Trp | Cys | Gly | |
| 1005 | | | | | 1010 | | | | | 1015 | | | | | | |

| | | | | | | | | | | | | | | | | |
|---|---|---|---|---|---|---|---|---|---|---|---|---|---|---|---|---|
| ATG | CCG | GAA | TTT | GGT | TAT | CAA | ATT | AGT | GAT | CCG | TTA | CCT | TCT | TTA | AAA | 1104 |
| Met | Pro | Glu | Phe | Gly | Tyr | Gln | Ile | Ser | Asp | Pro | Leu | Pro | Ser | Leu | Lys | |
| 1020 | | | | 1025 | | | | | 1030 | | | | | | 1035 | |
| GAT | TTT | GAA | GAA | CAA | TTT | TTA | AAT | ACA | ATT | AAA | GAA | GAC | AAA | GGG | TAT | 1152 |
| Asp | Phe | Glu | Glu | Gln | Phe | Leu | Asn | Thr | Ile | Lys | Glu | Asp | Lys | Gly | Tyr | |
| | | | | | | | 1040 | | | | 1045 | | | | 1050 | |
| ATG | AGT | ACA | AGC | TTA | TCG | AGT | GAA | CGT | CTT | GCA | GCT | TTT | GGA | TCT | AGA | 1200 |
| Met | Ser | Thr | Ser | Leu | Ser | Ser | Glu | Arg | Leu | Ala | Ala | Phe | Gly | Ser | Arg | |
| | | 1055 | | | | | | 1060 | | | | | | 1065 | | |
| AAA | ATT | ATA | TTA | CGC | TTA | CAA | GTT | CCG | AAA | GGA | AGT | ACG | GGG | GCG | TAT | 1248 |
| Lys | Ile | Ile | Leu | Arg | Leu | Gln | Val | Pro | Lys | Gly | Ser | Thr | Gly | Ala | Tyr | |
| | | | 1070 | | | | | 1075 | | | | | 1080 | | | |
| TTA | AGT | GCC | ATT | GGT | GGA | TTT | GCA | AGT | GAA | AAA | GAG | ATC | CTA | CTT | GAT | 1296 |
| Leu | Ser | Ala | Ile | Gly | Gly | Phe | Ala | Ser | Glu | Lys | Glu | Ile | Leu | Leu | Asp | |
| | | 1085 | | | | | 1090 | | | | | 1095 | | | | |
| AAA | GAT | AGT | AAA | TAT | CAT | ATT | GAT | AAA | GCA | ACA | GAG | GTA | ATC | ATT | AAA | 1344 |
| Lys | Asp | Ser | Lys | Tyr | His | Ile | Asp | Lys | Ala | Thr | Glu | Val | Ile | Ile | Lys | |
| 1100 | | | | | 1105 | | | | | 1110 | | | | | 1115 | |
| GGT | GTT | AAG | CGA | TAT | GTA | GTG | GAT | GCA | ACA | TTA | TTA | ACA | AAT | | | 1386 |
| Gly | Val | Lys | Arg | Tyr | Val | Val | Asp | Ala | Thr | Leu | Leu | Thr | Asn | | | |
| | | | | 1120 | | | | | 1125 | | | | | | | |
| TAAGGAG | ATG | AAA | AAT | ATG | AAG | AAA | AAG | TTA | GCA | AGT | GTT | GTA | ACC | TGT | | 1435 |
| | Met | Lys | Asn | Met | Lys | Lys | Lys | Leu | Ala | Ser | Val | Val | Thr | Cys | | |
| | 1 | | | | 5 | | | | | 10 | | | | | | |
| ATG | TTA | TTA | GCT | CCT | ATG | TTT | TTG | AAT | GGA | AAT | GTG | AAT | GCT | GTT | AAC | 1483 |
| Met | Leu | Leu | Ala | Pro | Met | Phe | Leu | Asn | Gly | Asn | Val | Asn | Ala | Val | Asn | |
| 15 | | | | | 20 | | | | | 25 | | | | | 30 | |
| GCG | GAT | AGT | AAA | ATA | AAT | CAG | ATT | TCT | ACA | ACG | CAG | GAA | AAC | CAA | CAG | 1531 |
| Ala | Asp | Ser | Lys | Ile | Asn | Gln | Ile | Ser | Thr | Thr | Gln | Glu | Asn | Gln | Gln | |
| | | | | 35 | | | | | 40 | | | | | 45 | | |
| AAA | GAG | ATG | GAC | CGA | AAG | GGA | TTA | TTG | GGA | TAT | TAT | TTC | AAA | GGA | AAA | 1579 |
| Lys | Glu | Met | Asp | Arg | Lys | Gly | Leu | Leu | Gly | Tyr | Tyr | Phe | Lys | Gly | Lys | |
| | | | 50 | | | | | 55 | | | | | 60 | | | |
| GAT | TTT | AAT | AAT | CTT | ACT | ATG | TTT | GCA | CCG | ACA | CGT | GAT | AAT | ACC | CTT | 1627 |
| Asp | Phe | Asn | Asn | Leu | Thr | Met | Phe | Ala | Pro | Thr | Arg | Asp | Asn | Thr | Leu | |
| | | 65 | | | | | 70 | | | | | 75 | | | | |
| ATG | TAT | GAC | CAA | CAA | ACA | GCG | AAT | GCA | TTA | TTA | GAT | AAA | AAA | CAA | CAA | 1675 |
| Met | Tyr | Asp | Gln | Gln | Thr | Ala | Asn | Ala | Leu | Leu | Asp | Lys | Lys | Gln | Gln | |
| | 80 | | | | | 85 | | | | | 90 | | | | | |
| GAA | TAT | CAG | TCC | ATT | CGT | TGG | ATT | GGT | TTG | ATT | CAG | CGT | AAA | GAA | ACG | 1723 |
| Glu | Tyr | Gln | Ser | Ile | Arg | Trp | Ile | Gly | Leu | Ile | Gln | Arg | Lys | Glu | Thr | |
| 95 | | | | | 100 | | | | | 105 | | | | | 110 | |
| GGC | GAT | TTC | ACA | TTT | AAC | TTA | TCA | AAG | GAT | GAA | CAG | GCA | ATT | ATA | GAA | 1771 |
| Gly | Asp | Phe | Thr | Phe | Asn | Leu | Ser | Lys | Asp | Glu | Gln | Ala | Ile | Ile | Glu | |
| | | | | 115 | | | | | 120 | | | | | 125 | | |
| ATC | GAT | GGG | AAA | ATC | ATT | TCT | AAT | AAA | GGG | AAA | GAA | AAG | CAA | GTT | GTC | 1819 |
| Ile | Asp | Gly | Lys | Ile | Ile | Ser | Asn | Lys | Gly | Lys | Glu | Lys | Gln | Val | Val | |
| | | | 130 | | | | | 135 | | | | | 140 | | | |
| CAT | TTA | GAA | AAA | GAA | AAA | TTA | GTT | CCA | ATC | AAA | ATA | GAG | TAT | CAA | TCA | 1867 |
| His | Leu | Glu | Lys | Glu | Lys | Leu | Val | Pro | Ile | Lys | Ile | Glu | Tyr | Gln | Ser | |
| | | 145 | | | | | 150 | | | | | 155 | | | | |
| GAT | ACG | AAA | TTT | AAT | ATT | GAT | AGT | AAA | ACA | TTT | AAA | GAA | CTT | AAA | TTA | 1915 |
| Asp | Thr | Lys | Phe | Asn | Ile | Asp | Ser | Lys | Thr | Phe | Lys | Glu | Leu | Lys | Leu | |
| | 160 | | | | | 165 | | | | | 170 | | | | | |
| TTT | AAA | ATA | GAT | AGT | CAA | AAC | CAA | TCT | CAA | CAA | GTT | CAA | CTG | AGA | AAC | 1963 |
| Phe | Lys | Ile | Asp | Ser | Gln | Asn | Gln | Ser | Gln | Gln | Val | Gln | Leu | Arg | Asn | |
| 175 | | | | | 180 | | | | | 185 | | | | | 190 | |
| CCT | GAA | TTT | AAC | AAA | AAA | GAA | TCA | CAG | GAA | TTT | TTA | GCA | AAA | GCA | TCA | 2011 |
| Pro | Glu | Phe | Asn | Lys | Lys | Glu | Ser | Gln | Glu | Phe | Leu | Ala | Lys | Ala | Ser | |
| | | | | 195 | | | | | 200 | | | | | 205 | | |

```
AAA  ACA  AAC  CTT  TTT  AAG  CAA  AAA  ATG  AAA  AGA  GAT  ATT  GAT  GAA  GAT    2059
Lys  Thr  Asn  Leu  Phe  Lys  Gln  Lys  Met  Lys  Arg  Asp  Ile  Asp  Glu  Asp
               210                 215                      220

ACG  GAT  ACA  GAT  GGA  GAC  TCC  ATT  CCT  GAT  CTT  TGG  GAA  GAA  AAT  GGG    2107
Thr  Asp  Thr  Asp  Gly  Asp  Ser  Ile  Pro  Asp  Leu  Trp  Glu  Glu  Asn  Gly
               225                 230                      235

TAC  ACG  ATT  CAA  AAT  AAA  GTT  GCT  GTC  AAA  TGG  GAT  GAT  TCG  CTA  GCA    2155
Tyr  Thr  Ile  Gln  Asn  Lys  Val  Ala  Val  Lys  Trp  Asp  Asp  Ser  Leu  Ala
     240                 245                      250

AGT  AAG  GGA  TAT  ACA  AAA  TTT  GTT  TCG  AAT  CCA  TTA  GAC  AGC  CAC  ACA    2203
Ser  Lys  Gly  Tyr  Thr  Lys  Phe  Val  Ser  Asn  Pro  Leu  Asp  Ser  His  Thr
255                      260                 265                           270

GTT  GGC  GAT  CCC  TAT  ACT  GAT  TAT  GAA  AAG  GCC  GCA  AGG  GAT  TTA  GAT    2251
Val  Gly  Asp  Pro  Tyr  Thr  Asp  Tyr  Glu  Lys  Ala  Ala  Arg  Asp  Leu  Asp
                    275                 280                           285

TTA  TCA  AAT  GCA  AAG  GAA  ACG  TTC  AAC  CCA  TTG  GTA  GCT  GCT  TTT  CCA    2299
Leu  Ser  Asn  Ala  Lys  Glu  Thr  Phe  Asn  Pro  Leu  Val  Ala  Ala  Phe  Pro
               290                 295                      300

AGT  GTG  AAT  GTT  AGT  ATG  GAA  AAG  GTG  ATA  TTA  TCA  CCA  AAT  GAA  AAT    2347
Ser  Val  Asn  Val  Ser  Met  Glu  Lys  Val  Ile  Leu  Ser  Pro  Asn  Glu  Asn
               305                 310                      315

TTA  TCC  AAT  AGT  GTA  GAG  TCT  CAT  TCA  TCC  ACG  AAT  TGG  TCT  TAT  ACG    2395
Leu  Ser  Asn  Ser  Val  Glu  Ser  His  Ser  Ser  Thr  Asn  Trp  Ser  Tyr  Thr
320                      325                 330

AAT  ACA  GAA  GGA  GCT  TCC  ATT  GAA  GCT  GGT  GGC  GGT  CCA  TTA  GGC  CTT    2443
Asn  Thr  Glu  Gly  Ala  Ser  Ile  Glu  Ala  Gly  Gly  Gly  Pro  Leu  Gly  Leu
335                      340                 345                           350

TCT  TTT  GGC  GTG  AGT  GTT  ACT  TAT  CAA  CAC  TCT  GAA  ACA  GTT  GCA  CAA    2491
Ser  Phe  Gly  Val  Ser  Val  Thr  Tyr  Gln  His  Ser  Glu  Thr  Val  Ala  Gln
               355                 360                      365

GAA  TGG  GGA  ACA  TCT  ACA  GGA  AAT  ACT  TCA  CAA  TTC  AAT  ACG  GCT  TCA    2539
Glu  Trp  Gly  Thr  Ser  Thr  Gly  Asn  Thr  Ser  Gln  Phe  Asn  Thr  Ala  Ser
               370                 375                      380

GCG  GGA  TAT  TTA  AAT  GCA  AAT  GTT  CGG  TAT  AAC  AAT  GTA  GGG  ACT  GGT    2587
Ala  Gly  Tyr  Leu  Asn  Ala  Asn  Val  Arg  Tyr  Asn  Asn  Val  Gly  Thr  Gly
          385                      390                 395

GCC  ATC  TAT  GAT  GTA  AAA  CCT  ACA  ACA  AGT  TTT  GTA  TTA  AAT  AAC  AAT    2635
Ala  Ile  Tyr  Asp  Val  Lys  Pro  Thr  Thr  Ser  Phe  Val  Leu  Asn  Asn  Asn
     400                 405                      410

ACC  ATC  GCA  ACG  ATT  ACA  GCA  AAA  TCA  AAT  TCA  ACA  GCT  TTA  CGT  ATA    2683
Thr  Ile  Ala  Thr  Ile  Thr  Ala  Lys  Ser  Asn  Ser  Thr  Ala  Leu  Arg  Ile
415                      420                 425                           430

TCT  CCG  GGG  GAT  AGT  TAT  CCA  GAA  ATA  GGA  GAA  AAC  GCT  ATT  GCG  ATT    2731
Ser  Pro  Gly  Asp  Ser  Tyr  Pro  Glu  Ile  Gly  Glu  Asn  Ala  Ile  Ala  Ile
               435                 440                      445

ACA  TCT  ATG  GAT  GAT  TTT  AAT  TCT  CAT  CCA  ATT  ACA  TTA  AAT  AAA  CAA    2779
Thr  Ser  Met  Asp  Asp  Phe  Asn  Ser  His  Pro  Ile  Thr  Leu  Asn  Lys  Gln
               450                 455                      460

CAG  GTA  AAT  CAA  TTG  ATA  AAT  AAT  AAG  CCA  ATT  ATG  CTA  GAG  ACA  GAC    2827
Gln  Val  Asn  Gln  Leu  Ile  Asn  Asn  Lys  Pro  Ile  Met  Leu  Glu  Thr  Asp
          465                      470                 475

CAA  ACA  GAT  GGT  GTT  TAT  AAA  ATA  AGA  GAT  ACA  CAT  GGA  AAT  ATT  GTA    2875
Gln  Thr  Asp  Gly  Val  Tyr  Lys  Ile  Arg  Asp  Thr  His  Gly  Asn  Ile  Val
     480                 485                      490

ACT  GGT  GGA  GAA  TGG  AAT  GGT  GTA  ACA  CAA  CAA  ATT  AAA  GCA  AAA  ACA    2923
Thr  Gly  Gly  Glu  Trp  Asn  Gly  Val  Thr  Gln  Gln  Ile  Lys  Ala  Lys  Thr
495                      500                 505                           510

GCG  TCT  ATT  ATT  GTG  GAT  GAC  GGG  AAA  CAG  GTA  GCA  GAA  AAA  CGT  GTG    2971
Ala  Ser  Ile  Ile  Val  Asp  Asp  Gly  Lys  Gln  Val  Ala  Glu  Lys  Arg  Val
               515                 520                      525
```

| | | | | | | | | | | | | | | | | |
|---|---|---|---|---|---|---|---|---|---|---|---|---|---|---|---|---|
| GCG | GCA | AAA | GAT | TAT | GGT | CAT | CCA | GAA | GAT | AAA | ACA | CCA | CCT | TTA | ACT | 3019 |
| Ala | Ala | Lys | Asp | Tyr | Gly | His | Pro | Glu | Asp | Lys | Thr | Pro | Pro | Leu | Thr | |
| | | 530 | | | | | 535 | | | | | 540 | | | | |
| TTA | AAA | GAT | ACC | CTG | AAG | CTT | TCA | TAC | CCA | GAT | GAA | ATA | AAA | GAA | ACT | 3067 |
| Leu | Lys | Asp | Thr | Leu | Lys | Leu | Ser | Tyr | Pro | Asp | Glu | Ile | Lys | Glu | Thr | |
| | | | 545 | | | | | 550 | | | | | 555 | | | |
| AAT | GGA | TTG | TTG | TAC | TAT | GAT | GAC | AAA | CCA | ATC | TAT | GAA | TCG | AGT | GTC | 3115 |
| Asn | Gly | Leu | Leu | Tyr | Tyr | Asp | Asp | Lys | Pro | Ile | Tyr | Glu | Ser | Ser | Val | |
| | 560 | | | | | | 565 | | | | | 570 | | | | |
| ATG | ACT | TAT | CTG | GAT | GAA | AAT | ACG | GCA | AAA | GAA | GTC | AAA | AAA | CAA | ATA | 3163 |
| Met | Thr | Tyr | Leu | Asp | Glu | Asn | Thr | Ala | Lys | Glu | Val | Lys | Lys | Gln | Ile | |
| 575 | | | | | 580 | | | | | 585 | | | | | 590 | |
| AAT | GAT | ACA | ACC | GGA | AAA | TTT | AAG | GAT | GTA | AAT | CAC | TTA | TAT | GAT | GTA | 3211 |
| Asn | Asp | Thr | Thr | Gly | Lys | Phe | Lys | Asp | Val | Asn | His | Leu | Tyr | Asp | Val | |
| | | | | 595 | | | | | 600 | | | | | 605 | | |
| AAA | CTG | ACT | CCA | AAA | ATG | AAT | TTT | ACG | ATT | AAA | ATG | GCT | TCC | TTG | TAT | 3259 |
| Lys | Leu | Thr | Pro | Lys | Met | Asn | Phe | Thr | Ile | Lys | Met | Ala | Ser | Leu | Tyr | |
| | | | 610 | | | | | 615 | | | | | 620 | | | |
| GAT | GGG | GCT | GAA | AAT | AAT | CAT | AAC | TCT | TTA | GGA | ACC | TGG | TAT | TTA | ACA | 3307 |
| Asp | Gly | Ala | Glu | Asn | Asn | His | Asn | Ser | Leu | Gly | Thr | Trp | Tyr | Leu | Thr | |
| | | 625 | | | | | 630 | | | | | 635 | | | | |
| TAT | AAT | GTT | GCT | GGT | GGA | AAT | ACT | GGG | AAG | AGA | CAA | TAT | CGT | TCA | GCT | 3355 |
| Tyr | Asn | Val | Ala | Gly | Gly | Asn | Thr | Gly | Lys | Arg | Gln | Tyr | Arg | Ser | Ala | |
| | 640 | | | | | 645 | | | | | 650 | | | | | |
| CAT | TCT | TGT | GCA | CAT | GTA | GCT | CTA | TCT | TCA | GAA | GCG | AAA | AAG | AAA | CTA | 3403 |
| His | Ser | Cys | Ala | His | Val | Ala | Leu | Ser | Ser | Glu | Ala | Lys | Lys | Lys | Leu | |
| 655 | | | | | 660 | | | | | 665 | | | | | 670 | |
| AAT | CAA | AAT | GCG | AAT | TAC | TAT | CTT | AGC | ATG | TAT | ATG | AAG | GCT | GAT | TCT | 3451 |
| Asn | Gln | Asn | Ala | Asn | Tyr | Tyr | Leu | Ser | Met | Tyr | Met | Lys | Ala | Asp | Ser | |
| | | | | 675 | | | | | 680 | | | | | 685 | | |
| ACT | ACG | GAA | CCT | ACA | ATA | GAA | GTA | GCT | GGG | GAA | AAA | TCT | GCA | ATA | ACA | 3499 |
| Thr | Thr | Glu | Pro | Thr | Ile | Glu | Val | Ala | Gly | Glu | Lys | Ser | Ala | Ile | Thr | |
| | | | 690 | | | | | 695 | | | | | 700 | | | |
| AGT | AAA | AAA | GTA | AAA | TTA | AAT | AAT | CAA | AAT | TAT | CAA | AGA | GTT | GAT | ATT | 3547 |
| Ser | Lys | Lys | Val | Lys | Leu | Asn | Asn | Gln | Asn | Tyr | Gln | Arg | Val | Asp | Ile | |
| | | 705 | | | | | 710 | | | | | 715 | | | | |
| TTA | GTG | AAA | AAT | TCT | GAA | AGA | AAT | CCA | ATG | GAT | AAA | ATA | TAT | ATA | AGA | 3595 |
| Leu | Val | Lys | Asn | Ser | Glu | Arg | Asn | Pro | Met | Asp | Lys | Ile | Tyr | Ile | Arg | |
| | 720 | | | | | 725 | | | | | 730 | | | | | |
| GGA | AAT | GGC | ACG | ACA | AAT | GTT | TAT | GGG | GAT | GAT | GTT | ACT | ATC | CCA | GAG | 3643 |
| Gly | Asn | Gly | Thr | Thr | Asn | Val | Tyr | Gly | Asp | Asp | Val | Thr | Ile | Pro | Glu | |
| 735 | | | | | 740 | | | | | 745 | | | | | 750 | |
| GTA | TCA | GCT | ATA | AAT | CCG | GCT | AGT | CTA | TCA | GAT | GAA | GAA | ATT | CAA | GAA | 3691 |
| Val | Ser | Ala | Ile | Asn | Pro | Ala | Ser | Leu | Ser | Asp | Glu | Glu | Ile | Gln | Glu | |
| | | | | 755 | | | | | 760 | | | | | 765 | | |
| ATA | TTT | AAA | GAC | TCA | ACT | ATT | GAA | TAT | GGA | AAT | CCT | AGT | TTC | GTT | GCT | 3739 |
| Ile | Phe | Lys | Asp | Ser | Thr | Ile | Glu | Tyr | Gly | Asn | Pro | Ser | Phe | Val | Ala | |
| | | | 770 | | | | | 775 | | | | | 780 | | | |
| GAT | GCC | GTA | ACA | TTT | AAA | AAT | ATA | AAA | CCT | TTA | CAA | AAT | TAT | GTA | AAG | 3787 |
| Asp | Ala | Val | Thr | Phe | Lys | Asn | Ile | Lys | Pro | Leu | Gln | Asn | Tyr | Val | Lys | |
| | | 785 | | | | | 790 | | | | | 795 | | | | |
| GAA | TAT | GAA | ATA | TAT | CAT | AAA | TCT | CAT | CGA | TAT | GAA | AAG | AAA | ACG | GTC | 3835 |
| Glu | Tyr | Glu | Ile | Tyr | His | Lys | Ser | His | Arg | Tyr | Glu | Lys | Lys | Thr | Val | |
| | 800 | | | | | 805 | | | | | 810 | | | | | |
| TTT | GAT | ATC | ATG | GGT | GTT | CAT | TAT | GAG | TAT | AGT | ATA | GCT | AGG | GAA | CAA | 3883 |
| Phe | Asp | Ile | Met | Gly | Val | His | Tyr | Glu | Tyr | Ser | Ile | Ala | Arg | Glu | Gln | |
| 815 | | | | | 820 | | | | | 825 | | | | | 830 | |
| AAG | AAA | GCC | GCA | TAATTTTAAA | AATAAAACTC | GTTAGAGTTT | ATTTAGCATG | | | | | | | | | 3935 |
| Lys | Lys | Ala | Ala | | | | | | | | | | | | | |

```
GTATTTTTAA GAATAATCAA TATGTTGAAC CGTTTGTAGC TGTTTTGGAA GGGAATTTCA      3995

TTTTATTTGG TCTCTTAAGT TGATGGGCAT GGGATATGTT CAGCATCCAA GCGTTTNGGG      4055

GGTTANAAAA TCCAATTTT                                                   4074
```

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Gln Arg Met Glu Gly Lys Leu Phe Val Val Ser Lys Thr Leu Gln
 1               5                  10                  15

Val Val Thr Arg Thr Val Leu Leu Ser Thr Val Tyr Ser Ile Thr Leu
            20                  25                  30

Leu Asn Asn Val Val Ile Lys Ala Asp Gln Leu Asn Ile Asn Ser Gln
        35                  40                  45

Ser Lys Tyr Thr Asn Leu Gln Asn Leu Lys Ile Pro Asp Asn Ala Glu
    50                  55                  60

Asp Phe Lys Glu Asp Lys Gly Lys Ala Lys Glu Trp Gly Lys Glu Lys
65                  70                  75                  80

Gly Glu Glu Trp Arg Pro Pro Ala Thr Glu Lys Gly Glu Met Asn Asn
                85                  90                  95

Phe Leu Asp Asn Lys Asn Asp Ile Lys Thr Asn Tyr Lys Glu Ile Thr
            100                 105                 110

Phe Ser Met Ala Gly Ser Cys Glu Asp Glu Ile Lys Asp Leu Glu Glu
        115                 120                 125

Ile Asp Lys Ile Phe Asp Lys Ala Asn Leu Ser Ser Ser Ile Ile Thr
    130                 135                 140

Tyr Lys Asn Val Glu Pro Ala Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Gly Lys Asp Met Lys Phe Asp Ser Tyr Leu Asp Thr His Leu
            180                 185                 190

Thr Ala Gln Gln Val Ser Ser Lys Lys Arg Val Ile Leu Lys Val Thr
        195                 200                 205

Val Pro Ser Gly Lys Gly Ser Thr Thr Pro Thr Lys Ala Gly Val Ile
    210                 215                 220

Leu Asn Asn Asn Glu Tyr Lys Met Leu Ile Asp Asn Gly Tyr Val Leu
225                 230                 235                 240

His Val Asp Lys Val Ser Lys Val Val Lys Lys Gly Met Glu Cys Leu
                245                 250                 255

Gln Val Glu Gly Thr Leu Lys Lys Ser Leu Asp Phe Lys Asn Asp Ile
            260                 265                 270

Asn Ala Glu Ala His Ser Trp Gly Met Lys Ile Tyr Glu Asp Trp Ala
        275                 280                 285

Lys Asn Leu Thr Ala Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Leu Lys Asn Ile Ser Asp Ala Leu
                325                 330                 335
```

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
        355                 360                 365

Asp Phe Glu Glu Gln Phe Leu Asn Thr Ile Lys Glu Asp Lys Gly Tyr
    370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
            405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Ala Thr Glu Val Ile Ile Lys
        435                 440                 445

Gly Val Lys Arg Tyr Val Val Asp Ala Thr Leu Leu Thr Asn
        450                 455                 460

(2) INFORMATION FOR SEQ ID NO:21:

(i) SEQUENCE CHARACTERISTICS:
      (A) LENGTH: 834 amino acids
      (B) TYPE: amino acid
      (D) TOPOLOGY: linear (ii) MOLECULE TYPE: protein (xi) SEQUENCE DESCRIPTION: SEQ ID NO:21:

Met Lys Asn Met Lys Lys Lys Leu Ala Ser Val Val Thr Cys Met Leu
 1               5                  10                  15

Leu Ala Pro Met Phe Leu Asn Gly Asn Val Asn Ala Val Asn Ala Asp
            20                  25                  30

Ser Lys Ile Asn Gln Ile Ser Thr Thr Gln Glu Asn Gln Gln Lys Glu
        35                  40                  45

Met Asp Arg Lys Gly Leu Leu Gly Tyr Tyr Phe Lys Gly Lys Asp Phe
    50                  55                  60

Asn Asn Leu Thr Met Phe Ala Pro Thr Arg Asp Asn Thr Leu Met Tyr
65                  70                  75                  80

Asp Gln Gln Thr Ala Asn Ala Leu Leu Asp Lys Lys Gln Gln Glu Tyr
                85                  90                  95

Gln Ser Ile Arg Trp Ile Gly Leu Ile Gln Arg Lys Glu Thr Gly Asp
            100                 105                 110

Phe Thr Phe Asn Leu Ser Lys Asp Glu Gln Ala Ile Ile Glu Ile Asp
        115                 120                 125

Gly Lys Ile Ile Ser Asn Lys Gly Lys Glu Lys Gln Val Val His Leu
    130                 135                 140

Glu Lys Glu Lys Leu Val Pro Ile Lys Ile Glu Tyr Gln Ser Asp Thr
145                 150                 155                 160

Lys Phe Asn Ile Asp Ser Lys Thr Phe Lys Glu Leu Lys Leu Phe Lys
                165                 170                 175

Ile Asp Ser Gln Asn Gln Ser Gln Gln Val Gln Leu Arg Asn Pro Glu
            180                 185                 190

Phe Asn Lys Lys Glu Ser Gln Glu Phe Leu Ala Lys Ala Ser Lys Thr
        195                 200                 205

Asn Leu Phe Lys Gln Lys Met Lys Arg Asp Ile Asp Glu Asp Thr Asp
    210                 215                 220

Thr Asp Gly Asp Ser Ile Pro Asp Leu Trp Glu Glu Asn Gly Tyr Thr

-continued

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |

Ile Gln Asn Lys Val Ala Val Lys Trp Asp Ser Leu Ala Ser Lys
              245                 250                 255

Gly Tyr Thr Lys Phe Val Ser Asn Pro Leu Asp Ser His Thr Val Gly
              260                 265                 270

Asp Pro Tyr Thr Asp Tyr Glu Lys Ala Ala Arg Asp Leu Asp Leu Ser
              275                 280                 285

Asn Ala Lys Glu Thr Phe Asn Pro Leu Val Ala Ala Phe Pro Ser Val
    290                 295                 300

Asn Val Ser Met Glu Lys Val Ile Leu Ser Pro Asn Glu Asn Leu Ser
305                 310                 315                 320

Asn Ser Val Glu Ser His Ser Ser Thr Asn Trp Ser Tyr Thr Asn Thr
              325                 330                 335

Glu Gly Ala Ser Ile Glu Ala Gly Gly Pro Leu Gly Leu Ser Phe
              340                 345                 350

Gly Val Ser Val Thr Tyr Gln His Ser Glu Thr Val Ala Gln Glu Trp
          355                 360                 365

Gly Thr Ser Thr Gly Asn Thr Ser Gln Phe Asn Thr Ala Ser Ala Gly
    370                 375                 380

Tyr Leu Asn Ala Asn Val Arg Tyr Asn Asn Val Gly Thr Gly Ala Ile
385                 390                 395                 400

Tyr Asp Val Lys Pro Thr Thr Ser Phe Val Leu Asn Asn Asn Thr Ile
              405                 410                 415

Ala Thr Ile Thr Ala Lys Ser Asn Ser Thr Ala Leu Arg Ile Ser Pro
              420                 425                 430

Gly Asp Ser Tyr Pro Glu Ile Gly Glu Asn Ala Ile Ala Ile Thr Ser
          435                 440                 445

Met Asp Asp Phe Asn Ser His Pro Ile Thr Leu Asn Lys Gln Gln Val
    450                 455                 460

Asn Gln Leu Ile Asn Asn Lys Pro Ile Met Leu Glu Thr Asp Gln Thr
465                 470                 475                 480

Asp Gly Val Tyr Lys Ile Arg Asp Thr His Gly Asn Ile Val Thr Gly
              485                 490                 495

Gly Glu Trp Asn Gly Val Thr Gln Gln Ile Lys Ala Lys Thr Ala Ser
          500                 505                 510

Ile Ile Val Asp Asp Gly Lys Gln Val Ala Glu Lys Arg Val Ala Ala
          515                 520                 525

Lys Asp Tyr Gly His Pro Glu Asp Lys Thr Pro Pro Leu Thr Leu Lys
    530                 535                 540

Asp Thr Leu Lys Leu Ser Tyr Pro Asp Glu Ile Lys Glu Thr Asn Gly
545                 550                 555                 560

Leu Leu Tyr Tyr Asp Asp Lys Pro Ile Tyr Glu Ser Ser Val Met Thr
              565                 570                 575

Tyr Leu Asp Glu Asn Thr Ala Lys Glu Val Lys Lys Gln Ile Asn Asp
          580                 585                 590

Thr Thr Gly Lys Phe Lys Asp Val Asn His Leu Tyr Asp Val Lys Leu
          595                 600                 605

Thr Pro Lys Met Asn Phe Thr Ile Lys Met Ala Ser Leu Tyr Asp Gly
    610                 615                 620

Ala Glu Asn Asn His Asn Ser Leu Gly Thr Trp Tyr Leu Thr Tyr Asn
625                 630                 635                 640

Val Ala Gly Gly Asn Thr Gly Lys Arg Gln Tyr Arg Ser Ala His Ser
              645                 650                 655

| Cys | Ala | His | Val | Ala | Leu | Ser | Ser | Glu | Ala | Lys | Lys | Lys | Leu | Asn | Gln |
|---|---|---|---|---|---|---|---|---|---|---|---|---|---|---|---|
| | | | 660 | | | | 665 | | | | | | 670 | | |

| Asn | Ala | Asn | Tyr | Tyr | Leu | Ser | Met | Tyr | Met | Lys | Ala | Asp | Ser | Thr | Thr |
|---|---|---|---|---|---|---|---|---|---|---|---|---|---|---|---|
| | | 675 | | | | | 680 | | | | | 685 | | | |

| Glu | Pro | Thr | Ile | Glu | Val | Ala | Gly | Glu | Lys | Ser | Ala | Ile | Thr | Ser | Lys |
|---|---|---|---|---|---|---|---|---|---|---|---|---|---|---|---|
| | 690 | | | | | 695 | | | | | 700 | | | | |

| Lys | Val | Lys | Leu | Asn | Asn | Gln | Asn | Tyr | Gln | Arg | Val | Asp | Ile | Leu | Val |
|---|---|---|---|---|---|---|---|---|---|---|---|---|---|---|---|
| 705 | | | | | 710 | | | | | 715 | | | | | 720 |

| Lys | Asn | Ser | Glu | Arg | Asn | Pro | Met | Asp | Lys | Ile | Tyr | Ile | Arg | Gly | Asn |
|---|---|---|---|---|---|---|---|---|---|---|---|---|---|---|---|
| | | | | 725 | | | | | 730 | | | | | 735 | |

| Gly | Thr | Thr | Asn | Val | Tyr | Gly | Asp | Asp | Val | Thr | Ile | Pro | Glu | Val | Ser |
|---|---|---|---|---|---|---|---|---|---|---|---|---|---|---|---|
| | | | 740 | | | | | 745 | | | | | 750 | | |

| Ala | Ile | Asn | Pro | Ala | Ser | Leu | Ser | Asp | Glu | Glu | Ile | Gln | Glu | Ile | Phe |
|---|---|---|---|---|---|---|---|---|---|---|---|---|---|---|---|
| | | 755 | | | | | 760 | | | | | 765 | | | |

| Lys | Asp | Ser | Thr | Ile | Glu | Tyr | Gly | Asn | Pro | Ser | Phe | Val | Ala | Asp | Ala |
|---|---|---|---|---|---|---|---|---|---|---|---|---|---|---|---|
| | 770 | | | | | 775 | | | | | 780 | | | | |

| Val | Thr | Phe | Lys | Asn | Ile | Lys | Pro | Leu | Gln | Asn | Tyr | Val | Lys | Glu | Tyr |
|---|---|---|---|---|---|---|---|---|---|---|---|---|---|---|---|
| 785 | | | | | 790 | | | | | 795 | | | | | 800 |

| Glu | Ile | Tyr | His | Lys | Ser | His | Arg | Tyr | Glu | Lys | Lys | Thr | Val | Phe | Asp |
|---|---|---|---|---|---|---|---|---|---|---|---|---|---|---|---|
| | | | | 805 | | | | | 810 | | | | | 815 | |

| Ile | Met | Gly | Val | His | Tyr | Glu | Tyr | Ser | Ile | Ala | Arg | Glu | Gln | Lys | Lys |
|---|---|---|---|---|---|---|---|---|---|---|---|---|---|---|---|
| | | | 820 | | | | | 825 | | | | | 830 | | |

| Ala | Ala |
|---|---|

( 2 ) INFORMATION FOR SEQ ID NO:22:

( i ) SEQUENCE CHARACTERISTICS:
        ( A ) LENGTH: 4041 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..4038
        ( D ) OTHER INFORMATION: /product="VIP1A(a)/VIP2A(a) fusion
            product"

( x i ) SEQUENCE DESCRIPTION: SEQ ID NO:22:

| ATG | AAA | AGA | ATG | GAG | GGA | AAG | TTG | TTT | ATG | GTG | TCA | AAA | AAA | TTA | CAA | 48 |
|---|---|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln | |
| 835 | | | | 840 | | | | | 845 | | | | | 850 | | |

| GTA | GTT | ACT | AAA | ACT | GTA | TTG | CTT | AGT | ACA | GTT | TTC | TCT | ATA | TCT | TTA | 96 |
|---|---|---|---|---|---|---|---|---|---|---|---|---|---|---|---|---|
| Val | Val | Thr | Lys | Thr | Val | Leu | Leu | Ser | Thr | Val | Phe | Ser | Ile | Ser | Leu | |
| | | | | 855 | | | | | 860 | | | | | 865 | | |

| TTA | AAT | AAT | GAA | GTG | ATA | AAA | GCT | GAA | CAA | TTA | AAT | ATA | AAT | TCT | CAA | 144 |
|---|---|---|---|---|---|---|---|---|---|---|---|---|---|---|---|---|
| Leu | Asn | Asn | Glu | Val | Ile | Lys | Ala | Glu | Gln | Leu | Asn | Ile | Asn | Ser | Gln | |
| | | | 870 | | | | | 875 | | | | | 880 | | | |

| AGT | AAA | TAT | ACT | AAC | TTG | CAA | AAT | CTA | AAA | ATC | ACT | GAC | AAG | GTA | GAG | 192 |
|---|---|---|---|---|---|---|---|---|---|---|---|---|---|---|---|---|
| Ser | Lys | Tyr | Thr | Asn | Leu | Gln | Asn | Leu | Lys | Ile | Thr | Asp | Lys | Val | Glu | |
| | | 885 | | | | | 890 | | | | | 895 | | | | |

| GAT | TTT | AAA | GAA | GAT | AAG | GAA | AAA | GCG | AAA | GAA | TGG | GGG | AAA | GAA | AAA | 240 |
|---|---|---|---|---|---|---|---|---|---|---|---|---|---|---|---|---|
| Asp | Phe | Lys | Glu | Asp | Lys | Glu | Lys | Ala | Lys | Glu | Trp | Gly | Lys | Glu | Lys | |
| | 900 | | | | | 905 | | | | | 910 | | | | | |

| GAA | AAA | GAG | TGG | AAA | CTA | ACT | GCT | ACT | GAA | AAA | GGA | AAA | ATG | AAT | AAT | 288 |
|---|---|---|---|---|---|---|---|---|---|---|---|---|---|---|---|---|
| Glu | Lys | Glu | Trp | Lys | Leu | Thr | Ala | Thr | Glu | Lys | Gly | Lys | Met | Asn | Asn | |
| 915 | | | | | 920 | | | | | 925 | | | | | 930 | |

| TTT | TTA | GAT | AAT | AAA | AAT | GAT | ATA | AAG | ACA | AAT | TAT | AAA | GAA | ATT | ACT | 336 |
|---|---|---|---|---|---|---|---|---|---|---|---|---|---|---|---|---|
| Phe | Leu | Asp | Asn | Lys | Asn | Asp | Ile | Lys | Thr | Asn | Tyr | Lys | Glu | Ile | Thr | |

```
                              935                       940                       945
TTT  TCT  ATG  GCA  GGC  TCA  TTT  GAA  GAT  GAA  ATA  AAA  GAT  TTA  AAA  GAA      384
Phe  Ser  Met  Ala  Gly  Ser  Phe  Glu  Asp  Glu  Ile  Lys  Asp  Leu  Lys  Glu
          950                      955                      960

ATT  GAT  AAG  ATG  TTT  GAT  AAA  ACC  AAT  CTA  TCA  AAT  TCT  ATT  ATC  ACC      432
Ile  Asp  Lys  Met  Phe  Asp  Lys  Thr  Asn  Leu  Ser  Asn  Ser  Ile  Ile  Thr
          965                      970                      975

TAT  AAA  AAT  GTG  GAA  CCG  ACA  ACA  ATT  GGA  TTT  AAT  AAA  TCT  TTA  ACA      480
Tyr  Lys  Asn  Val  Glu  Pro  Thr  Thr  Ile  Gly  Phe  Asn  Lys  Ser  Leu  Thr
          980                      985                      990

GAA  GGT  AAT  ACG  ATT  AAT  TCT  GAT  GCA  ATG  GCA  CAG  TTT  AAA  GAA  CAA      528
Glu  Gly  Asn  Thr  Ile  Asn  Ser  Asp  Ala  Met  Ala  Gln  Phe  Lys  Glu  Gln
995            1000                    1005                    1010

TTT  TTA  GAT  AGG  GAT  ATT  AAG  TTT  GAT  AGT  TAT  CTA  GAT  ACG  CAT  TTA      576
Phe  Leu  Asp  Arg  Asp  Ile  Lys  Phe  Asp  Ser  Tyr  Leu  Asp  Thr  His  Leu
               1015                     1020                    1025

ACT  GCT  CAA  CAA  GTT  TCC  AGT  AAA  GAA  AGA  GTT  ATT  TTG  AAG  GTT  ACG      624
Thr  Ala  Gln  Gln  Val  Ser  Ser  Lys  Glu  Arg  Val  Ile  Leu  Lys  Val  Thr
               1030                     1035                    1040

GTT  CCG  AGT  GGG  AAA  GGT  TCT  ACT  ACT  CCA  ACA  AAA  GCA  GGT  GTC  ATT      672
Val  Pro  Ser  Gly  Lys  Gly  Ser  Thr  Thr  Pro  Thr  Lys  Ala  Gly  Val  Ile
               1045                     1050                    1055

TTA  AAT  AAT  AGT  GAA  TAC  AAA  ATG  CTC  ATT  GAT  AAT  GGG  TAT  ATG  GTC      720
Leu  Asn  Asn  Ser  Glu  Tyr  Lys  Met  Leu  Ile  Asp  Asn  Gly  Tyr  Met  Val
               1060                     1065                    1070

CAT  GTA  GAT  AAG  GTA  TCA  AAA  GTG  GTG  AAA  AAA  GGG  GTG  GAG  TGC  TTA      768
His  Val  Asp  Lys  Val  Ser  Lys  Val  Val  Lys  Lys  Gly  Val  Glu  Cys  Leu
1075                     1080                    1085                    1090

CAA  ATT  GAA  GGG  ACT  TTA  AAA  AAG  AGT  CTT  GAC  TTT  AAA  AAT  GAT  ATA      816
Gln  Ile  Glu  Gly  Thr  Leu  Lys  Lys  Ser  Leu  Asp  Phe  Lys  Asn  Asp  Ile
               1095                     1100                    1105

AAT  GCT  GAA  GCG  CAT  AGC  TGG  GGT  ATG  AAG  AAT  TAT  GAA  GAG  TGG  GCT      864
Asn  Ala  Glu  Ala  His  Ser  Trp  Gly  Met  Lys  Asn  Tyr  Glu  Glu  Trp  Ala
               1110                     1115                    1120

AAA  GAT  TTA  ACC  GAT  TCG  CAA  AGG  GAA  GCT  TTA  GAT  GGG  TAT  GCT  AGG      912
Lys  Asp  Leu  Thr  Asp  Ser  Gln  Arg  Glu  Ala  Leu  Asp  Gly  Tyr  Ala  Arg
               1125                     1130                    1135

CAA  GAT  TAT  AAA  GAA  ATC  AAT  AAT  TAT  TTA  AGA  AAT  CAA  GGC  GGA  AGT      960
Gln  Asp  Tyr  Lys  Glu  Ile  Asn  Asn  Tyr  Leu  Arg  Asn  Gln  Gly  Gly  Ser
               1140                     1145                    1150

GGA  AAT  GAA  AAA  CTA  GAT  GCT  CAA  ATA  AAA  AAT  ATT  TCT  GAT  GCT  TTA     1008
Gly  Asn  Glu  Lys  Leu  Asp  Ala  Gln  Ile  Lys  Asn  Ile  Ser  Asp  Ala  Leu
1155                     1160                    1165                    1170

GGG  AAG  AAA  CCA  ATA  CCG  GAA  AAT  ATT  ACT  GTG  TAT  AGA  TGG  TGT  GGC     1056
Gly  Lys  Lys  Pro  Ile  Pro  Glu  Asn  Ile  Thr  Val  Tyr  Arg  Trp  Cys  Gly
               1175                     1180                    1185

ATG  CCG  GAA  TTT  GGT  TAT  CAA  ATT  AGT  GAT  CCG  TTA  CCT  TCT  TTA  AAA     1104
Met  Pro  Glu  Phe  Gly  Tyr  Gln  Ile  Ser  Asp  Pro  Leu  Pro  Ser  Leu  Lys
               1190                     1195                    1200

GAT  TTT  GAA  GAA  CAA  TTT  TTA  AAT  ACA  ATC  AAA  GAA  GAC  AAA  GGA  TAT     1152
Asp  Phe  Glu  Glu  Gln  Phe  Leu  Asn  Thr  Ile  Lys  Glu  Asp  Lys  Gly  Tyr
               1205                     1210                    1215

ATG  AGT  ACA  AGC  TTA  TCG  AGT  GAA  CGT  CTT  GCA  GCT  TTT  GGA  TCT  AGA     1200
Met  Ser  Thr  Ser  Leu  Ser  Ser  Glu  Arg  Leu  Ala  Ala  Phe  Gly  Ser  Arg
               1220                     1225                    1230

AAA  ATT  ATA  TTA  CGA  TTA  CAA  GTT  CCG  AAA  GGA  AGT  ACG  GGT  GCG  TAT     1248
Lys  Ile  Ile  Leu  Arg  Leu  Gln  Val  Pro  Lys  Gly  Ser  Thr  Gly  Ala  Tyr
1235                     1240                    1245                    1250

TTA  AGT  GCC  ATT  GGT  GGA  TTT  GCA  AGT  GAA  AAA  GAG  ATC  CTA  CTT  GAT     1296
Leu  Ser  Ala  Ile  Gly  Gly  Phe  Ala  Ser  Glu  Lys  Glu  Ile  Leu  Leu  Asp
```

```
                    1255                           1260                           1265
AAA  GAT  AGT  AAA  TAT  CAT  ATT  GAT  AAA  GTA  ACA  GAG  GTA  ATT  ATT  AAA        1344
Lys  Asp  Ser  Lys  Tyr  His  Ile  Asp  Lys  Val  Thr  Glu  Val  Ile  Ile  Lys
               1270               1275                         1280

GGT  GTT  AAG  CGA  TAT  GTA  GTG  GAT  GCA  ACA  TTA  TTA  ACA  AAT  ATG  AAA        1392
Gly  Val  Lys  Arg  Tyr  Val  Val  Asp  Ala  Thr  Leu  Leu  Thr  Asn  Met  Lys
               1285                    1290                    1295

AAT  ATG  AAG  AAA  AAG  TTA  GCA  AGT  GTT  GTA  ACG  TGT  ACG  TTA  TTA  GCT        1440
Asn  Met  Lys  Lys  Lys  Leu  Ala  Ser  Val  Val  Thr  Cys  Thr  Leu  Leu  Ala
     1300                    1305                         1310

CCT  ATG  TTT  TTG  AAT  GGA  AAT  GTG  AAT  GCT  GTT  TAC  GCA  GAC  AGC  AAA        1488
Pro  Met  Phe  Leu  Asn  Gly  Asn  Val  Asn  Ala  Val  Tyr  Ala  Asp  Ser  Lys
1315               1320                         1325                    1330

ACA  AAT  CAA  ATT  TCT  ACA  ACA  CAG  AAA  AAT  CAA  CAG  AAA  GAG  ATG  GAC        1536
Thr  Asn  Gln  Ile  Ser  Thr  Thr  Gln  Lys  Asn  Gln  Gln  Lys  Glu  Met  Asp
                         1335                    1340                    1345

CGA  AAA  GGA  TTA  CTT  GGG  TAT  TAT  TTC  AAA  GGA  AAA  GAT  TTT  AGT  AAT        1584
Arg  Lys  Gly  Leu  Leu  Gly  Tyr  Tyr  Phe  Lys  Gly  Lys  Asp  Phe  Ser  Asn
               1350                         1355                    1360

CTT  ACT  ATG  TTT  GCA  CCG  ACA  CGT  GAT  AGT  ACT  CTT  ATT  TAT  GAT  CAA        1632
Leu  Thr  Met  Phe  Ala  Pro  Thr  Arg  Asp  Ser  Thr  Leu  Ile  Tyr  Asp  Gln
          1365                         1370                    1375

CAA  ACA  GCA  AAT  AAA  CTA  TTA  GAT  AAA  AAA  CAA  CAA  GAA  TAT  CAG  TCT        1680
Gln  Thr  Ala  Asn  Lys  Leu  Leu  Asp  Lys  Lys  Gln  Gln  Glu  Tyr  Gln  Ser
     1380                    1385                         1390

ATT  CGT  TGG  ATT  GGT  TTG  ATT  CAG  AGT  AAA  GAA  ACG  GGA  GAT  TTC  ACA        1728
Ile  Arg  Trp  Ile  Gly  Leu  Ile  Gln  Ser  Lys  Glu  Thr  Gly  Asp  Phe  Thr
1395                    1400                         1405                    1410

TTT  AAC  TTA  TCT  GAG  GAT  GAA  CAG  GCA  ATT  ATA  GAA  ATC  AAT  GGG  AAA        1776
Phe  Asn  Leu  Ser  Glu  Asp  Glu  Gln  Ala  Ile  Ile  Glu  Ile  Asn  Gly  Lys
                         1415                    1420                    1425

ATT  ATT  TCT  AAT  AAA  GGG  AAA  GAA  AAG  CAA  GTT  GTC  CAT  TTA  GAA  AAA        1824
Ile  Ile  Ser  Asn  Lys  Gly  Lys  Glu  Lys  Gln  Val  Val  His  Leu  Glu  Lys
               1430                         1435                    1440

GGA  AAA  TTA  GTT  CCA  ATC  AAA  ATA  GAG  TAT  CAA  TCA  GAT  ACA  AAA  TTT        1872
Gly  Lys  Leu  Val  Pro  Ile  Lys  Ile  Glu  Tyr  Gln  Ser  Asp  Thr  Lys  Phe
          1445                         1450                    1455

AAT  ATT  GAC  AGT  AAA  ACA  TTT  AAA  GAA  CTT  AAA  TTA  TTT  AAA  ATA  GAT        1920
Asn  Ile  Asp  Ser  Lys  Thr  Phe  Lys  Glu  Leu  Lys  Leu  Phe  Lys  Ile  Asp
1460                    1465                         1470

AGT  CAA  AAC  CAA  CCC  CAG  CAA  GTC  CAG  CAA  GAT  GAA  CTG  AGA  AAT  CCT        1968
Ser  Gln  Asn  Gln  Pro  Gln  Gln  Val  Gln  Gln  Asp  Glu  Leu  Arg  Asn  Pro
1475                    1480                         1485                    1490

GAA  TTT  AAC  AAG  AAA  GAA  TCA  CAG  GAA  TTC  TTA  GCG  AAA  CCA  TCG  AAA        2016
Glu  Phe  Asn  Lys  Lys  Glu  Ser  Gln  Glu  Phe  Leu  Ala  Lys  Pro  Ser  Lys
                    1495                         1500                    1505

ATA  AAT  CTT  TTC  ACT  CAA  AAA  ATG  AAA  AGG  GAA  ATT  GAT  GAA  GAC  ACG        2064
Ile  Asn  Leu  Phe  Thr  Gln  Lys  Met  Lys  Arg  Glu  Ile  Asp  Glu  Asp  Thr
               1510                         1515                    1520

GAT  ACG  GAT  GGG  GAC  TCT  ATT  CCT  GAC  CTT  TGG  GAA  GAA  AAT  GGG  TAT        2112
Asp  Thr  Asp  Gly  Asp  Ser  Ile  Pro  Asp  Leu  Trp  Glu  Glu  Asn  Gly  Tyr
          1525                         1530                    1535

ACG  ATT  CAA  AAT  AGA  ATC  GCT  GTA  AAG  TGG  GAC  GAT  TCT  CTA  GCA  AGT        2160
Thr  Ile  Gln  Asn  Arg  Ile  Ala  Val  Lys  Trp  Asp  Asp  Ser  Leu  Ala  Ser
1540                    1545                         1550

AAA  GGG  TAT  ACG  AAA  TTT  GTT  TCA  AAT  CCA  CTA  GAA  AGT  CAC  ACA  GTT        2208
Lys  Gly  Tyr  Thr  Lys  Phe  Val  Ser  Asn  Pro  Leu  Glu  Ser  His  Thr  Val
1555                    1560                         1565                    1570

GGT  GAT  CCT  TAT  ACA  GAT  TAT  GAA  AAG  GCA  GCA  AGA  GAT  CTA  GAT  TTG        2256
Gly  Asp  Pro  Tyr  Thr  Asp  Tyr  Glu  Lys  Ala  Ala  Arg  Asp  Leu  Asp  Leu
```

-continued

|  |  |  | 1575 |  |  |  |  | 1580 |  |  |  |  | 1585 |  |  |  |
|---|---|---|---|---|---|---|---|---|---|---|---|---|---|---|---|---|
| TCA | AAT | GCA | AAG | GAA | ACG | TTT | AAC | CCA | TTG | GTA | GCT | GCT | TTT | CCA | AGT | 2304 |
| Ser | Asn | Ala | Lys | Glu | Thr | Phe | Asn | Pro | Leu | Val | Ala | Ala | Phe | Pro | Ser |  |
|  |  |  | 1590 |  |  |  |  | 1595 |  |  |  |  | 1600 |  |  |  |
| GTG | AAT | GTT | AGT | ATG | GAA | AAG | GTG | ATA | TTA | TCA | CCA | AAT | GAA | AAT | TTA | 2352 |
| Val | Asn | Val | Ser | Met | Glu | Lys | Val | Ile | Leu | Ser | Pro | Asn | Glu | Asn | Leu |  |
|  |  |  | 1605 |  |  |  |  | 1610 |  |  |  |  | 1615 |  |  |  |
| TCC | AAT | AGT | GTA | GAG | TCT | CAT | TCA | TCC | ACG | AAT | TGG | TCT | TAT | ACA | AAT | 2400 |
| Ser | Asn | Ser | Val | Glu | Ser | His | Ser | Ser | Thr | Asn | Trp | Ser | Tyr | Thr | Asn |  |
|  |  |  | 1620 |  |  |  |  | 1625 |  |  |  |  | 1630 |  |  |  |
| ACA | GAA | GGT | GCT | TCT | GTT | GAA | GCG | GGG | ATT | GGA | CCA | AAA | GGT | ATT | TCG | 2448 |
| Thr | Glu | Gly | Ala | Ser | Val | Glu | Ala | Gly | Ile | Gly | Pro | Lys | Gly | Ile | Ser |  |
|  |  |  | 1635 |  |  |  |  | 1640 |  |  |  |  | 1645 |  |  | 1650 |
| TTC | GGA | GTT | AGC | GTA | AAC | TAT | CAA | CAC | TCT | GAA | ACA | GTT | GCA | CAA | GAA | 2496 |
| Phe | Gly | Val | Ser | Val | Asn | Tyr | Gln | His | Ser | Glu | Thr | Val | Ala | Gln | Glu |  |
|  |  |  |  |  | 1655 |  |  |  |  | 1660 |  |  |  |  | 1665 |  |
| TGG | GGA | ACA | TCT | ACA | GGA | AAT | ACT | TCG | CAA | TTC | AAT | ACG | GCT | TCA | GCG | 2544 |
| Trp | Gly | Thr | Ser | Thr | Gly | Asn | Thr | Ser | Gln | Phe | Asn | Thr | Ala | Ser | Ala |  |
|  |  |  | 1670 |  |  |  |  | 1675 |  |  |  |  | 1680 |  |  |  |
| GGA | TAT | TTA | AAT | GCA | AAT | GTT | CGA | TAT | AAC | AAT | GTA | GGA | ACT | GGT | GCC | 2592 |
| Gly | Tyr | Leu | Asn | Ala | Asn | Val | Arg | Tyr | Asn | Asn | Val | Gly | Thr | Gly | Ala |  |
|  |  |  | 1685 |  |  |  |  | 1690 |  |  |  |  | 1695 |  |  |  |
| ATC | TAC | GAT | GTA | AAA | CCT | ACA | ACA | AGT | TTT | GTA | TTA | AAT | AAC | GAT | ACT | 2640 |
| Ile | Tyr | Asp | Val | Lys | Pro | Thr | Thr | Ser | Phe | Val | Leu | Asn | Asn | Asp | Thr |  |
|  |  |  | 1700 |  |  |  |  | 1705 |  |  |  |  | 1710 |  |  |  |
| ATC | GCA | ACT | ATT | ACG | GCG | AAA | TCT | AAT | TCT | ACA | GCC | TTA | AAT | ATA | TCT | 2688 |
| Ile | Ala | Thr | Ile | Thr | Ala | Lys | Ser | Asn | Ser | Thr | Ala | Leu | Asn | Ile | Ser |  |
| 1715 |  |  |  |  | 1720 |  |  |  |  | 1725 |  |  |  |  | 1730 |  |
| CCT | GGA | GAA | AGT | TAC | CCG | AAA | AAA | GGA | CAA | AAT | GGA | ATC | GCA | ATA | ACA | 2736 |
| Pro | Gly | Glu | Ser | Tyr | Pro | Lys | Lys | Gly | Gln | Asn | Gly | Ile | Ala | Ile | Thr |  |
|  |  |  |  |  | 1735 |  |  |  |  | 1740 |  |  |  |  | 1745 |  |
| TCA | ATG | GAT | GAT | TTT | AAT | TCC | CAT | CCG | ATT | ACA | TTA | AAT | AAA | AAA | CAA | 2784 |
| Ser | Met | Asp | Asp | Phe | Asn | Ser | His | Pro | Ile | Thr | Leu | Asn | Lys | Lys | Gln |  |
|  |  |  | 1750 |  |  |  |  | 1755 |  |  |  |  | 1760 |  |  |  |
| GTA | GAT | AAT | CTG | CTA | AAT | AAT | AAA | CCT | ATG | ATG | TTG | GAA | ACA | AAC | CAA | 2832 |
| Val | Asp | Asn | Leu | Leu | Asn | Asn | Lys | Pro | Met | Met | Leu | Glu | Thr | Asn | Gln |  |
|  |  |  | 1765 |  |  |  |  | 1770 |  |  |  |  | 1775 |  |  |  |
| ACA | GAT | GGT | GTT | TAT | AAG | ATA | AAA | GAT | ACA | CAT | GGA | AAT | ATA | GTA | ACT | 2880 |
| Thr | Asp | Gly | Val | Tyr | Lys | Ile | Lys | Asp | Thr | His | Gly | Asn | Ile | Val | Thr |  |
|  |  |  | 1780 |  |  |  |  | 1785 |  |  |  |  | 1790 |  |  |  |
| GGC | GGA | GAA | TGG | AAT | GGT | GTC | ATA | CAA | CAA | ATC | AAG | GCT | AAA | ACA | GCG | 2928 |
| Gly | Gly | Glu | Trp | Asn | Gly | Val | Ile | Gln | Gln | Ile | Lys | Ala | Lys | Thr | Ala |  |
| 1795 |  |  |  |  | 1800 |  |  |  |  | 1805 |  |  |  |  | 1810 |  |
| TCT | ATT | ATT | GTG | GAT | GAT | GGG | GAA | CGT | GTA | GCA | GAA | AAA | CGT | GTA | GCG | 2976 |
| Ser | Ile | Ile | Val | Asp | Asp | Gly | Glu | Arg | Val | Ala | Glu | Lys | Arg | Val | Ala |  |
|  |  |  |  |  | 1815 |  |  |  |  | 1820 |  |  |  |  | 1825 |  |
| GCA | AAA | GAT | TAT | GAA | AAT | CCA | GAA | GAT | AAA | ACA | CCG | TCT | TTA | ACT | TTA | 3024 |
| Ala | Lys | Asp | Tyr | Glu | Asn | Pro | Glu | Asp | Lys | Thr | Pro | Ser | Leu | Thr | Leu |  |
|  |  |  | 1830 |  |  |  |  | 1835 |  |  |  |  | 1840 |  |  |  |
| AAA | GAT | GCC | CTG | AAG | CTT | TCA | TAT | CCA | GAT | GAA | ATA | AAA | GAA | ATA | GAG | 3072 |
| Lys | Asp | Ala | Leu | Lys | Leu | Ser | Tyr | Pro | Asp | Glu | Ile | Lys | Glu | Ile | Glu |  |
|  |  |  | 1845 |  |  |  |  | 1850 |  |  |  |  | 1855 |  |  |  |
| GGA | TTA | TTA | TAT | TAT | AAA | AAC | AAA | CCG | ATA | TAC | GAA | TCG | AGC | GTT | ATG | 3120 |
| Gly | Leu | Leu | Tyr | Tyr | Lys | Asn | Lys | Pro | Ile | Tyr | Glu | Ser | Ser | Val | Met |  |
| 1860 |  |  |  |  | 1865 |  |  |  |  | 1870 |  |  |  |  |  |  |
| ACT | TAC | TTA | GAT | GAA | AAT | ACA | GCA | AAA | GAA | GTG | ACC | AAA | CAA | TTA | AAT | 3168 |
| Thr | Tyr | Leu | Asp | Glu | Asn | Thr | Ala | Lys | Glu | Val | Thr | Lys | Gln | Leu | Asn |  |
| 1875 |  |  |  |  | 1880 |  |  |  |  | 1885 |  |  |  |  | 1890 |  |
| GAT | ACC | ACT | GGG | AAA | TTT | AAA | GAT | GTA | AGT | CAT | TTA | TAT | GAT | GTA | AAA | 3216 |
| Asp | Thr | Thr | Gly | Lys | Phe | Lys | Asp | Val | Ser | His | Leu | Tyr | Asp | Val | Lys |  |

```
                      1 8 9 5                           1 9 0 0                           1 9 0 5
CTG  ACT  CCA  AAA  ATG  AAT  GTT  ACA  ATC  AAA  TTG  TCT  ATA  CTT  TAT  GAT        3264
Leu  Thr  Pro  Lys  Met  Asn  Val  Thr  Ile  Lys  Leu  Ser  Ile  Leu  Tyr  Asp
               1 9 1 0                    1 9 1 5                    1 9 2 0

AAT  GCT  GAG  TCT  AAT  GAT  AAC  TCA  ATT  GGT  AAA  TGG  ACA  AAC  ACA  AAT        3312
Asn  Ala  Glu  Ser  Asn  Asp  Asn  Ser  Ile  Gly  Lys  Trp  Thr  Asn  Thr  Asn
               1 9 2 5                    1 9 3 0                    1 9 3 5

ATT  GTT  TCA  GGT  GGA  AAT  AAC  GGA  AAA  AAA  CAA  TAT  TCT  TCT  AAT  AAT        3360
Ile  Val  Ser  Gly  Gly  Asn  Asn  Gly  Lys  Lys  Gln  Tyr  Ser  Ser  Asn  Asn
               1 9 4 0                    1 9 4 5                    1 9 5 0

CCG  GAT  GCT  AAT  TTG  ACA  TTA  AAT  ACA  GAT  GCT  CAA  GAA  AAA  TTA  AAT        3408
Pro  Asp  Ala  Asn  Leu  Thr  Leu  Asn  Thr  Asp  Ala  Gln  Glu  Lys  Leu  Asn
1 9 5 5                    1 9 6 0                    1 9 6 5                    1 9 7 0

AAA  AAT  CGT  GAC  TAT  TAT  ATA  AGT  TTA  TAT  ATG  AAG  TCA  GAA  AAA  AAC        3456
Lys  Asn  Arg  Asp  Tyr  Tyr  Ile  Ser  Leu  Tyr  Met  Lys  Ser  Glu  Lys  Asn
                    1 9 7 5                    1 9 8 0                    1 9 8 5

ACA  CAA  TGT  GAG  ATT  ACT  ATA  GAT  GGG  GAG  ATT  TAT  CCG  ATC  ACT  ACA        3504
Thr  Gln  Cys  Glu  Ile  Thr  Ile  Asp  Gly  Glu  Ile  Tyr  Pro  Ile  Thr  Thr
               1 9 9 0                    1 9 9 5                    2 0 0 0

AAA  ACA  GTG  AAT  GTG  AAT  AAA  GAC  AAT  TAC  AAA  AGA  TTA  GAT  ATT  ATA        3552
Lys  Thr  Val  Asn  Val  Asn  Lys  Asp  Asn  Tyr  Lys  Arg  Leu  Asp  Ile  Ile
               2 0 0 5                    2 0 1 0                    2 0 1 5

GCT  CAT  AAT  ATA  AAA  AGT  AAT  CCA  ATT  TCT  TCA  CTT  CAT  ATT  AAA  ACG        3600
Ala  His  Asn  Ile  Lys  Ser  Asn  Pro  Ile  Ser  Ser  Leu  His  Ile  Lys  Thr
               2 0 2 0                    2 0 2 5                    2 0 3 0

AAT  GAT  GAA  ATA  ACT  TTA  TTT  TGG  GAT  GAT  ATT  TCT  ATA  ACA  GAT  GTA        3648
Asn  Asp  Glu  Ile  Thr  Leu  Phe  Trp  Asp  Asp  Ile  Ser  Ile  Thr  Asp  Val
2 0 3 5                    2 0 4 0                    2 0 4 5                    2 0 5 0

GCA  TCA  ATA  AAA  CCG  GAA  AAT  TTA  ACA  GAT  TCA  GAA  ATT  AAA  CAG  ATT        3696
Ala  Ser  Ile  Lys  Pro  Glu  Asn  Leu  Thr  Asp  Ser  Glu  Ile  Lys  Gln  Ile
                    2 0 5 5                    2 0 6 0                    2 0 6 5

TAT  AGT  AGG  TAT  GGT  ATT  AAG  TTA  GAA  GAT  GGA  ATC  CTT  ATT  GAT  AAA        3744
Tyr  Ser  Arg  Tyr  Gly  Ile  Lys  Leu  Glu  Asp  Gly  Ile  Leu  Ile  Asp  Lys
               2 0 7 0                    2 0 7 5                    2 0 8 0

AAA  GGT  GGG  ATT  CAT  TAT  GGT  GAA  TTT  ATT  AAT  GAA  GCT  AGT  TTT  AAT        3792
Lys  Gly  Gly  Ile  His  Tyr  Gly  Glu  Phe  Ile  Asn  Glu  Ala  Ser  Phe  Asn
               2 0 8 5                    2 0 9 0                    2 0 9 5

ATT  GAA  CCA  TTG  CAA  AAT  TAT  GTG  ACC  AAA  TAT  GAA  GTT  ACT  TAT  AGT        3840
Ile  Glu  Pro  Leu  Gln  Asn  Tyr  Val  Thr  Lys  Tyr  Glu  Val  Thr  Tyr  Ser
2 1 0 0                    2 1 0 5                    2 1 1 0

AGT  GAG  TTA  GGA  CCA  AAC  GTG  AGT  GAC  ACA  CTT  GAA  AGT  GAT  AAA  ATT        3888
Ser  Glu  Leu  Gly  Pro  Asn  Val  Ser  Asp  Thr  Leu  Glu  Ser  Asp  Lys  Ile
2 1 1 5                    2 1 2 0                    2 1 2 5                    2 1 3 0

TAC  AAG  GAT  GGG  ACA  ATT  AAA  TTT  GAT  TTT  ACC  AAA  TAT  AGT  AAA  AAT        3936
Tyr  Lys  Asp  Gly  Thr  Ile  Lys  Phe  Asp  Phe  Thr  Lys  Tyr  Ser  Lys  Asn
                    2 1 3 5                    2 1 4 0                    2 1 4 5

GAA  CAA  GGA  TTA  TTT  TAT  GAC  AGT  GGA  TTA  AAT  TGG  GAC  TTT  AAA  ATT        3984
Glu  Gln  Gly  Leu  Phe  Tyr  Asp  Ser  Gly  Leu  Asn  Trp  Asp  Phe  Lys  Ile
               2 1 5 0                    2 1 5 5                    2 1 6 0

AAT  GCT  ATT  ACT  TAT  GAT  GGT  AAA  GAG  ATG  AAT  GTT  TTT  CAT  AGA  TAT        4032
Asn  Ala  Ile  Thr  Tyr  Asp  Gly  Lys  Glu  Met  Asn  Val  Phe  His  Arg  Tyr
               2 1 6 5                    2 1 7 0                    2 1 7 5

AAT  AAA  TAG                                                                          4041
Asn  Lys
     2 1 8 0
```

( 2 ) INFORMATION FOR SEQ ID NO:23:

( i ) SEQUENCE CHARACTERISTICS:
        ( A ) LENGTH: 1346 amino acids
        ( B ) TYPE: amino acid (D) TOPOLOGY: linear (ii) MOLECULE TYPE: protein (xi) SEQUENCE DESCRIPTION: SEQ ID NO:23:

| Met | Lys | Arg | Met | Glu | Gly | Lys | Leu | Phe | Met | Val | Ser | Lys | Lys | Leu | Gln |
|---|---|---|---|---|---|---|---|---|---|---|---|---|---|---|---|
| 1 | | | | 5 | | | | | 10 | | | | | 15 | |

| Val | Val | Thr | Lys | Thr | Val | Leu | Leu | Ser | Thr | Val | Phe | Ser | Ile | Ser | Leu |
|---|---|---|---|---|---|---|---|---|---|---|---|---|---|---|---|
| | | | 20 | | | | | 25 | | | | | 30 | | |

| Leu | Asn | Asn | Glu | Val | Ile | Lys | Ala | Glu | Gln | Leu | Asn | Ile | Asn | Ser | Gln |
|---|---|---|---|---|---|---|---|---|---|---|---|---|---|---|---|
| | | 35 | | | | | 40 | | | | | 45 | | | |

| Ser | Lys | Tyr | Thr | Asn | Leu | Gln | Asn | Leu | Lys | Ile | Thr | Asp | Lys | Val | Glu |
|---|---|---|---|---|---|---|---|---|---|---|---|---|---|---|---|
| | 50 | | | | | 55 | | | | | 60 | | | | |

| Asp | Phe | Lys | Glu | Asp | Lys | Glu | Lys | Ala | Lys | Glu | Trp | Gly | Lys | Glu | Lys |
|---|---|---|---|---|---|---|---|---|---|---|---|---|---|---|---|
| 65 | | | | | 70 | | | | | 75 | | | | | 80 |

| Glu | Lys | Glu | Trp | Lys | Leu | Thr | Ala | Thr | Glu | Lys | Gly | Lys | Met | Asn | Asn |
|---|---|---|---|---|---|---|---|---|---|---|---|---|---|---|---|
| | | | | 85 | | | | | 90 | | | | | 95 | |

| Phe | Leu | Asp | Asn | Lys | Asn | Asp | Ile | Lys | Thr | Asn | Tyr | Lys | Glu | Ile | Thr |
|---|---|---|---|---|---|---|---|---|---|---|---|---|---|---|---|
| | | | 100 | | | | | 105 | | | | | 110 | | |

| Phe | Ser | Met | Ala | Gly | Ser | Phe | Glu | Asp | Glu | Ile | Lys | Asp | Leu | Lys | Glu |
|---|---|---|---|---|---|---|---|---|---|---|---|---|---|---|---|
| | | | 115 | | | | | 120 | | | | | 125 | | |

| Ile | Asp | Lys | Met | Phe | Asp | Lys | Thr | Asn | Leu | Ser | Asn | Ser | Ile | Ile | Thr |
|---|---|---|---|---|---|---|---|---|---|---|---|---|---|---|---|
| | | 130 | | | | | 135 | | | | | 140 | | | |

| Tyr | Lys | Asn | Val | Glu | Pro | Thr | Thr | Ile | Gly | Phe | Asn | Lys | Ser | Leu | Thr |
|---|---|---|---|---|---|---|---|---|---|---|---|---|---|---|---|
| 145 | | | | | 150 | | | | | 155 | | | | | 160 |

| Glu | Gly | Asn | Thr | Ile | Asn | Ser | Asp | Ala | Met | Ala | Gln | Phe | Lys | Glu | Gln |
|---|---|---|---|---|---|---|---|---|---|---|---|---|---|---|---|
| | | | | 165 | | | | | 170 | | | | | 175 | |

| Phe | Leu | Asp | Arg | Asp | Ile | Lys | Phe | Asp | Ser | Tyr | Leu | Asp | Thr | His | Leu |
|---|---|---|---|---|---|---|---|---|---|---|---|---|---|---|---|
| | | | 180 | | | | | 185 | | | | | 190 | | |

| Thr | Ala | Gln | Gln | Val | Ser | Ser | Lys | Glu | Arg | Val | Ile | Leu | Lys | Val | Thr |
|---|---|---|---|---|---|---|---|---|---|---|---|---|---|---|---|
| | | | 195 | | | | | 200 | | | | | 205 | | |

| Val | Pro | Ser | Gly | Lys | Gly | Ser | Thr | Thr | Pro | Thr | Lys | Ala | Gly | Val | Ile |
|---|---|---|---|---|---|---|---|---|---|---|---|---|---|---|---|
| | 210 | | | | | 215 | | | | | 220 | | | | |

| Leu | Asn | Asn | Ser | Glu | Tyr | Lys | Met | Leu | Ile | Asp | Asn | Gly | Tyr | Met | Val |
|---|---|---|---|---|---|---|---|---|---|---|---|---|---|---|---|
| 225 | | | | | 230 | | | | | 235 | | | | | 240 |

| His | Val | Asp | Lys | Val | Ser | Lys | Val | Val | Lys | Lys | Gly | Val | Glu | Cys | Leu |
|---|---|---|---|---|---|---|---|---|---|---|---|---|---|---|---|
| | | | | 245 | | | | | 250 | | | | | 255 | |

| Gln | Ile | Glu | Gly | Thr | Leu | Lys | Lys | Ser | Leu | Asp | Phe | Lys | Asn | Asp | Ile |
|---|---|---|---|---|---|---|---|---|---|---|---|---|---|---|---|
| | | | 260 | | | | | 265 | | | | | 270 | | |

| Asn | Ala | Glu | Ala | His | Ser | Trp | Gly | Met | Lys | Asn | Tyr | Glu | Glu | Trp | Ala |
|---|---|---|---|---|---|---|---|---|---|---|---|---|---|---|---|
| | | 275 | | | | | 280 | | | | | 285 | | | |

| Lys | Asp | Leu | Thr | Asp | Ser | Gln | Arg | Glu | Ala | Leu | Asp | Gly | Tyr | Ala | Arg |
|---|---|---|---|---|---|---|---|---|---|---|---|---|---|---|---|
| | 290 | | | | | 295 | | | | | 300 | | | | |

| Gln | Asp | Tyr | Lys | Glu | Ile | Asn | Asn | Tyr | Leu | Arg | Asn | Gln | Gly | Gly | Ser |
|---|---|---|---|---|---|---|---|---|---|---|---|---|---|---|---|
| 305 | | | | | 310 | | | | | 315 | | | | | 320 |

| Gly | Asn | Glu | Lys | Leu | Asp | Ala | Gln | Ile | Lys | Asn | Ile | Ser | Asp | Ala | Leu |
|---|---|---|---|---|---|---|---|---|---|---|---|---|---|---|---|
| | | | | 325 | | | | | 330 | | | | | 335 | |

| Gly | Lys | Lys | Pro | Ile | Pro | Glu | Asn | Ile | Thr | Val | Tyr | Arg | Trp | Cys | Gly |
|---|---|---|---|---|---|---|---|---|---|---|---|---|---|---|---|
| | | | 340 | | | | | 345 | | | | | 350 | | |

| Met | Pro | Glu | Phe | Gly | Tyr | Gln | Ile | Ser | Asp | Pro | Leu | Pro | Ser | Leu | Lys |
|---|---|---|---|---|---|---|---|---|---|---|---|---|---|---|---|
| | | 355 | | | | | 360 | | | | | 365 | | | |

| Asp | Phe | Glu | Glu | Gln | Phe | Leu | Asn | Thr | Ile | Lys | Glu | Asp | Lys | Gly | Tyr |
|---|---|---|---|---|---|---|---|---|---|---|---|---|---|---|---|
| | 370 | | | | | 375 | | | | | 380 | | | | |

| Met | Ser | Thr | Ser | Leu | Ser | Ser | Glu | Arg | Leu | Ala | Ala | Phe | Gly | Ser | Arg |
|---|---|---|---|---|---|---|---|---|---|---|---|---|---|---|---|
| 385 | | | | | 390 | | | | | 395 | | | | | 400 |

```
Lys  Ile  Ile  Leu  Arg  Leu  Gln  Val  Pro  Lys  Gly  Ser  Thr  Gly  Ala  Tyr
               405                      410                     415

Leu  Ser  Ala  Ile  Gly  Gly  Phe  Ala  Ser  Glu  Lys  Glu  Ile  Leu  Leu  Asp
               420                      425                     430

Lys  Asp  Ser  Lys  Tyr  His  Ile  Asp  Lys  Val  Thr  Glu  Val  Ile  Ile  Lys
               435                      440                     445

Gly  Val  Lys  Arg  Tyr  Val  Asp  Ala  Thr  Leu  Leu  Thr  Asn  Met  Lys
450                      455                     460

Asn  Met  Lys  Lys  Lys  Leu  Ala  Ser  Val  Val  Thr  Cys  Thr  Leu  Leu  Ala
465                      470                     475                     480

Pro  Met  Phe  Leu  Asn  Gly  Asn  Val  Asn  Ala  Val  Tyr  Ala  Asp  Ser  Lys
               485                      490                     495

Thr  Asn  Gln  Ile  Ser  Thr  Thr  Gln  Lys  Asn  Gln  Lys  Glu  Met  Asp
               500                      505                     510

Arg  Lys  Gly  Leu  Leu  Gly  Tyr  Tyr  Phe  Lys  Gly  Lys  Asp  Phe  Ser  Asn
               515                      520                     525

Leu  Thr  Met  Phe  Ala  Pro  Thr  Arg  Asp  Ser  Thr  Leu  Ile  Tyr  Asp  Gln
          530                      535                     540

Gln  Thr  Ala  Asn  Lys  Leu  Leu  Asp  Lys  Lys  Gln  Gln  Glu  Tyr  Gln  Ser
545                      550                     555                     560

Ile  Arg  Trp  Ile  Gly  Leu  Ile  Gln  Ser  Lys  Glu  Thr  Gly  Asp  Phe  Thr
               565                      570                     575

Phe  Asn  Leu  Ser  Glu  Asp  Glu  Gln  Ala  Ile  Ile  Glu  Ile  Asn  Gly  Lys
               580                      585                     590

Ile  Ile  Ser  Asn  Lys  Gly  Lys  Glu  Lys  Gln  Val  Val  His  Leu  Glu  Lys
               595                      600                     605

Gly  Lys  Leu  Val  Pro  Ile  Lys  Ile  Glu  Tyr  Gln  Ser  Asp  Thr  Lys  Phe
     610                      615                     620

Asn  Ile  Asp  Ser  Lys  Thr  Phe  Lys  Glu  Leu  Lys  Leu  Phe  Lys  Ile  Asp
625                      630                     635                     640

Ser  Gln  Asn  Gln  Pro  Gln  Gln  Val  Gln  Gln  Asp  Glu  Leu  Arg  Asn  Pro
               645                      650                     655

Glu  Phe  Asn  Lys  Lys  Glu  Ser  Gln  Glu  Phe  Leu  Ala  Lys  Pro  Ser  Lys
               660                      665                     670

Ile  Asn  Leu  Phe  Thr  Gln  Lys  Met  Lys  Arg  Glu  Ile  Asp  Glu  Asp  Thr
               675                      680                     685

Asp  Thr  Asp  Gly  Asp  Ser  Ile  Pro  Asp  Leu  Trp  Glu  Glu  Asn  Gly  Tyr
     690                      695                     700

Thr  Ile  Gln  Asn  Arg  Ile  Ala  Val  Lys  Trp  Asp  Asp  Ser  Leu  Ala  Ser
705                      710                     715                     720

Lys  Gly  Tyr  Thr  Lys  Phe  Val  Ser  Asn  Pro  Leu  Glu  Ser  His  Thr  Val
               725                      730                     735

Gly  Asp  Pro  Tyr  Thr  Asp  Tyr  Glu  Lys  Ala  Ala  Arg  Asp  Leu  Asp  Leu
               740                      745                     750

Ser  Asn  Ala  Lys  Glu  Thr  Phe  Asn  Pro  Leu  Val  Ala  Ala  Phe  Pro  Ser
               755                      760                     765

Val  Asn  Val  Ser  Met  Glu  Lys  Val  Ile  Leu  Ser  Pro  Asn  Glu  Asn  Leu
     770                      775                     780

Ser  Asn  Ser  Val  Glu  Ser  His  Ser  Ser  Thr  Asn  Trp  Ser  Tyr  Thr  Asn
785                      790                     795                     800

Thr  Glu  Gly  Ala  Ser  Val  Glu  Ala  Gly  Ile  Gly  Pro  Lys  Gly  Ile  Ser
               805                      810                     815

Phe  Gly  Val  Ser  Val  Asn  Tyr  Gln  His  Ser  Glu  Thr  Val  Ala  Gln  Glu
```

-continued

|     |     |     |     |     | 820 |     |     |     | 825 |     |     |     | 830 |     |
|-----|-----|-----|-----|-----|-----|-----|-----|-----|-----|-----|-----|-----|-----|-----|
| Trp | Gly | Thr | Ser | Thr | Gly | Asn | Thr | Ser | Gln | Phe | Asn | Thr | Ala | Ser | Ala |
|     |     |     | 835 |     |     |     | 840 |     |     |     |     |     | 845 |     |
| Gly | Tyr | Leu | Asn | Ala | Asn | Val | Arg | Tyr | Asn | Asn | Val | Gly | Thr | Gly | Ala |
|     |     | 850 |     |     |     | 855 |     |     |     |     | 860 |     |     |     |
| Ile | Tyr | Asp | Val | Lys | Pro | Thr | Thr | Ser | Phe | Val | Leu | Asn | Asn | Asp | Thr |
| 865 |     |     |     |     | 870 |     |     |     | 875 |     |     |     |     | 880 |
| Ile | Ala | Thr | Ile | Thr | Ala | Lys | Ser | Asn | Ser | Thr | Ala | Leu | Asn | Ile | Ser |
|     |     |     |     | 885 |     |     |     |     | 890 |     |     |     |     | 895 |
| Pro | Gly | Glu | Ser | Tyr | Pro | Lys | Lys | Gly | Gln | Asn | Gly | Ile | Ala | Ile | Thr |
|     |     |     | 900 |     |     |     |     | 905 |     |     |     |     | 910 |     |
| Ser | Met | Asp | Asp | Phe | Asn | Ser | His | Pro | Ile | Thr | Leu | Asn | Lys | Lys | Gln |
|     |     |     | 915 |     |     |     | 920 |     |     |     |     | 925 |     |     |
| Val | Asp | Asn | Leu | Leu | Asn | Asn | Lys | Pro | Met | Met | Leu | Glu | Thr | Asn | Gln |
|     |     | 930 |     |     |     | 935 |     |     |     |     | 940 |     |     |     |
| Thr | Asp | Gly | Val | Tyr | Lys | Ile | Lys | Asp | Thr | His | Gly | Asn | Ile | Val | Thr |
| 945 |     |     |     |     | 950 |     |     |     | 955 |     |     |     |     | 960 |
| Gly | Gly | Glu | Trp | Asn | Gly | Val | Ile | Gln | Gln | Ile | Lys | Ala | Lys | Thr | Ala |
|     |     |     |     | 965 |     |     |     | 970 |     |     |     |     | 975 |     |
| Ser | Ile | Ile | Val | Asp | Asp | Gly | Glu | Arg | Val | Ala | Glu | Lys | Arg | Val | Ala |
|     |     |     | 980 |     |     |     | 985 |     |     |     |     | 990 |     |     |
| Ala | Lys | Asp | Tyr | Glu | Asn | Pro | Glu | Asp | Lys | Thr | Pro | Ser | Leu | Thr | Leu |
|     |     | 995 |     |     |     |     | 1000 |     |     |     | 1005 |     |     |     |
| Lys | Asp | Ala | Leu | Lys | Leu | Ser | Tyr | Pro | Asp | Glu | Ile | Lys | Glu | Ile | Glu |
|     |     | 1010 |     |     |     | 1015 |     |     |     |     | 1020 |     |     |     |
| Gly | Leu | Leu | Tyr | Tyr | Lys | Asn | Lys | Pro | Ile | Tyr | Glu | Ser | Ser | Val | Met |
| 1025 |     |     |     |     | 1030 |     |     |     | 1035 |     |     |     |     | 1040 |
| Thr | Tyr | Leu | Asp | Glu | Asn | Thr | Ala | Lys | Glu | Val | Thr | Lys | Gln | Leu | Asn |
|     |     |     |     | 1045 |     |     |     | 1050 |     |     |     |     | 1055 |     |
| Asp | Thr | Thr | Gly | Lys | Phe | Lys | Asp | Val | Ser | His | Leu | Tyr | Asp | Val | Lys |
|     |     |     | 1060 |     |     |     | 1065 |     |     |     |     | 1070 |     |     |
| Leu | Thr | Pro | Lys | Met | Asn | Val | Thr | Ile | Lys | Leu | Ser | Ile | Leu | Tyr | Asp |
|     |     |     | 1075 |     |     |     | 1080 |     |     |     | 1085 |     |     |     |
| Asn | Ala | Glu | Ser | Asn | Asp | Asn | Ser | Ile | Gly | Lys | Trp | Thr | Asn | Thr | Asn |
|     |     |     | 1090 |     |     |     | 1095 |     |     |     | 1100 |     |     |     |
| Ile | Val | Ser | Gly | Gly | Asn | Asn | Gly | Lys | Lys | Gln | Tyr | Ser | Ser | Asn | Asn |
| 1105 |     |     |     | 1110 |     |     |     |     | 1115 |     |     |     |     | 1120 |
| Pro | Asp | Ala | Asn | Leu | Thr | Leu | Asn | Thr | Asp | Ala | Gln | Glu | Lys | Leu | Asn |
|     |     |     |     | 1125 |     |     |     |     | 1130 |     |     |     |     | 1135 |
| Lys | Asn | Arg | Asp | Tyr | Tyr | Ile | Ser | Leu | Tyr | Met | Lys | Ser | Glu | Lys | Asn |
|     |     |     | 1140 |     |     |     | 1145 |     |     |     |     | 1150 |     |     |
| Thr | Gln | Cys | Glu | Ile | Thr | Ile | Asp | Gly | Glu | Ile | Tyr | Pro | Ile | Thr | Thr |
|     |     |     | 1155 |     |     |     | 1160 |     |     |     |     | 1165 |     |     |
| Lys | Thr | Val | Asn | Val | Asn | Lys | Asp | Asn | Tyr | Lys | Arg | Leu | Asp | Ile | Ile |
|     |     |     | 1170 |     |     |     | 1175 |     |     |     |     | 1180 |     |     |
| Ala | His | Asn | Ile | Lys | Ser | Asn | Pro | Ile | Ser | Ser | Leu | His | Ile | Lys | Thr |
| 1185 |     |     |     |     | 1190 |     |     |     | 1195 |     |     |     |     | 1200 |
| Asn | Asp | Glu | Ile | Thr | Leu | Phe | Trp | Asp | Asp | Ile | Ser | Ile | Thr | Asp | Val |
|     |     |     |     | 1205 |     |     |     | 1210 |     |     |     |     | 1215 |     |
| Ala | Ser | Ile | Lys | Pro | Glu | Asn | Leu | Thr | Asp | Ser | Glu | Ile | Lys | Gln | Ile |
|     |     |     | 1220 |     |     |     |     | 1225 |     |     |     |     | 1230 |     |
| Tyr | Ser | Arg | Tyr | Gly | Ile | Lys | Leu | Glu | Asp | Gly | Ile | Leu | Ile | Asp | Lys |
|     |     |     | 1235 |     |     |     | 1240 |     |     |     | 1245 |     |     |     |

-continued

Lys Gly Gly Ile His Tyr Gly Glu Phe Ile Asn Glu Ala Ser Phe Asn
1250 1255 1260

Ile Glu Pro Leu Gln Asn Tyr Val Thr Lys Tyr Glu Val Thr Tyr Ser
1265 1270 1275 1280

Ser Glu Leu Gly Pro Asn Val Ser Asp Thr Leu Glu Ser Asp Lys Ile
1285 1290 1295

Tyr Lys Asp Gly Thr Ile Lys Phe Asp Phe Thr Lys Tyr Ser Lys Asn
1300 1305 1310

Glu Gln Gly Leu Phe Tyr Asp Ser Gly Leu Asn Trp Asp Phe Lys Ile
1315 1320 1325

Asn Ala Ile Thr Tyr Asp Gly Lys Glu Met Asn Val Phe His Arg Tyr
1330 1335 1340

Asn Lys
1345

( 2 ) INFORMATION FOR SEQ ID NO:24:

( i ) SEQUENCE CHARACTERISTICS:
( A ) LENGTH: 1399 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..1386
( D ) OTHER INFORMATION: /note= "Maize optimized DNA sequence for VIP2A(a) protein from AB78"

( x i ) SEQUENCE DESCRIPTION: SEQ ID NO:24:

ATGAAGCGCA TGGAGGGCAA GCTGTTCATG GTGAGCAAGA AGCTCCAGGT GGTGACCAAG 60

ACCGTGCTGC TGAGCACCGT GTTCAGCATC AGCCTGCTGA ACAACGAGGT GATCAAGGCC 120

GAGCAGCTGA ACATCAACAG CCAGAGCAAG TACACCAACC TCCAGAACCT GAAGATCACC 180

GACAAGGTGG AGGACTTCAA GGAGGACAAG GAGAAGGCCA AGGAGTGGGG CAAGGAGAAG 240

GAGAAGGAGT GGAAGCTTAC CGCCACCGAG AAGGGCAAGA TGAACAACTT CCTGGACAAC 300

AAGAACGACA TCAAGACCAA CTACAAGGAG ATCACCTTCA GCATGGCCGG CAGCTTCGAG 360

GACGAGATCA AGGACCTGAA GGAGATCGAC AAGATGTTCG ACAAGACCAA CCTGAGCAAC 420

AGCATCATCA CCTACAAGAA CGTGGAGCCC ACCACCATCG GCTTCAACAA GAGCCTGACC 480

GAGGGCAACA CCATCAACAG CGACGCCATG GCCCAGTTCA AGGAGCAGTT CCTGGACCGC 540

GACATCAAGT TCGACAGCTA CCTGGACACC CACCTGACCG CCCAGCAGGT GAGCAGCAAG 600

GAGCGCGTGA TCCTGAAGGT GACCGTCCCC AGCGGCAAGG GCAGCACCAC CCCCACCAAG 660

GCCGGCGTGA TCCTGAACAA CAGCGAGTAC AAGATGCTGA TCGACAACGG CTACATGGTG 720

CACGTGGACA AGGTGAGCAA GGTGGTGAAG AAGGGCGTGG AGTGCCTCCA GATCGAGGGC 780

ACCCTGAAGA AGAGTCTAGA CTTCAAGAAC GACATCAACG CCGAGGCCCA CAGCTGGGGC 840

ATGAAGAACT ACGAGGAGTG GGCCAAGGAC CTGACCGACA GCCAGCGCGA GGCCCTGGAC 900

GGCTACGCCC GCCAGGACTA CAAGGAGATC AACAACTACC TGCGCAACCA GGGCGGCAGC 960

GGCAACGAGA AGCTGGACGC CCAGATCAAG AACATCAGCG ACGCCCTGGG CAAGAAGCCC 1020

ATCCCCGAGA ACATCACCGT GTACCGCTGG TGCGGCATGC CCGAGTTCGG CTACCAGATC 1080

AGCGACCCCC TGCCCAGCCT GAAGGACTTC GAGGAGCAGT TCCTGAACAC CATCAAGGAG 1140

GACAAGGGCT ACATGAGCAC CAGCCTGAGC AGCGAGCGCC TGGCCGCCTT CGGCAGCCGC 1200

-continued

AAGATCATCC TGCGCCTGCA GGTGCCCAAG GGCAGCACCG GCGCCTACCT GAGCGCCATC 1260

GGCGGCTTCG CCAGCGAGAA GGAGATCCTG CTGGACAAGG ACAGCAAGTA CCACATCGAC 1320

AAGGTGACCG AGGTGATCAT CAAGGGCGTG AAGCGCTACG TGGTGGACGC CACCCTGCTG 1380

ACCAACTAGA TCTGAGCTC 1399

( 2 ) INFORMATION FOR SEQ ID NO:25:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..19
( D ) OTHER INFORMATION: /note= "Secretion signal peptide to secrete VIP2 out of a cell"

( x i ) SEQUENCE DESCRIPTION: SEQ ID NO:25:

Gly Trp Ser Trp Ile Phe Leu Phe Leu Leu Ser Gly Ala Ala Gly Val
1 5 10 15

His Cys Leu ( 2 ) INFORMATION FOR SEQ ID NO:26:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..2655
( D ) OTHER INFORMATION: /note= "maize optimized DNA sequence encoding VIP1A(a)"

( x i ) SEQUENCE DESCRIPTION: SEQ ID NO:26:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

-continued

| | | | | | | |
|---|---|---|---|---|---|---|
| TACACCAAGT | TCGTGAGCAA | CCCCCTGGAG | AGCCACACCG | TGGGCGACCC | CTACACCGAC | 840 |
| TACGAGAAGG | CCGCCCGCGA | CCTGGACCTG | AGCAACGCCA | AGGAGACCTT | CAACCCCCTG | 900 |
| GTGGCCGCCT | TCCCCAGCGT | GAACGTGAGC | ATGGAGAAGG | TGATCCTGAG | CCCCAACGAG | 960 |
| AACCTGAGCA | ACAGCGTGGA | GAGCCACTCG | AGCACCAACT | GGAGCTACAC | CAACACCGAG | 1020 |
| GGCGCCAGCG | TGGAGGCCGG | CATCGGTCCC | AAGGGCATCA | GCTTCGGCGT | GAGCGTGAAC | 1080 |
| TACCAGCACA | GCGAGACCGT | GGCCCAGGAG | TGGGGCACCA | GCACCGGCAA | CACCAGCCAG | 1140 |
| TTCAACACCG | CCAGCGCCGG | CTACCTGAAC | GCCAACGTGC | GCTACAACAA | CGTGGGCACC | 1200 |
| GGCGCCATCT | ACGACGTGAA | GCCCACCACC | AGCTTCGTGC | TGAACAACGA | CACCATCGCC | 1260 |
| ACCATCACCG | CCAAGTCGAA | TTCCACCGCC | CTGAACATCA | GCCCCGGCGA | GAGCTACCCC | 1320 |
| AAGAAGGGCC | AGAACGGCAT | CGCCATCACC | AGCATGGACG | ACTTCAACAG | CCACCCCATC | 1380 |
| ACCCTGAACA | AGAAGCAGGT | GGACAACCTG | CTGAACAACA | AGCCCATGAT | GCTGGAGACC | 1440 |
| AACCAGACCG | ACGGCGTCTA | CAAGATCAAG | GACACCCACG | GCAACATCGT | GACGGGCGGC | 1500 |
| GAGTGGAACG | GCGTGATCCA | GCAGATCAAG | GCCAAGACCG | CCAGCATCAT | CGTCGACGAC | 1560 |
| GGCGAGCGCG | TGGCCGAGAA | GCGCGTGGCC | GCCAAGGACT | ACGAGAACCC | CGAGGACAAG | 1620 |
| ACCCCCAGCC | TGACCCTGAA | GGACGCCCTG | AAGCTGAGCT | ACCCCGACGA | GATCAAGGAG | 1680 |
| ATCGAGGGCT | TGCTGTACTA | CAAGAACAAG | CCCATCTACG | AGAGCAGCGT | GATGACCTAT | 1740 |
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | AGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:27:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature (B) LOCATION: 1..1389
(D) OTHER INFORMATION: /note= "maize optimized DNA sequence encoding VIP2A(a)"

(x i) SEQUENCE DESCRIPTION: SEQ ID NO:27:

| | | | | | | |
|---|---|---|---|---|---|---|
| ATGAAGCGCA | TGGAGGGCAA | GCTGTTCATG | GTGAGCAAGA | AGCTCCAGGT | GGTGACCAAG | 60 |
| ACCGTGCTGC | TGAGCACCGT | GTTCAGCATC | AGCCTGCTGA | CAACGAGGT | GATCAAGGCC | 120 |
| GAGCAGCTGA | ACATCAACAG | CCAGAGCAAG | TACACCAACC | TCCAGAACCT | GAAGATCACC | 180 |
| GACAAGGTGG | AGGACTTCAA | GGAGGACAAG | GAGAAGGCCA | AGGAGTGGGG | CAAGGAGAAG | 240 |
| GAGAAGGAGT | GGAAGCTTAC | CGCCACCGAG | AAGGGCAAGA | TGAACAACTT | CCTGGACAAC | 300 |
| AAGAACGACA | TCAAGACCAA | CTACAAGGAG | ATCACCTTCA | GCATAGCCGG | CAGCTTCGAG | 360 |
| GACGAGATCA | AGGACCTGAA | GGAGATCGAC | AAGATGTTCG | ACAAGACCAA | CCTGAGCAAC | 420 |
| AGCATCATCA | CCTACAAGAA | CGTGGAGCCC | ACCACCATCG | GCTTCAACAA | GAGCCTGACC | 480 |
| GAGGGCAACA | CCATCAACAG | CGACGCCATG | GCCCAGTTCA | AGGAGCAGTT | CCTGGACCGC | 540 |
| GACATCAAGT | TCGACAGCTA | CCTGGACACC | CACCTGACCG | CCCAGCAGGT | GAGCAGCAAG | 600 |
| GAGCGCGTGA | TCCTGAAGGT | GACCGTCCCC | AGCGGCAAGG | GCAGCACCAC | CCCCACCAAG | 660 |
| GCCGGCGTGA | TCCTGAACAA | CAGCGAGTAC | AAGATGCTGA | TCGACAACGG | CTACATGGTG | 720 |
| CACGTGGACA | AGGTGAGCAA | GGTGGTGAAG | AAGGGCGTGG | AGTGCCTCCA | GATCGAGGGC | 780 |
| ACCCTGAAGA | AGAGTCTAGA | CTTCAAGAAC | GACATCAACG | CCGAGGCCCA | CAGCTGGGGC | 840 |
| ATGAAGAACT | ACGAGGAGTG | GGCCAAGGAC | CTGACCGACA | GCCAGCGCGA | GGCCCTGGAC | 900 |
| GGCTACGCCC | GCCAGGACTA | CAAGGAGATC | AACAACTACC | TGCGCAACCA | GGGCGGCAGC | 960 |
| GGCAACGAGA | AGCTGGACGC | CCAGATCAAG | AACATCAGCG | ACGCCCTGGG | CAAGAAGCCC | 1020 |
| ATCCCCGAGA | ACATCACCGT | GTACCGCTGG | TGCGGCATGC | CCGAGTTCGG | CTACCAGATC | 1080 |
| AGCGACCCCC | TGCCCAGCCT | GAAGGACTTC | GAGGAGCAGT | TCCTGAACAC | CATCAAGGAG | 1140 |
| GACAAGGGCT | ACATGAGCAC | CAGCCTGAGC | AGCGAGCGCC | TGGCCGCCTT | CGGCAGCCGC | 1200 |
| AAGATCATCC | TGCGCCTGCA | GGTGCCCAAG | GGCAGCACTG | GTGCCTACCT | GAGCGCCATC | 1260 |
| GGCGGCTTCG | CCAGCGAGAA | GGAGATCCTG | CTGGATAAGG | ACAGCAAGTA | CCACATCGAC | 1320 |
| AAGGTGACCG | AGGTGATCAT | CAAGGGCGTG | AAGCGCTACG | TGGTGGACGC | CACCCTGCTG | 1380 |
| ACCAACTAG | | | | | | 1389 |

(2) INFORMATION FOR SEQ ID NO:28:

(i) SEQUENCE CHARACTERISTICS:
(A) LENGTH: 2378 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (ix) FEATURE:
(A) NAME/KEY: CDS
(B) LOCATION: 9..2375
(D) OTHER INFORMATION: /note= "Native DNA sequence encoding VIP3A(a) protein from AB88 as contained in pCIB7104"

(x i) SEQUENCE DESCRIPTION: SEQ ID NO:28:

```
AGATGAAC ATG AAC AAG AAT AAT ACT AAA TTA AGC ACA AGA GCC TTA CCA     50
         Met Asn Lys Asn Asn Thr Lys Leu Ser Thr Arg Ala Leu Pro
          1               5                  10
```

| | | | | | | | | | | | | | | | | |
|---|---|---|---|---|---|---|---|---|---|---|---|---|---|---|---|---|
| AGT | TTT | ATT | GAT | TAT | TTT | AAT | GGC | ATT | TAT | GGA | TTT | GCC | ACT | GGT | ATC | 98 |
| Ser | Phe | Ile | Asp | Tyr | Phe | Asn | Gly | Ile | Tyr | Gly | Phe | Ala | Thr | Gly | Ile | |
| 15 | | | | 20 | | | | | 25 | | | | | | 30 | |
| AAA | GAC | ATT | ATG | AAC | ATG | ATT | TTT | AAA | ACG | GAT | ACA | GGT | GGT | GAT | CTA | 146 |
| Lys | Asp | Ile | Met | Asn | Met | Ile | Phe | Lys | Thr | Asp | Thr | Gly | Gly | Asp | Leu | |
| | | | | 35 | | | | 40 | | | | | | 45 | | |
| ACC | CTA | GAC | GAA | ATT | TTA | AAG | AAT | CAG | CAG | TTA | CTA | AAT | GAT | ATT | TCT | 194 |
| Thr | Leu | Asp | Glu | Ile | Leu | Lys | Asn | Gln | Gln | Leu | Leu | Asn | Asp | Ile | Ser | |
| | | | 50 | | | | | 55 | | | | | 60 | | | |
| GGT | AAA | TTG | GAT | GGG | GTG | AAT | GGA | AGC | TTA | AAT | GAT | CTT | ATC | GCA | CAG | 242 |
| Gly | Lys | Leu | Asp | Gly | Val | Asn | Gly | Ser | Leu | Asn | Asp | Leu | Ile | Ala | Gln | |
| | 65 | | | | | 70 | | | | | 75 | | | | | |
| GGA | AAC | TTA | AAT | ACA | GAA | TTA | TCT | AAG | GAA | ATA | TTA | AAA | ATT | GCA | AAT | 290 |
| Gly | Asn | Leu | Asn | Thr | Glu | Leu | Ser | Lys | Glu | Ile | Leu | Lys | Ile | Ala | Asn | |
| | 80 | | | | | 85 | | | | | 90 | | | | | |
| GAA | CAA | AAT | CAA | GTT | TTA | AAT | GAT | GTT | AAT | AAC | AAA | CTC | GAT | GCG | ATA | 338 |
| Glu | Gln | Asn | Gln | Val | Leu | Asn | Asp | Val | Asn | Asn | Lys | Leu | Asp | Ala | Ile | |
| 95 | | | | | 100 | | | | | 105 | | | | | 110 | |
| AAT | ACG | ATG | CTT | CGG | GTA | TAT | CTA | CCT | AAA | ATT | ACC | TCT | ATG | TTG | AGT | 386 |
| Asn | Thr | Met | Leu | Arg | Val | Tyr | Leu | Pro | Lys | Ile | Thr | Ser | Met | Leu | Ser | |
| | | | | 115 | | | | | 120 | | | | | 125 | | |
| GAT | GTA | ATG | AAA | CAA | AAT | TAT | GCG | CTA | AGT | CTG | CAA | ATA | GAA | TAC | TTA | 434 |
| Asp | Val | Met | Lys | Gln | Asn | Tyr | Ala | Leu | Ser | Leu | Gln | Ile | Glu | Tyr | Leu | |
| | | | 130 | | | | | 135 | | | | | 140 | | | |
| AGT | AAA | CAA | TTG | CAA | GAG | ATT | TCT | GAT | AAG | TTG | GAT | ATT | ATT | AAT | GTA | 482 |
| Ser | Lys | Gln | Leu | Gln | Glu | Ile | Ser | Asp | Lys | Leu | Asp | Ile | Ile | Asn | Val | |
| | | 145 | | | | | 150 | | | | | 155 | | | | |
| AAT | GTA | CTT | ATT | AAC | TCT | ACA | CTT | ACT | GAA | ATT | ACA | CCT | GCG | TAT | CAA | 530 |
| Asn | Val | Leu | Ile | Asn | Ser | Thr | Leu | Thr | Glu | Ile | Thr | Pro | Ala | Tyr | Gln | |
| | 160 | | | | | 165 | | | | | 170 | | | | | |
| AGG | ATT | AAA | TAT | GTG | AAC | GAA | AAA | TTT | GAG | GAA | TTA | ACT | TTT | GCT | ACA | 578 |
| Arg | Ile | Lys | Tyr | Val | Asn | Glu | Lys | Phe | Glu | Glu | Leu | Thr | Phe | Ala | Thr | |
| 175 | | | | | 180 | | | | | 185 | | | | | 190 | |
| GAA | ACT | AGT | TCA | AAA | GTA | AAA | AAG | GAT | GGC | TCT | CCT | GCA | GAT | ATT | CTT | 626 |
| Glu | Thr | Ser | Ser | Lys | Val | Lys | Lys | Asp | Gly | Ser | Pro | Ala | Asp | Ile | Leu | |
| | | | | 195 | | | | | 200 | | | | | 205 | | |
| GAT | GAG | TTA | ACT | GAG | TTA | ACT | GAA | CTA | GCG | AAA | AGT | GTA | ACA | AAA | AAT | 674 |
| Asp | Glu | Leu | Thr | Glu | Leu | Thr | Glu | Leu | Ala | Lys | Ser | Val | Thr | Lys | Asn | |
| | | | 210 | | | | | 215 | | | | | 220 | | | |
| GAT | GTG | GAT | GGT | TTT | GAA | TTT | TAC | CTT | AAT | ACA | TTC | CAC | GAT | GTA | ATG | 722 |
| Asp | Val | Asp | Gly | Phe | Glu | Phe | Tyr | Leu | Asn | Thr | Phe | His | Asp | Val | Met | |
| | | 225 | | | | | 230 | | | | | 235 | | | | |
| GTA | GGA | AAT | AAT | TTA | TTC | GGG | CGT | TCA | GCT | TTA | AAA | ACT | GCA | TCG | GAA | 770 |
| Val | Gly | Asn | Asn | Leu | Phe | Gly | Arg | Ser | Ala | Leu | Lys | Thr | Ala | Ser | Glu | |
| | 240 | | | | | 245 | | | | | 250 | | | | | |
| TTA | ATT | ACT | AAA | GAA | AAT | GTG | AAA | ACA | AGT | GGC | AGT | GAG | GTC | GGA | AAT | 818 |
| Leu | Ile | Thr | Lys | Glu | Asn | Val | Lys | Thr | Ser | Gly | Ser | Glu | Val | Gly | Asn | |
| 255 | | | | | 260 | | | | | 265 | | | | | 270 | |
| GTT | TAT | AAC | TTC | TTA | ATT | GTA | TTA | ACA | GCT | CTG | CAA | GCC | CAA | GCT | TTT | 866 |
| Val | Tyr | Asn | Phe | Leu | Ile | Val | Leu | Thr | Ala | Leu | Gln | Ala | Gln | Ala | Phe | |
| | | | | 275 | | | | | 280 | | | | | 285 | | |
| CTT | ACT | TTA | ACA | ACA | TGC | CGA | AAA | TTA | TTA | GGC | TTA | GCA | GAT | ATT | GAT | 914 |
| Leu | Thr | Leu | Thr | Thr | Cys | Arg | Lys | Leu | Leu | Gly | Leu | Ala | Asp | Ile | Asp | |
| | | | 290 | | | | | 295 | | | | | 300 | | | |
| TAT | ACT | TCT | ATT | ATG | AAT | GAA | CAT | TTA | AAT | AAG | GAA | AAA | GAG | GAA | TTT | 962 |
| Tyr | Thr | Ser | Ile | Met | Asn | Glu | His | Leu | Asn | Lys | Glu | Lys | Glu | Glu | Phe | |
| | | 305 | | | | | 310 | | | | | 315 | | | | |
| AGA | GTA | AAC | ATC | CTC | CCT | ACA | CTT | TCT | AAT | ACT | TTT | TCT | AAT | CCT | AAT | 1010 |
| Arg | Val | Asn | Ile | Leu | Pro | Thr | Leu | Ser | Asn | Thr | Phe | Ser | Asn | Pro | Asn | |
| | 320 | | | | | 325 | | | | | 330 | | | | | |

| | | | | | | | | | | | | | | | | |
|---|---|---|---|---|---|---|---|---|---|---|---|---|---|---|---|---|
| TAT | GCA | AAA | GTT | AAA | GGA | AGT | GAT | GAA | GAT | GCA | AAG | ATG | ATT | GTG | GAA | 1058 |
| Tyr | Ala | Lys | Val | Lys | Gly | Ser | Asp | Glu | Asp | Ala | Lys | Met | Ile | Val | Glu | |
| 335 | | | | 340 | | | | | 345 | | | | | | 350 | |
| GCT | AAA | CCA | GGA | CAT | GCA | TTG | ATT | GGG | TTT | GAA | ATT | AGT | AAT | GAT | TCA | 1106 |
| Ala | Lys | Pro | Gly | His | Ala | Leu | Ile | Gly | Phe | Glu | Ile | Ser | Asn | Asp | Ser | |
| | | | | 355 | | | | 360 | | | | | 365 | | | |
| ATT | ACA | GTA | TTA | AAA | GTA | TAT | GAG | GCT | AAG | CTA | AAA | CAA | AAT | TAT | CAA | 1154 |
| Ile | Thr | Val | Leu | Lys | Val | Tyr | Glu | Ala | Lys | Leu | Lys | Gln | Asn | Tyr | Gln | |
| | | | 370 | | | | | 375 | | | | 380 | | | | |
| GTC | GAT | AAG | GAT | TCC | TTA | TCG | GAA | GTT | ATT | TAT | GGT | GAT | ATG | GAT | AAA | 1202 |
| Val | Asp | Lys | Asp | Ser | Leu | Ser | Glu | Val | Ile | Tyr | Gly | Asp | Met | Asp | Lys | |
| | | 385 | | | | | 390 | | | | | 395 | | | | |
| TTA | TTG | TGC | CCA | GAT | CAA | TCT | GAA | CAA | ATC | TAT | TAT | ACA | AAT | AAC | ATA | 1250 |
| Leu | Leu | Cys | Pro | Asp | Gln | Ser | Glu | Gln | Ile | Tyr | Tyr | Thr | Asn | Asn | Ile | |
| 400 | | | | | 405 | | | | | 410 | | | | | | |
| GTA | TTT | CCA | AAT | GAA | TAT | GTA | ATT | ACT | AAA | ATT | GAT | TTC | ACT | AAA | AAA | 1298 |
| Val | Phe | Pro | Asn | Glu | Tyr | Val | Ile | Thr | Lys | Ile | Asp | Phe | Thr | Lys | Lys | |
| 415 | | | | | 420 | | | | | 425 | | | | | 430 | |
| ATG | AAA | ACT | TTA | AGA | TAT | GAG | GTA | ACA | GCG | AAT | TTT | TAT | GAT | TCT | TCT | 1346 |
| Met | Lys | Thr | Leu | Arg | Tyr | Glu | Val | Thr | Ala | Asn | Phe | Tyr | Asp | Ser | Ser | |
| | | | | 435 | | | | 440 | | | | | 445 | | | |
| ACA | GGA | GAA | ATT | GAC | TTA | AAT | AAG | AAA | AAA | GTA | GAA | TCA | AGT | GAA | GCG | 1394 |
| Thr | Gly | Glu | Ile | Asp | Leu | Asn | Lys | Lys | Lys | Val | Glu | Ser | Ser | Glu | Ala | |
| | | | | 450 | | | | 455 | | | | 460 | | | | |
| GAG | TAT | AGA | ACG | TTA | AGT | GCT | AAT | GAT | GAT | GGG | GTG | TAT | ATG | CCG | TTA | 1442 |
| Glu | Tyr | Arg | Thr | Leu | Ser | Ala | Asn | Asp | Asp | Gly | Val | Tyr | Met | Pro | Leu | |
| | | 465 | | | | | 470 | | | | | 475 | | | | |
| GGT | GTC | ATC | AGT | GAA | ACA | TTT | TTG | ACT | CCG | ATT | AAT | GGG | TTT | GGC | CTC | 1490 |
| Gly | Val | Ile | Ser | Glu | Thr | Phe | Leu | Thr | Pro | Ile | Asn | Gly | Phe | Gly | Leu | |
| | | 480 | | | | | 485 | | | | | 490 | | | | |
| CAA | GCT | GAT | GAA | AAT | TCA | AGA | TTA | ATT | ACT | TTA | ACA | TGT | AAA | TCA | TAT | 1538 |
| Gln | Ala | Asp | Glu | Asn | Ser | Arg | Leu | Ile | Thr | Leu | Thr | Cys | Lys | Ser | Tyr | |
| 495 | | | | | 500 | | | | | 505 | | | | | 510 | |
| TTA | AGA | GAA | CTA | CTG | CTA | GCA | ACA | GAC | TTA | AGC | AAT | AAA | GAA | ACT | AAA | 1586 |
| Leu | Arg | Glu | Leu | Leu | Leu | Ala | Thr | Asp | Leu | Ser | Asn | Lys | Glu | Thr | Lys | |
| | | | | 515 | | | | 520 | | | | | 525 | | | |
| TTG | ATC | GTC | CCG | CCA | AGT | GGT | TTT | ATT | AGC | AAT | ATT | GTA | GAG | AAC | GGG | 1634 |
| Leu | Ile | Val | Pro | Pro | Ser | Gly | Phe | Ile | Ser | Asn | Ile | Val | Glu | Asn | Gly | |
| | | | 530 | | | | | 535 | | | | | 540 | | | |
| TCC | ATA | GAA | GAG | GAC | AAT | TTA | GAG | CCG | TGG | AAA | GCA | AAT | AAT | AAG | AAT | 1682 |
| Ser | Ile | Glu | Glu | Asp | Asn | Leu | Glu | Pro | Trp | Lys | Ala | Asn | Asn | Lys | Asn | |
| | | 545 | | | | | 550 | | | | | 555 | | | | |
| GCG | TAT | GTA | GAT | CAT | ACA | GGC | GGA | GTG | AAT | GGA | ACT | AAA | GCT | TTA | TAT | 1730 |
| Ala | Tyr | Val | Asp | His | Thr | Gly | Gly | Val | Asn | Gly | Thr | Lys | Ala | Leu | Tyr | |
| | 560 | | | | | 565 | | | | | 570 | | | | | |
| GTT | CAT | AAG | GAC | GGA | GGA | ATT | TCA | CAA | TTT | ATT | GGA | GAT | AAG | TTA | AAA | 1778 |
| Val | His | Lys | Asp | Gly | Gly | Ile | Ser | Gln | Phe | Ile | Gly | Asp | Lys | Leu | Lys | |
| 575 | | | | | 580 | | | | | 585 | | | | | 590 | |
| CCG | AAA | ACT | GAG | TAT | GTA | ATC | CAA | TAT | ACT | GTT | AAA | GGA | AAA | CCT | TCT | 1826 |
| Pro | Lys | Thr | Glu | Tyr | Val | Ile | Gln | Tyr | Thr | Val | Lys | Gly | Lys | Pro | Ser | |
| | | | | 595 | | | | | 600 | | | | | 605 | | |
| ATT | CAT | TTA | AAA | GAT | GAA | AAT | ACT | GGA | TAT | ATT | CAT | TAT | GAA | GAT | ACA | 1874 |
| Ile | His | Leu | Lys | Asp | Glu | Asn | Thr | Gly | Tyr | Ile | His | Tyr | Glu | Asp | Thr | |
| | | | 610 | | | | | 615 | | | | 620 | | | | |
| AAT | AAT | AAT | TTA | GAA | GAT | TAT | CAA | ACT | ATT | AAT | AAA | CGT | TTT | ACT | ACA | 1922 |
| Asn | Asn | Asn | Leu | Glu | Asp | Tyr | Gln | Thr | Ile | Asn | Lys | Arg | Phe | Thr | Thr | |
| | | 625 | | | | | 630 | | | | | 635 | | | | |
| GGA | ACT | GAT | TTA | AAG | GGA | GTG | TAT | TTA | ATT | TTA | AAA | AGT | CAA | AAT | GGA | 1970 |
| Gly | Thr | Asp | Leu | Lys | Gly | Val | Tyr | Leu | Ile | Leu | Lys | Ser | Gln | Asn | Gly | |
| 640 | | | | | 645 | | | | | 650 | | | | | | |

```
GAT  GAA  GCT  TGG  GGA  GAT  AAC  TTT  ATT  ATT  TTG  GAA  ATT  AGT  CCT  TCT      2018
Asp  Glu  Ala  Trp  Gly  Asp  Asn  Phe  Ile  Ile  Leu  Glu  Ile  Ser  Pro  Ser
655                      660                      665                      670

GAA  AAG  TTA  TTA  AGT  CCA  GAA  TTA  ATT  AAT  ACA  AAT  AAT  TGG  ACG  AGT      2066
Glu  Lys  Leu  Leu  Ser  Pro  Glu  Leu  Ile  Asn  Thr  Asn  Asn  Trp  Thr  Ser
                    675                      680                      685

ACG  GGA  TCA  ACT  AAT  ATT  AGC  GGT  AAT  ACA  CTC  ACT  CTT  TAT  CAG  GGA      2114
Thr  Gly  Ser  Thr  Asn  Ile  Ser  Gly  Asn  Thr  Leu  Thr  Leu  Tyr  Gln  Gly
               690                      695                      700

GGA  CGA  GGG  ATT  CTA  AAA  CAA  AAC  CTT  CAA  TTA  GAT  AGT  TTT  TCA  ACT      2162
Gly  Arg  Gly  Ile  Leu  Lys  Gln  Asn  Leu  Gln  Leu  Asp  Ser  Phe  Ser  Thr
          705                      710                      715

TAT  AGA  GTG  TAT  TTT  TCT  GTG  TCC  GGA  GAT  GCT  AAT  GTA  AGG  ATT  AGA      2210
Tyr  Arg  Val  Tyr  Phe  Ser  Val  Ser  Gly  Asp  Ala  Asn  Val  Arg  Ile  Arg
     720                      725                      730

AAT  TCT  AGG  GAA  GTG  TTA  TTT  GAA  AAA  AGA  TAT  ATG  AGC  GGT  GCT  AAA      2258
Asn  Ser  Arg  Glu  Val  Leu  Phe  Glu  Lys  Arg  Tyr  Met  Ser  Gly  Ala  Lys
735                      740                      745                      750

GAT  GTT  TCT  GAA  ATG  TTC  ACT  ACA  AAA  TTT  GAG  AAA  GAT  AAC  TTT  TAT      2306
Asp  Val  Ser  Glu  Met  Phe  Thr  Thr  Lys  Phe  Glu  Lys  Asp  Asn  Phe  Tyr
                    755                      760                      765

ATA  GAG  CTT  TCT  CAA  GGG  AAT  AAT  TTA  TAT  GGT  GGT  CCT  ATT  GTA  CAT      2354
Ile  Glu  Leu  Ser  Gln  Gly  Asn  Asn  Leu  Tyr  Gly  Gly  Pro  Ile  Val  His
               770                      775                      780

TTT  TAC  GAT  GTC  TCT  ATT  AAG  TAA                                               2378
Phe  Tyr  Asp  Val  Ser  Ile  Lys
               785
```

(2) INFORMATION FOR SEQ ID NO:29:

(i) SEQUENCE CHARACTERISTICS:
        (A) LENGTH: 789 amino acids
        (B) TYPE: amino acid
        (D) TOPOLOGY: linear (ii) MOLECULE TYPE: protein (xi) SEQUENCE DESCRIPTION: SEQ ID NO:29:

```
Met  Asn  Lys  Asn  Asn  Thr  Lys  Leu  Ser  Thr  Arg  Ala  Leu  Pro  Ser  Phe
1                   5                   10                      15

Ile  Asp  Tyr  Phe  Asn  Gly  Ile  Tyr  Gly  Phe  Ala  Thr  Gly  Ile  Lys  Asp
               20                      25                      30

Ile  Met  Asn  Met  Ile  Phe  Lys  Thr  Asp  Thr  Gly  Gly  Asp  Leu  Thr  Leu
          35                      40                      45

Asp  Glu  Ile  Leu  Lys  Asn  Gln  Gln  Leu  Leu  Asn  Asp  Ile  Ser  Gly  Lys
     50                      55                      60

Leu  Asp  Gly  Val  Asn  Gly  Ser  Leu  Asn  Asp  Leu  Ile  Ala  Gln  Gly  Asn
65                       70                      75                       80

Leu  Asn  Thr  Glu  Leu  Ser  Lys  Glu  Ile  Leu  Lys  Ile  Ala  Asn  Glu  Gln
                    85                      90                      95

Asn  Gln  Val  Leu  Asn  Asp  Val  Asn  Asn  Lys  Leu  Asp  Ala  Ile  Asn  Thr
               100                     105                     110

Met  Leu  Arg  Val  Tyr  Leu  Pro  Lys  Ile  Thr  Ser  Met  Leu  Ser  Asp  Val
          115                     120                     125

Met  Lys  Gln  Asn  Tyr  Ala  Leu  Ser  Leu  Gln  Ile  Glu  Tyr  Leu  Ser  Lys
     130                     135                     140

Gln  Leu  Gln  Glu  Ile  Ser  Asp  Lys  Leu  Asp  Ile  Ile  Asn  Val  Asn  Val
145                     150                     155                     160

Leu  Ile  Asn  Ser  Thr  Leu  Thr  Glu  Ile  Thr  Pro  Ala  Tyr  Gln  Arg  Ile
                    165                     170                     175
```

```
Lys  Tyr  Val  Asn  Glu  Lys  Phe  Glu  Glu  Leu  Thr  Phe  Ala  Thr  Glu  Thr
               180                 185                      190

Ser  Ser  Lys  Val  Lys  Lys  Asp  Gly  Ser  Pro  Ala  Asp  Ile  Leu  Asp  Glu
          195                 200                      205

Leu  Thr  Glu  Leu  Thr  Glu  Leu  Ala  Lys  Ser  Val  Thr  Lys  Asn  Asp  Val
     210                 215                      220

Asp  Gly  Phe  Glu  Phe  Tyr  Leu  Asn  Thr  Phe  His  Asp  Val  Met  Val  Gly
225                      230                 235                           240

Asn  Asn  Leu  Phe  Gly  Arg  Ser  Ala  Leu  Lys  Thr  Ala  Ser  Glu  Leu  Ile
                    245                      250                      255

Thr  Lys  Glu  Asn  Val  Lys  Thr  Ser  Gly  Ser  Glu  Val  Gly  Asn  Val  Tyr
               260                      265                      270

Asn  Phe  Leu  Ile  Val  Leu  Thr  Ala  Leu  Gln  Ala  Gln  Ala  Phe  Leu  Thr
               275                 280                      285

Leu  Thr  Thr  Cys  Arg  Lys  Leu  Leu  Gly  Leu  Ala  Asp  Ile  Asp  Tyr  Thr
     290                      295                      300

Ser  Ile  Met  Asn  Glu  His  Leu  Asn  Lys  Glu  Lys  Glu  Glu  Phe  Arg  Val
305                      310                 315                           320

Asn  Ile  Leu  Pro  Thr  Leu  Ser  Asn  Thr  Phe  Ser  Asn  Pro  Asn  Tyr  Ala
                    325                 330                      335

Lys  Val  Lys  Gly  Ser  Asp  Glu  Asp  Ala  Lys  Met  Ile  Val  Glu  Ala  Lys
               340                      345                      350

Pro  Gly  His  Ala  Leu  Ile  Gly  Phe  Glu  Ile  Ser  Asn  Asp  Ser  Ile  Thr
          355                      360                      365

Val  Leu  Lys  Val  Tyr  Glu  Ala  Lys  Leu  Lys  Gln  Asn  Tyr  Gln  Val  Asp
     370                      375                 380

Lys  Asp  Ser  Leu  Ser  Glu  Val  Ile  Tyr  Gly  Asp  Met  Asp  Lys  Leu  Leu
385                      390                      395                      400

Cys  Pro  Asp  Gln  Ser  Glu  Gln  Ile  Tyr  Tyr  Thr  Asn  Asn  Ile  Val  Phe
                    405                      410                      415

Pro  Asn  Glu  Tyr  Val  Ile  Thr  Lys  Ile  Asp  Phe  Thr  Lys  Lys  Met  Lys
               420                      425                      430

Thr  Leu  Arg  Tyr  Glu  Val  Thr  Ala  Asn  Phe  Tyr  Asp  Ser  Ser  Thr  Gly
          435                      440                      445

Glu  Ile  Asp  Leu  Asn  Lys  Lys  Lys  Val  Glu  Ser  Ser  Glu  Ala  Glu  Tyr
     450                      455                      460

Arg  Thr  Leu  Ser  Ala  Asn  Asp  Asp  Gly  Val  Tyr  Met  Pro  Leu  Gly  Val
465                      470                      475                      480

Ile  Ser  Glu  Thr  Phe  Leu  Thr  Pro  Ile  Asn  Gly  Phe  Gly  Leu  Gln  Ala
                    485                      490                      495

Asp  Glu  Asn  Ser  Arg  Leu  Ile  Thr  Leu  Thr  Cys  Lys  Ser  Tyr  Leu  Arg
               500                      505                      510

Glu  Leu  Leu  Leu  Ala  Thr  Asp  Leu  Ser  Asn  Lys  Glu  Thr  Lys  Leu  Ile
          515                      520                      525

Val  Pro  Pro  Ser  Gly  Phe  Ile  Ser  Asn  Ile  Val  Glu  Asn  Gly  Ser  Ile
     530                      535                      540

Glu  Glu  Asp  Asn  Leu  Glu  Pro  Trp  Lys  Ala  Asn  Asn  Lys  Asn  Ala  Tyr
545                      550                      555                      560

Val  Asp  His  Thr  Gly  Gly  Val  Asn  Gly  Thr  Lys  Ala  Leu  Tyr  Val  His
                    565                      570                      575

Lys  Asp  Gly  Gly  Ile  Ser  Gln  Phe  Ile  Gly  Asp  Lys  Leu  Lys  Pro  Lys
               580                      585                      590

Thr  Glu  Tyr  Val  Ile  Gln  Tyr  Thr  Val  Lys  Gly  Lys  Pro  Ser  Ile  His
```

|     |     |     |     |     | 595 |     |     |     |     | 600 |     |     |     |     | 605 |     |     |     |
| --- | --- | --- | --- | --- | --- | --- | --- | --- | --- | --- | --- | --- | --- | --- | --- | --- | --- | --- |
| Leu | Lys | Asp | Glu | Asn | Thr | Gly | Tyr | Ile | His | Tyr | Glu | Asp | Thr | Asn | Asn |
|     | 610 |     |     |     |     | 615 |     |     |     |     | 620 |
| Asn | Leu | Glu | Asp | Tyr | Gln | Thr | Ile | Asn | Lys | Arg | Phe | Thr | Thr | Gly | Thr |
| 625 |     |     |     |     | 630 |     |     |     |     | 635 |     |     |     |     | 640 |
| Asp | Leu | Lys | Gly | Val | Tyr | Leu | Ile | Leu | Lys | Ser | Gln | Asn | Gly | Asp | Glu |
|     |     |     |     | 645 |     |     |     |     | 650 |     |     |     |     | 655 |
| Ala | Trp | Gly | Asp | Asn | Phe | Ile | Ile | Leu | Glu | Ile | Ser | Pro | Ser | Glu | Lys |
|     |     |     | 660 |     |     |     |     | 665 |     |     |     |     | 670 |
| Leu | Leu | Ser | Pro | Glu | Leu | Ile | Asn | Thr | Asn | Asn | Trp | Thr | Ser | Thr | Gly |
|     |     | 675 |     |     |     |     | 680 |     |     |     |     | 685 |
| Ser | Thr | Asn | Ile | Ser | Gly | Asn | Thr | Leu | Thr | Leu | Tyr | Gln | Gly | Gly | Arg |
|     | 690 |     |     |     |     | 695 |     |     |     |     | 700 |
| Gly | Ile | Leu | Lys | Gln | Asn | Leu | Gln | Leu | Asp | Ser | Phe | Ser | Thr | Tyr | Arg |
| 705 |     |     |     |     | 710 |     |     |     |     | 715 |     |     |     |     | 720 |
| Val | Tyr | Phe | Ser | Val | Ser | Gly | Asp | Ala | Asn | Val | Arg | Ile | Arg | Asn | Ser |
|     |     |     |     | 725 |     |     |     |     | 730 |     |     |     |     | 735 |
| Arg | Glu | Val | Leu | Phe | Glu | Lys | Arg | Tyr | Met | Ser | Gly | Ala | Lys | Asp | Val |
|     |     |     | 740 |     |     |     |     | 745 |     |     |     |     | 750 |
| Ser | Glu | Met | Phe | Thr | Thr | Lys | Phe | Glu | Lys | Asp | Asn | Phe | Tyr | Ile | Glu |
|     |     | 755 |     |     |     |     | 760 |     |     |     |     | 765 |
| Leu | Ser | Gln | Gly | Asn | Asn | Leu | Tyr | Gly | Gly | Pro | Ile | Val | His | Phe | Tyr |
|     | 770 |     |     |     |     | 775 |     |     |     |     | 780 |
| Asp | Val | Ser | Ile | Lys |
| 785 |

( 2 ) INFORMATION FOR SEQ ID NO:30:

( i ) SEQUENCE CHARACTERISTICS:
    ( A ) LENGTH: 2403 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( i i i ) HYPOTHETICAL: NO ( i x ) FEATURE:
    ( A ) NAME/KEY: misc_feature
    ( B ) LOCATION: 11..2389
    ( D ) OTHER INFORMATION: /note= "maize optimized DNA
      sequence encoding VIP3A(a)"

( x i ) SEQUENCE DESCRIPTION: SEQ ID NO:30:

| | | | | | |
|---|---|---|---|---|---|
| GGATCCACCA | ATGAACATGA | ACAAGAACAA | CACCAAGCTG | AGCACCCGCG | CCCTGCCGAG | 60 |
| CTTCATCGAC | TACTTCAACG | GCATCTACGG | CTTCGCCACC | GGCATCAAGG | ACATCATGAA | 120 |
| CATGATCTTC | AAGACCGACA | CCGGCGGCGA | CCTGACCCTG | GACGAGATCC | TGAAGAACCA | 180 |
| GCAGCTGCTG | AACGACATCA | GCGGCAAGCT | GGACGGCGTG | AACGGCAGCC | TGAACGACCT | 240 |
| GATCGCCCAG | GGCAACCTGA | ACACCGAGCT | GAGCAAGGAG | ATCCTTAAGA | TCGCCAACGA | 300 |
| GCAGAACCAG | GTGCTGAACG | ACGTGAACAA | CAAGCTGGAC | GCCATCAACA | CCATGCTGCG | 360 |
| CGTGTACCTG | CCGAAGATCA | CCAGCATGCT | GAGCGACGTG | ATGAAGCAGA | ACTACGCCCT | 420 |
| GAGCCTGCAG | ATCGAGTACC | TGAGCAAGCA | GCTGCAGGAG | ATCAGCGACA | AGCTGGACAT | 480 |
| CATCAACGTG | AACGTCCTGA | TCAACAGCAC | CCTGACCGAG | ATCACCCCGG | CCTACCAGCG | 540 |
| CATCAAGTAC | GTGAACGAGA | AGTTCGAAGA | GCTGACCTTC | GCCACCGAGA | CCAGCAGCAA | 600 |

| | | | | | |
|---|---|---|---|---|---|
| GGTGAAGAAG | GACGGCAGCC | CGGCCGACAT | CCTGGACGAG | CTGACCGAGC | TGACCGAGCT | 660
| GGCCAAGAGC | GTGACCAAGA | ACGACGTGGA | CGGCTTCGAG | TTCTACCTGA | ACACCTTCCA | 720
| CGACGTGATG | GTGGGCAACA | ACCTGTTCGG | CCGCAGCGCC | CTGAAGACCG | CCAGCGAGCT | 780
| GATCACCAAG | GAGAACGTGA | AGACCAGCGG | CAGCGAGGTG | GGCAACGTGT | ACAACTTCCT | 840
| GATCGTGCTG | ACCGCCCTGC | AGGCCCAGGC | CTTCCTGACC | CTGACCACCT | GTCGCAAGCT | 900
| GCTGGGCCTG | GCCGACATCG | ACTACACCAG | CATCATGAAC | GAGCACTTGA | ACAAGGAGAA | 960
| GGAGGAGTTC | CGCGTGAACA | TCCTGCCGAC | CCTGAGCAAC | ACCTTCAGCA | ACCCGAACTA | 1020
| CGCCAAGGTG | AAGGGCAGCG | ACGAGGACGC | CAAGATGATC | GTGGAGGCTA | AGCCGGGCCA | 1080
| CGCGTTGATC | GGCTTCGAGA | TCAGCAACGA | CAGCATCACC | GTGCTGAAGG | TGTACGAGGC | 1140
| CAAGCTGAAG | CAGAACTACC | AGGTGGACAA | GGACAGCTTG | AGCGAGGTGA | TCTACGGCGA | 1200
| CATGGACAAG | CTGCTGTGTC | CGGACCAGAG | CGAGCAAATC | TACTACACCA | ACAACATCGT | 1260
| GTTCCCGAAC | GAGTACGTGA | TCACCAAGAT | CGACTTCACC | AAGAAGATGA | AGACCCTGCG | 1320
| CTACGAGGTG | ACCGCCAACT | TCTACGACAG | CAGCACCGGC | GAGATCGACC | TGAACAAGAA | 1380
| GAAGGTGGAG | AGCAGCGAGG | CCGAGTACCG | CACCCTGAGC | GCGAACGACG | ACGGCGTCTA | 1440
| CATGCCACTG | GGCGTGATCA | GCGAGACCTT | CCTGACCCCG | ATCAACGGCT | TTGGCCTGCA | 1500
| GGCCGACGAG | AACAGCCGCC | TGATCACCCT | GACCTGTAAG | AGCTACCTGC | GCGAGCTGCT | 1560
| GCTAGCCACC | GACCTGAGCA | ACAAGGAGAC | CAAGCTGATC | GTGCCACCGA | GCGGCTTCAT | 1620
| CAGCAACATC | GTGGAGAACG | GCAGCATCGA | GGAGGACAAC | CTGGAGCCGT | GGAAGGCCAA | 1680
| CAACAAGAAC | GCCTACGTGG | ACCACACCGG | CGGCGTGAAC | GGCACCAAGG | CCCTGTACGT | 1740
| GCACAAGGAC | GGCGGCATCA | GCCAGTTCAT | CGGCGACAAG | CTGAAGCCGA | AGACCGAGTA | 1800
| CGTGATCCAG | TACACCGTGA | AGGGCAAGCC | ATCGATTCAC | CTGAAGGACG | AGAACACCGG | 1860
| CTACATCCAC | TACGAGGACA | CCAACAACAA | CCTGGAGGAC | TACCAGACCA | TCAACAAGCG | 1920
| CTTCACCACC | GGCACCGACC | TGAAGGGCGT | GTACCTGATC | CTGAAGAGCC | AGAACGGCGA | 1980
| CGAGGCCTGG | GGCGACAACT | TCATCATCCT | GGAGATCAGC | CCGAGCGAGA | AGCTGCTGAG | 2040
| CCCGGAGCTG | ATCAACACCA | ACAACTGGAC | CAGCACCGGC | AGCACCAACA | TCAGCGGCAA | 2100
| CACCCTGACC | CTGTACCAGG | GCGGCCGCGG | CATCCTGAAG | CAGAACCTGC | AGCTGGACAG | 2160
| CTTCAGCACC | TACCGCGTGT | ACTTCAGCGT | GAGCGGCGAC | GCCAACGTGC | GCATCCGCAA | 2220
| CAGCCGCGAG | GTGCTGTTCG | AGAAGAGGTA | CATGAGCGGC | GCCAAGGACG | TGAGCGAGAT | 2280
| GTTCACCACC | AAGTTCGAGA | AGGACAACTT | CTACATCGAG | CTGAGCCAGG | GCAACAACCT | 2340
| GTACGGCGGC | CCGATCGTGC | ACTTCTACGA | CGTGAGCATC | AAGTTAACGT | AGAGCTCAGA | 2400
| TCT | | | | | | 2403

( 2 ) INFORMATION FOR SEQ ID NO:31:

( i ) SEQUENCE CHARACTERISTICS:
        ( A ) LENGTH: 2612 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 118..2484
        ( D ) OTHER INFORMATION: /note= "Native DNA sequence
            encoding VIP3A(b) from AB424"

( x i ) SEQUENCE DESCRIPTION: SEQ ID NO:31:

| ATTGAAATTG | ATAAAAGTT | ATGAGTGTTT | AATAATCAGT | AATTACCAAT | AAAGAATTAA | 60 |

| GAATACAAGT | TTACAAGAAA | TAAGTGTTAC | AAAAAATAGC | TGAAAAGGAA | GATGAAC | 117 |

| ATG | AAC | AAG | AAT | AAT | ACT | AAA | TTA | AGC | ACA | AGA | GCC | TTA | CCA | AGT | TTT | 165 |
|---|---|---|---|---|---|---|---|---|---|---|---|---|---|---|---|---|
| Met | Asn | Lys | Asn | Asn | Thr | Lys | Leu | Ser | Thr | Arg | Ala | Leu | Pro | Ser | Phe | |
| 790 | | | | | 795 | | | | 800 | | | | | | 805 | |

| ATT | GAT | TAT | TTC | AAT | GGC | ATT | TAT | GGA | TTT | GCC | ACT | GGT | ATC | AAA | GAC | 213 |
|---|---|---|---|---|---|---|---|---|---|---|---|---|---|---|---|---|
| Ile | Asp | Tyr | Phe | Asn | Gly | Ile | Tyr | Gly | Phe | Ala | Thr | Gly | Ile | Lys | Asp | |
| | | | | 810 | | | | | 815 | | | | | 820 | | |

| ATT | ATG | AAC | ATG | ATT | TTT | AAA | ACG | GAT | ACA | GGT | GGT | GAT | CTA | ACC | CTA | 261 |
|---|---|---|---|---|---|---|---|---|---|---|---|---|---|---|---|---|
| Ile | Met | Asn | Met | Ile | Phe | Lys | Thr | Asp | Thr | Gly | Gly | Asp | Leu | Thr | Leu | |
| | | | | 825 | | | | 830 | | | | | 835 | | | |

| GAC | GAA | ATT | TTA | AAG | AAT | CAG | CAG | CTA | CTA | AAT | GAT | ATT | TCT | GGT | AAA | 309 |
|---|---|---|---|---|---|---|---|---|---|---|---|---|---|---|---|---|
| Asp | Glu | Ile | Leu | Lys | Asn | Gln | Gln | Leu | Leu | Asn | Asp | Ile | Ser | Gly | Lys | |
| | | | 840 | | | | 845 | | | | | 850 | | | | |

| TTG | GAT | GGG | GTG | AAT | GGA | AGC | TTA | AAT | GAT | CTT | ATC | GCA | CAG | GGA | AAC | 357 |
|---|---|---|---|---|---|---|---|---|---|---|---|---|---|---|---|---|
| Leu | Asp | Gly | Val | Asn | Gly | Ser | Leu | Asn | Asp | Leu | Ile | Ala | Gln | Gly | Asn | |
| | | 855 | | | | | 860 | | | | | 865 | | | | |

| TTA | AAT | ACA | GAA | TTA | TCT | AAG | GAA | ATA | TTA | AAA | ATT | GCA | AAT | GAA | CAA | 405 |
|---|---|---|---|---|---|---|---|---|---|---|---|---|---|---|---|---|
| Leu | Asn | Thr | Glu | Leu | Ser | Lys | Glu | Ile | Leu | Lys | Ile | Ala | Asn | Glu | Gln | |
| 870 | | | | | 875 | | | | | 880 | | | | | 885 | |

| AAT | CAA | GTT | TTA | AAT | GAT | GTT | AAT | AAC | AAA | CTC | GAT | GCG | ATA | AAT | ACG | 453 |
|---|---|---|---|---|---|---|---|---|---|---|---|---|---|---|---|---|
| Asn | Gln | Val | Leu | Asn | Asp | Val | Asn | Asn | Lys | Leu | Asp | Ala | Ile | Asn | Thr | |
| | | | | 890 | | | | | 895 | | | | | 900 | | |

| ATG | CTT | CGG | GTA | TAT | CTA | CCT | AAA | ATT | ACC | TCT | ATG | TTG | AGT | GAT | GTA | 501 |
|---|---|---|---|---|---|---|---|---|---|---|---|---|---|---|---|---|
| Met | Leu | Arg | Val | Tyr | Leu | Pro | Lys | Ile | Thr | Ser | Met | Leu | Ser | Asp | Val | |
| | | | 905 | | | | | 910 | | | | | 915 | | | |

| ATG | AAA | CAA | AAT | TAT | GCG | CTA | AGT | CTG | CAA | ATA | GAA | TAC | TTA | AGT | AAA | 549 |
|---|---|---|---|---|---|---|---|---|---|---|---|---|---|---|---|---|
| Met | Lys | Gln | Asn | Tyr | Ala | Leu | Ser | Leu | Gln | Ile | Glu | Tyr | Leu | Ser | Lys | |
| | | 920 | | | | | 925 | | | | | 930 | | | | |

| CAA | TTG | CAA | GAG | ATT | TCT | GAT | AAG | TTG | GAT | ATT | ATT | AAT | GTA | AAT | GTA | 597 |
|---|---|---|---|---|---|---|---|---|---|---|---|---|---|---|---|---|
| Gln | Leu | Gln | Glu | Ile | Ser | Asp | Lys | Leu | Asp | Ile | Ile | Asn | Val | Asn | Val | |
| | 935 | | | | | 940 | | | | | 945 | | | | | |

| CTT | ATT | AAC | TCT | ACA | CTT | ACT | GAA | ATT | ACA | CCT | GCG | TAT | CAA | AGG | ATT | 645 |
|---|---|---|---|---|---|---|---|---|---|---|---|---|---|---|---|---|
| Leu | Ile | Asn | Ser | Thr | Leu | Thr | Glu | Ile | Thr | Pro | Ala | Tyr | Gln | Arg | Ile | |
| 950 | | | | | 955 | | | | | 960 | | | | | 965 | |

| AAA | TAT | GTG | AAC | GAA | AAA | TTT | GAG | GAA | TTA | ACT | TTT | GCT | ACA | GAA | ACT | 693 |
|---|---|---|---|---|---|---|---|---|---|---|---|---|---|---|---|---|
| Lys | Tyr | Val | Asn | Glu | Lys | Phe | Glu | Glu | Leu | Thr | Phe | Ala | Thr | Glu | Thr | |
| | | | | 970 | | | | | 975 | | | | | 980 | | |

| AGT | TCA | AAA | GTA | AAA | AAG | GAT | GGC | TCT | CCT | GCA | GAT | ATT | CGT | GAT | GAG | 741 |
|---|---|---|---|---|---|---|---|---|---|---|---|---|---|---|---|---|
| Ser | Ser | Lys | Val | Lys | Lys | Asp | Gly | Ser | Pro | Ala | Asp | Ile | Arg | Asp | Glu | |
| | | | 985 | | | | | 990 | | | | | 995 | | | |

| TTA | ACT | GAG | TTA | ACT | GAA | CTA | GCG | AAA | AGT | GTA | ACA | AAA | AAT | GAT | GTG | 789 |
|---|---|---|---|---|---|---|---|---|---|---|---|---|---|---|---|---|
| Leu | Thr | Glu | Leu | Thr | Glu | Leu | Ala | Lys | Ser | Val | Thr | Lys | Asn | Asp | Val | |
| | | 1000 | | | | | 1005 | | | | | 1010 | | | | |

| GAT | GGT | TTT | GAA | TTT | TAC | CTT | AAT | ACA | TTC | CAC | GAT | GTA | ATG | GTA | GGA | 837 |
|---|---|---|---|---|---|---|---|---|---|---|---|---|---|---|---|---|
| Asp | Gly | Phe | Glu | Phe | Tyr | Leu | Asn | Thr | Phe | His | Asp | Val | Met | Val | Gly | |
| | 1015 | | | | | 1020 | | | | | 1025 | | | | | |

| AAT | AAT | TTA | TTC | GGG | CGT | TCA | GCT | TTA | AAA | ACT | GCA | TCG | GAA | TTA | ATT | 885 |
|---|---|---|---|---|---|---|---|---|---|---|---|---|---|---|---|---|
| Asn | Asn | Leu | Phe | Gly | Arg | Ser | Ala | Leu | Lys | Thr | Ala | Ser | Glu | Leu | Ile | |
| 1030 | | | | | 1035 | | | | | 1040 | | | | | 1045 | |

| ACT | AAA | GAA | AAT | GTG | AAA | ACA | AGT | GGC | AGT | GAG | GTC | GGA | AAT | GTT | TAT | 933 |
|---|---|---|---|---|---|---|---|---|---|---|---|---|---|---|---|---|
| Thr | Lys | Glu | Asn | Val | Lys | Thr | Ser | Gly | Ser | Glu | Val | Gly | Asn | Val | Tyr | |
| | | | | 1050 | | | | | 1055 | | | | | 1060 | | |

| AAC | TTC | CTA | ATT | GTA | TTA | ACA | GCT | CTG | CAA | GCA | AAA | GCT | TTT | CTT | ACT | 981 |
|---|---|---|---|---|---|---|---|---|---|---|---|---|---|---|---|---|
| Asn | Phe | Leu | Ile | Val | Leu | Thr | Ala | Leu | Gln | Ala | Lys | Ala | Phe | Leu | Thr | |
| | | | 1065 | | | | | 1070 | | | | | 1075 | | | |

| TTA | ACA | CCA | TGC | CGA | AAA | TTA | TTA | GGC | TTA | GCA | GAT | ATT | GAT | TAT | ACT | 1029 |

|  |  |  |  |  |  |  |  |  |  |  |  |  |  |  |  |
|---|---|---|---|---|---|---|---|---|---|---|---|---|---|---|---|
| Leu | Thr | Pro | Cys | Arg | Lys | Leu | Leu | Gly | Leu | Ala | Asp | Ile | Asp | Tyr | Thr |
|  |  | 1080 |  |  | 1085 |  |  |  |  | 1090 |  |  |  |  |  |

| TCT | ATT | ATG | AAT | GAA | CAT | TTA | AAT | AAG | GAA | AAA | GAG | GAA | TTT | AGA | GTA | 1077 |
|---|---|---|---|---|---|---|---|---|---|---|---|---|---|---|---|---|
| Ser | Ile | Met | Asn | Glu | His | Leu | Asn | Lys | Glu | Lys | Glu | Glu | Phe | Arg | Val |  |
|  | 1095 |  |  |  | 1100 |  |  |  | 1105 |  |  |  |  |  |  |  |

| AAC | ATC | CTC | CCT | ACA | CTT | TCT | AAT | ACT | TTT | TCT | AAT | CCT | AAT | TAT | GCA | 1125 |
| Asn | Ile | Leu | Pro | Thr | Leu | Ser | Asn | Thr | Phe | Ser | Asn | Pro | Asn | Tyr | Ala |  |
| 1110 |  |  |  |  | 1115 |  |  |  |  | 1120 |  |  |  |  | 1125 |  |

| AAA | GTT | AAA | GGA | AGT | GAT | GAA | GAT | GCA | AAG | ATG | ATT | GTG | GAA | GCT | AAA | 1173 |
| Lys | Val | Lys | Gly | Ser | Asp | Glu | Asp | Ala | Lys | Met | Ile | Val | Glu | Ala | Lys |  |
|  |  |  |  | 1130 |  |  |  |  | 1135 |  |  |  |  | 1140 |  |  |

| CCA | GGA | CAT | GCA | TTG | ATT | GGG | TTT | GAA | ATT | AGT | AAT | GAT | TCA | ATT | ACA | 1221 |
| Pro | Gly | His | Ala | Leu | Ile | Gly | Phe | Glu | Ile | Ser | Asn | Asp | Ser | Ile | Thr |  |
|  |  |  |  | 1145 |  |  |  | 1150 |  |  |  |  | 1155 |  |  |  |

| GTA | TTA | AAA | GTA | TAT | GAG | GCT | AAG | CTA | AAA | CAA | AAT | TAT | CAA | GTC | GAT | 1269 |
| Val | Leu | Lys | Val | Tyr | Glu | Ala | Lys | Leu | Lys | Gln | Asn | Tyr | Gln | Val | Asp |  |
|  | 1160 |  |  |  |  | 1165 |  |  |  |  | 1170 |  |  |  |  |  |

| AAG | GAT | TCC | TTA | TCG | GAA | GTT | ATT | TAT | GGC | GAT | ATG | GAT | AAA | TTA | TTG | 1317 |
| Lys | Asp | Ser | Leu | Ser | Glu | Val | Ile | Tyr | Gly | Asp | Met | Asp | Lys | Leu | Leu |  |
|  | 1175 |  |  |  |  | 1180 |  |  |  |  | 1185 |  |  |  |  |  |

| TGC | CCA | GAT | CAA | TCT | GGA | CAA | ATC | TAT | TAT | ACA | AAT | AAC | ATA | GTA | TTT | 1365 |
| Cys | Pro | Asp | Gln | Ser | Gly | Gln | Ile | Tyr | Tyr | Thr | Asn | Asn | Ile | Val | Phe |  |
| 1190 |  |  |  |  | 1195 |  |  |  |  | 1200 |  |  |  |  | 1205 |  |

| CCA | AAT | GAA | TAT | GTA | ATT | ACT | AAA | ATT | GAT | TTC | ACT | AAA | AAA | ATG | AAA | 1413 |
| Pro | Asn | Glu | Tyr | Val | Ile | Thr | Lys | Ile | Asp | Phe | Thr | Lys | Lys | Met | Lys |  |
|  |  |  |  | 1210 |  |  |  |  | 1215 |  |  |  |  | 1220 |  |  |

| ACT | TTA | AGA | TAT | GAG | GTA | ACA | GCG | AAT | TTT | TAT | GAT | TCT | TCT | ACA | GGA | 1461 |
| Thr | Leu | Arg | Tyr | Glu | Val | Thr | Ala | Asn | Phe | Tyr | Asp | Ser | Ser | Thr | Gly |  |
|  |  | 1225 |  |  |  |  | 1230 |  |  |  |  | 1235 |  |  |  |  |

| GAA | ATT | GAC | TTA | AAT | AAG | AAA | AAA | GTA | GAA | TCA | AGT | GAA | GCG | GAG | TAT | 1509 |
| Glu | Ile | Asp | Leu | Asn | Lys | Lys | Lys | Val | Glu | Ser | Ser | Glu | Ala | Glu | Tyr |  |
|  | 1240 |  |  |  |  | 1245 |  |  |  |  | 1250 |  |  |  |  |  |

| AGA | ACG | TTA | AGT | GCT | AAT | GAT | GAT | GGG | GTG | TAT | ATG | CCG | TTA | GGT | GTC | 1557 |
| Arg | Thr | Leu | Ser | Ala | Asn | Asp | Asp | Gly | Val | Tyr | Met | Pro | Leu | Gly | Val |  |
|  | 1255 |  |  |  |  | 1260 |  |  |  |  | 1265 |  |  |  |  |  |

| ATC | AGT | GAA | ACA | TTT | TTG | ACT | CCG | ATT | AAT | GGG | TTT | GGC | CTC | CAA | GCT | 1605 |
| Ile | Ser | Glu | Thr | Phe | Leu | Thr | Pro | Ile | Asn | Gly | Phe | Gly | Leu | Gln | Ala |  |
| 1270 |  |  |  |  | 1275 |  |  |  |  | 1280 |  |  |  |  | 1285 |  |

| GAT | GAA | AAT | TCA | AGA | TTA | ATT | ACT | TTA | ACA | TGT | AAA | TCA | TAT | TTA | AGA | 1653 |
| Asp | Glu | Asn | Ser | Arg | Leu | Ile | Thr | Leu | Thr | Cys | Lys | Ser | Tyr | Leu | Arg |  |
|  |  |  |  | 1290 |  |  |  |  | 1295 |  |  |  |  | 1300 |  |  |

| GAA | CTA | CTG | CTA | GCA | ACA | GAC | TTA | AGC | AAT | AAA | GAA | ACT | AAA | TTG | ATC | 1701 |
| Glu | Leu | Leu | Leu | Ala | Thr | Asp | Leu | Ser | Asn | Lys | Glu | Thr | Lys | Leu | Ile |  |
|  |  |  | 1305 |  |  |  |  | 1310 |  |  |  |  | 1315 |  |  |  |

| GTC | CCG | CCA | AGT | GGT | TTT | ATT | AGC | AAT | ATT | GTA | GAG | AAC | GGG | TCC | ATA | 1749 |
| Val | Pro | Pro | Ser | Gly | Phe | Ile | Ser | Asn | Ile | Val | Glu | Asn | Gly | Ser | Ile |  |
|  |  | 1320 |  |  |  |  | 1325 |  |  |  |  | 1330 |  |  |  |  |

| GAA | GAG | GAC | AAT | TTA | GAG | CCG | TGG | AAA | GCA | AAT | AAT | AAG | AAT | GCG | TAT | 1797 |
| Glu | Glu | Asp | Asn | Leu | Glu | Pro | Trp | Lys | Ala | Asn | Asn | Lys | Asn | Ala | Tyr |  |
|  | 1335 |  |  |  |  | 1340 |  |  |  |  | 1345 |  |  |  |  |  |

| GTA | GAT | CAT | ACA | GGC | GGA | GTG | AAT | GGA | ACT | AAA | GCT | TTA | TAT | GTT | CAT | 1845 |
| Val | Asp | His | Thr | Gly | Gly | Val | Asn | Gly | Thr | Lys | Ala | Leu | Tyr | Val | His |  |
| 1350 |  |  |  |  | 1355 |  |  |  |  | 1360 |  |  |  |  | 1365 |  |

| AAG | GAC | GGA | GGA | ATT | TCA | CAA | TTT | ATT | GGA | GAT | AAG | TTA | AAA | CCG | AAA | 1893 |
| Lys | Asp | Gly | Gly | Ile | Ser | Gln | Phe | Ile | Gly | Asp | Lys | Leu | Lys | Pro | Lys |  |
|  |  |  |  | 1370 |  |  |  |  | 1375 |  |  |  |  | 1380 |  |  |

| ACT | GAG | TAT | GTA | ATC | CAA | TAT | ACT | GTT | AAA | GGA | AAA | CCT | TCT | ATT | CAT | 1941 |
| Thr | Glu | Tyr | Val | Ile | Gln | Tyr | Thr | Val | Lys | Gly | Lys | Pro | Ser | Ile | His |  |
|  |  |  | 1385 |  |  |  |  | 1390 |  |  |  |  | 1395 |  |  |  |

| TTA | AAA | GAT | GAA | AAT | ACT | GGA | TAT | ATT | CAT | TAT | GAA | GAT | ACA | AAT | AAT | 1989 |

| | | | | | | | | | | | | | | | |
|---|---|---|---|---|---|---|---|---|---|---|---|---|---|---|---|
| Leu | Lys | Asp | Glu | Asn | Thr | Gly | Tyr | Ile | His | Tyr | Glu | Asp | Thr | Asn | Asn |
| | | 1400 | | | | | 1405 | | | | 1410 | | | | |

| AAT | TTA | GAA | GAT | TAT | CAA | ACT | ATT | AAT | AAA | CGT | TTT | ACT | ACA | GGA | ACT | 2037 |
|---|---|---|---|---|---|---|---|---|---|---|---|---|---|---|---|---|
| Asn | Leu | Glu | Asp | Tyr | Gln | Thr | Ile | Asn | Lys | Arg | Phe | Thr | Thr | Gly | Thr | |
| 1415 | | | | | 1420 | | | | | 1425 | | | | | | |

| GAT | TTA | AAG | GGA | GTG | TAT | TTA | ATT | TTA | AAA | AGT | CAA | AAT | GGA | GAT | GAA | 2085 |
|---|---|---|---|---|---|---|---|---|---|---|---|---|---|---|---|---|
| Asp | Leu | Lys | Gly | Val | Tyr | Leu | Ile | Leu | Lys | Ser | Gln | Asn | Gly | Asp | Glu | |
| 1430 | | | | 1435 | | | | | 1440 | | | | | | 1445 | |

| GCT | TGG | GGA | GAT | AAC | TTT | ATT | ATT | TTG | GAA | ATT | AGT | CCT | TCT | GAA | AAG | 2133 |
|---|---|---|---|---|---|---|---|---|---|---|---|---|---|---|---|---|
| Ala | Trp | Gly | Asp | Asn | Phe | Ile | Ile | Leu | Glu | Ile | Ser | Pro | Ser | Glu | Lys | |
| | | | | 1450 | | | | | 1455 | | | | | 1460 | | |

| TTA | TTA | AGT | CCA | GAA | TTA | ATT | AAT | ACA | AAT | AAT | TGG | ACG | AGT | ACG | GGA | 2181 |
|---|---|---|---|---|---|---|---|---|---|---|---|---|---|---|---|---|
| Leu | Leu | Ser | Pro | Glu | Leu | Ile | Asn | Thr | Asn | Asn | Trp | Thr | Ser | Thr | Gly | |
| | | | 1465 | | | | | 1470 | | | | | 1475 | | | |

| TCA | ACT | AAT | ATT | AGC | GGT | AAT | ACA | CTC | ACT | CTT | TAT | CAG | GGA | GGA | CGA | 2229 |
|---|---|---|---|---|---|---|---|---|---|---|---|---|---|---|---|---|
| Ser | Thr | Asn | Ile | Ser | Gly | Asn | Thr | Leu | Thr | Leu | Tyr | Gln | Gly | Gly | Arg | |
| | | 1480 | | | | | 1485 | | | | | 1490 | | | | |

| GGG | ATT | CTA | AAA | CAA | AAC | CTT | CAA | TTA | GAT | AGT | TTT | TCA | ACT | TAT | AGA | 2277 |
|---|---|---|---|---|---|---|---|---|---|---|---|---|---|---|---|---|
| Gly | Ile | Leu | Lys | Gln | Asn | Leu | Gln | Leu | Asp | Ser | Phe | Ser | Thr | Tyr | Arg | |
| 1495 | | | | | 1500 | | | | | 1505 | | | | | | |

| GTG | TAT | TTC | TCT | GTG | TCC | GGA | GAT | GCT | AAT | GTA | AGG | ATT | AGA | AAT | TCT | 2325 |
|---|---|---|---|---|---|---|---|---|---|---|---|---|---|---|---|---|
| Val | Tyr | Phe | Ser | Val | Ser | Gly | Asp | Ala | Asn | Val | Arg | Ile | Arg | Asn | Ser | |
| 1510 | | | | 1515 | | | | | 1520 | | | | | | 1525 | |

| AGG | GAA | GTG | TTA | TTT | GAA | AAA | AGA | TAT | ATG | AGC | GGT | GCT | AAA | GAT | GTT | 2373 |
|---|---|---|---|---|---|---|---|---|---|---|---|---|---|---|---|---|
| Arg | Glu | Val | Leu | Phe | Glu | Lys | Arg | Tyr | Met | Ser | Gly | Ala | Lys | Asp | Val | |
| | | | | 1530 | | | | | 1535 | | | | | 1540 | | |

| TCT | GAA | ATG | TTC | ACT | ACA | AAA | TTT | GAG | AAA | GAT | AAC | TTC | TAT | ATA | GAG | 2421 |
|---|---|---|---|---|---|---|---|---|---|---|---|---|---|---|---|---|
| Ser | Glu | Met | Phe | Thr | Thr | Lys | Phe | Glu | Lys | Asp | Asn | Phe | Tyr | Ile | Glu | |
| | | | | 1545 | | | | | 1550 | | | | | 1555 | | |

| CTT | TCT | CAA | GGG | AAT | AAT | TTA | TAT | GGT | GGT | CCT | ATT | GTA | CAT | TTT | TAC | 2469 |
|---|---|---|---|---|---|---|---|---|---|---|---|---|---|---|---|---|
| Leu | Ser | Gln | Gly | Asn | Asn | Leu | Tyr | Gly | Gly | Pro | Ile | Val | His | Phe | Tyr | |
| | | | 1560 | | | | | 1565 | | | | | 1570 | | | |

| GAT | GTC | TCT | ATT | AAG | TAAGATCGGG | ATCTAATATT | AACAGTTTTT | AGAAGCTAAT | 2524 |
|---|---|---|---|---|---|---|---|---|---|
| Asp | Val | Ser | Ile | Lys | | | | | |
| | | 1575 | | | | | | | |

TCTTGTATAA TGTCCTTGAT TATGGAAAAA CACAATTTTG TTTGCTAAGA TGTATATATA 2584

GCTCACTCAT TAAAAGGCAA TCAAGCTT 2612

( 2 ) INFORMATION FOR SEQ ID NO:32:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| | | | | | | | | | | | | | | | |
|---|---|---|---|---|---|---|---|---|---|---|---|---|---|---|---|
| Met | Asn | Lys | Asn | Asn | Thr | Lys | Leu | Ser | Thr | Arg | Ala | Leu | Pro | Ser | Phe |
| 1 | | | | 5 | | | | | 10 | | | | | 15 | |

| Ile | Asp | Tyr | Phe | Asn | Gly | Ile | Tyr | Gly | Phe | Ala | Thr | Gly | Ile | Lys | Asp |
|---|---|---|---|---|---|---|---|---|---|---|---|---|---|---|---|
| | | | 20 | | | | | 25 | | | | | 30 | | |

| Ile | Met | Asn | Met | Ile | Phe | Lys | Thr | Asp | Thr | Gly | Gly | Asp | Leu | Thr | Leu |
|---|---|---|---|---|---|---|---|---|---|---|---|---|---|---|---|
| | | | 35 | | | | | 40 | | | | | 45 | | |

| Asp | Glu | Ile | Leu | Lys | Asn | Gln | Gln | Leu | Leu | Asn | Asp | Ile | Ser | Gly | Lys |
|---|---|---|---|---|---|---|---|---|---|---|---|---|---|---|---|
| | 50 | | | | | 55 | | | | | 60 | | | | |

| Leu | Asp | Gly | Val | Asn | Gly | Ser | Leu | Asn | Asp | Leu | Ile | Ala | Gln | Gly | Asn |
|---|---|---|---|---|---|---|---|---|---|---|---|---|---|---|---|
| 65 | | | | | 70 | | | | | 75 | | | | | 80 |

| Leu | Asn | Thr | Glu | Leu | Ser | Lys | Glu | Ile | Leu | Lys | Ile | Ala | Asn | Glu | Gln |
|---|---|---|---|---|---|---|---|---|---|---|---|---|---|---|---|
| | | | | 85 | | | | | 90 | | | | | 95 | |

| | | | | | | | | | | | | | |
|---|---|---|---|---|---|---|---|---|---|---|---|---|---|
| Asn | Gln | Val | Leu | Asn | Asp | Val | Asn | Asn | Lys | Leu | Asp | Ala | Ile | Asn | Thr |
| | | | 100 | | | | 105 | | | | | 110 | | | |
| Met | Leu | Arg | Val | Tyr | Leu | Pro | Lys | Ile | Thr | Ser | Met | Leu | Ser | Asp | Val |
| | | 115 | | | | 120 | | | | | 125 | | | | |
| Met | Lys | Gln | Asn | Tyr | Ala | Leu | Ser | Leu | Gln | Ile | Glu | Tyr | Leu | Ser | Lys |
| | 130 | | | | | 135 | | | | | 140 | | | | |
| Gln | Leu | Gln | Glu | Ile | Ser | Asp | Lys | Leu | Asp | Ile | Ile | Asn | Val | Asn | Val |
| 145 | | | | | 150 | | | | | 155 | | | | | 160 |
| Leu | Ile | Asn | Ser | Thr | Leu | Thr | Glu | Ile | Thr | Pro | Ala | Tyr | Gln | Arg | Ile |
| | | | | 165 | | | | | 170 | | | | | 175 | |
| Lys | Tyr | Val | Asn | Glu | Lys | Phe | Glu | Glu | Leu | Thr | Phe | Ala | Thr | Glu | Thr |
| | | | 180 | | | | | 185 | | | | | 190 | | |
| Ser | Ser | Lys | Val | Lys | Lys | Asp | Gly | Ser | Pro | Ala | Asp | Ile | Arg | Asp | Glu |
| | | 195 | | | | | 200 | | | | | 205 | | | |
| Leu | Thr | Glu | Leu | Thr | Glu | Leu | Ala | Lys | Ser | Val | Thr | Lys | Asn | Asp | Val |
| | 210 | | | | | 215 | | | | | 220 | | | | |
| Asp | Gly | Phe | Glu | Phe | Tyr | Leu | Asn | Thr | Phe | His | Asp | Val | Met | Val | Gly |
| 225 | | | | | 230 | | | | | 235 | | | | | 240 |
| Asn | Asn | Leu | Phe | Gly | Arg | Ser | Ala | Leu | Lys | Thr | Ala | Ser | Glu | Leu | Ile |
| | | | | 245 | | | | | 250 | | | | | 255 | |
| Thr | Lys | Glu | Asn | Val | Lys | Thr | Ser | Gly | Ser | Glu | Val | Gly | Asn | Val | Tyr |
| | | | 260 | | | | | 265 | | | | | 270 | | |
| Asn | Phe | Leu | Ile | Val | Leu | Thr | Ala | Leu | Gln | Ala | Lys | Ala | Phe | Leu | Thr |
| | | 275 | | | | | 280 | | | | | 285 | | | |
| Leu | Thr | Pro | Cys | Arg | Lys | Leu | Leu | Gly | Leu | Ala | Asp | Ile | Asp | Tyr | Thr |
| | 290 | | | | | 295 | | | | | 300 | | | | |
| Ser | Ile | Met | Asn | Glu | His | Leu | Asn | Lys | Glu | Lys | Glu | Glu | Phe | Arg | Val |
| 305 | | | | | 310 | | | | | 315 | | | | | 320 |
| Asn | Ile | Leu | Pro | Thr | Leu | Ser | Asn | Thr | Phe | Ser | Asn | Pro | Asn | Tyr | Ala |
| | | | | 325 | | | | | 330 | | | | | 335 | |
| Lys | Val | Lys | Gly | Ser | Asp | Glu | Asp | Ala | Lys | Met | Ile | Val | Glu | Ala | Lys |
| | | | 340 | | | | | 345 | | | | | 350 | | |
| Pro | Gly | His | Ala | Leu | Ile | Gly | Phe | Glu | Ile | Ser | Asn | Asp | Ser | Ile | Thr |
| | | 355 | | | | | 360 | | | | | 365 | | | |
| Val | Leu | Lys | Val | Tyr | Glu | Ala | Lys | Leu | Lys | Gln | Asn | Tyr | Gln | Val | Asp |
| | 370 | | | | | 375 | | | | | 380 | | | | |
| Lys | Asp | Ser | Leu | Ser | Glu | Val | Ile | Tyr | Gly | Asp | Met | Asp | Lys | Leu | Leu |
| 385 | | | | | 390 | | | | | 395 | | | | | 400 |
| Cys | Pro | Asp | Gln | Ser | Gly | Gln | Ile | Tyr | Tyr | Thr | Asn | Asn | Ile | Val | Phe |
| | | | | 405 | | | | | 410 | | | | | 415 | |
| Pro | Asn | Glu | Tyr | Val | Ile | Thr | Lys | Ile | Asp | Phe | Thr | Lys | Lys | Met | Lys |
| | | | 420 | | | | | 425 | | | | | 430 | | |
| Thr | Leu | Arg | Tyr | Glu | Val | Thr | Ala | Asn | Phe | Tyr | Asp | Ser | Ser | Thr | Gly |
| | | 435 | | | | | 440 | | | | | 445 | | | |
| Glu | Ile | Asp | Leu | Asn | Lys | Lys | Lys | Val | Glu | Ser | Ser | Glu | Ala | Glu | Tyr |
| | 450 | | | | | 455 | | | | | 460 | | | | |
| Arg | Thr | Leu | Ser | Ala | Asn | Asp | Asp | Gly | Val | Tyr | Met | Pro | Leu | Gly | Val |
| 465 | | | | | 470 | | | | | 475 | | | | | 480 |
| Ile | Ser | Glu | Thr | Phe | Leu | Thr | Pro | Ile | Asn | Gly | Phe | Gly | Leu | Gln | Ala |
| | | | | 485 | | | | | 490 | | | | | 495 | |
| Asp | Glu | Asn | Ser | Arg | Leu | Ile | Thr | Leu | Thr | Cys | Lys | Ser | Tyr | Leu | Arg |
| | | | 500 | | | | | 505 | | | | | 510 | | |
| Glu | Leu | Leu | Leu | Ala | Thr | Asp | Leu | Ser | Asn | Lys | Glu | Thr | Lys | Leu | Ile |

| | | | | 515 | | | | | 520 | | | | | 525 | |
|---|---|---|---|---|---|---|---|---|---|---|---|---|---|---|---|
| Val | Pro 530 | Pro | Ser | Gly | Phe | Ile 535 | Ser | Asn | Ile | Val | Glu 540 | Asn | Gly | Ser | Ile |
| Glu 545 | Glu | Asp | Asn | Leu | Glu 550 | Pro | Trp | Lys | Ala | Asn 555 | Asn | Lys | Asn | Ala | Tyr 560 |
| Val | Asp | His | Thr | Gly 565 | Gly | Val | Asn | Gly | Thr 570 | Lys | Ala | Leu | Tyr | Val 575 | His |
| Lys | Asp | Gly | Gly 580 | Ile | Ser | Gln | Phe | Ile 585 | Gly | Asp | Lys | Leu | Lys 590 | Pro | Lys |
| Thr | Glu | Tyr 595 | Val | Ile | Gln | Tyr | Thr 600 | Val | Lys | Gly | Lys | Pro 605 | Ser | Ile | His |
| Leu | Lys 610 | Asp | Glu | Asn | Thr | Gly 615 | Tyr | Ile | His | Tyr | Glu 620 | Asp | Thr | Asn | Asn |
| Asn 625 | Leu | Glu | Asp | Tyr | Gln 630 | Thr | Ile | Asn | Lys | Arg 635 | Phe | Thr | Thr | Gly | Thr 640 |
| Asp | Leu | Lys | Gly | Val 645 | Tyr | Leu | Ile | Leu | Lys 650 | Ser | Gln | Asn | Gly | Asp 655 | Glu |
| Ala | Trp | Gly | Asp 660 | Asn | Phe | Ile | Ile | Leu 665 | Glu | Ile | Ser | Pro | Ser 670 | Glu | Lys |
| Leu | Leu | Ser 675 | Pro | Glu | Leu | Ile | Asn 680 | Thr | Asn | Asn | Trp | Thr 685 | Ser | Thr | Gly |
| Ser | Thr 690 | Asn | Ile | Ser | Gly | Asn 695 | Thr | Leu | Thr | Leu | Tyr 700 | Gln | Gly | Gly | Arg |
| Gly 705 | Ile | Leu | Lys | Gln | Asn 710 | Leu | Gln | Leu | Asp | Ser 715 | Phe | Ser | Thr | Tyr | Arg 720 |
| Val | Tyr | Phe | Ser | Val 725 | Ser | Gly | Asp | Ala | Asn 730 | Val | Arg | Ile | Arg | Asn 735 | Ser |
| Arg | Glu | Val | Leu 740 | Phe | Glu | Lys | Arg | Tyr 745 | Met | Ser | Gly | Ala | Lys 750 | Asp | Val |
| Ser | Glu | Met 755 | Phe | Thr | Thr | Lys | Phe 760 | Glu | Lys | Asp | Asn | Phe 765 | Tyr | Ile | Glu |
| Leu | Ser 770 | Gln | Gly | Asn | Asn | Leu 775 | Tyr | Gly | Gly | Pro | Ile 780 | Val | His | Phe | Tyr |
| Asp 785 | Val | Ser | Ile | Lys | | | | | | | | | | | |

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make pCIB5526"

( i i i ) HYPOTHETICAL: NO ( x i ) SEQUENCE DESCRIPTION: SEQ ID NO:33:

GGATCCACCA TGAAGACCAA CCAGATCAGC        30

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (i i) MOLECULE TYPE: other nucleic acid
    (A) DESCRIPTION: /desc = "reverse primer used to make pCIB5526"

(i i i) HYPOTHETICAL: NO (x i) SEQUENCE DESCRIPTION: SEQ ID NO:34:

AAGCTTCAGC TCCTT                                                                                           15

(2) INFORMATION FOR SEQ ID NO:35:

(i) SEQUENCE CHARACTERISTICS:
        (A) LENGTH: 2576 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(i i i) HYPOTHETICAL: NO (i x) FEATURE:
        (A) NAME/KEY: CDS
        (B) LOCATION: 9..2564
        (D) OTHER INFORMATION: /note= "Maize optimized sequence
            encoding VIP1A(a) with the Bacillus secretion signal
            removed as contained in pCIB5526"

(x i) SEQUENCE DESCRIPTION: SEQ ID NO:35:

```
GATCCACC ATG AAG ACC AAC CAG ATC AGC ACC ACC CAG AAG AAC CAG CAG      50
         Met Lys Thr Asn Gln Ile Ser Thr Thr Gln Lys Asn Gln Gln
                     825                 830                 835

AAG GAG ATG GAC CGC AAG GGC CTG CTG GGC TAC TAC TTC AAG GGC AAG       98
Lys Glu Met Asp Arg Lys Gly Leu Leu Gly Tyr Tyr Phe Lys Gly Lys
                840                 845                 850

GAC TTC AGC AAC CTG ACC ATG TTC GCC CCC ACG CGT GAC AGC ACC CTG      146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG      194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC      242
Glu Tyr Gln Ser Ile Arg Trp Ile Gly Leu Ile Gln Ser Lys Glu Thr
    885                 890                 895

GGC GAC TTC ACC TTC AAC CTG AGC GAG GAC GAG CAG GCC ATC ATC GAG      290
Gly Asp Phe Thr Phe Asn Leu Ser Glu Asp Glu Gln Ala Ile Ile Glu
900                 905                 910                 915

ATC AAC GGC AAG ATC ATC AGC AAC AAG GGC AAG GAG AAG CAG GTG GTG      338
Ile Asn Gly Lys Ile Ile Ser Asn Lys Gly Lys Glu Lys Gln Val Val
                920                 925                 930

CAC CTG GAG AAG GGC AAG CTG GTG CCC ATC AAG ATC GAG TAC CAG AGC      386
His Leu Glu Lys Gly Lys Leu Val Pro Ile Lys Ile Glu Tyr Gln Ser
            935                 940                 945

GAC ACC AAG TTC AAC ATC GAC AGC AAG ACC TTC AAG GAG CTG AAG CTT      434
Asp Thr Lys Phe Asn Ile Asp Ser Lys Thr Phe Lys Glu Leu Lys Leu
        950                 955                 960

TTC AAG ATC GAC AGC CAG AAC CAG CCC CAG CAG GTG CAG CAG GAC GAG      482
Phe Lys Ile Asp Ser Gln Asn Gln Pro Gln Gln Val Gln Gln Asp Glu
    965                 970                 975

CTG CGC AAC CCC GAG TTC AAC AAG AAG GAG AGC CAG GAG TTC CTG GCC      530
Leu Arg Asn Pro Glu Phe Asn Lys Lys Glu Ser Gln Glu Phe Leu Ala
980                 985                 990                 995

AAG CCC AGC AAG ATC AAC CTG TTC ACC CAG CAG ATG AAG CGC GAG ATC      578
Lys Pro Ser Lys Ile Asn Leu Phe Thr Gln Gln Met Lys Arg Glu Ile
```

-continued

|   |   |   |   |   |   |   |   |   |   |   |   |   |   |   |   |
|---|---|---|---|---|---|---|---|---|---|---|---|---|---|---|---|
|   |   |   |   |   | 1000 |   |   |   |   | 1005 |   |   |   |   | 1010 |

```
GAC GAG GAC ACC GAC ACC GAC GGC GAC AGC ATC CCC GAC CTG TGG GAG        626
Asp Glu Asp Thr Asp Thr Asp Gly Asp Ser Ile Pro Asp Leu Trp Glu
        1015            1020            1025

GAG AAC GGC TAC ACC ATC CAG AAC CGC ATC GCC GTG AAG TGG GAC GAC        674
Glu Asn Gly Tyr Thr Ile Gln Asn Arg Ile Ala Val Lys Trp Asp Asp
        1030            1035            1040

AGC CTG GCT AGC AAG GGC TAC ACC AAG TTC GTG AGC AAC CCC CTG GAG        722
Ser Leu Ala Ser Lys Gly Tyr Thr Lys Phe Val Ser Asn Pro Leu Glu
        1045            1050            1055

AGC CAC ACC GTG GGC GAC CCC TAC ACC GAC TAC GAG AAG GCC GCC CGC        770
Ser His Thr Val Gly Asp Pro Tyr Thr Asp Tyr Glu Lys Ala Ala Arg
1060            1065            1070            1075

GAC CTG GAC CTG AGC AAC GCC AAG GAG ACC TTC AAC CCC CTG GTG GCC        818
Asp Leu Asp Leu Ser Asn Ala Lys Glu Thr Phe Asn Pro Leu Val Ala
            1080            1085            1090

GCC TTC CCC AGC GTG AAC GTG AGC ATG GAG AAG GTG ATC CTG AGC CCC        866
Ala Phe Pro Ser Val Asn Val Ser Met Glu Lys Val Ile Leu Ser Pro
        1095            1100            1105

AAC GAG AAC CTG AGC AAC AGC GTG GAG AGC CAC TCG AGC ACC AAC TGG        914
Asn Glu Asn Leu Ser Asn Ser Val Glu Ser His Ser Ser Thr Asn Trp
    1110            1115            1120

AGC TAC ACC AAC ACC GAG GGC GCC AGC GTG GAG GCC GGC ATC GGT CCC        962
Ser Tyr Thr Asn Thr Glu Gly Ala Ser Val Glu Ala Gly Ile Gly Pro
        1125            1130            1135

AAG GGC ATC AGC TTC GGC GTG AGC GTG AAC TAC CAG CAC AGC GAG ACC       1010
Lys Gly Ile Ser Phe Gly Val Ser Val Asn Tyr Gln His Ser Glu Thr
1140            1145            1150            1155

GTG GCC CAG GAG TGG GGC ACC AGC ACC GGC AAC ACC AGC CAG TTC AAC       1058
Val Ala Gln Glu Trp Gly Thr Ser Thr Gly Asn Thr Ser Gln Phe Asn
            1160            1165            1170

ACC GCC AGC GCC GGC TAC CTG AAC GCC AAC GTG CGC TAC AAC AAC GTG       1106
Thr Ala Ser Ala Gly Tyr Leu Asn Ala Asn Val Arg Tyr Asn Asn Val
        1175            1180            1185

GGC ACC GGC GCC ATC TAC GAC GTG AAG CCC ACC ACC AGC TTC GTG CTG       1154
Gly Thr Gly Ala Ile Tyr Asp Val Lys Pro Thr Thr Ser Phe Val Leu
    1190            1195            1200

AAC AAC GAC ACC ATC GCC ACC ATC ACC GCC AAG TCG AAT TCC ACC GCC       1202
Asn Asn Asp Thr Ile Ala Thr Ile Thr Ala Lys Ser Asn Ser Thr Ala
        1205            1210            1215

CTG AAC ATC AGC CCC GGC GAG AGC TAC CCC AAG AAG GGC CAG AAC GGC       1250
Leu Asn Ile Ser Pro Gly Glu Ser Tyr Pro Lys Lys Gly Gln Asn Gly
1220            1225            1230            1235

ATC GCC ATC ACC AGC ATG GAC GAC TTC AAC AGC CAC CCC ATC ACC CTG       1298
Ile Ala Ile Thr Ser Met Asp Asp Phe Asn Ser His Pro Ile Thr Leu
            1240            1245            1250

AAC AAG AAG CAG GTG GAC AAC CTG CTG AAC AAC AAG CCC ATG ATG CTG       1346
Asn Lys Lys Gln Val Asp Asn Leu Leu Asn Asn Lys Pro Met Met Leu
        1255            1260            1265

GAG ACC AAC CAG ACC GAC GGC GTC TAC AAG ATC AAG GAC ACC CAC GGC       1394
Glu Thr Asn Gln Thr Asp Gly Val Tyr Lys Ile Lys Asp Thr His Gly
    1270            1275            1280

AAC ATC GTG ACG GGC GGC GAG TGG AAC GGC GTG ATC CAG CAG ATC AAG       1442
Asn Ile Val Thr Gly Gly Glu Trp Asn Gly Val Ile Gln Gln Ile Lys
        1285            1290            1295

GCC AAG ACC GCC AGC ATC ATC GTC GAC GAC GGC GAG CGC GTG GCC GAG       1490
Ala Lys Thr Ala Ser Ile Ile Val Asp Asp Gly Glu Arg Val Ala Glu
1300            1305            1310            1315

AAG CGC GTG GCC GCC AAG GAC TAC GAG AAC CCC GAG GAC AAG ACC CCC       1538
Lys Arg Val Ala Ala Lys Asp Tyr Glu Asn Pro Glu Asp Lys Thr Pro
```

|  |  |  |  |  |  |  |  |  |  |  |  |  |  |  |  |  |
|---|---|---|---|---|---|---|---|---|---|---|---|---|---|---|---|---|
|  |  |  | 1320 |  |  |  |  | 1325 |  |  |  |  |  | 1330 |  |  |
| AGC | CTG | ACC | CTG | AAG | GAC | GCC | CTG | AAG | CTG | AGC | TAC | CCC | GAC | GAG | ATC | 1586 |
| Ser | Leu | Thr | Leu | Lys | Asp | Ala | Leu | Lys | Leu | Ser | Tyr | Pro | Asp | Glu | Ile |  |
|  |  |  | 1335 |  |  |  |  | 1340 |  |  |  |  |  | 1345 |  |  |
| AAG | GAG | ATC | GAG | GGC | TTG | CTG | TAC | TAC | AAG | AAC | AAG | CCC | ATC | TAC | GAG | 1634 |
| Lys | Glu | Ile | Glu | Gly | Leu | Leu | Tyr | Tyr | Lys | Asn | Lys | Pro | Ile | Tyr | Glu |  |
|  |  |  | 1350 |  |  |  |  | 1355 |  |  |  |  |  | 1360 |  |  |
| AGC | AGC | GTG | ATG | ACC | TAT | CTA | GAC | GAG | AAC | ACC | GCC | AAG | GAG | GTG | ACC | 1682 |
| Ser | Ser | Val | Met | Thr | Tyr | Leu | Asp | Glu | Asn | Thr | Ala | Lys | Glu | Val | Thr |  |
|  |  |  | 1365 |  |  |  |  | 1370 |  |  |  |  |  | 1375 |  |  |
| AAG | CAG | CTG | AAC | GAC | ACC | ACC | GGC | AAG | TTC | AAG | GAC | GTG | AGC | CAC | CTG | 1730 |
| Lys | Gln | Leu | Asn | Asp | Thr | Thr | Gly | Lys | Phe | Lys | Asp | Val | Ser | His | Leu |  |
| 1380 |  |  |  |  | 1385 |  |  |  |  | 1390 |  |  |  |  | 1395 |  |
| TAC | GAC | GTG | AAG | CTG | ACC | CCC | AAG | ATG | AAC | GTG | ACC | ATC | AAG | CTG | AGC | 1778 |
| Tyr | Asp | Val | Lys | Leu | Thr | Pro | Lys | Met | Asn | Val | Thr | Ile | Lys | Leu | Ser |  |
|  |  |  | 1400 |  |  |  |  | 1405 |  |  |  |  |  | 1410 |  |  |
| ATC | CTG | TAC | GAC | AAC | GCC | GAG | AGC | AAC | GAC | AAC | AGC | ATC | GGC | AAG | TGG | 1826 |
| Ile | Leu | Tyr | Asp | Asn | Ala | Glu | Ser | Asn | Asp | Asn | Ser | Ile | Gly | Lys | Trp |  |
|  |  |  | 1415 |  |  |  |  | 1420 |  |  |  |  |  | 1425 |  |  |
| ACC | AAC | ACC | AAC | ATC | GTG | AGC | GGC | GGC | AAC | AAC | GGC | AAG | AAG | CAG | TAC | 1874 |
| Thr | Asn | Thr | Asn | Ile | Val | Ser | Gly | Gly | Asn | Asn | Gly | Lys | Lys | Gln | Tyr |  |
|  |  |  | 1430 |  |  |  |  | 1435 |  |  |  |  |  | 1440 |  |  |
| AGC | AGC | AAC | AAC | CCC | GAC | GCC | AAC | CTG | ACC | CTG | AAC | ACC | GAC | GCC | CAG | 1922 |
| Ser | Ser | Asn | Asn | Pro | Asp | Ala | Asn | Leu | Thr | Leu | Asn | Thr | Asp | Ala | Gln |  |
|  |  |  | 1445 |  |  |  |  | 1450 |  |  |  |  |  | 1455 |  |  |
| GAG | AAG | CTG | AAC | AAG | AAC | CGC | GAC | TAC | TAC | ATC | AGC | CTG | TAC | ATG | AAG | 1970 |
| Glu | Lys | Leu | Asn | Lys | Asn | Arg | Asp | Tyr | Tyr | Ile | Ser | Leu | Tyr | Met | Lys |  |
| 1460 |  |  |  |  | 1465 |  |  |  |  | 1470 |  |  |  |  | 1475 |  |
| AGC | GAG | AAG | AAC | ACC | CAG | TGC | GAG | ATC | ACC | ATC | GAC | GGC | GAG | ATA | TAC | 2018 |
| Ser | Glu | Lys | Asn | Thr | Gln | Cys | Glu | Ile | Thr | Ile | Asp | Gly | Glu | Ile | Tyr |  |
|  |  |  | 1480 |  |  |  |  | 1485 |  |  |  |  |  | 1490 |  |  |
| CCC | ATC | ACC | ACC | AAG | ACC | GTG | AAC | GTG | AAC | AAG | GAC | AAC | TAC | AAG | CGC | 2066 |
| Pro | Ile | Thr | Thr | Lys | Thr | Val | Asn | Val | Asn | Lys | Asp | Asn | Tyr | Lys | Arg |  |
|  |  |  | 1495 |  |  |  |  | 1500 |  |  |  |  |  | 1505 |  |  |
| CTG | GAC | ATC | ATC | GCC | CAC | AAC | ATC | AAG | AGC | AAC | CCC | ATC | AGC | AGC | CTG | 2114 |
| Leu | Asp | Ile | Ile | Ala | His | Asn | Ile | Lys | Ser | Asn | Pro | Ile | Ser | Ser | Leu |  |
|  |  |  | 1510 |  |  |  |  | 1515 |  |  |  |  |  | 1520 |  |  |
| CAC | ATC | AAG | ACC | AAC | GAC | GAG | ATC | ACC | CTG | TTC | TGG | GAC | GAC | ATA | TCG | 2162 |
| His | Ile | Lys | Thr | Asn | Asp | Glu | Ile | Thr | Leu | Phe | Trp | Asp | Asp | Ile | Ser |  |
|  |  |  | 1525 |  |  |  |  | 1530 |  |  |  |  |  | 1535 |  |  |
| ATT | ACC | GAC | GTC | GCC | AGC | ATC | AAG | CCC | GAG | AAC | CTG | ACC | GAC | AGC | GAG | 2210 |
| Ile | Thr | Asp | Val | Ala | Ser | Ile | Lys | Pro | Glu | Asn | Leu | Thr | Asp | Ser | Glu |  |
| 1540 |  |  |  |  | 1545 |  |  |  |  | 1550 |  |  |  |  | 1555 |  |
| ATC | AAG | CAG | ATA | TAC | AGT | CGC | TAC | GGC | ATC | AAG | CTG | GAG | GAC | GGC | ATC | 2258 |
| Ile | Lys | Gln | Ile | Tyr | Ser | Arg | Tyr | Gly | Ile | Lys | Leu | Glu | Asp | Gly | Ile |  |
|  |  |  | 1560 |  |  |  |  | 1565 |  |  |  |  |  | 1570 |  |  |
| CTG | ATC | GAC | AAG | AAA | GGC | GGC | ATC | CAC | TAC | GGC | GAG | TTC | ATC | AAC | GAG | 2306 |
| Leu | Ile | Asp | Lys | Lys | Gly | Gly | Ile | His | Tyr | Gly | Glu | Phe | Ile | Asn | Glu |  |
|  |  |  | 1575 |  |  |  |  | 1580 |  |  |  |  |  | 1585 |  |  |
| GCC | AGC | TTC | AAC | ATC | GAG | CCC | CTG | CAG | AAC | TAC | GTG | ACC | AAG | TAC | GAG | 2354 |
| Ala | Ser | Phe | Asn | Ile | Glu | Pro | Leu | Gln | Asn | Tyr | Val | Thr | Lys | Tyr | Glu |  |
|  |  |  | 1590 |  |  |  |  | 1595 |  |  |  |  |  | 1600 |  |  |
| GTG | ACC | TAC | AGC | AGC | GAG | CTG | GGC | CCC | AAC | GTG | AGC | GAC | ACC | CTG | GAG | 2402 |
| Val | Thr | Tyr | Ser | Ser | Glu | Leu | Gly | Pro | Asn | Val | Ser | Asp | Thr | Leu | Glu |  |
|  |  |  | 1605 |  |  |  |  | 1610 |  |  |  |  |  | 1615 |  |  |
| AGC | GAC | AAG | ATT | TAC | AAG | GAC | GGC | ACC | ATC | AAG | TTC | GAC | TTC | ACC | AAG | 2450 |
| Ser | Asp | Lys | Ile | Tyr | Lys | Asp | Gly | Thr | Ile | Lys | Phe | Asp | Phe | Thr | Lys |  |
| 1620 |  |  |  |  | 1625 |  |  |  |  | 1630 |  |  |  |  | 1635 |  |
| TAC | AGC | AAG | AAC | GAG | CAG | GGC | CTG | TTC | TAC | GAC | AGC | GGC | CTG | AAC | TGG | 2498 |
| Tyr | Ser | Lys | Asn | Glu | Gln | Gly | Leu | Phe | Tyr | Asp | Ser | Gly | Leu | Asn | Trp |  |

|     |     |     |     |     |     |     |     |     |     |     |     |     |     |     |     |     |
|---|---|---|---|---|---|---|---|---|---|---|---|---|---|---|---|---|
|     |     |     |     | 1640 |     |     |     |     | 1645 |     |     |     |     | 1650 |     |     |
| GAC | TTC | AAG | ATC | AAC | GCC | ATC | ACC | TAC | GAC | GGC | AAG | GAG | ATG | AAC | GTG | 2546 |
| Asp | Phe | Lys | Ile | Asn | Ala | Ile | Thr | Tyr | Asp | Gly | Lys | Glu | Met | Asn | Val |     |
|     |     |     | 1655 |     |     |     | 1660 |     |     |     |     | 1665 |     |     |     |     |
| TTC | CAC | CGC | TAC | AAC | AAG | TAGATCTGAG | CT |     |     |     |     |     |     |     |     | 2576 |
| Phe | His | Arg | Tyr | Asn | Lys |     |     |     |     |     |     |     |     |     |     |     |
|     |     |     | 1670 |     |     |     |     |     |     |     |     |     |     |     |     |     |

( 2 ) INFORMATION FOR SEQ ID NO:36:

( i ) SEQUENCE CHARACTERISTICS:
        ( A ) LENGTH: 852 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| Met | Lys | Thr | Asn | Gln | Ile | Ser | Thr | Thr | Gln | Lys | Asn | Gln | Gln | Lys | Glu |
|---|---|---|---|---|---|---|---|---|---|---|---|---|---|---|---|
| 1 |     |     |     | 5 |     |     |     |     | 10 |     |     |     |     | 15 |     |
| Met | Asp | Arg | Lys | Gly | Leu | Leu | Gly | Tyr | Tyr | Phe | Lys | Gly | Lys | Asp | Phe |
|     |     |     | 20 |     |     |     | 25 |     |     |     |     | 30 |     |     |     |
| Ser | Asn | Leu | Thr | Met | Phe | Ala | Pro | Thr | Arg | Asp | Ser | Thr | Leu | Ile | Tyr |
|     |     | 35 |     |     |     |     | 40 |     |     |     |     | 45 |     |     |     |
| Asp | Gln | Gln | Thr | Ala | Asn | Lys | Leu | Leu | Asp | Lys | Lys | Gln | Gln | Glu | Tyr |
|     | 50 |     |     |     |     | 55 |     |     |     |     |     | 60 |     |     |     |
| Gln | Ser | Ile | Arg | Trp | Ile | Gly | Leu | Ile | Gln | Ser | Lys | Glu | Thr | Gly | Asp |
| 65 |     |     |     |     | 70 |     |     |     |     | 75 |     |     |     |     | 80 |
| Phe | Thr | Phe | Asn | Leu | Ser | Glu | Asp | Glu | Gln | Ala | Ile | Ile | Glu | Ile | Asn |
|     |     |     |     | 85 |     |     |     |     | 90 |     |     |     |     | 95 |     |
| Gly | Lys | Ile | Ile | Ser | Asn | Lys | Gly | Lys | Glu | Lys | Gln | Val | Val | His | Leu |
|     |     |     | 100 |     |     |     | 105 |     |     |     |     | 110 |     |     |     |
| Glu | Lys | Gly | Lys | Leu | Val | Pro | Ile | Lys | Ile | Glu | Tyr | Gln | Ser | Asp | Thr |
|     |     | 115 |     |     |     |     | 120 |     |     |     |     | 125 |     |     |     |
| Lys | Phe | Asn | Ile | Asp | Ser | Lys | Thr | Phe | Lys | Glu | Leu | Lys | Leu | Phe | Lys |
|     | 130 |     |     |     |     | 135 |     |     |     |     | 140 |     |     |     |     |
| Ile | Asp | Ser | Gln | Asn | Gln | Pro | Gln | Gln | Val | Gln | Gln | Asp | Glu | Leu | Arg |
| 145 |     |     |     |     | 150 |     |     |     |     | 155 |     |     |     |     | 160 |
| Asn | Pro | Glu | Phe | Asn | Lys | Lys | Glu | Ser | Gln | Glu | Phe | Leu | Ala | Lys | Pro |
|     |     |     |     | 165 |     |     |     |     | 170 |     |     |     |     | 175 |     |
| Ser | Lys | Ile | Asn | Leu | Phe | Thr | Gln | Gln | Met | Lys | Arg | Glu | Ile | Asp | Glu |
|     |     |     | 180 |     |     |     |     | 185 |     |     |     |     | 190 |     |     |
| Asp | Thr | Asp | Thr | Asp | Gly | Asp | Ser | Ile | Pro | Asp | Leu | Trp | Glu | Glu | Asn |
|     |     | 195 |     |     |     |     | 200 |     |     |     |     | 205 |     |     |     |
| Gly | Tyr | Thr | Ile | Gln | Asn | Arg | Ile | Ala | Val | Lys | Trp | Asp | Asp | Ser | Leu |
|     | 210 |     |     |     |     | 215 |     |     |     |     | 220 |     |     |     |     |
| Ala | Ser | Lys | Gly | Tyr | Thr | Lys | Phe | Val | Ser | Asn | Pro | Leu | Glu | Ser | His |
| 225 |     |     |     |     | 230 |     |     |     |     | 235 |     |     |     |     | 240 |
| Thr | Val | Gly | Asp | Pro | Tyr | Thr | Asp | Tyr | Glu | Lys | Ala | Ala | Arg | Asp | Leu |
|     |     |     |     | 245 |     |     |     |     | 250 |     |     |     |     | 255 |     |
| Asp | Leu | Ser | Asn | Ala | Lys | Glu | Thr | Phe | Asn | Pro | Leu | Val | Ala | Ala | Phe |
|     |     |     | 260 |     |     |     |     | 265 |     |     |     |     | 270 |     |     |
| Pro | Ser | Val | Asn | Val | Ser | Met | Glu | Lys | Val | Ile | Leu | Ser | Pro | Asn | Glu |
|     |     | 275 |     |     |     |     | 280 |     |     |     |     | 285 |     |     |     |
| Asn | Leu | Ser | Asn | Ser | Val | Glu | Ser | His | Ser | Ser | Thr | Asn | Trp | Ser | Tyr |
|     | 290 |     |     |     |     | 295 |     |     |     |     | 300 |     |     |     |     |
| Thr | Asn | Thr | Glu | Gly | Ala | Ser | Val | Glu | Ala | Gly | Ile | Gly | Pro | Lys | Gly |

-continued

```
            305                     310                     315                     320
Ile  Ser  Phe  Gly  Val  Ser  Val  Asn  Tyr  Gln  His  Ser  Glu  Thr  Val  Ala
                    325                     330                     335
Gln  Glu  Trp  Gly  Thr  Ser  Thr  Gly  Asn  Thr  Ser  Gln  Phe  Asn  Thr  Ala
                    340                     345                     350
Ser  Ala  Gly  Tyr  Leu  Asn  Ala  Asn  Val  Arg  Tyr  Asn  Asn  Val  Gly  Thr
                    355                     360                     365
Gly  Ala  Ile  Tyr  Asp  Val  Lys  Pro  Thr  Thr  Ser  Phe  Val  Leu  Asn  Asn
          370                     375                     380
Asp  Thr  Ile  Ala  Thr  Ile  Thr  Ala  Lys  Ser  Asn  Ser  Thr  Ala  Leu  Asn
385                     390                     395                          400
Ile  Ser  Pro  Gly  Glu  Ser  Tyr  Pro  Lys  Lys  Gly  Gln  Asn  Gly  Ile  Ala
                    405                     410                     415
Ile  Thr  Ser  Met  Asp  Asp  Phe  Asn  Ser  His  Pro  Ile  Thr  Leu  Asn  Lys
                    420                     425                     430
Lys  Gln  Val  Asp  Asn  Leu  Leu  Asn  Asn  Lys  Pro  Met  Met  Leu  Glu  Thr
                    435                     440                     445
Asn  Gln  Thr  Asp  Gly  Val  Tyr  Lys  Ile  Lys  Asp  Thr  His  Gly  Asn  Ile
          450                     455                     460
Val  Thr  Gly  Gly  Glu  Trp  Asn  Gly  Val  Ile  Gln  Gln  Ile  Lys  Ala  Lys
465                     470                     475                          480
Thr  Ala  Ser  Ile  Ile  Val  Asp  Asp  Gly  Glu  Arg  Val  Ala  Glu  Lys  Arg
                    485                     490                     495
Val  Ala  Ala  Lys  Asp  Tyr  Glu  Asn  Pro  Glu  Asp  Lys  Thr  Pro  Ser  Leu
                    500                     505                     510
Thr  Leu  Lys  Asp  Ala  Leu  Lys  Leu  Ser  Tyr  Pro  Asp  Glu  Ile  Lys  Glu
                    515                     520                     525
Ile  Glu  Gly  Leu  Leu  Tyr  Tyr  Lys  Asn  Lys  Pro  Ile  Tyr  Glu  Ser  Ser
          530                     535                     540
Val  Met  Thr  Tyr  Leu  Asp  Glu  Asn  Thr  Ala  Lys  Glu  Val  Thr  Lys  Gln
545                     550                     555                          560
Leu  Asn  Asp  Thr  Thr  Gly  Lys  Phe  Lys  Asp  Val  Ser  His  Leu  Tyr  Asp
                    565                     570                     575
Val  Lys  Leu  Thr  Pro  Lys  Met  Asn  Val  Thr  Ile  Lys  Leu  Ser  Ile  Leu
                    580                     585                     590
Tyr  Asp  Asn  Ala  Glu  Ser  Asn  Asp  Asn  Ser  Ile  Gly  Lys  Trp  Thr  Asn
                    595                     600                     605
Thr  Asn  Ile  Val  Ser  Gly  Gly  Asn  Asn  Gly  Lys  Lys  Gln  Tyr  Ser  Ser
          610                     615                     620
Asn  Asn  Pro  Asp  Ala  Asn  Leu  Thr  Leu  Asn  Thr  Asp  Ala  Gln  Glu  Lys
625                     630                     635                          640
Leu  Asn  Lys  Asn  Arg  Asp  Tyr  Tyr  Ile  Ser  Leu  Tyr  Met  Lys  Ser  Glu
                    645                     650                     655
Lys  Asn  Thr  Gln  Cys  Glu  Ile  Thr  Ile  Asp  Gly  Glu  Ile  Tyr  Pro  Ile
                    660                     665                     670
Thr  Thr  Lys  Thr  Val  Asn  Val  Asn  Lys  Asp  Asn  Tyr  Lys  Arg  Leu  Asp
                    675                     680                     685
Ile  Ile  Ala  His  Asn  Ile  Lys  Ser  Asn  Pro  Ile  Ser  Ser  Leu  His  Ile
                    690                     695                     700
Lys  Thr  Asn  Asp  Glu  Ile  Thr  Leu  Phe  Trp  Asp  Asp  Ile  Ser  Ile  Thr
705                     710                     715                          720
Asp  Val  Ala  Ser  Ile  Lys  Pro  Glu  Asn  Leu  Thr  Asp  Ser  Glu  Ile  Lys
                    725                     730                     735
```

| Gln | Ile | Tyr | Ser | Arg | Tyr | Gly | Ile | Lys | Leu | Glu | Asp | Gly | Ile | Leu | Ile |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Asp | Lys | Lys | Gly | Gly | Ile | His | Tyr | Gly | Glu | Phe | Ile | Asn | Glu | Ala | Ser |
|-----|-----|-----|-----|-----|-----|-----|-----|-----|-----|-----|-----|-----|-----|-----|-----|
|     |     | 755 |     |     |     |     | 760 |     |     |     |     | 765 |     |     |     |

| Phe | Asn | Ile | Glu | Pro | Leu | Gln | Asn | Tyr | Val | Thr | Lys | Tyr | Glu | Val | Thr |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Tyr | Ser | Ser | Glu | Leu | Gly | Pro | Asn | Val | Ser | Asp | Thr | Leu | Glu | Ser | Asp |
|-----|-----|-----|-----|-----|-----|-----|-----|-----|-----|-----|-----|-----|-----|-----|-----|
| 785 |     |     |     |     | 790 |     |     |     |     | 795 |     |     |     |     | 800 |

| Lys | Ile | Tyr | Lys | Asp | Gly | Thr | Ile | Lys | Phe | Asp | Phe | Thr | Lys | Tyr | Ser |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Lys | Asn | Glu | Gln | Gly | Leu | Phe | Tyr | Asp | Ser | Gly | Leu | Asn | Trp | Asp | Phe |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Lys | Ile | Asn | Ala | Ile | Thr | Tyr | Asp | Gly | Lys | Glu | Met | Asn | Val | Phe | His |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Arg | Tyr | Asn | Lys |
|-----|-----|-----|-----|
|     | 850 |     |     |

( 2 ) INFORMATION FOR SEQ ID NO:37:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make pCIB5527"

( i i i ) HYPOTHETICAL: NO ( x i ) SEQUENCE DESCRIPTION: SEQ ID NO:37:

GGATCCACCA TGCTGCAGAA CCTGAAGATC AC      32

( 2 ) INFORMATION FOR SEQ ID NO:38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make pCIB5527"

( i i i ) HYPOTHETICAL: NO ( x i ) SEQUENCE DESCRIPTION: SEQ ID NO:38:

AAGCTTCCAC TCCTTCTC      18

( 2 ) INFORMATION FOR SEQ ID NO:39:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA -continued sequence encoding VIP2A(a) with the Bacillus secretion
signal removed as contained in pCIB5527"

( x i ) SEQUENCE DESCRIPTION: SEQ ID NO:39:

| | | | | | | | | | | | | | | | | |
|---|---|---|---|---|---|---|---|---|---|---|---|---|---|---|---|---|
| GATCCACC | ATG | CTG | CAG | AAC | CTG | AAG | ATC | ACC | GAC | AAG | GTG | GAG | GAC | TTC | | 50 |
| | Met | Leu | Gln | Asn | Leu | Lys | Ile | Thr | Asp | Lys | Val | Glu | Asp | Phe | | |
| | | | 855 | | | | | 860 | | | | | | 865 | | |
| AAG | GAG | GAC | AAG | GAG | AAG | GCC | AAG | GAG | TGG | GGC | AAG | GAG | AAG | GAG | AAG | 98 |
| Lys | Glu | Asp | Lys | Glu | Lys | Ala | Lys | Glu | Trp | Gly | Lys | Glu | Lys | Glu | Lys | |
| | | | 870 | | | | | 875 | | | | | 880 | | | |
| GAG | TGG | AAG | CTT | ACC | GCC | ACC | GAG | AAG | GGC | AAG | ATG | AAC | AAC | TTC | CTG | 146 |
| Glu | Trp | Lys | Leu | Thr | Ala | Thr | Glu | Lys | Gly | Lys | Met | Asn | Asn | Phe | Leu | |
| | | 885 | | | | | 890 | | | | | 895 | | | | |
| GAC | AAC | AAG | AAC | GAC | ATC | AAG | ACC | AAC | TAC | AAG | GAG | ATC | ACC | TTC | AGC | 194 |
| Asp | Asn | Lys | Asn | Asp | Ile | Lys | Thr | Asn | Tyr | Lys | Glu | Ile | Thr | Phe | Ser | |
| | 900 | | | | | 905 | | | | | 910 | | | | | |
| ATA | GCC | GGC | AGC | TTC | GAG | GAC | GAG | ATC | AAG | GAC | CTG | AAG | GAG | ATC | GAC | 242 |
| Ile | Ala | Gly | Ser | Phe | Glu | Asp | Glu | Ile | Lys | Asp | Leu | Lys | Glu | Ile | Asp | |
| 915 | | | | | 920 | | | | | 925 | | | | | 930 | |
| AAG | ATG | TTC | GAC | AAG | ACC | AAC | CTG | AGC | AAC | AGC | ATC | ATC | ACC | TAC | AAG | 290 |
| Lys | Met | Phe | Asp | Lys | Thr | Asn | Leu | Ser | Asn | Ser | Ile | Ile | Thr | Tyr | Lys | |
| | | | 935 | | | | | 940 | | | | | 945 | | | |
| AAC | GTG | GAG | CCC | ACC | ACC | ATC | GGC | TTC | AAC | AAG | AGC | CTG | ACC | GAG | GGC | 338 |
| Asn | Val | Glu | Pro | Thr | Thr | Ile | Gly | Phe | Asn | Lys | Ser | Leu | Thr | Glu | Gly | |
| | | | 950 | | | | | 955 | | | | | 960 | | | |
| AAC | ACC | ATC | AAC | AGC | GAC | GCC | ATG | GCC | CAG | TTC | AAG | GAG | CAG | TTC | CTG | 386 |
| Asn | Thr | Ile | Asn | Ser | Asp | Ala | Met | Ala | Gln | Phe | Lys | Glu | Gln | Phe | Leu | |
| | | 965 | | | | | 970 | | | | | 975 | | | | |
| GAC | CGC | GAC | ATC | AAG | TTC | GAC | AGC | TAC | CTG | GAC | ACC | CAC | CTG | ACC | GCC | 434 |
| Asp | Arg | Asp | Ile | Lys | Phe | Asp | Ser | Tyr | Leu | Asp | Thr | His | Leu | Thr | Ala | |
| | 980 | | | | | 985 | | | | | 990 | | | | | |
| CAG | CAG | GTG | AGC | AGC | AAG | GAG | CGC | GTG | ATC | CTG | AAG | GTG | ACC | GTC | CCC | 482 |
| Gln | Gln | Val | Ser | Ser | Lys | Glu | Arg | Val | Ile | Leu | Lys | Val | Thr | Val | Pro | |
| 995 | | | | | 1000 | | | | | 1005 | | | | | 1010 | |
| AGC | GGC | AAG | GGC | AGC | ACC | ACC | CCC | ACC | AAG | GCC | GGC | GTG | ATC | CTG | AAC | 530 |
| Ser | Gly | Lys | Gly | Ser | Thr | Thr | Pro | Thr | Lys | Ala | Gly | Val | Ile | Leu | Asn | |
| | | | | 1015 | | | | | 1020 | | | | | 1025 | | |
| AAC | AGC | GAG | TAC | AAG | ATG | CTG | ATC | GAC | AAC | GGC | TAC | ATG | GTG | CAC | GTG | 578 |
| Asn | Ser | Glu | Tyr | Lys | Met | Leu | Ile | Asp | Asn | Gly | Tyr | Met | Val | His | Val | |
| | | | | 1030 | | | | | 1035 | | | | | 1040 | | |
| GAC | AAG | GTG | AGC | AAG | GTG | GTG | AAG | AAG | GGC | GTG | GAG | TGC | CTC | CAG | ATC | 626 |
| Asp | Lys | Val | Ser | Lys | Val | Val | Lys | Lys | Gly | Val | Glu | Cys | Leu | Gln | Ile | |
| | | | 1045 | | | | | 1050 | | | | | 1055 | | | |
| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala | |
| | | | 1060 | | | | | 1065 | | | | | 1070 | | | |
| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp | |
| 1075 | | | | | 1080 | | | | | 1085 | | | | | 1090 | |
| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp | |
| | | | | 1095 | | | | | 1100 | | | | | 1105 | | |
| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn | |
| | | | | 1110 | | | | | 1115 | | | | | 1120 | | |
| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys | |
| | | | 1125 | | | | | 1130 | | | | | 1135 | | | |
| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro | |
| | | | 1140 | | | | | 1145 | | | | | 1150 | | | |

```
GAG  TTC  GGC  TAC  CAG  ATC  AGC  GAC  CCC  CTG  CCC  AGC  CTG  AAG  GAC  TTC      962
Glu  Phe  Gly  Tyr  Gln  Ile  Ser  Asp  Pro  Leu  Pro  Ser  Leu  Lys  Asp  Phe
1155                     1160                    1165                    1170

GAG  GAG  CAG  TTC  CTG  AAC  ACC  ATC  AAG  GAG  GAC  AAG  GGC  TAC  ATG  AGC     1010
Glu  Glu  Gln  Phe  Leu  Asn  Thr  Ile  Lys  Glu  Asp  Lys  Gly  Tyr  Met  Ser
                    1175                    1180                    1185

ACC  AGC  CTG  AGC  AGC  GAG  CGC  CTG  GCC  GCC  TTC  GGC  AGC  CGC  AAG  ATC     1058
Thr  Ser  Leu  Ser  Ser  Glu  Arg  Leu  Ala  Ala  Phe  Gly  Ser  Arg  Lys  Ile
               1190                    1195                    1200

ATC  CTG  CGC  CTG  CAG  GTG  CCC  AAG  GGC  AGC  ACT  GGT  GCC  TAC  CTG  AGC     1106
Ile  Leu  Arg  Leu  Gln  Val  Pro  Lys  Gly  Ser  Thr  Gly  Ala  Tyr  Leu  Ser
          1205                    1210                    1215

GCC  ATC  GGC  GGC  TTC  GCC  AGC  GAG  AAG  GAG  ATC  CTG  CTG  GAT  AAG  GAC     1154
Ala  Ile  Gly  Gly  Phe  Ala  Ser  Glu  Lys  Glu  Ile  Leu  Leu  Asp  Lys  Asp
     1220                    1225                    1230

AGC  AAG  TAC  CAC  ATC  GAC  AAG  GTG  ACC  GAG  GTG  ATC  ATC  AAG  GGC  GTG     1202
Ser  Lys  Tyr  His  Ile  Asp  Lys  Val  Thr  Glu  Val  Ile  Ile  Lys  Gly  Val
1235                     1240                    1245                    1250

AAG  CGC  TAC  GTG  GTG  GAC  GCC  ACC  CTG  CTG  ACC  AAC  TAG                    1241
Lys  Arg  Tyr  Val  Val  Asp  Ala  Thr  Leu  Leu  Thr  Asn
                    1255                    1260
```

( 2 ) INFORMATION FOR SEQ ID NO:40:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Met  Leu  Gln  Asn  Leu  Lys  Ile  Thr  Asp  Lys  Val  Glu  Asp  Phe  Lys  Glu
 1                    5                   10                    15

Asp  Lys  Glu  Lys  Ala  Lys  Glu  Trp  Gly  Lys  Glu  Lys  Glu  Lys  Glu  Trp
               20                    25                    30

Lys  Leu  Thr  Ala  Thr  Glu  Lys  Gly  Lys  Met  Asn  Asn  Phe  Leu  Asp  Asn
               35                    40                    45

Lys  Asn  Asp  Ile  Lys  Thr  Asn  Tyr  Lys  Glu  Ile  Thr  Phe  Ser  Ile  Ala
          50                    55                    60

Gly  Ser  Phe  Glu  Asp  Glu  Ile  Lys  Asp  Leu  Lys  Glu  Ile  Asp  Lys  Met
65                    70                    75                         80

Phe  Asp  Lys  Thr  Asn  Leu  Ser  Asn  Ser  Ile  Ile  Thr  Tyr  Lys  Asn  Val
                    85                    90                    95

Glu  Pro  Thr  Thr  Ile  Gly  Phe  Asn  Lys  Ser  Leu  Thr  Glu  Gly  Asn  Thr
                    100                   105                   110

Ile  Asn  Ser  Asp  Ala  Met  Ala  Gln  Phe  Lys  Glu  Gln  Phe  Leu  Asp  Arg
               115                   120                   125

Asp  Ile  Lys  Phe  Asp  Ser  Tyr  Leu  Asp  Thr  His  Leu  Thr  Ala  Gln  Gln
     130                   135                   140

Val  Ser  Ser  Lys  Glu  Arg  Val  Ile  Leu  Lys  Val  Thr  Val  Pro  Ser  Gly
145                   150                   155                        160

Lys  Gly  Ser  Thr  Thr  Pro  Thr  Lys  Ala  Gly  Val  Ile  Leu  Asn  Asn  Ser
                    165                   170                   175

Glu  Tyr  Lys  Met  Leu  Ile  Asp  Asn  Gly  Tyr  Met  Val  His  Val  Asp  Lys
               180                   185                   190

Val  Ser  Lys  Val  Val  Lys  Lys  Gly  Val  Glu  Cys  Leu  Gln  Ile  Glu  Gly
          195                   200                   205
```

| | | | | | | | | | | | | | |
|---|---|---|---|---|---|---|---|---|---|---|---|---|---|
| Thr | Leu | Lys | Lys | Ser | Leu | Asp | Phe | Lys | Asn | Asp | Ile | Asn | Ala | Glu | Ala |
| | 210 | | | | 215 | | | | | 220 | | | | | |
| His | Ser | Trp | Gly | Met | Lys | Asn | Tyr | Glu | Glu | Trp | Ala | Lys | Asp | Leu | Thr |
| 225 | | | | | 230 | | | | | 235 | | | | | 240 |
| Asp | Ser | Gln | Arg | Glu | Ala | Leu | Asp | Gly | Tyr | Ala | Arg | Gln | Asp | Tyr | Lys |
| | | | | 245 | | | | | 250 | | | | | 255 | |
| Glu | Ile | Asn | Asn | Tyr | Leu | Arg | Asn | Gln | Gly | Gly | Ser | Gly | Asn | Glu | Lys |
| | | | 260 | | | | | 265 | | | | | 270 | | |
| Leu | Asp | Ala | Gln | Ile | Lys | Asn | Ile | Ser | Asp | Ala | Leu | Gly | Lys | Lys | Pro |
| | | 275 | | | | | 280 | | | | | 285 | | | |
| Ile | Pro | Glu | Asn | Ile | Thr | Val | Tyr | Arg | Trp | Cys | Gly | Met | Pro | Glu | Phe |
| | 290 | | | | | 295 | | | | | 300 | | | | |
| Gly | Tyr | Gln | Ile | Ser | Asp | Pro | Leu | Pro | Ser | Leu | Lys | Asp | Phe | Glu | Glu |
| 305 | | | | | 310 | | | | | 315 | | | | | 320 |
| Gln | Phe | Leu | Asn | Thr | Ile | Lys | Glu | Asp | Lys | Gly | Tyr | Met | Ser | Thr | Ser |
| | | | | 325 | | | | | 330 | | | | | 335 | |
| Leu | Ser | Ser | Glu | Arg | Leu | Ala | Ala | Phe | Gly | Ser | Arg | Lys | Ile | Ile | Leu |
| | | | 340 | | | | | 345 | | | | | 350 | | |
| Arg | Leu | Gln | Val | Pro | Lys | Gly | Ser | Thr | Gly | Ala | Tyr | Leu | Ser | Ala | Ile |
| | | 355 | | | | | 360 | | | | | 365 | | | |
| Gly | Gly | Phe | Ala | Ser | Glu | Lys | Glu | Ile | Leu | Leu | Asp | Lys | Asp | Ser | Lys |
| | 370 | | | | | 375 | | | | | 380 | | | | |
| Tyr | His | Ile | Asp | Lys | Val | Thr | Glu | Val | Ile | Ile | Lys | Gly | Val | Lys | Arg |
| 385 | | | | | 390 | | | | | 395 | | | | | 400 |
| Tyr | Val | Val | Asp | Ala | Thr | Leu | Leu | Thr | Asn | | | | | | |
| | | | | 405 | | | | | 410 | | | | | | |

( 2 ) INFORMATION FOR SEQ ID NO:41:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            eukaryotic secretion signal used to construct pCIB5527"

( i i i ) HYPOTHETICAL: NO ( x i ) SEQUENCE DESCRIPTION: SEQ ID NO:41:

| | | | | | |
|---|---|---|---|---|---|
| GGATCCACCA | TGGGCTGGAG | CTGGATCTTC | CTGTTCCTGC | TGAGCGGCGC | CGCGGGCGTG | 60 |
| CACTGCCTGC | AG | | | | | 72 |

( 2 ) INFORMATION FOR SEQ ID NO:42:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
            signal removed and the eukaryotic secretion signal -continued inserted as contained in pCIB5528"

(xi) SEQUENCE DESCRIPTION: SEQ ID NO:42:

| | | | | | | | | | | | | | | | | |
|---|---|---|---|---|---|---|---|---|---|---|---|---|---|---|---|---|
| GATCCACC | ATG | CTG | CAG | AAC | CTG | AAG | ATC | ACC | GAC | AAG | GTG | GAG | GAC | TTC | | 50 |
| | Met | Leu | Gln | Asn | Leu | Lys | Ile | Thr | Asp | Lys | Val | Glu | Asp | Phe | | |
| | | | | 415 | | | | | | 420 | | | | | | |
| AAG | GAG | GAC | AAG | GAG | AAG | GCC | AAG | GAG | TGG | GGC | AAG | GAG | AAG | GAG | AAG | 98 |
| Lys | Glu | Asp | Lys | Glu | Lys | Ala | Lys | Glu | Trp | Gly | Lys | Glu | Lys | Glu | Lys | |
| 425 | | | | 430 | | | | | 435 | | | | | | 440 | |
| GAG | TGG | AAG | CTT | ACC | GCC | ACC | GAG | AAG | GGC | AAG | ATG | AAC | AAC | TTC | CTG | 146 |
| Glu | Trp | Lys | Leu | Thr | Ala | Thr | Glu | Lys | Gly | Lys | Met | Asn | Asn | Phe | Leu | |
| | | | | 445 | | | | | 450 | | | | | 455 | | |
| GAC | AAC | AAG | AAC | GAC | ATC | AAG | ACC | AAC | TAC | AAG | GAG | ATC | ACC | TTC | AGC | 194 |
| Asp | Asn | Lys | Asn | Asp | Ile | Lys | Thr | Asn | Tyr | Lys | Glu | Ile | Thr | Phe | Ser | |
| | | | 460 | | | | | 465 | | | | | 470 | | | |
| ATA | GCC | GGC | AGC | TTC | GAG | GAC | GAG | ATC | AAG | GAC | CTG | AAG | GAG | ATC | GAC | 242 |
| Ile | Ala | Gly | Ser | Phe | Glu | Asp | Glu | Ile | Lys | Asp | Leu | Lys | Glu | Ile | Asp | |
| | | 475 | | | | | 480 | | | | | 485 | | | | |
| AAG | ATG | TTC | GAC | AAG | ACC | AAC | CTG | AGC | AAC | AGC | ATC | ATC | ACC | TAC | AAG | 290 |
| Lys | Met | Phe | Asp | Lys | Thr | Asn | Leu | Ser | Asn | Ser | Ile | Ile | Thr | Tyr | Lys | |
| | 490 | | | | | 495 | | | | | 500 | | | | | |
| AAC | GTG | GAG | CCC | ACC | ACC | ATC | GGC | TTC | AAC | AAG | AGC | CTG | ACC | GAG | GGC | 338 |
| Asn | Val | Glu | Pro | Thr | Thr | Ile | Gly | Phe | Asn | Lys | Ser | Leu | Thr | Glu | Gly | |
| 505 | | | | 510 | | | | | 515 | | | | | 520 | | |
| AAC | ACC | ATC | AAC | AGC | GAC | GCC | ATG | GCC | CAG | TTC | AAG | GAG | CAG | TTC | CTG | 386 |
| Asn | Thr | Ile | Asn | Ser | Asp | Ala | Met | Ala | Gln | Phe | Lys | Glu | Gln | Phe | Leu | |
| | | | | 525 | | | | | 530 | | | | | 535 | | |
| GAC | CGC | GAC | ATC | AAG | TTC | GAC | AGC | TAC | CTG | GAC | ACC | CAC | CTG | ACC | GCC | 434 |
| Asp | Arg | Asp | Ile | Lys | Phe | Asp | Ser | Tyr | Leu | Asp | Thr | His | Leu | Thr | Ala | |
| | | | 540 | | | | | 545 | | | | | 550 | | | |
| CAG | CAG | GTG | AGC | AGC | AAG | GAG | CGC | GTG | ATC | CTG | AAG | GTG | ACC | GTC | CCC | 482 |
| Gln | Gln | Val | Ser | Ser | Lys | Glu | Arg | Val | Ile | Leu | Lys | Val | Thr | Val | Pro | |
| | | 555 | | | | | 560 | | | | | 565 | | | | |
| AGC | GGC | AAG | GGC | AGC | ACC | ACC | CCC | ACC | AAG | GCC | GGC | GTG | ATC | CTG | AAC | 530 |
| Ser | Gly | Lys | Gly | Ser | Thr | Thr | Pro | Thr | Lys | Ala | Gly | Val | Ile | Leu | Asn | |
| | | 570 | | | | 575 | | | | | 580 | | | | | |
| AAC | AGC | GAG | TAC | AAG | ATG | CTG | ATC | GAC | AAC | GGC | TAC | ATG | GTG | CAC | GTG | 578 |
| Asn | Ser | Glu | Tyr | Lys | Met | Leu | Ile | Asp | Asn | Gly | Tyr | Met | Val | His | Val | |
| 585 | | | | | 590 | | | | | 595 | | | | | 600 | |
| GAC | AAG | GTG | AGC | AAG | GTG | GTG | AAG | AAG | GGC | GTG | GAG | TGC | CTC | CAG | ATC | 626 |
| Asp | Lys | Val | Ser | Lys | Val | Val | Lys | Lys | Gly | Val | Glu | Cys | Leu | Gln | Ile | |
| | | | | 605 | | | | | 610 | | | | | 615 | | |
| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala | |
| | | | 620 | | | | | 625 | | | | | 630 | | | |
| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp | |
| | | 635 | | | | | 640 | | | | | 645 | | | | |
| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp | |
| | 650 | | | | 655 | | | | | 660 | | | | | | |
| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn | |
| 665 | | | | | 670 | | | | | 675 | | | | | 680 | |
| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys | |
| | | | | 685 | | | | | 690 | | | | | 695 | | |
| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro | |
| | | | 700 | | | | | 705 | | | | | 710 | | | |

| | | | | | | | | | | | | | | | | |
|---|---|---|---|---|---|---|---|---|---|---|---|---|---|---|---|---|
| GAG | TTC | GGC | TAC | CAG | ATC | AGC | GAC | CCC | CTG | CCC | AGC | CTG | AAG | GAC | TTC | 962 |
| Glu | Phe | Gly | Tyr | Gln | Ile | Ser | Asp | Pro | Leu | Pro | Ser | Leu | Lys | Asp | Phe | |
| | | 715 | | | | | 720 | | | | | 725 | | | | |
| GAG | GAG | CAG | TTC | CTG | AAC | ACC | ATC | AAG | GAG | GAC | AAG | GGC | TAC | ATG | AGC | 1010 |
| Glu | Glu | Gln | Phe | Leu | Asn | Thr | Ile | Lys | Glu | Asp | Lys | Gly | Tyr | Met | Ser | |
| 730 | | | | | 735 | | | | | 740 | | | | | | |
| ACC | AGC | CTG | AGC | AGC | GAG | CGC | CTG | GCC | GCC | TTC | GGC | AGC | CGC | AAG | ATC | 1058 |
| Thr | Ser | Leu | Ser | Ser | Glu | Arg | Leu | Ala | Ala | Phe | Gly | Ser | Arg | Lys | Ile | |
| 745 | | | | | 750 | | | | | 755 | | | | | 760 | |
| ATC | CTG | CGC | CTG | CAG | GTG | CCC | AAG | GGC | AGC | ACT | GGT | GCC | TAC | CTG | AGC | 1106 |
| Ile | Leu | Arg | Leu | Gln | Val | Pro | Lys | Gly | Ser | Thr | Gly | Ala | Tyr | Leu | Ser | |
| | | | | 765 | | | | | 770 | | | | | 775 | | |
| GCC | ATC | GGC | GGC | TTC | GCC | AGC | GAG | AAG | GAG | ATC | CTG | CTG | GAT | AAG | GAC | 1154 |
| Ala | Ile | Gly | Gly | Phe | Ala | Ser | Glu | Lys | Glu | Ile | Leu | Leu | Asp | Lys | Asp | |
| | | | 780 | | | | | 785 | | | | | 790 | | | |
| AGC | AAG | TAC | CAC | ATC | GAC | AAG | GTG | ACC | GAG | GTG | ATC | ATC | AAG | GGC | GTG | 1202 |
| Ser | Lys | Tyr | His | Ile | Asp | Lys | Val | Thr | Glu | Val | Ile | Ile | Lys | Gly | Val | |
| | | 795 | | | | | 800 | | | | | 805 | | | | |
| AAG | CGC | TAC | GTG | GTG | GAC | GCC | ACC | CTG | CTG | ACC | AAC | TAG | | | | 1241 |
| Lys | Arg | Tyr | Val | Val | Asp | Ala | Thr | Leu | Leu | Thr | Asn | | | | | |
| | 810 | | | | | 815 | | | | | 820 | | | | | |

( 2 ) INFORMATION FOR SEQ ID NO:43:

( i ) SEQUENCE CHARACTERISTICS:
  ( A ) LENGTH: 410 amino acids
  ( B ) TYPE: amino acid
  ( D ) TOPOLOGY: linear ( i i ) MOLECULE TYPE: protein ( x i ) SEQUENCE DESCRIPTION: SEQ ID NO:43:

| | | | | | | | | | | | | | | |
|---|---|---|---|---|---|---|---|---|---|---|---|---|---|---|
| Met | Leu | Gln | Asn | Leu | Lys | Ile | Thr | Asp | Lys | Val | Glu | Asp | Phe | Lys | Glu |
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | | 25 | | | | | 30 | | |
| Lys | Leu | Thr | Ala | Thr | Glu | Lys | Gly | Lys | Met | Asn | Asn | Phe | Leu | Asp | Asn |
| | | | 35 | | | | | 40 | | | | | 45 | | |
| Lys | Asn | Asp | Ile | Lys | Thr | Asn | Tyr | Lys | Glu | Ile | Thr | Phe | Ser | Ile | Ala |
| | | 50 | | | | | 55 | | | | | 60 | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |
| | | | | 85 | | | | | 90 | | | | | 95 | |
| Glu | Pro | Thr | Thr | Ile | Gly | Phe | Asn | Lys | Ser | Leu | Thr | Glu | Gly | Asn | Thr |
| | | | 100 | | | | | 105 | | | | | 110 | | |
| Ile | Asn | Ser | Asp | Ala | Met | Ala | Gln | Phe | Lys | Glu | Gln | Phe | Leu | Asp | Arg |
| | | 115 | | | | | 120 | | | | | 125 | | | |
| Asp | Ile | Lys | Phe | Asp | Ser | Tyr | Leu | Asp | Thr | His | Leu | Thr | Ala | Gln | Gln |
| | 130 | | | | | 135 | | | | | 140 | | | | |
| Val | Ser | Ser | Lys | Glu | Arg | Val | Ile | Leu | Lys | Val | Thr | Val | Pro | Ser | Gly |
| 145 | | | | | 150 | | | | | 155 | | | | | 160 |
| Lys | Gly | Ser | Thr | Thr | Pro | Thr | Lys | Ala | Gly | Val | Ile | Leu | Asn | Asn | Ser |
| | | | | 165 | | | | | 170 | | | | | 175 | |
| Glu | Tyr | Lys | Met | Leu | Ile | Asp | Asn | Gly | Tyr | Met | Val | His | Val | Asp | Lys |
| | | | 180 | | | | | 185 | | | | | 190 | | |
| Val | Ser | Lys | Val | Val | Lys | Lys | Gly | Val | Glu | Cys | Leu | Gln | Ile | Glu | Gly |
| | | 195 | | | | | 200 | | | | | 205 | | | |
| Thr | Leu | Lys | Lys | Ser | Leu | Asp | Phe | Lys | Asn | Asp | Ile | Asn | Ala | Glu | Ala |

|   |   |   |   |   | 210 |   |   |   |   | 215 |   |   |   |   | 220 |   |   |   |   |
|---|---|---|---|---|---|---|---|---|---|---|---|---|---|---|---|---|---|---|---|

His Ser Trp Gly Met Lys Asn Tyr Glu Glu Trp Ala Lys Asp Leu Thr
225                     230                     235                     240

Asp Ser Gln Arg Glu Ala Leu Asp Gly Tyr Ala Arg Gln Asp Tyr Lys
                245                     250                     255

Glu Ile Asn Asn Tyr Leu Arg Asn Gln Gly Gly Ser Gly Asn Glu Lys
            260                     265                     270

Leu Asp Ala Gln Ile Lys Asn Ile Ser Asp Ala Leu Gly Lys Lys Pro
        275                     280                     285

Ile Pro Glu Asn Ile Thr Val Tyr Arg Trp Cys Gly Met Pro Glu Phe
    290                     295                     300

Gly Tyr Gln Ile Ser Asp Pro Leu Pro Ser Leu Lys Asp Phe Glu Glu
305                     310                     315                     320

Gln Phe Leu Asn Thr Ile Lys Glu Asp Lys Gly Tyr Met Ser Thr Ser
                325                     330                     335

Leu Ser Ser Glu Arg Leu Ala Ala Phe Gly Ser Arg Lys Ile Ile Leu
            340                     345                     350

Arg Leu Gln Val Pro Lys Gly Ser Thr Gly Ala Tyr Leu Ser Ala Ile
        355                     360                     365

Gly Gly Phe Ala Ser Glu Lys Glu Ile Leu Leu Asp Lys Asp Ser Lys
370                     375                     380

Tyr His Ile Asp Lys Val Thr Glu Val Ile Ile Lys Gly Val Lys Arg
385                     390                     395                     400

Tyr Val Val Asp Ala Thr Leu Leu Thr Asn
                405                     410

(2) INFORMATION FOR SEQ ID NO:44:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide encoding
            vacuolar targetting peptide used to construct pCIB5533"

(iii) HYPOTHETICAL: NO (xi) SEQUENCE DESCRIPTION: SEQ ID NO:44:

CCGCGGGCGT GCACTGCCTC AGCAGCAGCA GCTTCGCCGA CAGCAACCCC ATCCGCGTGA 60

CCGACCGCGC CGCCAGCACC CTGCAG 86

(2) INFORMATION FOR SEQ ID NO:45:

(i) SEQUENCE CHARACTERISTICS:
        (A) LENGTH: 1358 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1355
        (D) OTHER INFORMATION: /note= "Maize optimized VIP2A(a)
            with the Bacillus secretion signal removed and the
            vacuolar targetting signal inserted as contained
            in pCIB5533"

( x i ) SEQUENCE DESCRIPTION: SEQ ID NO:45:

| | | | | | | | | | | | | | | | | |
|---|---|---|---|---|---|---|---|---|---|---|---|---|---|---|---|---|
| GATCCACC | ATG | GGC | TGG | AGC | TGG | ATC | TTC | CTG | TTC | CTG | CTG | AGC | GGC | GCC | | 50 |
| | Met | Gly | Trp | Ser | Trp | Ile | Phe | Leu | Phe | Leu | Leu | Ser | Gly | Ala | | |
| | | | | 415 | | | | | 420 | | | | | | | |
| GCG | GGC | GTG | CAC | TGC | CTC | AGC | AGC | AGC | AGC | TTC | GCC | GAC | AGC | AAC | CCC | 98 |
| Ala | Gly | Val | His | Cys | Leu | Ser | Ser | Ser | Ser | Phe | Ala | Asp | Ser | Asn | Pro | |
| 425 | | | | 430 | | | | | 435 | | | | | 440 | | |
| ATC | CGC | GTG | ACC | GAC | CGC | GCC | GCC | AGC | ACC | CTG | CAG | AAC | CTG | AAG | ATC | 146 |
| Ile | Arg | Val | Thr | Asp | Arg | Ala | Ala | Ser | Thr | Leu | Gln | Asn | Leu | Lys | Ile | |
| | | | | 445 | | | | | 450 | | | | | 455 | | |
| ACC | GAC | AAG | GTG | GAG | GAC | TTC | AAG | GAG | GAC | AAG | GAG | AAG | GCC | AAG | GAG | 194 |
| Thr | Asp | Lys | Val | Glu | Asp | Phe | Lys | Glu | Asp | Lys | Glu | Lys | Ala | Lys | Glu | |
| | | | 460 | | | | 465 | | | | 470 | | | | | |
| TGG | GGC | AAG | GAG | AAG | GAG | AAG | GAG | TGG | AAG | CTT | ACC | GCC | ACC | GAG | AAG | 242 |
| Trp | Gly | Lys | Glu | Lys | Glu | Lys | Glu | Trp | Lys | Leu | Thr | Ala | Thr | Glu | Lys | |
| | | 475 | | | | 480 | | | | | 485 | | | | | |
| GGC | AAG | ATG | AAC | AAC | TTC | CTG | GAC | AAC | AAG | AAC | GAC | ATC | AAG | ACC | AAC | 290 |
| Gly | Lys | Met | Asn | Asn | Phe | Leu | Asp | Asn | Lys | Asn | Asp | Ile | Lys | Thr | Asn | |
| | 490 | | | | 495 | | | | | 500 | | | | | | |
| TAC | AAG | GAG | ATC | ACC | TTC | AGC | ATA | GCC | GGC | AGC | TTC | GAG | GAC | GAG | ATC | 338 |
| Tyr | Lys | Glu | Ile | Thr | Phe | Ser | Ile | Ala | Gly | Ser | Phe | Glu | Asp | Glu | Ile | |
| 505 | | | | 510 | | | | | 515 | | | | | 520 | | |
| AAG | GAC | CTG | AAG | GAG | ATC | GAC | AAG | ATG | TTC | GAC | AAG | ACC | AAC | CTG | AGC | 386 |
| Lys | Asp | Leu | Lys | Glu | Ile | Asp | Lys | Met | Phe | Asp | Lys | Thr | Asn | Leu | Ser | |
| | | | | 525 | | | | | 530 | | | | | 535 | | |
| AAC | AGC | ATC | ATC | ACC | TAC | AAG | AAC | GTG | GAG | CCC | ACC | ACC | ATC | GGC | TTC | 434 |
| Asn | Ser | Ile | Ile | Thr | Tyr | Lys | Asn | Val | Glu | Pro | Thr | Thr | Ile | Gly | Phe | |
| | | | 540 | | | | | 545 | | | | | 550 | | | |
| AAC | AAG | AGC | CTG | ACC | GAG | GGC | AAC | ACC | ATC | AAC | AGC | GAC | GCC | ATG | GCC | 482 |
| Asn | Lys | Ser | Leu | Thr | Glu | Gly | Asn | Thr | Ile | Asn | Ser | Asp | Ala | Met | Ala | |
| | | 555 | | | | | 560 | | | | | 565 | | | | |
| CAG | TTC | AAG | GAG | CAG | TTC | CTG | GAC | CGC | GAC | ATC | AAG | TTC | GAC | AGC | TAC | 530 |
| Gln | Phe | Lys | Glu | Gln | Phe | Leu | Asp | Arg | Asp | Ile | Lys | Phe | Asp | Ser | Tyr | |
| | 570 | | | | 575 | | | | | 580 | | | | | | |
| CTG | GAC | ACC | CAC | CTG | ACC | GCC | CAG | CAG | GTG | AGC | AGC | AAG | GAG | CGC | GTG | 578 |
| Leu | Asp | Thr | His | Leu | Thr | Ala | Gln | Gln | Val | Ser | Ser | Lys | Glu | Arg | Val | |
| 585 | | | | 590 | | | | | 595 | | | | | 600 | | |
| ATC | CTG | AAG | GTG | ACC | GTC | CCC | AGC | GGC | AAG | GGC | AGC | ACC | ACC | CCC | ACC | 626 |
| Ile | Leu | Lys | Val | Thr | Val | Pro | Ser | Gly | Lys | Gly | Ser | Thr | Thr | Pro | Thr | |
| | | | | 605 | | | | | 610 | | | | | 615 | | |
| AAG | GCC | GGC | GTG | ATC | CTG | AAC | AAC | AGC | GAG | TAC | AAG | ATG | CTG | ATC | GAC | 674 |
| Lys | Ala | Gly | Val | Ile | Leu | Asn | Asn | Ser | Glu | Tyr | Lys | Met | Leu | Ile | Asp | |
| | | | 620 | | | | | 625 | | | | | 630 | | | |
| AAC | GGC | TAC | ATG | GTG | CAC | GTG | GAC | AAG | GTG | AGC | AAG | GTG | GTG | AAG | AAG | 722 |
| Asn | Gly | Tyr | Met | Val | His | Val | Asp | Lys | Val | Ser | Lys | Val | Val | Lys | Lys | |
| | | 635 | | | | | 640 | | | | | 645 | | | | |
| GGC | GTG | GAG | TGC | CTC | CAG | ATC | GAG | GGC | ACC | CTG | AAG | AAG | AGT | CTA | GAC | 770 |
| Gly | Val | Glu | Cys | Leu | Gln | Ile | Glu | Gly | Thr | Leu | Lys | Lys | Ser | Leu | Asp | |
| | 650 | | | | | 655 | | | | | 660 | | | | | |
| TTC | AAG | AAC | GAC | ATC | AAC | GCC | GAG | GCC | CAC | AGC | TGG | GGC | ATG | AAG | AAC | 818 |
| Phe | Lys | Asn | Asp | Ile | Asn | Ala | Glu | Ala | His | Ser | Trp | Gly | Met | Lys | Asn | |
| 665 | | | | 670 | | | | | 675 | | | | | 680 | | |
| TAC | GAG | GAG | TGG | GCC | AAG | GAC | CTG | ACC | GAC | AGC | CAG | CGC | GAG | GCC | CTG | 866 |
| Tyr | Glu | Glu | Trp | Ala | Lys | Asp | Leu | Thr | Asp | Ser | Gln | Arg | Glu | Ala | Leu | |
| | | | | 685 | | | | | 690 | | | | | 695 | | |
| GAC | GGC | TAC | GCC | CGC | CAG | GAC | TAC | AAG | GAG | ATC | AAC | AAC | TAC | CTG | CGC | 914 |
| Asp | Gly | Tyr | Ala | Arg | Gln | Asp | Tyr | Lys | Glu | Ile | Asn | Asn | Tyr | Leu | Arg | |
| | | | 700 | | | | | 705 | | | | | 710 | | | |
| AAC | CAG | GGC | GGC | AGC | GGC | AAC | GAG | AAG | CTG | GAC | GCC | CAG | ATC | AAG | AAC | 962 |

```
Asn  Gln  Gly  Gly  Ser  Gly  Asn  Glu  Lys  Leu  Asp  Ala  Gln  Ile  Lys  Asn
          715                      720                     725

ATC  AGC  GAC  GCC  CTG  GGC  AAG  AAG  CCC  ATC  CCC  GAG  AAC  ATC  ACC  GTG         1010
Ile  Ser  Asp  Ala  Leu  Gly  Lys  Lys  Pro  Ile  Pro  Glu  Asn  Ile  Thr  Val
     730                      735                     740

TAC  CGC  TGG  TGC  GGC  ATG  CCC  GAG  TTC  GGC  TAC  CAG  ATC  AGC  GAC  CCC         1058
Tyr  Arg  Trp  Cys  Gly  Met  Pro  Glu  Phe  Gly  Tyr  Gln  Ile  Ser  Asp  Pro
745                      750                     755                      760

CTG  CCC  AGC  CTG  AAG  GAC  TTC  GAG  GAG  CAG  TTC  CTG  AAC  ACC  ATC  AAG         1106
Leu  Pro  Ser  Leu  Lys  Asp  Phe  Glu  Glu  Gln  Phe  Leu  Asn  Thr  Ile  Lys
                765                      770                     775

GAG  GAC  AAG  GGC  TAC  ATG  AGC  ACC  AGC  CTG  AGC  AGC  GAG  CGC  CTG  GCC         1154
Glu  Asp  Lys  Gly  Tyr  Met  Ser  Thr  Ser  Leu  Ser  Ser  Glu  Arg  Leu  Ala
                780                      785                     790

GCC  TTC  GGC  AGC  CGC  AAG  ATC  ATC  CTG  CGC  CTG  CAG  GTG  CCC  AAG  GGC         1202
Ala  Phe  Gly  Ser  Arg  Lys  Ile  Ile  Leu  Arg  Leu  Gln  Val  Pro  Lys  Gly
          795                      800                     805

AGC  ACT  GGT  GCC  TAC  CTG  AGC  GCC  ATC  GGC  GGC  TTC  GCC  AGC  GAG  AAG         1250
Ser  Thr  Gly  Ala  Tyr  Leu  Ser  Ala  Ile  Gly  Gly  Phe  Ala  Ser  Glu  Lys
     810                      815                     820

GAG  ATC  CTG  CTG  GAT  AAG  GAC  AGC  AAG  TAC  CAC  ATC  GAC  AAG  GTG  ACC         1298
Glu  Ile  Leu  Leu  Asp  Lys  Asp  Ser  Lys  Tyr  His  Ile  Asp  Lys  Val  Thr
825                      830                     835                      840

GAG  GTG  ATC  ATC  AAG  GGC  GTG  AAG  CGC  TAC  GTG  GTG  GAC  GCC  ACC  CTG         1346
Glu  Val  Ile  Ile  Lys  Gly  Val  Lys  Arg  Tyr  Val  Val  Asp  Ala  Thr  Leu
                845                      850                     855

CTG  ACC  AAC  TAG                                                                      1358
Leu  Thr  Asn
```

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Met  Gly  Trp  Ser  Trp  Ile  Phe  Leu  Phe  Leu  Leu  Ser  Gly  Ala  Ala  Gly
1                   5                    10                     15

Val  His  Cys  Leu  Ser  Ser  Ser  Phe  Ala  Asp  Ser  Asn  Pro  Ile  Arg
               20                   25                     30

Val  Thr  Asp  Arg  Ala  Ala  Ser  Thr  Leu  Gln  Asn  Leu  Lys  Ile  Thr  Asp
          35                        40                     45

Lys  Val  Glu  Asp  Phe  Lys  Glu  Asp  Lys  Glu  Lys  Ala  Lys  Glu  Trp  Gly
     50                   55                       60

Lys  Glu  Lys  Glu  Lys  Glu  Trp  Lys  Leu  Thr  Ala  Thr  Glu  Lys  Gly  Lys
65                        70                        75                      80

Met  Asn  Asn  Phe  Leu  Asp  Asn  Lys  Asn  Asp  Ile  Lys  Thr  Asn  Tyr  Lys
                    85                       90                      95

Glu  Ile  Thr  Phe  Ser  Ile  Ala  Gly  Ser  Phe  Glu  Asp  Glu  Ile  Lys  Asp
                    100                      105                     110

Leu  Lys  Glu  Ile  Asp  Lys  Met  Phe  Asp  Lys  Thr  Asn  Leu  Ser  Asn  Ser
               115                      120                      125

Ile  Ile  Thr  Tyr  Lys  Asn  Val  Glu  Pro  Thr  Thr  Ile  Gly  Phe  Asn  Lys
     130                      135                      140

Ser  Leu  Thr  Glu  Gly  Asn  Thr  Ile  Asn  Ser  Asp  Ala  Met  Ala  Gln  Phe
145                      150                       155                     160
```

| | | | | | | | | | | | | | | |
|---|---|---|---|---|---|---|---|---|---|---|---|---|---|---|
| Lys | Glu | Gln | Phe | Leu<br>165 | Asp | Arg | Asp | Ile | Lys<br>170 | Phe | Asp | Ser | Tyr | Leu<br>175 | Asp |
| Thr | His | Leu | Thr<br>180 | Ala | Gln | Gln | Val | Ser<br>185 | Ser | Lys | Glu | Arg | Val<br>190 | Ile | Leu |
| Lys | Val | Thr<br>195 | Val | Pro | Ser | Gly | Lys<br>200 | Gly | Ser | Thr | Thr | Pro<br>205 | Thr | Lys | Ala |
| Gly | Val<br>210 | Ile | Leu | Asn | Asn | Ser | Glu<br>215 | Tyr | Lys | Met | Leu<br>220 | Ile | Asp | Asn | Gly |
| Tyr<br>225 | Met | Val | His | Val | Asp<br>230 | Lys | Val | Ser | Lys | Val<br>235 | Val | Lys | Lys | Gly | Val<br>240 |
| Glu | Cys | Leu | Gln | Ile<br>245 | Glu | Gly | Thr | Leu | Lys<br>250 | Lys | Ser | Leu | Asp | Phe<br>255 | Lys |
| Asn | Asp | Ile | Asn<br>260 | Ala | Glu | Ala | His | Ser<br>265 | Trp | Gly | Met | Lys | Asn<br>270 | Tyr | Glu |
| Glu | Trp | Ala<br>275 | Lys | Asp | Leu | Thr | Asp<br>280 | Ser | Gln | Arg | Glu | Ala<br>285 | Leu | Asp | Gly |
| Tyr | Ala<br>290 | Arg | Gln | Asp | Tyr | Lys<br>295 | Glu | Ile | Asn | Asn | Tyr<br>300 | Leu | Arg | Asn | Gln |
| Gly<br>305 | Gly | Ser | Gly | Asn | Glu<br>310 | Lys | Leu | Asp | Ala | Gln<br>315 | Ile | Lys | Asn | Ile | Ser<br>320 |
| Asp | Ala | Leu | Gly | Lys<br>325 | Lys | Pro | Ile | Pro | Glu<br>330 | Asn | Ile | Thr | Val | Tyr<br>335 | Arg |
| Trp | Cys | Gly | Met<br>340 | Pro | Glu | Phe | Gly | Tyr<br>345 | Gln | Ile | Ser | Asp | Pro<br>350 | Leu | Pro |
| Ser | Leu | Lys<br>355 | Asp | Phe | Glu | Glu | Gln<br>360 | Phe | Leu | Asn | Thr | Ile<br>365 | Lys | Glu | Asp |
| Lys | Gly<br>370 | Tyr | Met | Ser | Thr | Ser<br>375 | Leu | Ser | Ser | Glu | Arg<br>380 | Leu | Ala | Ala | Phe |
| Gly<br>385 | Ser | Arg | Lys | Ile | Ile<br>390 | Leu | Arg | Leu | Gln | Val<br>395 | Pro | Lys | Gly | Ser | Thr<br>400 |
| Gly | Ala | Tyr | Leu | Ser<br>405 | Ala | Ile | Gly | Gly | Phe<br>410 | Ala | Ser | Glu | Lys | Glu<br>415 | Ile |
| Leu | Leu | Asp | Lys<br>420 | Asp | Ser | Lys | Tyr | His<br>425 | Ile | Asp | Lys | Val | Thr<br>430 | Glu | Val |
| Ile | Ile | Lys<br>435 | Gly | Val | Lys | Arg | Tyr<br>440 | Val | Val | Asp | Ala | Thr<br>445 | Leu | Leu | Thr |
| Asn | | | | | | | | | | | | | | | |

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Peptide
        (B) LOCATION: 1..16
        (D) OTHER INFORMATION: /note= "linker peptide for fusion
            of VIP1A(a) and VIP2A(a) used to construct pCIB5533"

(x) SEQUENCE DESCRIPTION: SEQ ID NO:47:

| | | |

( 2 ) INFORMATION FOR SEQ ID NO:48:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA encoding linker peptide
              used to construct pCIB5533"

( i i i ) HYPOTHETICAL: NO ( x i ) SEQUENCE DESCRIPTION: SEQ ID NO:48:

```
CCCGGGCCTT  CTACTCCCCC  AACTCCCTCT  CCTAGCACGC  CTCCGACACC  TAGCGATATC      60

GGATCC                                                                      66
```

( 2 ) INFORMATION FOR SEQ ID NO:49:

( i ) SEQUENCE CHARACTERISTICS:
        ( A ) LENGTH: 4031 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 6..4019
        ( D ) OTHER INFORMATION: /note= "Maize optimized DNA
              sequence encoding a VIP2A(a) - VIP1A(a) fusion protein as
              contained in pCIB5531"

( x i ) SEQUENCE DESCRIPTION: SEQ ID NO:49:

```
GATCC ATG AAG CGC ATG GAG GGC AAG CTG TTC ATG GTG AGC AAG AAG     47
      Met Lys Arg Met Glu Gly Lys Leu Phe Met Val Ser Lys Lys
      450                     455                     460

CTC CAG GTG GTG ACC AAG ACC GTG CTG CTG AGC ACC GTG TTC AGC ATC   95
Leu Gln Val Val Thr Lys Thr Val Leu Leu Ser Thr Val Phe Ser Ile
    465                     470                     475

AGC CTG CTG AAC AAC GAG GTG ATC AAG GCC GAG CAG CTG AAC ATC AAC  143
Ser Leu Leu Asn Asn Glu Val Ile Lys Ala Glu Gln Leu Asn Ile Asn
480                     485                     490                 495

AGC CAG AGC AAG TAC ACC AAC CTC CAG AAC CTG AAG ATC ACC GAC AAG  191
Ser Gln Ser Lys Tyr Thr Asn Leu Gln Asn Leu Lys Ile Thr Asp Lys
                500                     505                     510

GTG GAG GAC TTC AAG GAG GAC AAG GAG AAG GCC AAG GAG TGG GGC AAG  239
Val Glu Asp Phe Lys Glu Asp Lys Glu Lys Ala Lys Glu Trp Gly Lys
            515                     520                     525

GAG AAG GAG AAG GAG TGG AAG CTT ACC GCC ACC GAG AAG GGC AAG ATG  287
Glu Lys Glu Lys Glu Trp Lys Leu Thr Ala Thr Glu Lys Gly Lys Met
        530                     535                     540

AAC AAC TTC CTG GAC AAC AAG AAC GAC ATC AAG ACC AAC TAC AAG GAG  335
Asn Asn Phe Leu Asp Asn Lys Asn Asp Ile Lys Thr Asn Tyr Lys Glu
    545                     550                     555

ATC ACC TTC AGC ATA GCC GGC AGC TTC GAG GAC GAG ATC AAG GAC CTG  383
Ile Thr Phe Ser Ile Ala Gly Ser Phe Glu Asp Glu Ile Lys Asp Leu
560                     565                     570                 575

AAG GAG ATC GAC AAG ATG TTC GAC AAG ACC AAC CTG AGC AAC AGC ATC  431
Lys Glu Ile Asp Lys Met Phe Asp Lys Thr Asn Leu Ser Asn Ser Ile
                580                     585                     590
```

| | | | | | | | | | | | | | | | | |
|---|---|---|---|---|---|---|---|---|---|---|---|---|---|---|---|---|
| ATC | ACC | TAC | AAG | AAC | GTG | GAG | CCC | ACC | ACC | ATC | GGC | TTC | AAC | AAG | AGC | 479 |
| Ile | Thr | Tyr | Lys | Asn | Val | Glu | Pro | Thr | Thr | Ile | Gly | Phe | Asn | Lys | Ser | |
| | | 595 | | | | 600 | | | | | 605 | | | | | |
| CTG | ACC | GAG | GGC | AAC | ACC | ATC | AAC | AGC | GAC | GCC | ATG | GCC | CAG | TTC | AAG | 527 |
| Leu | Thr | Glu | Gly | Asn | Thr | Ile | Asn | Ser | Asp | Ala | Met | Ala | Gln | Phe | Lys | |
| | | 610 | | | | 615 | | | | 620 | | | | | | |
| GAG | CAG | TTC | CTG | GAC | CGC | GAC | ATC | AAG | TTC | GAC | AGC | TAC | CTG | GAC | ACC | 575 |
| Glu | Gln | Phe | Leu | Asp | Arg | Asp | Ile | Lys | Phe | Asp | Ser | Tyr | Leu | Asp | Thr | |
| 625 | | | | | 630 | | | | | 635 | | | | | | |
| CAC | CTG | ACC | GCC | CAG | CAG | GTG | AGC | AGC | AAG | GAG | CGC | GTG | ATC | CTG | AAG | 623 |
| His | Leu | Thr | Ala | Gln | Gln | Val | Ser | Ser | Lys | Glu | Arg | Val | Ile | Leu | Lys | |
| 640 | | | | | 645 | | | | 650 | | | | | | 655 | |
| GTG | ACC | GTC | CCC | AGC | GGC | AAG | GGC | AGC | ACC | ACC | CCC | ACC | AAG | GCC | GGC | 671 |
| Val | Thr | Val | Pro | Ser | Gly | Lys | Gly | Ser | Thr | Thr | Pro | Thr | Lys | Ala | Gly | |
| | | | | 660 | | | | | 665 | | | | | 670 | | |
| GTG | ATC | CTG | AAC | AAC | AGC | GAG | TAC | AAG | ATG | CTG | ATC | GAC | AAC | GGC | TAC | 719 |
| Val | Ile | Leu | Asn | Asn | Ser | Glu | Tyr | Lys | Met | Leu | Ile | Asp | Asn | Gly | Tyr | |
| | | | 675 | | | | | 680 | | | | | 685 | | | |
| ATG | GTG | CAC | GTG | GAC | AAG | GTG | AGC | AAG | GTG | GTG | AAG | AAG | GGC | GTG | GAG | 767 |
| Met | Val | His | Val | Asp | Lys | Val | Ser | Lys | Val | Val | Lys | Lys | Gly | Val | Glu | |
| | | 690 | | | | | 695 | | | | | 700 | | | | |
| TGC | CTC | CAG | ATC | GAG | GGC | ACC | CTG | AAG | AAG | AGT | CTA | GAC | TTC | AAG | AAC | 815 |
| Cys | Leu | Gln | Ile | Glu | Gly | Thr | Leu | Lys | Lys | Ser | Leu | Asp | Phe | Lys | Asn | |
| | 705 | | | | | 710 | | | | | 715 | | | | | |
| GAC | ATC | AAC | GCC | GAG | GCC | CAC | AGC | TGG | GGC | ATG | AAG | AAC | TAC | GAG | GAG | 863 |
| Asp | Ile | Asn | Ala | Glu | Ala | His | Ser | Trp | Gly | Met | Lys | Asn | Tyr | Glu | Glu | |
| 720 | | | | | 725 | | | | | 730 | | | | | 735 | |
| TGG | GCC | AAG | GAC | CTG | ACC | GAC | AGC | CAG | CGC | GAG | GCC | CTG | GAC | GGC | TAC | 911 |
| Trp | Ala | Lys | Asp | Leu | Thr | Asp | Ser | Gln | Arg | Glu | Ala | Leu | Asp | Gly | Tyr | |
| | | | | 740 | | | | 745 | | | | | 750 | | | |
| GCC | CGC | CAG | GAC | TAC | AAG | GAG | ATC | AAC | AAC | TAC | CTG | CGC | AAC | CAG | GGC | 959 |
| Ala | Arg | Gln | Asp | Tyr | Lys | Glu | Ile | Asn | Asn | Tyr | Leu | Arg | Asn | Gln | Gly | |
| | | | 755 | | | | | 760 | | | | | 765 | | | |
| GGC | AGC | GGC | AAC | GAG | AAG | CTG | GAC | GCC | CAG | ATC | AAG | AAC | ATC | AGC | GAC | 1007 |
| Gly | Ser | Gly | Asn | Glu | Lys | Leu | Asp | Ala | Gln | Ile | Lys | Asn | Ile | Ser | Asp | |
| | | 770 | | | | | 775 | | | | 780 | | | | | |
| GCC | CTG | GGC | AAG | AAG | CCC | ATC | CCC | GAG | AAC | ATC | ACC | GTG | TAC | CGC | TGG | 1055 |
| Ala | Leu | Gly | Lys | Lys | Pro | Ile | Pro | Glu | Asn | Ile | Thr | Val | Tyr | Arg | Trp | |
| | 785 | | | | | 790 | | | | | 795 | | | | | |
| TGC | GGC | ATG | CCC | GAG | TTC | GGC | TAC | CAG | ATC | AGC | GAC | CCC | CTG | CCC | AGC | 1103 |
| Cys | Gly | Met | Pro | Glu | Phe | Gly | Tyr | Gln | Ile | Ser | Asp | Pro | Leu | Pro | Ser | |
| 800 | | | | | 805 | | | | | 810 | | | | | 815 | |
| CTG | AAG | GAC | TTC | GAG | GAG | CAG | TTC | CTG | AAC | ACC | ATC | AAG | GAG | GAC | AAG | 1151 |
| Leu | Lys | Asp | Phe | Glu | Glu | Gln | Phe | Leu | Asn | Thr | Ile | Lys | Glu | Asp | Lys | |
| | | | | 820 | | | | | 825 | | | | | 830 | | |
| GGC | TAC | ATG | AGC | ACC | AGC | CTG | AGC | AGC | GAG | CGC | CTG | GCC | GCC | TTC | GGC | 1199 |
| Gly | Tyr | Met | Ser | Thr | Ser | Leu | Ser | Ser | Glu | Arg | Leu | Ala | Ala | Phe | Gly | |
| | | | 835 | | | | | 840 | | | | | 845 | | | |
| AGC | CGC | AAG | ATC | ATC | CTG | CGC | CTG | CAG | GTG | CCC | AAG | GGC | AGC | ACT | GGT | 1247 |
| Ser | Arg | Lys | Ile | Ile | Leu | Arg | Leu | Gln | Val | Pro | Lys | Gly | Ser | Thr | Gly | |
| | | 850 | | | | | 855 | | | | | 860 | | | | |
| GCC | TAC | CTG | AGC | GCC | ATC | GGC | GGC | TTC | GCC | AGC | GAG | AAG | GAG | ATC | CTG | 1295 |
| Ala | Tyr | Leu | Ser | Ala | Ile | Gly | Gly | Phe | Ala | Ser | Glu | Lys | Glu | Ile | Leu | |
| | 865 | | | | | 870 | | | | | 875 | | | | | |
| CTG | GAT | AAG | GAC | AGC | AAG | TAC | CAC | ATC | GAC | AAG | GTG | ACC | GAG | GTG | ATC | 1343 |
| Leu | Asp | Lys | Asp | Ser | Lys | Tyr | His | Ile | Asp | Lys | Val | Thr | Glu | Val | Ile | |
| 880 | | | | | 885 | | | | | 890 | | | | | 895 | |
| ATC | AAG | GGC | GTG | AAG | CGC | TAC | GTG | GTG | GAC | GCC | ACC | CTG | CTG | ACC | AAC | 1391 |
| Ile | Lys | Gly | Val | Lys | Arg | Tyr | Val | Val | Asp | Ala | Thr | Leu | Leu | Thr | Asn | |
| | | | | 900 | | | | | 905 | | | | | 910 | | |

```
TCC CGG GGG CCT TCT ACT CCC CCA ACT CCC TCT CCT AGC ACG CCT CCG    1439
Ser Arg Gly Pro Ser Thr Pro Pro Thr Pro Ser Pro Ser Thr Pro Pro
        915                 920                 925

ACA CCT AGC GAT ATC GGA TCC ACC ATG AAG ACC AAC CAG ATC AGC ACC    1487
Thr Pro Ser Asp Ile Gly Ser Thr Met Lys Thr Asn Gln Ile Ser Thr
        930                 935                 940

ACC CAG AAG AAC CAG CAG AAG GAG ATG GAC CGC AAG GGC CTG CTG GGC    1535
Thr Gln Lys Asn Gln Gln Lys Glu Met Asp Arg Lys Gly Leu Leu Gly
        945                 950                 955

TAC TAC TTC AAG GGC AAG GAC TTC AGC AAC CTG ACC ATG TTC GCC CCC    1583
Tyr Tyr Phe Lys Gly Lys Asp Phe Ser Asn Leu Thr Met Phe Ala Pro
960                 965                 970                 975

ACG CGT GAC AGC ACC CTG ATC TAC GAC CAG CAG ACC GCC AAC AAG CTG    1631
Thr Arg Asp Ser Thr Leu Ile Tyr Asp Gln Gln Thr Ala Asn Lys Leu
            980                 985                 990

CTG GAC AAG AAG CAG CAG GAG TAC CAG AGC ATC CGC TGG ATC GGC CTG    1679
Leu Asp Lys Lys Gln Gln Glu Tyr Gln Ser Ile Arg Trp Ile Gly Leu
                995                 1000                1005

ATC CAG AGC AAG GAG ACC GGC GAC TTC ACC TTC AAC CTG AGC GAG GAC    1727
Ile Gln Ser Lys Glu Thr Gly Asp Phe Thr Phe Asn Leu Ser Glu Asp
        1010                1015                1020

GAG CAG GCC ATC ATC GAG ATC AAC GGC AAG ATC ATC AGC AAC AAG GGC    1775
Glu Gln Ala Ile Ile Glu Ile Asn Gly Lys Ile Ile Ser Asn Lys Gly
        1025                1030                1035

AAG GAG AAG CAG GTG GTG CAC CTG GAG AAG GGC AAG CTG GTG CCC ATC    1823
Lys Glu Lys Gln Val Val His Leu Glu Lys Gly Lys Leu Val Pro Ile
1040                1045                1050                1055

AAG ATC GAG TAC CAG AGC GAC ACC AAG TTC AAC ATC GAC AGC AAG ACC    1871
Lys Ile Glu Tyr Gln Ser Asp Thr Lys Phe Asn Ile Asp Ser Lys Thr
                1060                1065                1070

TTC AAG GAG CTG AAG CTT TTC AAG ATC GAC AGC CAG AAC CAG CCC CAG    1919
Phe Lys Glu Leu Lys Leu Phe Lys Ile Asp Ser Gln Asn Gln Pro Gln
                1075                1080                1085

CAG GTG CAG CAG GAC GAG CTG CGC AAC CCC GAG TTC AAC AAG AAG GAG    1967
Gln Val Gln Gln Asp Glu Leu Arg Asn Pro Glu Phe Asn Lys Lys Glu
        1090                1095                1100

AGC CAG GAG TTC CTG GCC AAG CCC AGC AAG ATC AAC CTG TTC ACC CAG    2015
Ser Gln Glu Phe Leu Ala Lys Pro Ser Lys Ile Asn Leu Phe Thr Gln
        1105                1110                1115

CAG ATG AAG CGC GAG ATC GAC GAG GAC ACC GAC ACC GAC GGC GAC AGC    2063
Gln Met Lys Arg Glu Ile Asp Glu Asp Thr Asp Thr Asp Gly Asp Ser
1120                1125                1130                1135

ATC CCC GAC CTG TGG GAG GAG AAC GGC TAC ACC ATC CAG AAC CGC ATC    2111
Ile Pro Asp Leu Trp Glu Glu Asn Gly Tyr Thr Ile Gln Asn Arg Ile
                1140                1145                1150

GCC GTG AAG TGG GAC GAC AGC CTG GCT AGC AAG GGC TAC ACC AAG TTC    2159
Ala Val Lys Trp Asp Asp Ser Leu Ala Ser Lys Gly Tyr Thr Lys Phe
                1155                1160                1165

GTG AGC AAC CCC CTG GAG AGC CAC ACC GTG GGC GAC CCC TAC ACC GAC    2207
Val Ser Asn Pro Leu Glu Ser His Thr Val Gly Asp Pro Tyr Thr Asp
        1170                1175                1180

TAC GAG AAG GCC GCC CGC GAC CTG GAC CTG AGC AAC GCC AAG GAG ACC    2255
Tyr Glu Lys Ala Ala Arg Asp Leu Asp Leu Ser Asn Ala Lys Glu Thr
        1185                1190                1195

TTC AAC CCC CTG GTG GCC GCC TTC CCC AGC GTG AAC GTG AGC ATG GAG    2303
Phe Asn Pro Leu Val Ala Ala Phe Pro Ser Val Asn Val Ser Met Glu
1200                1205                1210                1215

AAG GTG ATC CTG AGC CCC AAC GAG AAC CTG AGC AAC AGC GTG GAG AGC    2351
Lys Val Ile Leu Ser Pro Asn Glu Asn Leu Ser Asn Ser Val Glu Ser
                1220                1225                1230
```

```
CAC  TCG  AGC  ACC  AAC  TGG  AGC  TAC  ACC  AAC  ACC  GAG  GGC  GCC  AGC  GTG      2399
His  Ser  Ser  Thr  Asn  Trp  Ser  Tyr  Thr  Asn  Thr  Glu  Gly  Ala  Ser  Val
               1235                1240                1245

GAG  GCC  GGC  ATC  GGT  CCC  AAG  GGC  ATC  AGC  TTC  GGC  GTG  AGC  GTG  AAC      2447
Glu  Ala  Gly  Ile  Gly  Pro  Lys  Gly  Ile  Ser  Phe  Gly  Val  Ser  Val  Asn
          1250                1255                1260

TAC  CAG  CAC  AGC  GAG  ACC  GTG  GCC  CAG  GAG  TGG  GGC  ACC  AGC  ACC  GGC      2495
Tyr  Gln  His  Ser  Glu  Thr  Val  Ala  Gln  Glu  Trp  Gly  Thr  Ser  Thr  Gly
               1265                1270                1275

AAC  ACC  AGC  CAG  TTC  AAC  ACC  GCC  AGC  GCC  GGC  TAC  CTG  AAC  GCC  AAC      2543
Asn  Thr  Ser  Gln  Phe  Asn  Thr  Ala  Ser  Ala  Gly  Tyr  Leu  Asn  Ala  Asn
1280                1285                1290                     1295

GTG  CGC  TAC  AAC  AAC  GTG  GGC  ACC  GGC  GCC  ATC  TAC  GAC  GTG  AAG  CCC      2591
Val  Arg  Tyr  Asn  Asn  Val  Gly  Thr  Gly  Ala  Ile  Tyr  Asp  Val  Lys  Pro
                    1300                1305                1310

ACC  ACC  AGC  TTC  GTG  CTG  AAC  AAC  GAC  ACC  ATC  GCC  ACC  ATC  ACC  GCC      2639
Thr  Thr  Ser  Phe  Val  Leu  Asn  Asn  Asp  Thr  Ile  Ala  Thr  Ile  Thr  Ala
               1315                1320                1325

AAG  TCG  AAT  TCC  ACC  GCC  CTG  AAC  ATC  AGC  CCC  GGC  GAG  AGC  TAC  CCC      2687
Lys  Ser  Asn  Ser  Thr  Ala  Leu  Asn  Ile  Ser  Pro  Gly  Glu  Ser  Tyr  Pro
               1330                1335                1340

AAG  AAG  GGC  CAG  AAC  GGC  ATC  GCC  ATC  ACC  AGC  ATG  GAC  GAC  TTC  AAC      2735
Lys  Lys  Gly  Gln  Asn  Gly  Ile  Ala  Ile  Thr  Ser  Met  Asp  Asp  Phe  Asn
               1345                1350                1355

AGC  CAC  CCC  ATC  ACC  CTG  AAC  AAG  AAG  CAG  GTG  GAC  AAC  CTG  CTG  AAC      2783
Ser  His  Pro  Ile  Thr  Leu  Asn  Lys  Lys  Gln  Val  Asp  Asn  Leu  Leu  Asn
1360                1365                1370                     1375

AAC  AAG  CCC  ATG  ATG  CTG  GAG  ACC  AAC  CAG  ACC  GAC  GGC  GTC  TAC  AAG      2831
Asn  Lys  Pro  Met  Met  Leu  Glu  Thr  Asn  Gln  Thr  Asp  Gly  Val  Tyr  Lys
                    1380                1385                1390

ATC  AAG  GAC  ACC  CAC  GGC  AAC  ATC  GTG  ACG  GGC  GGC  GAG  TGG  AAC  GGC      2879
Ile  Lys  Asp  Thr  His  Gly  Asn  Ile  Val  Thr  Gly  Gly  Glu  Trp  Asn  Gly
               1395                1400                1405

GTG  ATC  CAG  CAG  ATC  AAG  GCC  AAG  ACC  GCC  AGC  ATC  ATC  GTC  GAC  GAC      2927
Val  Ile  Gln  Gln  Ile  Lys  Ala  Lys  Thr  Ala  Ser  Ile  Ile  Val  Asp  Asp
          1410                1415                1420

GGC  GAG  CGC  GTG  GCC  GAG  AAG  CGC  GTG  GCC  GCC  AAG  GAC  TAC  GAG  AAC      2975
Gly  Glu  Arg  Val  Ala  Glu  Lys  Arg  Val  Ala  Ala  Lys  Asp  Tyr  Glu  Asn
          1425                1430                1435

CCC  GAG  GAC  AAG  ACC  CCC  AGC  CTG  ACC  CTG  AAG  GAC  GCC  CTG  AAG  CTG      3023
Pro  Glu  Asp  Lys  Thr  Pro  Ser  Leu  Thr  Leu  Lys  Asp  Ala  Leu  Lys  Leu
1440                1445                1450                     1455

AGC  TAC  CCC  GAC  GAG  ATC  AAG  GAG  ATC  GAG  GGC  TTG  CTG  TAC  TAC  AAG      3071
Ser  Tyr  Pro  Asp  Glu  Ile  Lys  Glu  Ile  Glu  Gly  Leu  Leu  Tyr  Tyr  Lys
                    1460                1465                1470

AAC  AAG  CCC  ATC  TAC  GAG  AGC  AGC  GTG  ATG  ACC  TAT  CTA  GAC  GAG  AAC      3119
Asn  Lys  Pro  Ile  Tyr  Glu  Ser  Ser  Val  Met  Thr  Tyr  Leu  Asp  Glu  Asn
               1475                1480                1485

ACC  GCC  AAG  GAG  GTG  ACC  AAG  CAG  CTG  AAC  GAC  ACC  ACC  GGC  AAG  TTC      3167
Thr  Ala  Lys  Glu  Val  Thr  Lys  Gln  Leu  Asn  Asp  Thr  Thr  Gly  Lys  Phe
          1490                1495                1500

AAG  GAC  GTG  AGC  CAC  CTG  TAC  GAC  GTG  AAG  CTG  ACC  CCC  AAG  ATG  AAC      3215
Lys  Asp  Val  Ser  His  Leu  Tyr  Asp  Val  Lys  Leu  Thr  Pro  Lys  Met  Asn
          1505                1510                1515

GTG  ACC  ATC  AAG  CTG  AGC  ATC  CTG  TAC  GAC  AAC  GCC  GAG  AGC  AAC  GAC      3263
Val  Thr  Ile  Lys  Leu  Ser  Ile  Leu  Tyr  Asp  Asn  Ala  Glu  Ser  Asn  Asp
1520                1525                1530                     1535

AAC  AGC  ATC  GGC  AAG  TGG  ACC  AAC  ACC  AAC  ATC  GTG  AGC  GGC  GGC  AAC      3311
Asn  Ser  Ile  Gly  Lys  Trp  Thr  Asn  Thr  Asn  Ile  Val  Ser  Gly  Gly  Asn
               1540                1545                1550
```

| | | | | | | | | | | | | | | | |
|---|---|---|---|---|---|---|---|---|---|---|---|---|---|---|---|
| AAC | GGC | AAG | AAG | CAG | TAC | AGC | AGC | AAC | AAC | CCC | GAC | GCC | AAC | CTG | ACC | 3359
| Asn | Gly | Lys | Lys | Gln | Tyr | Ser | Ser | Asn | Asn | Pro | Asp | Ala | Asn | Leu | Thr |
| | | | 1555 | | | | 1560 | | | | | 1565 | | | |
| CTG | AAC | ACC | GAC | GCC | CAG | GAG | AAG | CTG | AAC | AAG | AAC | CGC | GAC | TAC | TAC | 3407
| Leu | Asn | Thr | Asp | Ala | Gln | Glu | Lys | Leu | Asn | Lys | Asn | Arg | Asp | Tyr | Tyr |
| | | 1570 | | | | | 1575 | | | | 1580 | | | | |
| ATC | AGC | CTG | TAC | ATG | AAG | AGC | GAG | AAG | AAC | ACC | CAG | TGC | GAG | ATC | ACC | 3455
| Ile | Ser | Leu | Tyr | Met | Lys | Ser | Glu | Lys | Asn | Thr | Gln | Cys | Glu | Ile | Thr |
| | 1585 | | | | | 1590 | | | | | 1595 | | | | |
| ATC | GAC | GGC | GAG | ATA | TAC | CCC | ATC | ACC | ACC | AAG | ACC | GTG | AAC | GTG | AAC | 3503
| Ile | Asp | Gly | Glu | Ile | Tyr | Pro | Ile | Thr | Thr | Lys | Thr | Val | Asn | Val | Asn |
| 1600 | | | | | 1605 | | | | 1610 | | | | | | 1615 |
| AAG | GAC | AAC | TAC | AAG | CGC | CTG | GAC | ATC | ATC | GCC | CAC | AAC | ATC | AAG | AGC | 3551
| Lys | Asp | Asn | Tyr | Lys | Arg | Leu | Asp | Ile | Ile | Ala | His | Asn | Ile | Lys | Ser |
| | | | | 1620 | | | | | 1625 | | | | | 1630 | |
| AAC | CCC | ATC | AGC | AGC | CTG | CAC | ATC | AAG | ACC | AAC | GAC | GAG | ATC | ACC | CTG | 3599
| Asn | Pro | Ile | Ser | Ser | Leu | His | Ile | Lys | Thr | Asn | Asp | Glu | Ile | Thr | Leu |
| | | | 1635 | | | | | 1640 | | | | | 1645 | | |
| TTC | TGG | GAC | GAC | ATA | TCG | ATT | ACC | GAC | GTC | GCC | AGC | ATC | AAG | CCC | GAG | 3647
| Phe | Trp | Asp | Asp | Ile | Ser | Ile | Thr | Asp | Val | Ala | Ser | Ile | Lys | Pro | Glu |
| | | 1650 | | | | | 1655 | | | | | 1660 | | | |
| AAC | CTG | ACC | GAC | AGC | GAG | ATC | AAG | CAG | ATA | TAC | AGT | CGC | TAC | GGC | ATC | 3695
| Asn | Leu | Thr | Asp | Ser | Glu | Ile | Lys | Gln | Ile | Tyr | Ser | Arg | Tyr | Gly | Ile |
| | 1665 | | | | | 1670 | | | | | 1675 | | | | |
| AAG | CTG | GAG | GAC | GGC | ATC | CTG | ATC | GAC | AAG | AAA | GGC | GGC | ATC | CAC | TAC | 3743
| Lys | Leu | Glu | Asp | Gly | Ile | Leu | Ile | Asp | Lys | Lys | Gly | Gly | Ile | His | Tyr |
| 1680 | | | | | 1685 | | | | | 1690 | | | | | 1695 |
| GGC | GAG | TTC | ATC | AAC | GAG | GCC | AGC | TTC | AAC | ATC | GAG | CCC | CTG | CAG | AAC | 3791
| Gly | Glu | Phe | Ile | Asn | Glu | Ala | Ser | Phe | Asn | Ile | Glu | Pro | Leu | Gln | Asn |
| | | | | 1700 | | | | | 1705 | | | | | 1710 | |
| TAC | GTG | ACC | AAG | TAC | GAG | GTG | ACC | TAC | AGC | AGC | GAG | CTG | GGC | CCC | AAC | 3839
| Tyr | Val | Thr | Lys | Tyr | Glu | Val | Thr | Tyr | Ser | Ser | Glu | Leu | Gly | Pro | Asn |
| | | | 1715 | | | | | 1720 | | | | | 1725 | | |
| GTG | AGC | GAC | ACC | CTG | GAG | AGC | GAC | AAG | ATT | TAC | AAG | GAC | GGC | ACC | ATC | 3887
| Val | Ser | Asp | Thr | Leu | Glu | Ser | Asp | Lys | Ile | Tyr | Lys | Asp | Gly | Thr | Ile |
| | | | 1730 | | | | | 1735 | | | | | 1740 | | |
| AAG | TTC | GAC | TTC | ACC | AAG | TAC | AGC | AAG | AAC | GAG | CAG | GGC | CTG | TTC | TAC | 3935
| Lys | Phe | Asp | Phe | Thr | Lys | Tyr | Ser | Lys | Asn | Glu | Gln | Gly | Leu | Phe | Tyr |
| | 1745 | | | | | 1750 | | | | | 1755 | | | | |
| GAC | AGC | GGC | CTG | AAC | TGG | GAC | TTC | AAG | ATC | AAC | GCC | ATC | ACC | TAC | GAC | 3983
| Asp | Ser | Gly | Leu | Asn | Trp | Asp | Phe | Lys | Ile | Asn | Ala | Ile | Thr | Tyr | Asp |
| 1760 | | | | | 1765 | | | | | 1770 | | | | | 1775 |
| GGC | AAG | GAG | ATG | AAC | GTG | TTC | CAC | CGC | TAC | AAC | AAG | TAGATCTGAG | | | | 4029
| Gly | Lys | Glu | Met | Asn | Val | Phe | His | Arg | Tyr | Asn | Lys | | | | |
| | | | | 1780 | | | | | 1785 | | | | | | |
| CT | | | | | | | | | | | | | | | | 4031

( 2 ) INFORMATION FOR SEQ ID NO:50:

( i ) SEQUENCE CHARACTERISTICS:
        ( A ) LENGTH: 1338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| | | | | | | | | | | | | | | |
|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 |
| Val | Val | Thr | Lys | Thr | Val | Leu | Leu | Ser | Thr | Val | Phe | Ser | Ile | Ser | Leu |
| | | | 20 | | | | | 25 | | | | | 30 | |

```
Leu  Asn  Asn  Glu  Val  Ile  Lys  Ala  Glu  Gln  Leu  Asn  Ile  Asn  Ser  Gln
          35                      40                      45

Ser  Lys  Tyr  Thr  Asn  Leu  Gln  Asn  Leu  Lys  Ile  Thr  Asp  Lys  Val  Glu
     50                      55                      60

Asp  Phe  Lys  Glu  Asp  Lys  Gly  Lys  Ala  Lys  Glu  Trp  Gly  Lys  Glu  Lys
65                      70                      75                           80

Glu  Lys  Glu  Trp  Lys  Leu  Thr  Ala  Thr  Glu  Lys  Gly  Lys  Met  Asn  Asn
               85                      90                           95

Phe  Leu  Asp  Asn  Lys  Asn  Asp  Ile  Lys  Thr  Asn  Tyr  Lys  Glu  Ile  Thr
               100                     105                     110

Phe  Ser  Ile  Ala  Gly  Ser  Phe  Glu  Asp  Glu  Ile  Lys  Asp  Leu  Lys  Glu
          115                     120                     125

Ile  Asp  Lys  Met  Phe  Asp  Lys  Thr  Asn  Leu  Ser  Asn  Ser  Ile  Ile  Thr
     130                     135                     140

Tyr  Lys  Asn  Val  Glu  Pro  Thr  Thr  Ile  Gly  Phe  Asn  Lys  Ser  Leu  Thr
145                     150                     155                     160

Glu  Gly  Asn  Thr  Ile  Asn  Ser  Asp  Ala  Met  Ala  Gln  Phe  Lys  Glu  Gln
                    165                     170                     175

Phe  Leu  Asp  Arg  Asp  Ile  Lys  Phe  Asp  Ser  Tyr  Leu  Asp  Thr  His  Leu
               180                     185                     190

Thr  Ala  Gln  Gln  Val  Ser  Ser  Lys  Glu  Arg  Val  Ile  Leu  Lys  Val  Thr
          195                     200                     205

Val  Pro  Ser  Gly  Lys  Gly  Ser  Thr  Thr  Pro  Thr  Lys  Ala  Gly  Val  Ile
     210                     215                     220

Leu  Asn  Asn  Ser  Glu  Tyr  Lys  Met  Leu  Ile  Asp  Asn  Gly  Tyr  Met  Val
225                     230                     235                     240

His  Val  Asp  Lys  Val  Ser  Lys  Val  Val  Lys  Lys  Gly  Val  Glu  Cys  Leu
               245                     250                     255

Gln  Ile  Glu  Gly  Thr  Leu  Lys  Lys  Ser  Leu  Asp  Phe  Lys  Asn  Asp  Ile
               260                     265                     270

Asn  Ala  Glu  Ala  His  Ser  Trp  Gly  Met  Lys  Asn  Tyr  Glu  Glu  Trp  Ala
          275                     280                     285

Lys  Asp  Leu  Thr  Asp  Ser  Gln  Arg  Glu  Ala  Leu  Asp  Gly  Tyr  Ala  Arg
     290                     295                     300

Gln  Asp  Tyr  Lys  Glu  Ile  Asn  Asn  Tyr  Leu  Arg  Asn  Gln  Gly  Gly  Ser
305                     310                     315                     320

Gly  Asn  Glu  Lys  Leu  Asp  Ala  Gln  Ile  Lys  Asn  Ile  Ser  Asp  Ala  Leu
               325                     330                     335

Gly  Lys  Lys  Pro  Ile  Pro  Glu  Asn  Ile  Thr  Val  Tyr  Arg  Trp  Cys  Gly
               340                     345                     350

Met  Pro  Glu  Phe  Gly  Tyr  Gln  Ile  Ser  Asp  Pro  Leu  Pro  Ser  Leu  Lys
          355                     360                     365

Asp  Phe  Glu  Glu  Gln  Phe  Leu  Asn  Thr  Ile  Lys  Glu  Asp  Lys  Gly  Tyr
     370                     375                     380

Met  Ser  Thr  Ser  Leu  Ser  Ser  Glu  Arg  Leu  Ala  Ala  Phe  Gly  Ser  Arg
385                     390                     395                     400

Lys  Ile  Ile  Leu  Arg  Leu  Gln  Val  Pro  Lys  Gly  Ser  Thr  Gly  Ala  Tyr
               405                     410                     415

Leu  Ser  Ala  Ile  Gly  Gly  Phe  Ala  Ser  Glu  Lys  Glu  Ile  Leu  Leu  Asp
          420                     425                     430

Lys  Asp  Ser  Lys  Tyr  His  Ile  Asp  Lys  Val  Thr  Glu  Val  Ile  Ile  Lys
               435                     440                     445

Gly  Val  Lys  Arg  Tyr  Val  Val  Asp  Ala  Thr  Leu  Leu  Thr  Asn  Ser  Arg
     450                     455                     460
```

```
Gly  Pro  Ser  Thr  Pro  Pro  Thr  Pro  Ser  Pro  Ser  Thr  Pro  Pro  Thr  Pro
465            470                      475                      480

Ser  Asp  Ile  Gly  Ser  Thr  Met  Lys  Thr  Asn  Gln  Ile  Ser  Thr  Thr  Gln
                    485                 490                      495

Lys  Asn  Gln  Gln  Lys  Glu  Met  Asp  Arg  Lys  Gly  Leu  Leu  Gly  Tyr  Tyr
               500                      505                      510

Phe  Lys  Gly  Lys  Asp  Phe  Ser  Asn  Leu  Thr  Met  Phe  Ala  Pro  Thr  Arg
          515                 520                      525

Asp  Ser  Thr  Leu  Ile  Tyr  Asp  Gln  Gln  Thr  Ala  Asn  Lys  Leu  Leu  Asp
530                      535                      540

Lys  Lys  Gln  Gln  Glu  Tyr  Gln  Ser  Ile  Arg  Trp  Ile  Gly  Leu  Ile  Gln
545                      550                 555                           560

Ser  Lys  Glu  Thr  Gly  Asp  Phe  Thr  Phe  Asn  Leu  Ser  Glu  Asp  Glu  Gln
               565                      570                      575

Ala  Ile  Ile  Glu  Ile  Asn  Gly  Lys  Ile  Ile  Ser  Asn  Lys  Gly  Lys  Glu
               580                 585                      590

Lys  Gln  Val  Val  His  Leu  Glu  Lys  Gly  Lys  Leu  Val  Pro  Ile  Lys  Ile
          595                      600                 605

Glu  Tyr  Gln  Ser  Asp  Thr  Lys  Phe  Asn  Ile  Asp  Ser  Lys  Thr  Phe  Lys
     610                 615                      620

Glu  Leu  Lys  Leu  Phe  Lys  Ile  Asp  Ser  Gln  Asn  Gln  Pro  Gln  Gln  Val
625                 630                      635                           640

Gln  Gln  Asp  Glu  Leu  Arg  Asn  Pro  Glu  Phe  Asn  Lys  Lys  Glu  Ser  Gln
                    645                      650                      655

Glu  Phe  Leu  Ala  Lys  Pro  Ser  Lys  Ile  Asn  Leu  Phe  Thr  Gln  Gln  Met
               660                      665                 670

Lys  Arg  Glu  Ile  Asp  Glu  Asp  Thr  Asp  Thr  Asp  Gly  Asp  Ser  Ile  Pro
          675                 680                      685

Asp  Leu  Trp  Glu  Glu  Asn  Gly  Tyr  Thr  Ile  Gln  Asn  Arg  Ile  Ala  Val
          690                 695                      700

Lys  Trp  Asp  Asp  Ser  Leu  Ala  Ser  Lys  Gly  Tyr  Thr  Lys  Phe  Val  Ser
705                      710                      715                      720

Asn  Pro  Leu  Glu  Ser  His  Thr  Val  Gly  Asp  Pro  Tyr  Thr  Asp  Tyr  Glu
                    725                      730                      735

Lys  Ala  Ala  Arg  Asp  Leu  Asp  Leu  Ser  Asn  Ala  Lys  Glu  Thr  Phe  Asn
               740                      745                      750

Pro  Leu  Val  Ala  Ala  Phe  Pro  Ser  Val  Asn  Val  Ser  Met  Glu  Lys  Val
          755                      760                      765

Ile  Leu  Ser  Pro  Asn  Glu  Asn  Leu  Ser  Asn  Ser  Val  Glu  Ser  His  Ser
     770                      775                      780

Ser  Thr  Asn  Trp  Ser  Tyr  Thr  Asn  Thr  Glu  Gly  Ala  Ser  Val  Glu  Ala
785                      790                      795                      800

Gly  Ile  Gly  Pro  Lys  Gly  Ile  Ser  Phe  Gly  Val  Ser  Val  Asn  Tyr  Gln
               805                      810                      815

His  Ser  Glu  Thr  Val  Ala  Gln  Glu  Trp  Gly  Thr  Ser  Thr  Gly  Asn  Thr
               820                      825                      830

Ser  Gln  Phe  Asn  Thr  Ala  Ser  Ala  Gly  Tyr  Leu  Asn  Ala  Asn  Val  Arg
          835                      840                      845

Tyr  Asn  Asn  Val  Gly  Thr  Gly  Ala  Ile  Tyr  Asp  Val  Lys  Pro  Thr  Thr
     850                      855                      860

Ser  Phe  Val  Leu  Asn  Asn  Asp  Thr  Ile  Ala  Thr  Ile  Thr  Ala  Lys  Ser
865                      870                      875                      880

Asn  Ser  Thr  Ala  Leu  Asn  Ile  Ser  Pro  Gly  Glu  Ser  Tyr  Pro  Lys  Lys
```

-continued

|     |     |     | 885 |     |     |     |     | 890 |     |     |     |     | 895 |     |
| --- | --- | --- | --- | --- | --- | --- | --- | --- | --- | --- | --- | --- | --- | --- |

Gly Gln Asn Gly Ile Ala Ile Thr Ser Met Asp Asp Phe Asn Ser His
            900                905                910

Pro Ile Thr Leu Asn Lys Lys Gln Val Asp Asn Leu Leu Asn Asn Lys
        915                920                925

Pro Met Met Leu Glu Thr Asn Gln Thr Asp Gly Val Tyr Lys Ile Lys
        930                935                940

Asp Thr His Gly Asn Ile Val Thr Gly Gly Glu Trp Asn Gly Val Ile
945                950                955                960

Gln Gln Ile Lys Ala Lys Thr Ala Ser Ile Ile Val Asp Asp Gly Glu
                965                970                975

Arg Val Ala Glu Lys Arg Val Ala Ala Lys Asp Tyr Glu Asn Pro Glu
            980                985                990

Asp Lys Thr Pro Ser Leu Thr Leu Lys Asp Ala Leu Lys Leu Ser Tyr
        995                1000                1005

Pro Asp Glu Ile Lys Glu Ile Glu Gly Leu Leu Tyr Lys Asn Lys
    1010                1015                1020

Pro Ile Tyr Glu Ser Ser Val Met Thr Tyr Leu Asp Glu Asn Thr Ala
1025                1030                1035                1040

Lys Glu Val Thr Lys Gln Leu Asn Asp Thr Thr Gly Lys Phe Lys Asp
            1045                1050                1055

Val Ser His Leu Tyr Asp Val Lys Leu Thr Pro Lys Met Asn Val Thr
            1060                1065                1070

Ile Lys Leu Ser Ile Leu Tyr Asp Asn Ala Glu Ser Asn Asp Asn Ser
        1075                1080                1085

Ile Gly Lys Trp Thr Asn Thr Asn Ile Val Ser Gly Gly Asn Asn Gly
    1090                1095                1100

Lys Lys Gln Tyr Ser Ser Asn Asn Pro Asp Ala Asn Leu Thr Leu Asn
1105                1110                1115                1120

Thr Asp Ala Gln Glu Lys Leu Asn Lys Asn Arg Asp Tyr Tyr Ile Ser
                1125                1130                1135

Leu Tyr Met Lys Ser Glu Lys Asn Thr Gln Cys Glu Ile Thr Ile Asp
            1140                1145                1150

Gly Glu Ile Tyr Pro Ile Thr Thr Lys Thr Val Asn Val Asn Lys Asp
        1155                1160                1165

Asn Tyr Lys Arg Leu Asp Ile Ile Ala His Asn Ile Lys Ser Asn Pro
1170                1175                1180

Ile Ser Ser Leu His Ile Lys Thr Asn Asp Glu Ile Thr Leu Phe Trp
1185                1190                1195                1200

Asp Asp Ile Ser Ile Thr Asp Val Ala Ser Ile Lys Pro Glu Asn Leu
            1205                1210                1215

Thr Asp Ser Glu Ile Lys Gln Ile Tyr Ser Arg Tyr Gly Ile Lys Leu
        1220                1225                1230

Glu Asp Gly Ile Leu Ile Asp Lys Lys Gly Gly Ile His Tyr Gly Glu
            1235                1240                1245

Phe Ile Asn Glu Ala Ser Phe Asn Ile Glu Pro Leu Gln Asn Tyr Val
        1250                1255                1260

Thr Lys Tyr Glu Val Thr Tyr Ser Ser Glu Leu Gly Pro Asn Val Ser
1265                1270                1275                1280

Asp Thr Leu Glu Ser Asp Lys Ile Tyr Lys Asp Gly Thr Ile Lys Phe
            1285                1290                1295

Asp Phe Thr Lys Tyr Ser Lys Asn Glu Gln Gly Leu Phe Tyr Asp Ser
            1300                1305                1310

-continued

```
Gly Leu Asn Trp Asp Phe Lys Ile Asn Ala Ile Thr Tyr Asp Gly Lys
        1315                1320                1325

Glu Met Asn Val Phe His Arg Tyr Asn Lys
    1330            1335
```